United States Patent
Cui et al.

(10) Patent No.: US 7,772,246 B2
(45) Date of Patent: Aug. 10, 2010

(54) PYRAZOLE COMPOUNDS AS RAF INHIBITORS

(75) Inventors: Jingrong Jean Cui, San Diego, CA (US); Judith Gail Deal, Wildomar, CA (US); Danlin Gu, San Diego, CA (US); Chuangxing Guo, San Diego, CA (US); Mary Catherine Johnson, San Diego, CA (US); Robert Steven Kania, San Diego, CA (US); Susan Elizabeth Kephart, San Diego, CA (US); Maria Angelica Linton, San Diego, CA (US); Indrawan James McAlpine, San Diego, CA (US); Mason Alan Pairish, San Diego, CA (US); Cynthia Louise Palmer, La Mesa, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 12/182,977

(22) Filed: Jul. 30, 2008

(65) Prior Publication Data

US 2009/0221608 A1 Sep. 3, 2009

Related U.S. Application Data

(60) Provisional application No. 61/080,054, filed on Jul. 11, 2008, provisional application No. 60/953,235, filed on Aug. 1, 2007.

(51) Int. Cl.
*A61K 31/505* (2006.01)
(52) U.S. Cl. .................. 514/275; 544/331; 546/113; 548/373.1
(58) Field of Classification Search .................. 514/275; 544/331; 546/113; 548/373.1
See application file for complete search history.

(56) References Cited

U.S. PATENT DOCUMENTS

| | | | |
|---|---|---|---|
| 6,423,713 | B1 | 7/2002 | Anantanarayan et al. |
| 6,884,804 | B2 * | 4/2005 | Choon-Moon ............. 514/275 |
| 7,247,734 | B2 | 7/2007 | Drysdale et al. |
| 7,429,665 | B2 | 9/2008 | Verhoest et al. |
| 7,501,430 | B2 | 3/2009 | Lapierre et al. |
| 2004/0082551 | A1 | 4/2004 | Benson et al. |
| 2006/0106027 | A1 | 5/2006 | Furet et al. |
| 2007/0281955 | A1 | 12/2007 | Lapierre et al. |
| 2009/0111985 | A1 | 4/2009 | Ashwell et al. |

FOREIGN PATENT DOCUMENTS

| | | |
|---|---|---|
| GB | 2 306 108 | 4/1997 |
| WO | WO 01/30154 | 5/2001 |
| WO | WO 02/062787 | 8/2002 |
| WO | WO 02/066462 | 8/2002 |
| WO | WO 2004/026306 | 4/2004 |
| WO | WO 2004/072033 | * 8/2004 |
| WO | WO 2007/105058 | 9/2007 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Chong, H. et al., "Positive and negative regulation of Raf Kinase activity and function by Phosphorylation," *The EMBO Journal*, 2001, 20:3716-3727.
Davies, H. et al., "Mutations of the BRAF gene in human cancer," *Nature*, 2002, 417:949-954.
Hayes, J., et al., "A Novel and Efficient Synthesis of a Tetra-Substituted Imidazole," *Tetrahedron Letters*, 1994, 273-274, vol. 35, No. 2.
Jonkers, J. et al., "Oncogene addition: Sometimes a temporary slavery," *Cancer Cell*, 2004, 6:535-538.
Monia, B. et al., "Antitumor activity of a phosphorothioate antisense oligodeoxynucleotide targeted against C-raf kinase," *Nature Medicine*, 1996, 2:668-675.
Sawyer, J., et al., "Synthesis and Activity of New Aryl- and Heteroaryl-Substituted Pyrazole Inhibitors of the Transforming Growth Factor-β Type I Receptor Kinase Domain," *Journal of Medicinal Chemistry*, 2003, 3953-3956, vol. 46, No. 19.
Takle, A., et al., "The identification of potent, selective and CNS penetrant furan-based inhibitors of B-Raf kinase," *Bioorganic & Medicinal Chemistry Letters*, 2008, 4373-4376, vol. 18, No. 15.
Wellbrock, C., "The Raf Proteins Take Centre Stage," *Nature Reviews—Molecular Cell Biology*, 2004, 11:875-885.

* cited by examiner

*Primary Examiner*—James O Wilson
*Assistant Examiner*—Douglas M Willis
(74) *Attorney, Agent, or Firm*—Jeffrey H. Tidwell; Vincent P. Liptak

(57) ABSTRACT

The present invention is directed to compounds of Formula (I),

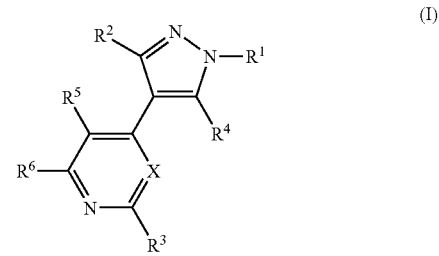

and to pharmaceutically acceptable salts thereof, their synthesis, and their use as Raf inhibitors.

2 Claims, No Drawings

PYRAZOLE COMPOUNDS AS RAF INHIBITORS

This application claims the benefit of U.S. Provisional Application No. 60/953,235 filed Aug. 1, 2007, and U.S. Provisional Application No. 61/080,054 filed Jul. 11, 2008, the contents of which are hereby incorporated by reference in their entireties.

FIELD OF THE INVENTION

The present invention is directed to compounds, their synthesis, and their use as modulators or inhibitors of the Raf enzyme. The compounds of the present invention are useful for modulating (e.g. inhibiting) Raf activity and for treating diseases or conditions mediated by Raf, such as for example, disease states associated with abnormal cell growth such as cancer.

BACKGROUND

The "Erk pathway" is an intracellular signal transduction pathway used by nearly all types of human cells to translate extracellular signals to cellular decisions, including proliferation, differentiation, senescence, or apoptosis (Wellbrock et al., *Nat. Rev. Mol. Cell Biol.* 11:875-885 (2004)). One of the invariant components of this pathway is the Ras GTPase, which receives signals from membrane receptors and activates the Raf protein kinases, which activate the Mek protein kinases, which in turn activate the Erk protein kinases. Activated Erk kinases phosphorylate a number of nuclear and cytoplasmic targets to initiate various cellular decisions. The biological importance of Raf in the Erk pathway is underscored by the finding that mutated forms of Raf are associated with certain human malignancies (see e.g. Monia et al., *Nature Medicine* 2:668-675 (1996); Davies et al., *Nature* 417:949-954 (2002)). Three distinct genes have been identified in mammals that encode Raf proteins; a-Raf, b-Raf and c-Raf (also known as Raf-1) and isoformic variants that result from differential splicing of mRNA are known (Chong et al., *EMBO J.* 20:3716-3727 (2001)). The Erk pathway is mutationally activated in a number of human cancers, most often by mutation of the Ras or b-Raf genes. Mutations in Ras and b-Raf genes generally occur in the same tumor types, including cancers of the colon, lung and pancreas and melanoma, but are usually mutually exclusive. This suggests that activation of either Ras or Raf is sufficient for pathway activation and cancer progression.

Since tumor cells frequently become dependent, or 'addicted' to one or two key signaling pathways for their survival (see, e.g. Jonkers et al., *Cancer Cell.* 6:535-538 (2004)), the Erk pathway represents a highly attractive target for drug intervention to treat cancer. Protein kinases in general are considered desirable targets for drug therapy, as evidenced by recent successes in targeting growth factor receptor and intracellular tyrosine kinases. Inhibitors of Mek have shown promise in clinical trials, however, there is ample evidence to indicate Mek-independent Raf signaling that may also contribute to cancer progression (Wellbrock et al, *Nat. Rev. Mol. Cell Biol.* 11:875-885 (2004)). Therefore, targeting Raf kinases promises an alternative and complementary approach to treating tumors in which Ras or Raf genes are mutated.

SUMMARY

In one embodiment, the present invention is a compound of Formula (I)

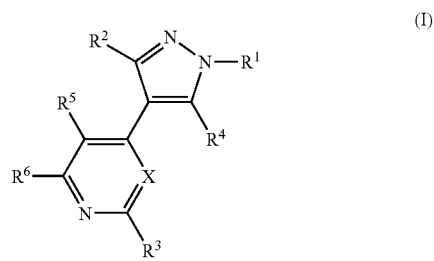

wherein:

X is N or $CR^7$;

$R^1$ is H, $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, or $C_2$-$C_8$ heteroaryl, wherein each of said $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, and $C_2$-$C_9$ heteroaryl is optionally substituted with one or more $R^8$;

$R^2$ is $C_2$-$C_9$ cycloheteroalkyl or $C_5$-$C_{14}$ heteroaryl, wherein each of said $C_2$-$C_9$ cycloheteroalkyl and $C_5$-$C_{14}$ heteroaryl is optionally substituted with one or more $R^8$;

$R^3$ is H or —$NR^9R^{10}$;

$R^4$, $R^5$, $R^6$, $R^7$ are each independently H, —$NR^9R^{10}$, —CN, —$C(O)R^9$, —$C(O)OR^9$, —$NO_2$, —$SR^9$, —$OR^9$, $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, or $C_2$-$C_8$ heteroaryl wherein each of said $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, or $C_2$-$C_9$ heteroaryl is optionally substituted with one or more $R^8$;

each $R^8$ is independently —OH, fluorine, chlorine, bromine, cyano, —$NR^9R^{10}$, —$C(O)N(R^9R^{10})$, —$C(O)R^9$, —$C(O)OR^9$, —$NO_2$, $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, $C_2$-$C_8$ heteroaryl, or —$(CH_2)_nC(O)R^9$, wherein each of said $C_3$-$C_8$ cycloalkyl, $C_6$-$C_{14}$ aryl, $C_2$-$C_9$ cycloheteroalkyl, and $C_2$-$C_9$ heteroaryl is optionally substituted with one or more $R^{11}$;

$R^9$ and $R^{10}$ are each independently H, $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, or $C_2$-$C_8$ heteroaryl, wherein each of said $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, and $C_2$-$C_8$ heteroaryl is optionally substituted with at least one $R^{11}$; or $R^9$ and $R^{10}$ taken together with the nitrogen to which they are attached combine to form a 4-7 membered ring optionally substituted with one or more $R^{11}$;

each $R^{11}$ is independently fluorine, chlorine, bromine, —OH, cyano, $C_1$-$C_6$ alkyl, $C_1$-$C_{11}$ heteroalkyl, $C_3$-$C_8$ cycloalkyl, —O—($C_3$-$C_8$ cycloalkyl), —S—($C_3$-$C_8$ cycloalkyl), $C_6$-$C_{14}$ aryl, —O—($C_6$-$C_{14}$ aryl), —S—($C_6$-$C_{14}$ aryl), $C_2$-$C_9$ cycloheteroalkyl, and $C_2$-$C_8$ heteroaryl, wherein each of $C_3$-$C_8$ cycloalkyl, —O—($C_3$-$C_8$ cycloalkyl), —S— ($C_3$-$C_8$ cycloalkyl), $C_6$-$C_{14}$ aryl, —O—($C_6$-$C_{14}$ aryl), —S—

($C_6$-$C_{14}$ aryl), $C_2$-$C_8$ cycloheteroalkyl, and $C_2$-$C_8$ heteroaryl, is optionally substituted with one or more group selected from fluorine, chlorine, bromine, —OH, cyano, and $C_1$-$C_6$ alkyl;

n is 0, 1, 2, 3, or 4;

or a pharmaceutically acceptable salt thereof.

In one aspect of this embodiment, X is N. In another aspect of this embodiment, X is $CR^7$. In a further aspect, $R^4$ is H. In a further aspect of this embodiment, $R^5$ is H. In a further aspect of this embodiment, $R^6$ is H. I still a further aspect of this embodiment, $R^4$, $R^5$, and $R^6$ are H. In a further aspect of this embodiment, $R^1$ is $C_1$-$C_6$ alkyl optionally substituted with one or more $R^8$. In a further aspect of this embodiment, $R^1$ is $C_1$-$C_6$ alkyl substituted with at least one $R^3$. In a further aspect of this embodiment, $R^1$ is selected from methyl, isopropyl, (3-methyloxetan-3-yl)methyl, 2,2-difluoroethyl, and acetonitrile. In another aspect of this embodiment, $R^3$ is —$NR^9R^{10}$.

In another aspect of this embodiment, $R^2$ is selected from the group consisting of

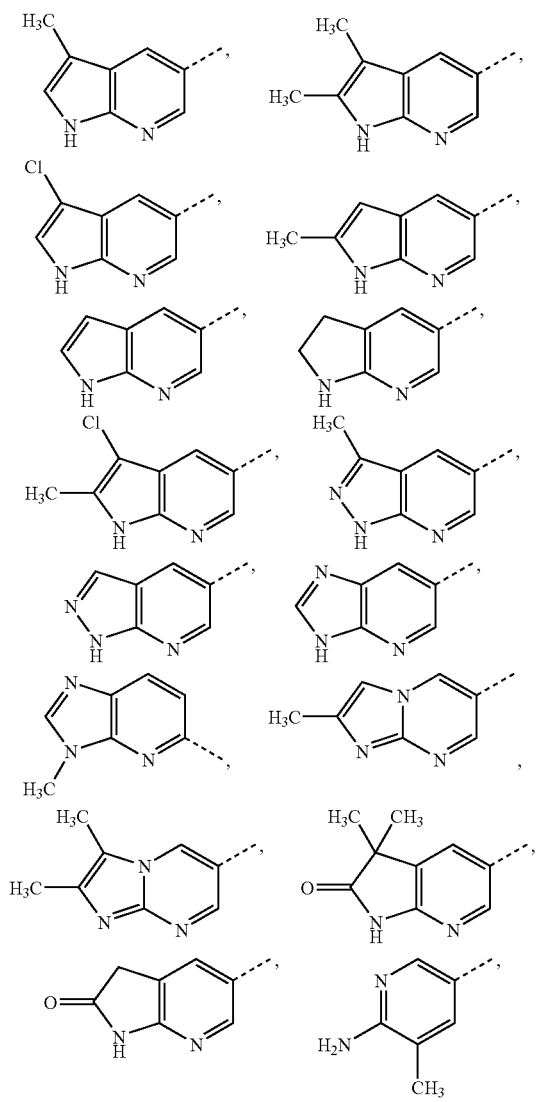

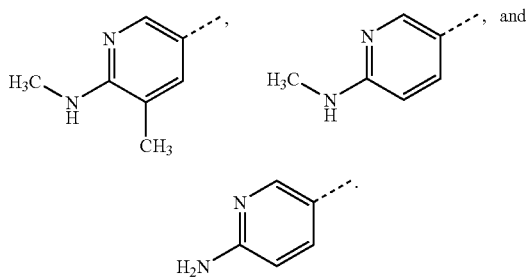

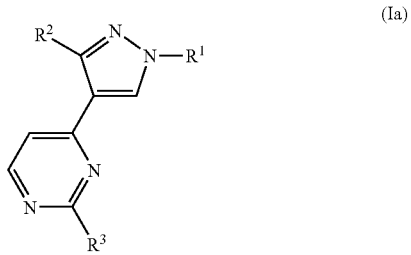

In a further embodiment, the invention is a compound of Formula (Ia) having the following structure:

(Ia)

wherein:

$R^1$ is $C_1$-$C_6$ alkyl optionally substituted with one or more $R^8$;

$R^2$ is $C_2$-$C_9$ cycloheteroalkyl or $C_5$-$C_{14}$ heteroaryl, wherein each of said $C_3$-$C_{12}$ cycloheteroalkyl and $C_2$-$C_8$ heteroaryl is optionally substituted with one or more $R^8$;

$R^3$ is H or —$NR^9R^{10}$;

each $R^8$ is independently —OH, fluorine, chlorine, bromine, cyano, —$NR^9R^{10}$, —$C(O)N(R^9R^{10})$, $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, $C_2$-$C_8$ heteroaryl, or —$(CH_2)_nC(O)R^9$, wherein each of said $C_3$-$C_8$ cycloalkyl, $C_6$-$C_{14}$ aryl, $C_2$-$C_9$ cycloheteroalkyl, and $C_2$-$C_8$ heteroaryl is optionally substituted with one or more $R^{11}$;

$R^9$ and $R^{10}$ are each independently H, $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_3$-$C_9$ cycloheteroalkyl, or $C_5$-$C_8$ heteroaryl, wherein each of said $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, and $C_2$-$C_8$ heteroaryl are optionally substituted with at least one $R^{11}$; or $R^9$ and $R^{10}$ taken together with the nitrogen to which they are attached combine to form a 4-7 membered ring optionally substituted with one or more $R^{11}$;

each $R^{11}$ is independently fluorine, chlorine, bromine, —OH, cyano, $C_1$-$C_6$ alkyl, $C_1$-$C_{11}$ heteroalkyl, $C_3$-$C_8$ cycloalkyl, —O—($C_3$-$C_8$ cycloalkyl), —S—($C_3$-$C_8$ cycloalkyl), $C_6$-$C_{14}$ aryl, —O—($C_6$-$C_{14}$ aryl), —S—($C_6$-$C_{14}$ aryl), $C_2$-$C_9$ cycloheteroalkyl, and $C_2$-$C_8$ heteroaryl, wherein each of $C_3$-$C_8$ cycloalkyl, —O—($C_3$-$C_8$ cycloalkyl), —S—($C_3$-$C_8$ cycloalkyl), $C_6$-$C_{14}$ aryl, —O—($C_6$-$C_{14}$ aryl), —S—($C_6$-$C_{14}$ aryl), $C_2$-$C_8$ cycloheteroalkyl, and $C_2$-$C_8$ heteroaryl, is optionally substituted with one or more group selected from fluorine, chlorine, bromine, —OH, cyano, and $C_1$-$C_6$ alkyl;

or a pharmaceutically acceptable salt thereof.

In one aspect of this embodiment, $R^1$ is selected from methyl, isopropyl, (3-methyloxetan-3-yl)methyl, 2,2-difluoroethyl, and acetonitrile. In another aspect of this embodiment, $R^3$ is —$NR^9R^{10}$.

In another aspect of this embodiment, $R^2$ is selected from the group consisting of

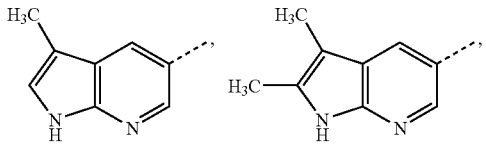
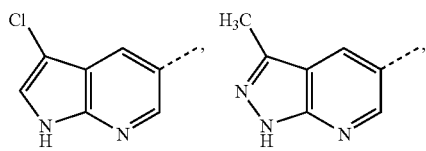
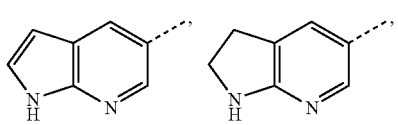
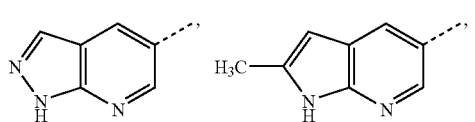
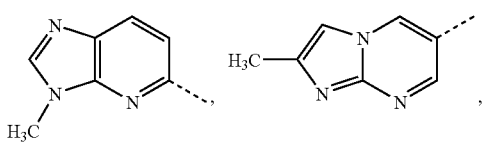
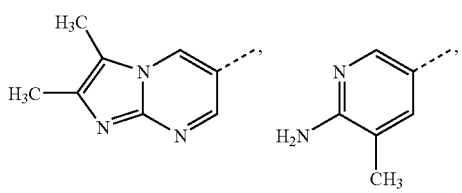
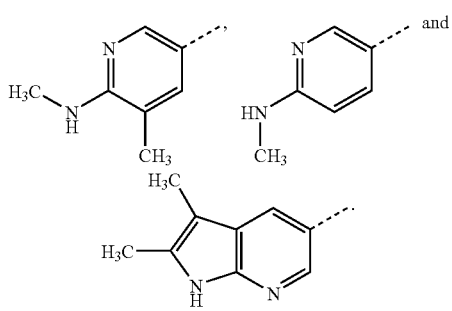

In another embodiment, the present invention is a compound of Formula (II)

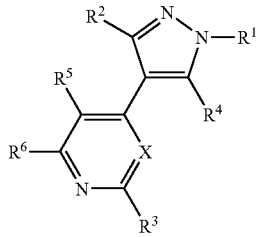

wherein:

X is N or $CR^7$;

$R^1$ is H, $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, or $C_2$-$C_8$ heteroaryl, wherein each of said $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, and $C_2$-$C_9$ heteroaryl is optionally substituted with one or more $R^8$;

$R^2$ is $C_2$-$C_9$ cycloheteroalkyl or $C_2$-$C_8$ heteroaryl, wherein each of said $C_2$-$C_9$ cycloheteroalkyl and $C_5$-$C_{14}$ heteroaryl is optionally substituted with one or more $R^8$; or optionally where $R^2$ is $C_2$-$C_8$ heteroaryl, the hydrogen atoms on any 2 adjacent ring atoms may combine to form a 5-7 membered cycloalkyl optionally substituted by one or more $R^8$, a 5-7 membered cycloheteroalkyl optionally substituted by one or more $R^8$, or a 5-7 membered heteroaryl optionally substituted by one or more $R^3$;

$R^3$ is H or —$NR^9R^{10}$; or where X is $CR^7$, $R^3$ may combine with $R^7$ to form a 5-7 membered heteroaryl optionally substituted by one or more $R^8$, 5-7 membered cycloheteroalkyl optionally substituted by one or more $R^8$, phenyl optionally substituted by one or more $R^8$, or 5-7 membered cycloalkyl optionally substituted by one or more $R^8$.

$R^4$, $R^5$, $R^6$, $R^7$ are each independently H, —$NR^{11}R^{12}$, —CN, —$C(O)R^{11}$, —$C(O)OR^{11}$, —$NO_2$, —$SR^{11}$, —$S(O)_2R^{11}$, —$OR^{11}$, $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, or $C_2$-$C_8$ heteroaryl wherein each of said $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, or $C_2$-$C_8$ heteroaryl is optionally substituted with one or more $R^8$;

each $R^8$ is independently —$OR^{11}$, fluorine, chlorine, bromine, oxo, cyano, —$NR^{13}R^{14}$, —$C(O)N(R^{13}R^{14})$, —$C(O)R^{13}$, —$C(O)OR^{13}$, —$NO_2$, $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, $C_2$-$C_8$ heteroaryl, or —$(CH_2)_nC(O)R^{11}$, wherein each of said $C_3$-$C_8$ cycloalkyl, $C_6$-$C_{14}$ aryl, $C_2$-$C_9$ cycloheteroalkyl, and $C_2$-$C_8$ heteroaryl is optionally substituted with one or more $R^{11}$;

$R^9$ and $R^{10}$ are each independently H, —$C(O)N(R^{13}R^{14})$, —$C(O)R^{13}$, —$C(O)OR^{13}$, $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, or $C_2$-$C_8$ heteroaryl, wherein each of said $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, and $C_2$-$C_8$ heteroaryl is optionally substituted with at least one $R^{11}$; or $R^9$ and $R^{10}$ taken together with the nitrogen to which they are attached combine to form a 4-7 membered cycloheteroalkyl ring optionally substituted with one or more $R^{11}$;

each $R^{11}$ and $R^{12}$ is independently fluorine, chlorine, bromine, —OH, —$C(O)R^{13}$, —$C(O)OR^{13}$, —$SR^{13}$, —$S(O)_2$ $R^{13}$, —$OR^{13}$, —$NR^{13}R^{14}$, —$C(O)N(R^{13}R^{14})$, cyano, $C_1$-$C_6$ alkyl, $C_1$-$C_{11}$ heteroalkyl, $C_3$-$C_8$ cycloalkyl, —O—($C_3$-$C_8$ cycloalkyl), —S—($C_3$-$C_8$ cycloalkyl), $C_6$-$C_{14}$ aryl, —O—($C_6$-$C_{14}$ aryl), —S—($C_6$-$C_{14}$ aryl), $C_2$-$C_9$ cycloheteroalkyl, and $C_2$-$C_8$ heteroaryl, wherein each of $C_3$-$C_8$ cycloalkyl, —O—($C_3$-$C_8$ cycloalkyl), —S—($C_3$-$C_8$ cycloalkyl), $C_6$-$C_{14}$ aryl, —O—($C_6$-$C_{14}$ aryl), —S—($C_6$-$C_{14}$ aryl), $C_2$-$C_8$ cycloheteroalkyl, and $C_2$-$C_8$ heteroaryl, is optionally substituted with one or more $R^{13}$;

each $R^{13}$ and $R^{14}$ is independently H, oxo, $C_1$-$C_6$ alkyl, $C_1$-$C_{11}$ heteroalkyl, $C_3$-$C_8$ cycloalkyl, —O—($C_3$-$C_8$ cycloalkyl), —S—($C_3$-$C_8$ cycloalkyl), $C_6$-$C_{14}$ aryl, —O—($C_6$-$C_{14}$ aryl), —S—($C_6$-$C_{14}$ aryl), $C_2$-$C_9$ cycloheteroalkyl, and $C_2$-$C_8$ heteroaryl, wherein each of $C_3$-$C_8$ cycloalkyl, —O—($C_3$-$C_8$ cycloalkyl), —S—($C_3$-$C_8$ cycloalkyl), $C_6$-$C_{14}$ aryl, —O—($C_6$-$C_{14}$ aryl), —S—($C_6$-$C_{14}$ aryl), $C_2$-$C_9$ cycloheteroalkyl, and $C_2$-$C_8$ heteroaryl, is optionally substituted with one or more group selected from fluorine, chlorine, bromine, —OH, cyano, and $C_1$-$C_6$ alkyl;

n is 0, 1, 2, 3, or 4;

or a pharmaceutically acceptable salt thereof.

In one aspect of this embodiment, X is N, or a pharmaceutically acceptable salt thereof. In another aspect of this embodiment, X is $CR^7$, or a pharmaceutically acceptable salt thereof. In a further aspect, $R^4$ is H, or a pharmaceutically acceptable salt thereof. In a further aspect of this embodiment, $R^5$ is H, or a pharmaceutically acceptable salt thereof. In a further aspect of this embodiment, $R^6$ is H, or a pharmaceutically acceptable salt thereof. In still a further aspect of this embodiment, $R^4$, $R^5$, and $R^5$ are H, or a pharmaceutically acceptable salt thereof. In a further aspect of this embodiment, $R^1$ is $C_1$-$C_6$ alkyl optionally substituted with one or more $R^8$, or a pharmaceutically acceptable salt thereof. In a further aspect of this embodiment, $R^1$ is $C_1$-$C_6$ alkyl substituted with at least one $R^8$, or a pharmaceutically acceptable salt thereof.

In one aspect of this embodiment, $R^1$ is selected from methyl, ethyl, isopropyl, cyclopropyl, 2,2-difluoroethyl, cyanomethyl, difluorocyclobutanyl, (3-methyloxetan-3-yl)methyl, 1,1-dimethyl-2-hydroxyethyl, 1-methyl-1-cyanoethyl, difluoromethyl, tert-butyl, 3-hydroxypropan-2-yl, piperidinyl, N-acetyl-piperidinyl, H, tetrahydro-2H-pyranyl, tetrahydrofuranyl, 4-cyanophenyl, cis-fluorocyclobutanyl, trans-fluorocyclobutanyl, oxetanyl, and N-methyl-piperidinyl, or a pharmaceutically acceptable salt thereof.

In a further aspect of this embodiment, $R^1$ is selected from methyl, isopropyl, (3-methyloxetan-3-yl)methyl, 2,2-difluoroethyl, and acetonitrile, or a pharmaceutically acceptable salt thereof. In another aspect of this embodiment, $R^3$ is —$NR^9R^{10}$, or a pharmaceutically acceptable salt thereof.

In another aspect of this embodiment, $R^2$ is selected from the group consisting of

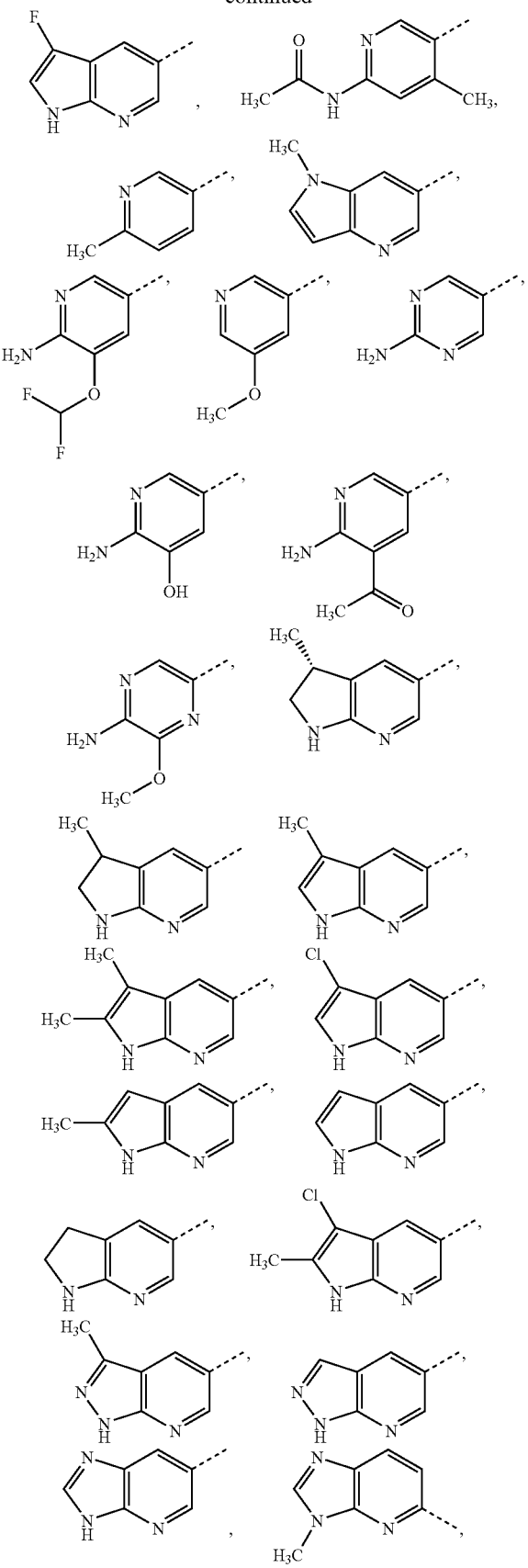

or a pharmaceutically acceptable salt thereof.

In a further embodiment, the invention is a compound of Formula (IIa) having the following structure:

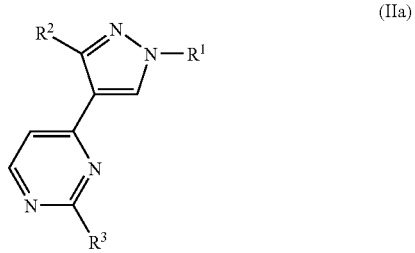

(IIa)

wherein:
R¹ is $C_1$-$C_6$ alkyl optionally substituted with one or more $R^8$;

R² is $C_2$-$C_9$ cycloheteroalkyl or $C_5$-$C_{14}$ heteroaryl, wherein each of said $C_3$-$C_{12}$ cycloheteroalkyl and $C_2$-$C_8$ heteroaryl is optionally substituted with one or more $R^8$;

R³ is H or —NR⁹R¹⁰;

each R⁸ is independently —OR¹¹, fluorine, chlorine, bromine, oxo, cyano, —NR¹³R¹⁴, —C(O)N(R¹³R¹⁴), —C(O)R¹³, —C(O)OR¹³, —NO₂, $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, $C_2$-$C_8$ heteroaryl, or —(CH₂)ₙC(O)R⁹, wherein each of said $C_3$-$C_8$ cycloalkyl, $C_6$-$C_{14}$ aryl, $C_2$-$C_9$ cycloheteroalkyl, and $C_2$-$C_8$ heteroaryl is optionally substituted with one or more R¹¹;

R⁹ and R¹⁰ are each independently H, —C(O)N(R¹³R¹⁴), —C(O)R¹³, —C(O)OR¹³, $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, or $C_2$-$C_8$ heteroaryl, wherein each of said $C_1$-$C_6$ alkyl, $C_2$-$C_8$ alkenyl, $C_2$-$C_8$ alkynyl, $C_3$-$C_8$ cycloalkyl, $C_6$-$C_{14}$ aryl, $C_2$-$C_9$ cycloheteroalkyl, and $C_2$-$C_8$ heteroaryl is optionally substituted with at least one $R^{11}$; or $R^9$ and $R^{10}$ taken together with the nitrogen to which they are attached combine to form a 4-7 membered cycloheteroalkyl ring optionally substituted with one or more $R^{11}$;

each $R^{11}$ and $R^{12}$ is independently fluorine, chlorine, bromine, —OH, —C(O)$R^{13}$, —C(O)O$R^{13}$, —S$R^{13}$, —S(O)$_2$ $R^{13}$, —O$R^{13}$, —N$R^{13}R^{14}$, —C(O)N($R^{13}R^{14}$), cyano, $C_1$-$C_6$ alkyl, $C_1$-$C_{11}$ heteroalkyl, $C_3$-$C_8$ cycloalkyl, —O—($C_3$-$C_8$ cycloalkyl), —S—($C_3$-$C_8$ cycloalkyl), $C_6$-$C_{14}$ aryl, —O—($C_6$-$C_{14}$ aryl), —S—($C_6$-$C_{14}$ aryl), $C_2$-$C_9$ cycloheteroalkyl, and $C_2$-$C_8$ heteroaryl, wherein each of $C_3$-$C_8$ cycloalkyl, —O—($C_3$-$C_8$ cycloalkyl), —S—($C_3$-$C_8$ cycloalkyl), $C_6$-$C_{14}$ aryl, —O—($C_6$-$C_{14}$ aryl), —S—($C_6$-$C_{14}$ aryl), $C_2$-$C_9$ cycloheteroalkyl, and $C_2$-$C_8$ heteroaryl, is optionally substituted with one or more $R^{13}$ each $R^{13}$ and $R^{14}$ is independently H, oxo, $C_1$-$C_6$ alkyl, $C_1$-$C_{11}$ heteroalkyl, $C_3$-$C_8$ cycloalkyl, —O—($C_3$-$C_8$ cycloalkyl), —S—($C_3$-$C_8$ cycloalkyl), $C_6$-$C_{14}$ aryl, —O—($C_6$-$C_{14}$ aryl), —S—($C_6$-$C_{14}$ aryl), $C_2$-$C_9$ cycloheteroalkyl, and $C_2$-$C_8$ heteroaryl, wherein each of $C_3$-$C_8$ cycloalkyl, —O—($C_3$-$C_8$ cycloalkyl), —S—($C_3$-$C_8$ cycloalkyl), $C_6$-$C_{14}$ aryl, —O—($C_6$-$C_{14}$ aryl), —S—($C_6$-$C_{14}$ aryl), $C_2$-$C_9$ cycloheteroalkyl, and $C_2$-$C_8$ heteroaryl, is optionally substituted with one or more group selected from fluorine, chlorine, bromine, —OH, cyano, and $C_1$-$C_6$ alkyl;

or a pharmaceutically acceptable salt thereof.

In one aspect of this embodiment, $R^1$ is selected from methyl, ethyl, isopropyl, cyclopropyl, 2,2-difluoroethyl, cyanomethyl, difluorocyclobutanyl, (3-methyloxetan-3-yl)methyl, 1,1-dimethyl-2-hydroxyethyl, 1-methyl-1-cyanoethyl, difluoromethyl, tert-butyl, 3-hydroxypropan-2-yl, piperidinyl, N-acetyl-piperidinyl, H, tetrahydro-2H-pyranyl, tetrahydrofuranyl, 4-cyanophenyl, cis-fluorocyclobutanyl, trans-fluorocyclobutanyl, oxetanyl, and N-methyl-piperidinyl, or a pharmaceutically acceptable salt thereof.

In another aspect of this embodiment, $R^2$ is selected from the group consisting of

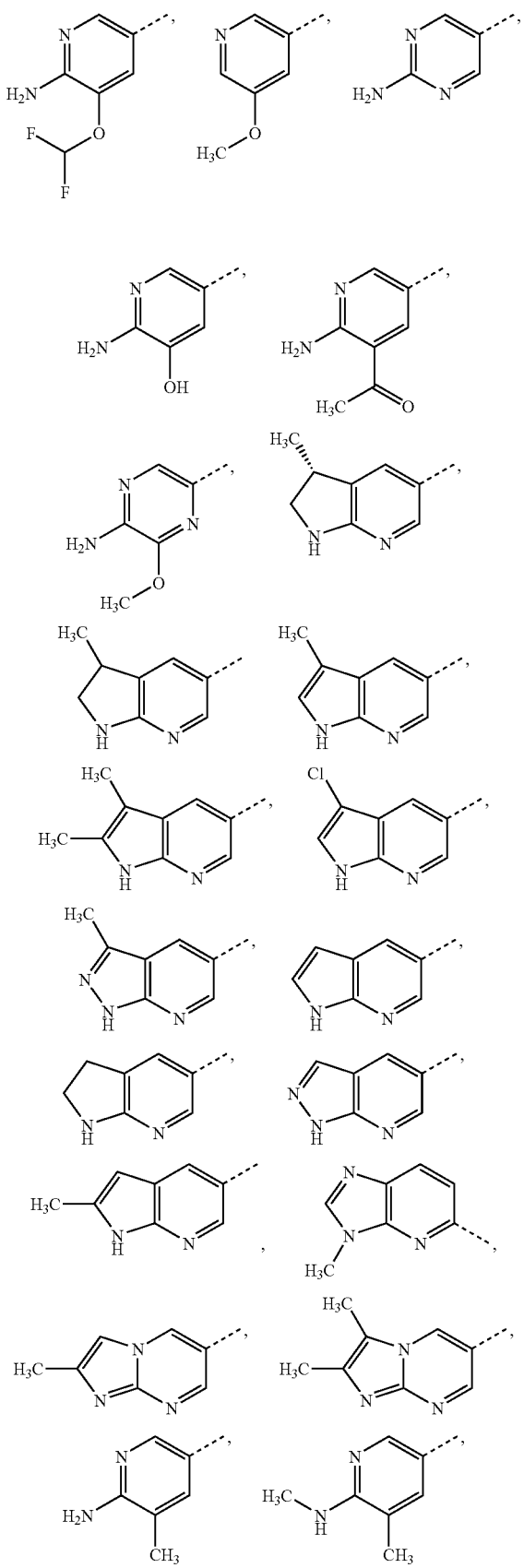

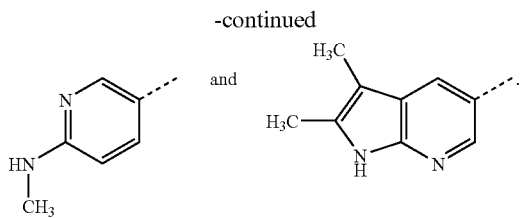 and 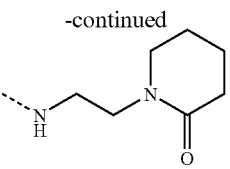

or a pharmaceutically acceptable salt thereof.

In another aspect of this embodiment, $R^3$ is $-NR^9R^{10}$. In another aspect of this embodiment, $R^3$ is $NH_2$, H,

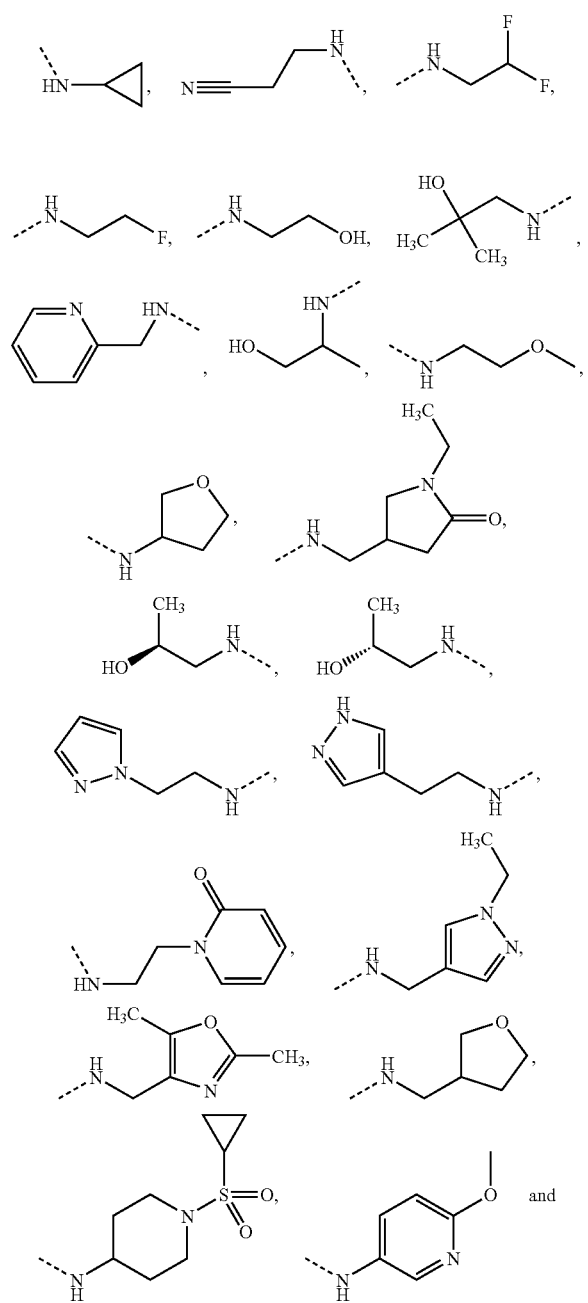

or a pharmaceutically acceptable salt thereof.

In a further embodiment, the present invention is a compound selected from the group consisting of (2S)-1-(4-(1-isopropyl-3-(3-methyl-1H-pyrrolo[2,3-b]pyridin-5-yl)-1H-pyrazol-4-yl)pyrimidin-2-ylamino)propan-2-ol, (2S)-1-(4-(3-(3-chloro-1H-pyrrolo[2,3-b]pyridin-5-yl)-1-isopropyl-1H-pyrazol-4-yl)pyrimidin-2-ylamino)propan-2-ol, (2S)-1-(4-(3-(2,3-dimethyl-1H-pyrrolo[2,3-b]pyridin-5-yl)-1-isopropyl-1H-pyrazol-4-yl)pyrimidin-2-ylamino)propan-2-ol, (2S)-1-(4-(1-isopropyl-3-(3-methyl-1H-pyrazolo[3,4-b]pyridin-5-yl)-1H-pyrazol-4-yl)pyrimidin-2-ylamino)propan-2-ol, 4-[1-isopropyl-3-(1H-pyrrolo[2,3-b]pyridin-5-yl)-1H-pyrazol-4-yl]-N-[2-(1H-pyrazol-1-yl)ethyl]pyrimidin-2-amine, (2S)-1-(4-(1-isopropyl-3-(1H-pyrrolo[2,3-b]pyridin-5-yl)-1H-pyrazol-4-yl)pyrimidin-2-ylamino)propan-2-ol, N-(2-fluoroethyl)-4-[1-isopropyl-3-(1H-pyrrolo[2,3-b]pyridin-5-yl)-1H-pyrazol-4-yl]pyrimidin-2-amine, (2S)-1-(4-(3-(3-chloro-1H-pyrrolo[2,3-b]pyridin-5-yl)-1-methyl-1H-pyrazol-4-yl)pyrimidin-2-ylamino)propan-2-ol, 2-({4-[1-isopropyl-3-(1H-pyrrolo[2,3-b]pyridin-5-yl)-1H-pyrazol-4-yl]pyrimidin-2-yl}amino)ethanol, 4-[1-isopropyl-3-(1H-pyrrolo[2,3-b]pyridin-5-yl)-1H-pyrazol-4-yl]-N-[2-(1H-pyrazol-4-yl)ethyl]pyrimidin-2-amine, (2S)-1-(4-(3-(2,3-dihydro-1H-pyrrolo[2,3-b]pyridin-5-yl)-1-isopropyl-1H-pyrazol-4-yl)pyrimidin-2-ylamino)propan-2-ol, [4-[2-((S)-2-Hydroxy-propylamino)-pyrimidin-4-yl]-3-(1H-pyrrolo[2,3-b]pyridin-5-yl)-pyrazol-1-yl]-acetonitrile, 1-[2-({4-[1-isopropyl-3-(1H-pyrrolo[2,3-b]pyridin-5-yl)-1H-pyrazol-4-yl]pyrimidin-2-yl}amino)ethyl]pyridin-2(1H)-one, (2R)-2-({4-[1-isopropyl-3-(1H-pyrrolo[2,3-b]pyridin-5-yl)-1H-pyrazol-4-yl]pyrimidin-2-yl}amino)propan-1-ol, N-[(1-ethyl-1H-pyrazol-4-yl)methyl]-4-[1-isopropyl-3-(1H-pyrrolo[2,3-b]pyridin-5-yl)-1H-pyrazol-4-yl]pyrimidin-2-amine, N-[(2,5-dimethyl-1,3-oxazol-4-yl)methyl]-4-[1-isopropyl-3-(1H-pyrrolo[2,3-b]pyridin-5-yl)-1H-pyrazol-4-yl]pyrimidin-2-amine, 4-[1-isopropyl-3-(1H-pyrrolo[2,3-b]pyridin-5-yl)-1H-pyrazol-4-yl]-N-(tetrahydrofuran-3-ylmethyl)pyrimidin-2-amine, 4-(1-isopropyl-3-(1H-pyrrolo[2,3-b]pyridin-5-yl)-1H-pyrazol-4-yl)-N-(pyridin-2-ylmethyl)pyrimidin-2-amine, (2S)-1-(4-(1-isopropyl-3-(1H-pyrazolo[3,4-b]pyridin-5-yl)-1H-pyrazol-4-yl)pyrimidin-2-ylamino)propan-2-ol, 4-[1-isopropyl-3-(1H-pyrrolo[2,3-b]pyridin-5-yl)-1H-pyrazol-4-yl]-N-(2-methoxyethyl)pyrimidin-2-amine, 1-ethyl-4-[({4-[1-isopropyl-3-(1H-pyrrolo[2,3-b]pyridin-5-yl)-1H-pyrazol-4-yl]pyrimidin-2-yl}amino)methyl]pyrrolidin-2-one, (2S)-1-(4-(1-isopropyl-3-(5-methyl-6-(methylamino)pyridin-3-yl)-1H-pyrazol-4-yl)pyrimidin-2-ylamino)propan-2-ol, (2S)-1-(4-(1-isopropyl-3-(2-methyl-1H-pyrrolo[2,3-b]pyridin-5-yl)-1H-pyrazol-4-yl)pyrimidin-2-ylamino)propan-2-ol, (2S)-1-(4-(1-isopropyl-3-(5-methyl-5H-pyrrolo[2,3-b]pyrazin-3-yl)-1H-pyrazol-4-yl)pyrimidin-2-ylamino)propan-2-ol, (2S)-1-(4-(1-methyl-3-(1H-pyrrolo[2,3-b]pyridin-5-yl)-1H-pyrazol-4-yl)pyrimidin-2-ylamino)propan-2-ol, (2S)-1-(4-(1-isopropyl-3-(2-methylimidazo[1,2-a]pyrimidin-6-yl)-1H-pyrazol-4-yl)pyrimidin-2-ylamino)propan-2-ol, (2S)-1-(4-(1-isopropyl-3-(6-(methylamino)

pyridin-3-yl)-1H-pyrazol-4-yl)pyrimidin-2-ylamino)propan-2-ol, (2S)-1-(4-(3-(2,3-dimethylimidazo[1,2-a]pyrimidin-6-yl)-1-isopropyl-1H-pyrazol-4-yl)pyrimidin-2-ylamino)propan-2-ol, (2S)-1-(4-(1-(2,2-difluoroethyl)-3-(1H-pyrrolo[2,3-b]pyridin-5-yl)-1H-pyrazol-4-yl)pyrimidin-2-ylamino)propan-2-ol, (2S)-1-(4-(3-(3-chloro-1H-pyrrolo[2,3-b]pyridin-5-yl)-1-(2,2-difluoroethyl)-1H-pyrazol-4-yl)pyrimidin-2-ylamino)propan-2-ol, (2S)-1-(4-(3-(3-chloro-2-methyl-1H-pyrrolo[2,3-b]pyridin-5-yl)-1-isopropyl-1H-pyrazol-4-yl)pyrimidin-2-ylamino)propan-2-ol, (2S)-1-(4-(1-((3-methyloxetan-3-yl)methyl)-3-(1H-pyrrolo[2,3-b]pyridin-5-yl)-1H-pyrazol-4-yl)pyrimidin-2-ylamino)propan-2-ol, 5-(4-(2-((S)-2-hydroxypropylamino)pyrimidin-4-yl)-1-isopropyl-1H-pyrazol-3-yl)-3,3-dimethyl-1H-pyrrolo[2,3-b]pyridin-2(3H)-one, (2S)-1-(4-(3-(3,3-dimethyl-2,3-dihydro-1H-pyrrolo[2,3-b]pyridin-5-yl)-1-methyl-1H-pyrazol-4-yl)pyrimidin-2-ylamino)propan-2-ol and (2S)-1-(4-(3-(3-chloro-1H-pyrrolo[2,3-b]pyridin-5-yl)-1-((3-methyloxetan-3-yl)methyl)-1H-pyrazol-4-yl)pyrimidin-2-ylamino)propan-2-ol, or a pharmaceutically acceptable salt thereof.

In a further embodiment, the present invention is a compound selected from the group consisting of (2S)-1-(4-(1-isopropyl-3-(3-methyl-1H-pyrrolo[2,3-b]pyridin-5-yl)-1H-pyrazol-4-yl)pyrimidin-2-ylamino)propan-2-ol, (2S)-1-(4-(3-(3-chloro-1H-pyrrolo[2,3-b]pyridin-5-yl)-1-isopropyl-1H-pyrazol-4-yl)pyrimidin-2-ylamino)propan-2-ol, (2S)-1-(4-(3-(2,3-dimethyl-1H-pyrrolo[2,3-b]pyridin-5-yl)-1-isopropyl-1H-pyrazol-4-yl)pyrimidin-2-ylamino)propan-2-ol, (2S)-1-(4-(3-(3-chloro-1H-pyrrolo[2,3-b]pyridin-5-yl)-1-(2,2-difluoroethyl)-1H-pyrazol-4-yl)pyrimidin-2-ylamino)propan-2-ol and (2S)-1-(4-(1-isopropyl-3-(3-methyl-1H-pyrazolo[3,4-b]pyridin-5-yl)-1H-pyrazol-4-yl)pyrimidin-2-ylamino)propan-2-ol; or a pharmaceutically acceptable salt thereof. In a further embodiment, the compound is (2S)-1-(4-(1-isopropyl-3-(3-methyl-1H-pyrrolo[2,3-b]pyridin-5-yl)-1H-pyrazol-4-yl)pyrimidin-2-ylamino)propan-2-ol, or a pharmaceutically acceptable salt thereof. In a further embodiment, the compound is (2S)-1-(4-(3-(3-chloro-1H-pyrrolo[2,3-b]pyridin-5-yl)-1-isopropyl-1H-pyrazol-4-yl)pyrimidin-2-ylamino)propan-2-ol, or a pharmaceutically acceptable salt thereof. In a further embodiment, the compound is (2S)-1-(4-(3-(2,3-dimethyl-1H-pyrrolo[2,3-b]pyridin-5-yl)-1-isopropyl-1H-pyrazol-4-yl)pyrimidin-2-ylamino)propan-2-ol, or a pharmaceutically acceptable salt thereof. In a further embodiment, the compound is (2S)-1-(4-(3-(3-chloro-1H-pyrrolo[2,3-b]pyridin-5-yl)-1-(2,2-difluoroethyl)-1H-pyrazol-4-yl)pyrimidin-2-ylamino)propan-2-ol, or a pharmaceutically acceptable salt thereof.

In a further embodiment, the compound is selected from 4-[3-(6-amino-5-methoxypyridin-3-yl)-1-isopropyl-1H-pyrazol-4-yl]-N-cyclopropylpyrimidin-2-amine, (2S)-1-({4-[3-(3-chloro-1H-pyrrolo[2,3-b]pyridin-5-yl)-1-(3,3-difluorocyclobutyl)-1H-pyrazol-4-yl]pyrimidin-2-yl}amino)propan-2-ol, (2S)-1-({4-[3-(6-amino-5-methylpyridin-3-yl)-1-(2,2-difluoroethyl)-1H-pyrazol-4-yl]pyrimidin-2-yl}amino)propan-2-ol, 3-({4-[3-(3-fluoro-1H-pyrrolo[2,3-b]pyridin-5-yl)-1-isopropyl-1H-pyrazol-4-yl]pyrimidin-2-yl}amino)propanenitrile, 3-({4-[3-(2,3-dihydro-1H-pyrrolo[2,3-b]pyridin-5-yl)-1-isopropyl-1H-pyrazol-4-yl]pyrimidin-2-yl}amino)propanenitrile, 3-({4-[1-(2,2-difluoroethyl)-3-(3-fluoro-1H-pyrrolo[2,3-b]pyridin-5-yl)-1H-pyrazol-4-yl]pyrimidin-2-yl}amino)propanenitrile, 3-({4-[3-(2,3-dihydro-1H-pyrrolo[2,3-b]pyridin-5-yl)-1-(2-hydroxy-1,1-dimethylethyl)-1H-pyrazol-4-yl]pyrimidin-2-yl}amino)propanenitrile, 3-({4-[1-(2-hydroxy-1,1-dimethylethyl)-3-(3-methyl-1H-pyrrolo[2,3-b]pyridin-5-yl)-1H-pyrazol-4-yl]pyrimidin-2-yl}amino)propanenitrile, 3-({4-[3-(3-fluoro-1H-pyrrolo[2,3-b]pyridin-5-yl)-1-(2-hydroxy-1,1-dimethylethyl)-1H-pyrazol-4-yl]pyrimidin-2-yl}amino)propanenitrile, 3-({4-[1-(2-hydroxy-1,1-dimethylethyl)-3-(1H-pyrrolo[2,3-b]pyridin-5-yl)-1H-pyrazol-4-yl]pyrimidin-2-yl}amino)propanenitrile, N-{5-[4-{2-[(2-cyanoethyl)amino]pyrimidin-4-yl}-1-(2,2-difluoroethyl)-1H-pyrazol-3-yl]-4-methylpyridin-2-yl}acetamide, N-[1-(cyclopropyl-sulfonyl)piperidin-4-yl]-4-[1-(2,2-difluoroethyl)-3-(1H-pyrrolo[2,3-b]pyridin-5-yl)-1H-pyrazol-4-yl]pyrimidin-2-amine, 3-({4-[1-(2,2-difluoroethyl)-3-(6-methylpyridin-3-yl)-1H-pyrazol-4-yl]pyrimidin-2-yl}amino)propanenitrile, (2S)-1-({4-[1-(2,2-difluoroethyl)-3-(1H-pyrrolo[2,3-b]pyridin-4-yl)-1H-pyrazol-4-yl]pyrimidin-2-yl}amino)propan-2-ol, 3-({4-[3-(5-amino-6-methoxypyrazin-2-yl)-1-tert-butyl-1H-pyrazol-4-yl]pyrimidin-2-yl}amino)propanenitrile, 3-({4-[3-(5-amino-6-methoxypyrazin-2-yl)-1-isopropyl-1H-pyrazol-4-yl]pyrimidin-2-yl}amino)propanenitrile, 3-({4-[3-(5-amino-6-methoxypyrazin-2-yl)-1-(2,2-difluoroethyl)-1H-pyrazol-4-yl]pyrimidin-2-yl}amino)propanenitrile, 3-({4-[3-(5-amino-6-methoxypyrazin-2-yl)-1-(2,2-difluoroethyl)-1H-pyrazol-4-yl]pyrimidin-2-yl}amino)propanenitrile, 2-[3-(3-chloro-1H-pyrrolo[2,3-b]pyridin-5-yl)-4-(2-{[(2S)-2-hydroxypropyl]amino}pyrimidin-4-yl)-1H-pyrazol-1-yl]-2-methylpropanenitrile, (2S)-1-({4-[1-(2,2-difluoroethyl)-3-(1-methyl-1H-pyrrolo[3,2-b]pyridin-6-yl)-1H-pyrazol-4-yl]pyrimidin-2-yl}amino)propan-2-ol, 3-({4-[1-(2,2-difluoroethyl)-3-(1H-pyrrolo[3,2-b]pyridin-6-yl)-1H-pyrazol-4-yl]pyrimidin-2-yl}amino)propanenitrile, and 3-({4-[1-(2-hydroxy-1,1-dimethylethyl)-3-(1-methyl-1H-pyrrolo[3,2-b]pyridin-6-yl)-1H-pyrazol-4-yl]pyrimidin-2-yl}amino)propanenitrile, or a pharmaceutically acceptable salt thereof.

In a further embodiment, the compound is selected from 3-({4-[1-(2-hydroxy-1,1-dimethylethyl)-3-(1-methyl-1H-pyrrolo[3,2-b]pyridin-6-yl)-1H-pyrazol-4-yl]pyrimidin-2-yl}amino)propanenitrile, (2S)-1-[(4-{3-[6-amino-5-(difluoromethoxy)-pyridin-3-yl]-1-isopropyl-1H-pyrazol-4-yl}pyrimidin-2-yl)amino]propan-2-ol, 4-[1-(difluoromethyl)-3-(3-methyl-1H-pyrrolo[2,3-b]pyridin-5-yl)-1H-pyrazol-4-yl]pyrimidin-2-amine, (2S)-1-({4-[3-(6-amino-5-methoxypyridin-3-yl)-1-(difluoromethyl)-1H-pyrazol-4-yl]pyrimidin-2-yl}amino)propan-2-ol, (2S)-1-({4-[3-(2-aminopyrimidin-5-yl)-1-isopropyl-1H-pyrazol-4-yl]pyrimidin-2-yl}amino)propan-2-ol, 4-[3-(3-chloro-1H-pyrrolo[2,3-b]pyridin-5-yl)-1-(difluoromethyl)-1H-pyrazol-4-yl]pyrimidin-2-amine, 3-({4-[1-(difluoromethyl)-3-(3-methyl-1H-pyrrolo[2,3-b]pyridin-5-yl)-1H-pyrazol-4-yl]pyrimidin-2-yl}amino)-propanenitrile, 2-amino-5-[4-(2-{[(2S)-2-hydroxypropyl]-amino}pyrimidin-4-yl)-1-isopropyl-1H-pyrazol-3-yl]pyridin-3-ol, 3-({4-[1-(2,2-difluoroethyl)-3-(5-methoxypyridin-3-yl)-1H-pyrazol-4-yl]pyrimidin-2-yl}amino)propanenitrile, 3-({4-[3-(6-amino-5-methylpyridin-3-yl)-1-(2-hydroxy-1,1-dimethylethyl)-1H-pyrazol-4-yl]pyrimidin-2-yl}amino)-propanenitrile, 2-[4-{2-[(2,2-difluoroethyl)amino]pyrimidin-4-yl}-3-(1H-pyrrolo[2,3-b]pyridin-5-yl)-1H-pyrazol-1-yl]-2-methylpropan-1-ol, 3-({4-[1-(2-hydroxy-1,1-dimethylethyl)-3-(5-methoxypyridin-3-yl)-1H-pyrazol-4-yl]pyrimidin-2-yl}amino)propanenitrile, 3-({4-[1-isopropyl-3-(1H-pyrrolo[2,3-b]pyridin-5-yl)-1H-pyrazol-4-yl]pyrimidin-2-yl}amino)-propanenitrile, 3-({4-[1-isopropyl-3-(3-methyl-1H-pyrazolo[3,4-b]pyridin-5-yl)-1H-pyrazol-4-yl]pyrimidin-2-yl}amino)propanenitrile, 3-({4-[3-(5-acetyl-6-aminopyridin-3-yl)-1-isopropyl-1H- pyrazol-4-yl]pyrimidin-2-yl}amino)propanenitrile, 3-{[4-(1-isopropyl-3-pyridin-3-yl-1H-pyrazol-4-yl)pyrimidin-2-yl]amino}-propanenitrile, 4-[3-(6-amino-5-methoxypyridin-3-yl)-1-tert-butyl-1H-pyrazol-4-yl]-N-(2,2-difluoroethyl)pyrimidin-2-amine, (2R)-2-[4-(2-aminopyrimidin-4-yl)-3-(3-chloro-1H-pyrrolo[2,3-b]pyridin-5-yl)-1H-pyrazol-1-yl]propan-1-ol, 4-[3-(6-amino-5-methoxypyridin-3-yl)-1-cyclopropyl-1H-pyrazol-4-yl]pyrimidin-2-amine, 3-({4-[3-(6-amino-5-methoxypyridin-3-yl)-1-cyclopropyl-1H-pyrazol-4-yl]pyrimidin-2-yl}amino)-propanenitrile, 2-[4-(2-aminopyrimidin-4-yl)-3-(3-methyl-1H-pyrrolo[2,3-b]pyridin-5-yl)-1H-pyrazol-1-yl]-2-methylpropan-1-ol, 4-[3-(6-amino-5-methoxypyridin-3-yl)-1-cyclopropyl-1H-pyrazol-4-yl]-N-(2,2-difluoroethyl)pyrimidin-2-amine, and 4-[3-(3-chloro-1H-pyrrolo[2,3-b]pyridin-5-yl)-1-isopropyl-1H-pyrazol-4-yl]pyrimidin-2-amine, or a pharmaceutically acceptable salt thereof.

In a further embodiment, the compound is selected from (2S)-1-({4-[3-(3-chloro-1H-pyrrolo[2,3-b]pyridin-5-yl)-1-ethyl-1H-pyrazol-4-yl]pyrimidin-2-yl}amino)propan-2-ol, 4-[1-isopropyl-3-(3-methyl-1H-pyrrolo[2,3-b]pyridin-5-yl)-1H-pyrazol-4-yl]pyrimidin-2-amine, 4-[3-(3-chloro-1H-pyrrolo[2,3-b]pyridin-5-yl)-1-piperidin-4-yl-1H-pyrazol-4-yl]pyrimidin-2-amine, 3-chloro-5-(1-piperidin-4-yl-4-pyrimidin-4-yl-1H-pyrazol-3-yl)-1H-pyrrolo[2,3-b]pyridine, 4-[1-tert-butyl-3-(3-chloro-1H-pyrrolo[2,3-b]pyridin-5-yl)-1H-pyrazol-4-yl]pyrimidin-2-amine, (2S)-1-({4-[1-tert-butyl-3-(3-methyl-1H-pyrrolo[2,3-b]pyridin-5-yl)-1H-pyrazol-4-yl]pyrimidin-2-yl}amino)propan-2-ol, 4-[1-(1-acetylpiperidin-4-yl)-3-(3-chloro-1H-pyrrolo[2,3-b]pyridin-5-yl)-1H-pyrazol-4-yl]-N-(2,2-difluoroethyl)-pyrimidin-2-amine, 4-[3-(6-amino-5-methoxypyridin-3-yl)-1H-pyrazol-4-yl]-N-(2,2-difluoroethyl)-pyrimidin-2-amine, 3-({4-[3-(6-amino-5-methoxypyridin-3-yl)-1-(tetrahydro-2H-pyran-4-yl)-1H-pyrazol-4-yl]pyrimidin-2-yl}amino)propanenitrile, 4-[3-(6-amino-5-methoxypyridin-3-yl)-1-(tetrahydro-2H-pyran-4-yl)-1H-pyrazol-4-yl]-N-(2,2-difluoroethyl)-pyrimidin-2-amine, 3-({4-[1-tert-butyl-3-(3-methyl-1H-pyrazolo[3,4-b]pyridin-5-yl)-1H-pyrazol-4-yl]pyrimidin-2-yl}amino)propanenitrile, 3-({4-[1-tert-butyl-3-(2,3-dihydro-1H-pyrrolo[2,3-b]pyridin-5-yl)-1H-pyrazol-4-yl]pyrimidin-2-yl}amino)propanenitrile, 3-[(4-{3-(5-methoxypyridin-3-yl)-1-[(3R)-tetrahydrofuran-3-yl]-1H-pyrazol-4-yl}pyrimidin-2-yl)amino]propanenitrile, 3-({4-[1-tert-butyl-3-(1H-pyrrolo[2,3-b]pyridin-5-yl)-1H-pyrazol-4-yl]pyrimidin-2-yl}amino)-propanenitrile, 3-[(4-{3-(1H-pyrrolo[2,3-b]pyridin-5-yl)-1-[(3R)-tetrahydrofuran-3-yl]-1H-pyrazol-4-yl}pyrimidin-2-yl)amino]propanenitrile, (2S)-1-({4-[3-(3-chloro-1H-pyrrolo[2,3-b]pyridin-5-yl)-1-(tetrahydro-2H-pyran-4-yl)-1H-pyrazol-4-yl]pyrimidin-2-yl}amino)propan-2-ol, 4-[3-(3-chloro-1H-pyrrolo[2,3-b]pyridin-5-yl)-1-piperidin-4-yl-1H-pyrazol-4-yl]-N-(2,2-difluoroethyl)pyrimidin-2-amine, 3-(4-(3-(5-acetyl-6-aminopyridin-3-yl)-1-(2,2-difluoroethyl)-1H-pyrazol-4-yl)pyrimidin-2-ylamino)-propanenitrile, 3-({4-[3-(5-amino-6-methoxypyrazin-2-yl)-1-(2,2-difluoroethyl)-1H-pyrazol-4-yl]pyrimidin-2-yl}amino)propanenitrile, 4-[3-(6-amino-5-methoxypyridin-3-yl)-4-{2-[(2-hydroxyethyl)-amino]pyrimidin-4-yl}-1H-pyrazol-1-yl]-benzonitrile, 4-[1-(2,2-difluoroethyl)-3-(1H-pyrrolo[2,3-b]pyridin-5-yl)-1H-pyrazol-4-yl]-N-(6-methoxypyridin-3-yl)pyrimidin-2-amine, 3-(4-(3-(6-amino-5-methoxypyridin-3-yl)-1-(2,2-difluoroethyl)-1H-pyrazol-4-yl)pyrimidin-2-ylamino)propanenitrile, 3-(4-(3-(6-amino-5-methoxypyridin-3-yl)-1-(2,2-difluoroethyl)-1H-pyrazol-4-yl)pyrimidin-2-ylamino)-propanenitrile, (S)-1-(4-(3-(3-chloro-1H-pyrrolo[2,3-b]pyridin-5-yl)-1-((1s,3s)-3-fluorocyclobutyl)-1H-pyrazol-4-yl)pyrimidin-2-ylamino)propan-2-ol, (S)-1-(4-(3-(6-amino-5-methoxypyridin-3-yl)-1-((1r,3r)-3-fluorocyclobutyl)-1H-pyrazol-4-yl)pyrimidin-2-ylamino)propan-2-ol, (S)-1-(4-(3-(3-chloro-1H-pyrrolo[2,3-b]pyridin-5-yl)-1-((1r,3r)-3-fluorocyclobutyl)-1H-pyrazol-4-yl)pyrimidin-2-ylamino)propan-2-ol, (2S)-1-(4-(1-(2,2-difluoroethyl)-3-(3-methyl-2,3-dihydro-1H-pyrrolo[2,3-b]pyridin-5-yl)-1H-pyrazol-4-yl)pyrimidin-2-ylamino)propan-2-ol, 3-(4-(1-(2,2-difluoroethyl)-3-(2,3-dihydro-1H-pyrrolo[2,3-b]pyridin-5-yl)-1H-pyrazol-4-yl)pyrimidin-2-ylamino)propanenitrile, and 1-(4-(1-(2,2-difluoroethyl)-3-(2,3-dihydro-1H-pyrrolo[2,3-b]pyridin-5-yl)-1H-pyrazol-4-yl)pyrimidin-2-ylamino)-2-methylpropan-2-ol, or a pharmaceutically acceptable salt thereof.

In a further embodiment, the compound is selected from N-(2,2-difluoroethyl)-4-(1-(2,2-difluoroethyl)-3-(2,3-dihydro-1H-pyrrolo[2,3-b]pyridin-5-yl)-1H-pyrazol-4-yl)pyrimidin-2-amine, 3-(4-(1-(2,2-difluoroethyl)-3-(3-methyl-1H-pyrazolo[3,4-b]pyridin-5-yl)-1H-pyrazol-4-yl)pyrimidin-2-ylamino)propanenitrile, (S)-1-(4-(1-(2,2-difluoroethyl)-3-((R)-3-methyl-2,3-dihydro-1H-pyrrolo[2,3-b]pyridin-5-yl)-1H-pyrazol-4-yl)pyrimidin-2-ylamino)propan-2-ol, 3-(4-(1-(2,2-difluoroethyl)-3-(3-methyl-1H-pyrrolo[2,3-b]pyridin-5-yl)-1H-pyrazol-4-yl)pyrimidin-2-ylamino)propanenitrile, 3-(4-(1-(1-hydroxy-2-methylpropan-2-yl)-3-(3-methyl-1H-pyrazolo[3,4-b]pyridin-5-yl)-1H-pyrazol-4-yl)pyrimidin-2-ylamino)propanenitrile, 3-(4-(1-(2,2-difluoroethyl)-3-(2-oxo-2,3-dihydro-1H-pyrrolo[2,3-b]pyridin-5-yl)-1H-pyrazol-4-yl)-pyrimidin-2-ylamino)propanenitrile, (2S)-1-({4-[3-(3-chloro-1H-pyrrolo[2,3-b]pyridin-5-yl)-1-(2,2-difluoroethyl)-1H-pyrazol-4-yl]pyrimidin-2-yl}amino)propan-2-ol, (2S)-1-({4-[3-(3-chloro-2-methyl-1H-pyrrolo[2,3-b]pyridin-5-yl)-1-isopropyl-1H-pyrazol-4-yl]pyrimidin-2-yl}amino)propan-2-ol, (2S)-1-[(4-{3-(3-chloro-1H-pyrrolo[2,3-b]pyridin-5-yl)-1-[(3-methyloxetan-3-yl)methyl]-1H-pyrazol-4-yl}pyrimidin-2-yl)amino]propan-2-ol, (2S)-1-({4-[3-(3-chloro-1H-pyrrolo[2,3-b]pyridin-5-yl)-1-oxetan-3-yl-1H-pyrazol-4-yl]pyrimidin-2-yl}amino)propan-2-ol, (2S)-1-({4-[1-(2,2-difluoroethyl)-3-(3-methyl-1H-pyrrolo[2,3-b]pyridin-5-yl)-1H-pyrazol-4-yl]pyrimidin-2-yl}amino)propan-2-ol, (2S)-1-({4-[1-(2,2-difluoroethyl)-3-(3-fluoro-1H-pyrrolo[2,3-b]pyridin-5-yl)-1H-pyrazol-4-yl]pyrimidin-2-yl}amino)propan-2-ol, (2S)-1-({4-[1-(2,2-difluoroethyl)-3-(2,3-dihydro-1H-pyrrolo[2,3-b]pyridin-5-yl)-1H-pyrazol-4-yl]pyrimidin-2-yl}amino)propan-2-ol, 5-[1-(2,2-difluoroethyl)-4-(2-{[(2S)-2-hydroxypropyl]amino}pyrimidin-4-yl)-1H-pyrazol-3-yl]-1H-pyrrolo[2,3-b]pyridine-3-carbonitrile, (2S)-1-({4-[3-(6-amino-5-methoxypyridin-3-yl)-1-(2,2-difluoroethyl)-1H-pyrazol-4-yl]pyrimidin-2-yl}amino)propan-2-ol, 2-({4-[1-(2,2-difluoroethyl)-3-(3-methyl-1H-pyrrolo[2,3-b]pyridin-5-yl)-1H-pyrazol-4-yl]pyrimidin-2-yl}amino)ethanol, 2-({4-[3-(3-chloro-1H-pyrrolo[2,3-b]pyridin-5-yl)-1-(2,2-difluoroethyl)-1H-pyrazol-4-yl]pyrimidin-2-yl}amino)ethanol, 4-[3-(3-chloro-1H-pyrrolo[2,3-b]pyridin-5-yl)-1-(2,2-difluoroethyl)-1H-pyrazol-4-yl]pyrimidin-2-amine, 4-[1-(2,2-difluoroethyl)-3-(3-methyl-1H-pyrrolo[2,3-b]pyridin-5-yl)-1H-pyrazol-4-yl]pyrimidin-2-amine, (2S)-1-({4-[3-(3-chloro-1H-pyrrolo[2,3-b]pyridin-5-yl)-1-(1-methylpiperidin-4-yl)-1H-pyrazol-4-yl]pyrimidin-2-yl}amino)propan-2-ol, (2S)-1-({4-[3-(3-chloro-1H-pyrrolo[2,3-b]pyridin-5-yl)-1-(3-methoxypropyl)-1H-pyrazol-4-yl]pyrimidin-2-yl}amino)propan-2-ol, (2S)-1-({4-[3-(6-amino-5-methoxypyridin-3-yl)-1-isopropyl-1H-pyrazol-4-yl]pyrimidin-2-yl}amino)propan-2-ol, (2S)-1-({4-[3-(3-chloro-1H-pyrrolo[2,3-b]pyridin-5-yl)-1-(1-methylpiperidin-4-yl)-1H-pyrazol-4-yl]pyrimidin-2- yl}amino)propan-2-ol, N-(2,2-difluoroethyl)-4-[1-(1-methylpiperidin-4-yl)-3-(3-methyl-1H-pyrrolo[2,3-b]pyridin-5-yl)-1H-pyrazol-4-yl]pyrimidin-2-amine, 4-[3-(3-chloro-1H-pyrrolo[2,3-b]pyridin-5-yl)-1-(1-methylpiperidin-4-yl)-1H-pyrazol-4-yl]-N-(2,2-difluoroethyl)pyrimidin-2-amine, 4-[3-(6-amino-5-methoxypyridin-3-yl)-1H-pyrazol-4-yl]pyrimidin-2-amine, 3-(4-(1-(2,2-difluoroethyl)-3-(1-cyanoethyl-1H-pyrrolo[2,3-b]pyridin-5-yl)-1H-pyrazol-4-yl)pyrimidin-2-ylamino)propanenitrile, 3-({4-[3-(3-chloro-1H-pyrrolo[2,3-b]pyridin-5-yl)-1-(2-hydroxy-1,1-dimethylethyl)-1H-pyrazol-4-yl]pyrimidin-2-yl}amino)-propanenitrile, 2-[4-(2-aminopyrimidin-4-yl)-3-(3-chloro-1H-pyrrolo[2,3-b]pyridin-5-yl)-1H-pyrazol-1-yl]-2-methylpropan-1-ol, 3-chloro-5-(1-isopropyl-4-pyrimidin-4-yl-1H-pyrazol-3-yl)-1H-pyrrolo[2,3-b]pyridine, 3-chloro-5-[1-(1-methylpiperidin-4-yl)-4-pyrimidin-4-yl-1H-pyrazol-3-yl]-1H-pyrrolo[2,3-b]pyridine, 5-(1-tert-butyl-4-pyrimidin-4-yl-1H-pyrazol-3-yl)-3-methoxypyridin-2-amine, (2S)-1-(4-(3-(3-chloro-1H-pyrrolo[2,3-b]pyridin-5-yl)-1-(tetrahydrofuran-3-yl)-1H-pyrazol-4-yl)pyrimidin-2-ylamino)propan-2-ol, 3-({4-[3-(6-amino-5-methoxypyridin-3-yl)-1-methyl-1H-pyrazol-4-yl]pyrimidin-2-yl}amino)propanenitrile, N-(2,2-difluoroethyl)-4-[1-(2,2-difluoroethyl)-3-(3-methyl-1H-pyrazolo[3,4-b]pyridin-5-yl)-1H-pyrazol-4-yl]pyrimidin-2-amine, 4-[1-(2,2-difluoroethyl)-3-(3-methyl-1H-pyrazolo[3,4-b]pyridin-5-yl)-1H-pyrazol-4-yl]-N-(tetrahydrofuran-3-yl)pyrimidin-2-amine, 2-[3-(3-chloro-1H-pyrrolo[2,3-b]pyridin-5-yl)-4-{2-[(2-hydroxyethyl)amino]pyrimidin-4-yl}-1H-pyrazol-1-yl]-2-methylpropanenitrile, 2-[4-(2-aminopyrimidin-4-yl)-3-(3-chloro-1H-pyrrolo[2,3-b]pyridin-5-yl)-1H-pyrazol-1-yl]-2-methylpropanenitrile, 3-(4-(3-(6-amino-5-methylpyridin-3-yl)-1-(2,2-difluoroethyl)-1H-pyrazol-4-yl)pyrimidin-2-ylamino)-propanenitrile, 4-(3-(3-chloro-1H-pyrrolo[2,3-b]pyridin-5-yl)-1-isopropyl-1H-pyrazol-4-yl)pyridin-2-amine, 4-(1-isopropyl-3-(1H-pyrrolo[2,3-b]pyridin-5-yl)-1H-pyrazol-4-yl)pyridin-2-amine, 4-(1-isopropyl-3-(1H-pyrrolo[2,3-b]pyridin-5-yl)-1H-pyrazol-4-yl)-1H-pyrrolo[2,3-b]pyridine, 3-chloro-5-(1-isopropyl-4-(1H-pyrrolo[2,3-b]pyridin-4-yl)-1H-pyrazol-3-yl)-1H-pyrrolo[2,3-b]pyridine, (2S)-1-({4-[3-(5-amino-6-methoxypyrazin-2-yl)-1-(2,2-difluoroethyl)-1H-pyrazol-4-yl]pyrimidin-2-yl}amino)propan-2-ol, (2S)-1-({4-[3-(7-chloro-5H-pyrrolo[2,3-b]pyrazin-2-yl)-1-isopropyl-1H-pyrazol-4-yl]pyrimidin-2-yl}amino)propan-2-ol, or a pharmaceutically acceptable salt thereof.

In a further embodiment, the compound is selected from 3-({4-[1-(2-hydroxy-1,1-dimethylethyl)-3-(5-methoxypyridin-3-yl)-1H-pyrazol-4-yl]pyrimidin-2-yl}amino)propanenitrile, 3-({4-[1-(2,2-difluoroethyl)-3-(1H-pyrrolo[2,3-b]pyridin-5-yl)-1H-pyrazol-4-yl]pyrimidin-2-yl}amino)propanenitrile, 3-({4-[3-(5-amino-6-methoxypyrazin-2-yl)-1-(2,2-difluoroethyl)-1H-pyrazol-4-yl]pyrimidin-2-yl}amino)propanenitrile, (2S)-1-(4-(1-isopropyl-3-(3-methyl-1H-pyrazolo[3,4-b]pyridin-5-yl)-1H-pyrazol-4-yl)pyrimidin-2-ylamino)propan-2-ol and 3-(4-(3-(5-acetyl-6-aminopyridin-3-yl)-1-(2,2-difluoroethyl)-1H-pyrazol-4-yl)pyrimidin-2-ylamino)-propanenitrile, or a pharmaceutically acceptable salt thereof.

In a further embodiment, the compound is selected from 3-({4-[1-(2-hydroxy-1,1-dimethylethyl)-3-(5-methoxypyridin-3-yl)-1H-pyrazol-4-yl]pyrimidin-2-yl}amino)propanenitrile, 3-({4-[1-(2,2-difluoroethyl)-3-(1H-pyrrolo[2,3-b]pyridin-5-yl)-1H-pyrazol-4-yl]pyrimidin-2-yl}amino)propanenitrile, 3-({4-[3-(5-amino-6-methoxypyrazin-2-yl)-1-(2,2-difluoroethyl)-1H-pyrazol-4-yl]pyrimidin-2-yl}amino)propanenitrile, and 3-(4-(3-(5-acetyl-6-aminopyridin-3-yl)-1-(2,2-difluoroethyl)-1H-pyrazol-4-yl)pyrimidin-2-ylamino)-propanenitrile, or a pharmaceutically acceptable salt thereof.

In a further embodiment, the compound is (2S)-1-(4-(1-isopropyl-3-(3-methyl-1H-pyrazolo[3,4-b]pyridin-5-yl)-1H-pyrazol-4-yl)pyrimidin-2-ylamino)propan-2-ol, or a pharmaceutically acceptable salt thereof. In a further embodiment, the compound is (2S)-1-(4-(1-isopropyl-3-(3-methyl-1H-pyrrolo[2,3-b]pyridin-5-yl)-1H-pyrazol-4-yl)pyrimidin-2-ylamino)propan-2-ol, or a pharmaceutically acceptable salt thereof. In a further embodiment, the compound is (2S)-1-(4-(3-(3-chloro-1H-pyrrolo[2,3-b]pyridin-5-yl)-1-isopropyl-1H-pyrazol-4-yl)pyrimidin-2-ylamino)propan-2-ol, or a pharmaceutically acceptable salt thereof. In a further embodiment, the compound is (2S)-1-(4-(3-(2,3-dimethyl-1H-pyrrolo[2,3-b]pyridin-5-yl)-1-isopropyl-1H-pyrazol-4-yl)pyrimidin-2-ylamino)propan-2-ol, or a pharmaceutically acceptable salt thereof. In a further embodiment, the compound is (2S)-1-(4-(3-(3-chloro-1H-pyrrolo[2,3-b]pyridin-5-yl)-1-(2,2-difluoroethyl)-1H-pyrazol-4-yl)pyrimidin-2-ylamino)propan-2-ol, or a pharmaceutically acceptable salt thereof. In a further embodiment, the compound is 3-({4-[1-(2-hydroxy-1,1-dimethylethyl)-3-(5-methoxypyridin-3-yl)-1H-pyrazol-4-yl]pyrimidin-2-yl}amino)propanenitrile, or a pharmaceutically acceptable salt thereof. In a further embodiment, the compound is 3-({4-[1-(2,2-difluoroethyl)-3-(1H-pyrrolo[2,3-b]pyridin-5-yl)-1H-pyrazol-4-yl]pyrimidin-2-yl}amino)propanenitrile, or a pharmaceutically acceptable salt thereof. In a further embodiment, the compound is 3-({4-[3-(5-amino-6-methoxypyrazin-2-yl)-1-(2,2-difluoroethyl)-1H-pyrazol-4-yl]pyrimidin-2-yl}amino)propanenitrile, or a pharmaceutically acceptable salt thereof. In a further embodiment, the compound is 3-(4-(3-(5-acetyl-6-aminopyridin-3-yl)-1-(2,2-difluoroethyl)-1H-pyrazol-4-yl)pyrimidin-2-ylamino)-propanenitrile, or a pharmaceutically acceptable salt thereof.

In a further embodiment, the compound is selected from any group of 10 compounds found in Table 1, or a pharmaceutically acceptable salt thereof.

In a further embodiment is any of the aspects described above in combination with any of the other aspects described above which is not inconsistent therewith.

The present invention also relates to a pharmaceutical composition, comprising at least one compound as described herein, or a pharmaceutically acceptable salt thereof, and a pharmaceutically acceptable carrier or diluent.

The present invention also relates to a method of treating abnormal cell growth, or any Raf-mediated disease or condition, in a mammal in need thereof, comprising the step of administering to said mammal a therapeutically effective amount of at least one compound as described herein, or a pharmaceutically acceptable salt thereof. For example, in one embodiment the abnormal cell growth is cancerous. In a further embodiment, the abnormal cell growth in non-cancerous.

The present invention further relates to a method of inhibiting Raf enzymatic activity, comprising contacting a Raf enzyme with a Raf-inhibiting amount of at least one compound as described herein, or a pharmaceutically acceptable salt thereof.

The present invention further relates to the use of any of the compounds as described herein, or a salt or solvate thereof, in the manufacture of a medicament for the treatment of abnormal cell growth in a mammal.

The present invention further relates to methods of making the compounds as described herein using the methods as shown in the specific examples herein and in the general synthetic methods A, B, C, D, E, F, G, H and I as described herein.

The present invention further relates to any of the compounds described above, or salts or solvates thereof, for use as a medicament. The present invention further relates to the use of any of the compounds described above, or salts or solvates thereof, for the manufacture of a medicament for the treatment of abnormal cell growth.

DETAILED DESCRIPTION

As used herein, the terms "comprising" and "including" are used in their open, non-limiting sense.

The terms "halo" and/or "halogen" refer to fluorine, chlorine, bromine or iodine.

The term "oxo" as used herein refers to an oxygen covalently attached to a carbon atom on an alkyl, cycloalkyl, or cycloheteroalkyl by a double bond such that the carbon is in the sp$^2$ hydridization state and the resultant functional group is a ketone.

The term "$C_1$-$C_6$ alkyl" refers to a saturated aliphatic hydrocarbon radical including straight chain and branched chain groups of 1 to 6 carbon atoms. Examples of ($C_1$ to $C_6$) alkyl groups include methyl, ethyl, propyl, 2-propyl, n-butyl, iso-butyl, tert-butyl, pentyl, and the like.

The term "$C_2$-$C_8$ alkenyl", as used herein, means an alkyl moiety comprising 2 to 8 carbons having at least one carbon-carbon double bond. The carbon-carbon double bond in such a group may be anywhere along the 2 to 8 carbon chain that will result in a stable compound. Such groups include both the E and Z isomers of said alkenyl moiety. Examples of such groups include, but are not limited to, ethenyl, propenyl, butenyl, allyl, and pentenyl. The term "allyl," as used herein, means a —$CH_2CH$=$CH_2$ group. The term, "C(R)=C(R)," as used herein, represents a carbon-carbon double bond in which each carbon is substituted by an R group.

As used herein, the term "$C_2$-$C_8$ alkynyl" means an alkyl moiety comprising from 2 to 8 carbon atoms and having at least one carbon-carbon triple bond. The carbon-carbon triple bond in such a group may be anywhere along the 2 to 8 carbon chain that will result in a stable compound. Examples of such groups include, but are not limited to, ethyne, propyne, 1-butyne, 2-butyne, 1-pentyne, 2-pentyne, 1-hexyne, 2-hexyne, and 3-hexyne.

The term "$C_1$-$C_6$ alkoxy", as used herein, means an O-alkyl group wherein said alkyl group contains from 1 to 6 carbon atoms and is straight, branched, or cyclic. Alternatively, "$C_1$-$C_6$ alkoxy" is used interchangeably herein with "—O—$C_1$-$C_6$ alkyl". Examples of such groups include, but are not limited to, methoxy, ethoxy, n-propyloxy, iso-propyloxy, n-butoxy, iso-butoxy, tert-butoxy, cyclopentyloxy, and cyclohexyloxy.

The term "$C_1$-$C_{11}$ heteroalkyl" refers to a straight- or branched-chain alkyl group having a total of from 2 to 12 atoms in the chain, including from 1 to 11 carbon atoms, and one or more atoms of which is a heteroatom selected from S, O, and N, with the proviso that said chain may not contain two adjacent O atoms or two adjacent S atoms. The S atoms in said chains may be optionally oxidized with one or two oxygen atoms, to afford sulfides and sulfones, respectively. Furthermore, the $C_1$-$C_{11}$ heteroalkyl groups in the compounds of the present invention can contain an oxo group at any carbon or heteroatom that will result in a stable compound. Exemplary $C_1$-$C_{11}$ heteroalkyl groups include, but are not limited to, alcohols, alkyl ethers, primary, secondary, and tertiary alkyl amines, amides, ketones, esters, sulfides, and sulfones.

The term "$C_6$-$C_{14}$ aryl", as used herein, means a group derived from an aromatic hydrocarbon containing from 6 to 14 carbon atoms that can be, for example, monocyclic, bicyclic or tricyclic. Examples of such groups include, but are not limited to, phenyl or naphthyl. The terms "Ph" and "phenyl," as used herein, means a —$C_6H_5$ group. The term "benzyl," as used herein, means a —$CH_2C_6H_5$ group.

The term "$C_6$-$C_{14}$ aryloxy", as used herein, means an O-aryl group wherein said aryl group is a group derived from an aromatic hydrocarbon containing from 6 to 14 carbon atoms that can be, for example, monocyclic, bicyclic or tricyclic. Alternatively, "$C_6$-$C_{14}$ aryloxy" is used interchangeably herein with "—O—$C_6$-$C_{14}$ aryl". Examples of such groups include, but are not limited to phenolyl or naphtholyl.

The term "—S—$C_6$-$C_{14}$ aryl", as used herein, means an S-aryl group wherein said aryl group is a group derived from an aromatic hydrocarbon containing from 6 to 14 carbon atoms that can be, for example, monocyclic, bicyclic or tricyclic.

"$C_2$-$C_9$ heteroaryl", as used herein, means an aromatic heterocyclic group having a total of from 5 to 10 atoms in its ring, and containing from 2 to 9 carbon atoms and from one to four heteroatoms each independently selected from O, S and N, and with the proviso that the ring of said group does not contain two adjacent O atoms or two adjacent S atoms. The heterocyclic groups include benzo-fused ring systems. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, 1H-pyrrolo[2,3-b]pyridinyl, 1H-pyrazolo[3,4-b]pyridinyl, 3H-imidazo[4,5-b]pyridinyl, imidazo[1,2-a]pyrimidinyl and furopyridinyl. The $C_4$ to $C_9$ heteroaryl groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

"$C_2$-$C_9$ cycloheteroalkyl", as used herein, means a non-aromatic, monocyclic, bicyclic, tricyclic, spirocyclic, or tetracyclic group having a total of from 4 to 13 atoms in its ring system, and containing from 2 to 9 carbon atoms and from 1 to 4 heteroatoms each independently selected from O, S and N, and with the proviso that the ring of said group does not contain two adjacent O atoms or two adjacent S atoms. Furthermore, such $C_2$ to $C_9$ cycloheteroalkyl groups may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a $C_2$ to $C_9$ cycloheteroalkyl group contains a sulfur atom, said sulfur atom may be oxidized with one or two oxygen atoms to afford either a sulfoxide or sulfone. An example of a 4 membered cycloheteroalkyl group is azetidinyl (derived from azetidine). An example of a 5 membered cycloheteroalkyl group is pyrrolidinyl. An example of a 6 membered cycloheteroalkyl group is piperidinyl. An example of a 9 membered cycloheteroalkyl group is indolinyl. An example of a 10 membered cycloheteroalkyl group is 4H-quinolizinyl. Further examples of such $C_2$ to $C_9$ cycloheteroalkyl groups include, but are not limited to, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl quinolizinyl, 3-oxopiperazinyl, 4-methylpiperazinyl, 4-ethylpiperazinyl, 1-oxo-2,8,diazaspiro[4.5]dec-8-yl, 1H-pyrrolo[2,3-b]pyridin-2(3H)-one, 2,3-dihydro-1H-pyrrolo[2,3-b]pyridinyl and 6,7-dihydro-5H-pyrrolo[3,4-d]pyrimidinyl.

The term "$C_3$-$C_8$ cycloalkyl group" means a saturated, monocyclic, fused, spirocyclic, or polycyclic ring structure having a total of from 3 to 8 carbon ring atoms. Examples of such groups include, but are not limited to, cyclopropyl, cyclobutyl, cyclopentyl, cyclopentenyl, cyclohexyl, cycloheptyl, and adamantyl.

The term "cyano" refers to a —C≡N group.

The term "substituted," means that the specified group or moiety bears one or more substituents. The term "unsubstituted," means that the specified group bears no substituents. The term "optionally substituted" means that the specified group is unsubstituted or substituted by one or more substituents. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$ aryl group, also called "phenyl" herein, is substituted with one additional substituent, one of ordinary skill in the art would understand that such a group has 4 open positions left on carbon atoms of the $C_6$ aryl ring (6 initial positions, minus one to which the remainder of the compound of the present invention is bonded, minus an additional substituent, to leave 4). In such cases, the remaining 4 carbon atoms are each bound to one hydrogen atom to fill their valencies. Similarly, if a $C_6$ aryl group in the present compounds is said to be "disubstituted," one of ordinary skill in the art would understand it to mean that the $C_6$ aryl has 3 carbon atoms remaining that are unsubstituted. Those three unsubstituted carbon atoms are each bound to one hydrogen atom to fill their valencies.

The term "solvate," is used to describe a molecular complex between compounds of the present invention and solvent molecules. Examples of solvates include, but are not limited to, compounds of the invention in combination water, isopropanol, ethanol, methanol, dimethylsulfoxide (DMSO), ethyl acetate, acetic acid, ethanolamine, or mixtures thereof. The term "hydrate" can be used when said solvent is water. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

The term "pharmaceutically acceptable salt," as used herein, means a salt of a compound of the present invention that retains the biological effectiveness of the free acids and bases of the specified derivative and that is not biologically or otherwise undesirable.

The term "pharmaceutically acceptable formulation," as used herein, means a combination of a compound of the invention, or a salt or solvate thereof, and a carrier, diluent, and/or excipient(s) that are compatible with a compound of the present invention, and is not deleterious to the recipient thereof. Pharmaceutical formulations can be prepared by procedures known to those of ordinary skill in the art. For example, the compounds of the present invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be pills, tablets, powders, lozenges, saches, cachets, or sterile packaged powders, and the like, depending on the type of excipient used. Additionally, it is specifically contemplated that pharmaceutically acceptable formulations of the present invention can contain more than one active ingredient. For example, such formulations may contain more than one compound according to the present invention. Alternatively, such formulations may contain one or more compounds of the present invention and one or more additional agents that reduce abnormal cell growth.

The term "Raf-inhibiting amount" as used herein, refers to the amount of a compound of the present invention, or a salt or solvate thereof, required to inhibit the enzymatic activity of Raf in vivo, such as in a mammal, or in vitro. The amount of such compounds required to cause such inhibition can be determined without undue experimentation using methods described herein and those known to those of ordinary skill in the art.

The term "inhibiting Raf enzyme activity," as used herein, means decreasing the activity or functioning of the Raf enzyme either in vitro or in vivo, such as in a mammal, such as a human, by contacting the enzyme with a compound of the present invention.

The term "Raf" as used herein means a-Raf, b-Raf, c-Raf, or mutants thereof, or any of the known Raf isoformic splice variants.

The term "therapeutically effective amount," as used herein, means an amount of a compound of the present invention, or a salt or solvate thereof, that, when administered to a mammal in need of such treatment, is sufficient to effect treatment, as defined herein. Thus, a therapeutically effective amount of a compound of the present invention, or a salt or solvate thereof, is a quantity sufficient to modulate or inhibit the activity of the Raf enzyme such that a disease condition that is mediated by activity of the Raf enzyme is reduced or alleviated.

The terms "treat", "treating", and "treatment" with reference to abnormal cell growth, or to any Raf mediated disease or condition, in a mammal, particularly a human, include: (i) preventing the disease or condition from occurring in a subject which may be predisposed to the condition, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating the disease or condition or the symptoms resulting from the disease or condition, e.g., relieving an inflammatory response without addressing the underlying disease or condition. With regard to abnormal cell growth, such as cancer, these terms simply mean that the life expectancy of an individual affected with abnormal cell growth will be increased or that one or more of the symptoms of the disease will be reduced.

Unless indicated otherwise, all references herein to the inventive compounds include references to salts, solvates, and complexes thereof, including polymorphs, stereoisomers, tautomers, and isotopically labeled versions thereof. For example, compounds of the present invention can be pharmaceutically acceptable salts and/or pharmaceutically acceptable solvates.

"Abnormal cell growth", as used herein, unless otherwise indicated, refers to cell growth that is independent of normal regulatory mechanisms (e.g., loss of contact inhibition), including the abnormal growth of normal cells and the growth of abnormal cells. This includes, but is not limited to, the abnormal growth of: tumor cells (tumors) that proliferate by expressing a mutated tyrosine kinase or overexpression of a receptor tyrosine kinase; benign and malignant cells of other proliferative diseases in which aberrant tyrosine kinase activation occurs; any tumors that proliferate by receptor tyrosine kinases; any tumors that proliferate by aberrant serine/threonine kinase activation; benign and malignant cells of other proliferative diseases in which aberrant serine/threonine kinase activation occurs; tumors, both benign and malignant, expressing an activated Ras oncogene; tumor cells, both benign and malignant, in which the Ras protein is activated as a result of oncogenic mutation in another gene; benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase.

The terms "abnormal cell growth" and "hyperproliferative disorder" are used interchangeably in this application.

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. The terms "racemic" or "racemic mixture," as used herein, refer to a 1:1 mixture of enantiomers of a particular compound. The term "diastereomers", on the other hand, refers to the relationship between a pair of stereoisomers that comprise two or more asymmetric centers and are not mirror images of one another.

The compounds of the present invention are useful for modulating or inhibiting Raf activity. Accordingly, these compounds are useful for the prevention and/or treatment of disease states associated with abnormal cell growth such as cancer, alone or in combination with other anti-cancer agents.

In accordance with a convention used in the art, the symbol

⁃ is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

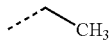

represents an ethyl group, and

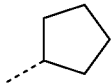

represents a cyclopentyl group, etc.

The compounds of the present invention may have asymmetric carbon atoms. The carbon-carbon bonds of the compounds of the present invention may be depicted herein using a solid line (-), a solid wedge (◀▬), or a dotted wedge (⠐⠐⠐⠐⠐). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the present invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art. See, e.g. "Stereochemistry of Organic Compounds" by E L Eliel (Wiley, New York, 1994), the disclosure of which is incorporated herein by reference in its entirety.

Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. Examples of tautomerism include keto and enol tautomers. A single compound may exhibit more than one type of isomerism. Included within the scope of the invention are all stereoisomers, geometric isomers and tautomeric forms of the inventive compounds, including compounds exhibiting more than one type of isomerism, and mixtures of one or more thereof. Cis/trans isomers may be separated by conventional techniques well known to those skilled in the art, for example, chromatography and fractional crystallization.

The compounds of the present invention may be administered as prodrugs. Thus certain derivatives of compounds of Formula (I), which may have little or no pharmacological activity themselves can, when administered to a mammal, be converted into a compound of Formula (I) having the desired activity, for example, by hydrolytic cleavage. Such derivatives are referred to as "prodrugs". Prodrugs can, for example, be produced by replacing appropriate functionalities present in the compound of Formula (I) with certain moieties known to those skilled in the art. See, e.g. "Pro-drugs as Novel Delivery Systems", Vol. 14, ACS Symposium Series (T Higuchi and W Stella) and "Bioreversible Carriers in Drug Design", Pergamon Press, 1987 (ed. E B Roche, American Pharmaceutical Association), the disclosures of which are incorporated herein by reference in their entireties. Some examples of such prodrugs include: an ester moiety in the place of a carboxylic acid functional group; an ether moiety or an amide moiety in place of an alcohol functional group; and an amide moiety in place of a primary or secondary amino functional group. Further examples of replacement groups are known to those of skill in the art. See, e.g. "Design of Prodrugs" by H Bundgaard (Elsevier, 1985), the disclosure of which is incorporated herein by reference in its entirety. It is also possible that certain compounds of Formula (I) may themselves act as prodrugs of other compounds of Formula (I).

Salts of the present invention can be prepared according to methods known to those of skill in the art. Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

If the inventive compound is a base, the desired salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified formulas.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The compounds of the present invention may be formulated into pharmaceutical compositions as described below in any pharmaceutical form recognizable to the skilled artisan as being suitable. Pharmaceutical compositions of the invention comprise a therapeutically effective amount of at least one compound of the present invention and an inert, pharmaceutically acceptable carrier or diluent.

To treat or prevent diseases or conditions mediated by Raf, a pharmaceutical composition of the invention is administered in a suitable formulation prepared by combining a therapeutically effective amount (i.e., a Raf modulating, regulating, or inhibiting amount effective to achieve therapeutic efficacy) of at least one compound of the present invention (as an active ingredient) with one or more pharmaceutically suitable carriers, which may be selected, for example, from diluents, excipients and auxiliaries that facilitate processing of the active compounds into the final pharmaceutical preparations.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g. parenteral or oral administration.

To obtain a stable water-soluble dose form, a salt of a compound of the present invention may be dissolved in an aqueous solution of an organic or inorganic acid, such as a 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin and the like in concentrations ranging from 0 to 60% of the total volume. In an exemplary embodiment, a compound of the present invention is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, the agents of the compounds of the present invention may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g. sterile pyrogen-free water, before use.

In addition to the formulations described above, the compounds of the present invention may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt. A pharmaceutical carrier for hydrophobic compounds is a co-solvent system comprising benzyl alcohol, a non-polar surfactant, a water-miscible organic polymer, and an aqueous phase. The co-solvent system may be a VPD co-solvent system. VPD is a solution of 3% w/v benzyl alcohol, 8% w/v of the non-polar surfactant polysorbate 80, and 65% w/v polyethylene glycol 300, made up to volume in absolute ethanol. The VPD co-solvent system (VPD: 5W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity non-polar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol® Transcutol® and the like may be used.

Further, the pharmaceutical composition may be incorporated into a skin patch for delivery of the drug directly onto the skin.

It will be appreciated that the actual dosages of the agents of this invention will vary according to the particular agent being used, the particular composition formulated, the mode of administration, and the particular site, host, and disease being treated. Those skilled in the art using conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals.

Furthermore, the pharmaceutically acceptable formulations of the present invention may contain a compound of the present invention, or a salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg.

Additionally, the pharmaceutically acceptable formulations of the present invention may contain a compound of the present invention, or a salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

The compounds of the present invention, or salts or solvates thereof, may be administered to a mammal suffering from abnormal cell growth, such as a human, either alone or as part of a pharmaceutically acceptable formulation, once a day, twice a day, three times a day, or four times a day, or even more frequently.

Those of ordinary skill in the art will understand that with respect to the compounds of the present invention, the particular pharmaceutical formulation, the dosage, and the number of doses given per day to a mammal requiring such treatment, are all choices within the knowledge of one of ordinary skill in the art and can be determined without undue experimentation.

This invention also relates to a method for the treatment of abnormal cell growth in a mammal, including a human, comprising administering to said mammal an amount of a compound of the Formula (I), as defined above, or a salt or solvate thereof, that is effective in treating abnormal cell growth.

In one embodiment of this method, the abnormal cell growth is cancer, including, but not limited to, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In one embodiment of the present invention the cancer is selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non hodgkins's lymphoma, spinal axis tumors, or a combination of one or more of the foregoing cancers.

In another embodiment of the present invention the cancer is selected from lung cancer (NSCLC and SCLC), ovarian cancer, colon cancer, rectal cancer, cancer of the anal region, or a combination of one or more of the foregoing cancers.

In another embodiment of the present invention the cancer is selected from lung cancer (NSCLC and SCLC), ovarian cancer, colon cancer, rectal cancer, or a combination of one or more of the foregoing cancers.

In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of the present invention, or a salt or solvate thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

In one embodiment of the present invention the anti-tumor agent used in conjunction with a compound of the present invention and pharmaceutical compositions described herein is an anti-angiogenesis agent, kinase inhibitor, pan kinase inhibitor or growth factor inhibitor. Preferred pan kinase inhibitors include Sutent™ (sunitinib), described in U.S. Pat. No. 6,573,293 (Pfizer, Inc, NY, USA). Anti-angiogenesis agents, include but are not limited to the following agents, such as EGF inhibitors, EGFR inhibitors, VEGF inhibitors, VEGFR inhibitors, TIE2 inhibitors, IGF1R inhibitors, COX-11 (cyclooxygenase 11) inhibitors, MMP-2 (matrix-metalloprotienase 2) inhibitors, and MMP-9 (matrix-metalloprotienase 9) inhibitors.

Preferred VEGF inhibitors, include for example, Avastin (bevacizumab), an anti-VEGF monoclonal antibody of Genentech, Inc. of South San Francisco, Calif. Additional VEGF inhibitors include CP-547,632 (Pfizer Inc., NY, USA), AG13736 (Pfizer Inc.), ZD-6474 (AstraZeneca), AEE788 (Novartis), AZD-2171, VEGF Trap (Regeneron/Aventis), Vatalanib (also known as PTK-787, ZK-222584: Novartis & Schering AG), Macugen (pegaptanib octasodium, NX-1838, EYE-001, Pfizer Inc./Gilead/Eyetech), IM862 (Cytran Inc. of Kirkland, Wash., USA); and angiozyme, a synthetic ribozyme from Ribozyme (Boulder, Colo.) and Chiron (Emeryville, Calif.) and combinations thereof.

VEGF inhibitors useful in the practice of the present invention are described in U.S. Pat. Nos. 6,534,524 and 6,235,764, both of which are incorporated in their entirety for all purposes. Additional VEGF inhibitors are described in, for example in WO 99/24440, in WO 95/21613, WO 99/61422, U.S. Pat. No. 5,834,504, WO 98/50356, U.S. Pat. No. 5,883, 113 U.S. Pat. No. 5,886,020, U.S. Pat. No. 5,792,783, U.S. Pat. No. 6,653,308, WO 99/10349, WO 97/32856, WO 97/22596, WO 98/54093, WO 98/02438, WO 99/16755, and WO 98/02437, all of which are herein incorporated by reference in their entirety.

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain, Vitaxin and combinations thereof.

Other antiproliferative agents that may be used in combination with the compounds of the present invention include inhibitors of the enzyme farnesyl protein transferase and inhibitors of the receptor tyrosine kinase PDGFr, including the compounds disclosed and claimed in the following: U.S. Pat. No. 6,080,769; U.S. Pat. No. 6,194,438; U.S. Pat. No. 6,258,824; U.S. Pat. No. 6,586,447; U.S. Pat. No. 6,071,935; U.S. Pat. No. 6,495,564; and U.S. Pat. No. 6,150,377; U.S. Pat. No. 6,596,735; U.S. Pat. No. 6,479,513; WO 01/40217; U.S. 2003-0166675. Each of the foregoing patents and patent applications is herein incorporated by reference in their entirety.

PDGRr inhibitors include but are not limited to those disclosed in international patent application publication numbers WO01/40217 and WO2004/020431, the contents of which are incorporated in their entirety for all purposes. Preferred PDGFr inhibitors include Pfizer's CP-673,451 and CP-868,596 and its salts.

Preferred GARF inhibitors include Pfizer's AG-2037 (pelitrexol and its salts). GARF inhibitors useful in the practice of the present invention are disclosed in U.S. Pat. No. 5,608,082 which is incorporated in its entirety for all purposes.

Examples of useful COX-11 inhibitors which can be used in conjunction with a compound of Formula (I) and pharmaceutical compositions disclosed herein include CELEBREX™ (celecoxib), parecoxib, deracoxib, ABT-963, MK-663 (etoricoxib), COX-189 (Lumiracoxib), BMS 347070, RS 57067, NS-398, Bextra (valdecoxib), paracoxib, Vioxx (rofecoxib), SD-8381, 4-Methyl-2-(3,4-dimethylphenyl)-1-(4-sulfamoyl-phenyl)-1H-pyrrole, 2-(4-Ethoxyphenyl)-4-methyl-1-(4-sulfamoylphenyl)-1H-pyrrole, T-614, JTE-522, S-2474, SVT-2016, CT-3, SC-58125 and Arcoxia (etoricoxib). Additionally, COX-11 inhibitors are disclosed in U.S. Patent Applications US 2005-0148627 and US 2005-0148777, the contents of which are incorporated in their entirety for all purposes.

In a particular embodiment the anti-tumor agent is celecoxib (U.S. Pat. No. 5,466,823), valdecoxib (U.S. Pat. No. 5,633,272), parecoxib (U.S. Pat. No. 5,932,598), deracoxib (U.S. Pat. No. 5,521,207), SD-8381 (U.S. Pat. No. 6,034,256, Example 175), ABT-963 (WO 2002/24719), rofecoxib (CAS No. 162011-90-7), MK-663 (or etoricoxib) as disclosed in WO 1998/03484, COX-189 (Lumiracoxib) as disclosed in WO 1999/11605, BMS-347070 (U.S. Pat. No. 6,180,651), NS-398 (CAS 123653-11-2), RS 57067 (CAS 17932-91-3), 4-Methyl-2-(3,4-dimethylphenyl)-1-(4-sulfamoyl-phenyl)-1H-pyrrole, 2-(4-Ethoxyphenyl)-4-methyl-1-(4-sulfamoylphenyl)-1H-pyrrole, or meloxicam.

Other useful inhibitors as anti-tumor agents used in combination with a compound of the present invention and pharmaceutical compositions disclosed herein include aspirin, and non-steroidal anti-inflammatory drugs (NSAIDs) which inhibit the enzyme that makes prostaglandins (cyclooxygenase I and II), resulting in lower levels of prostaglandins, include but are not limited to the following, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol), Oxaprozin (Daypro) and combinations thereof.

Preferred COX-1 inhibitors include ibuprofen (Motrin), nuprin, naproxen (Aleve), indomethacin (Indocin), nabumetone (Relafen) and combinations thereof.

Targeted agents used in combination with a compound of the present invention and pharmaceutical compositions disclosed herein include EGFr inhibitors such as Iressa (gefitinib, AstraZeneca), Tarceva (erlotinib or OSI-774, OSI Pharmaceuticals Inc.), Erbitux (cetuximab, Imclone Pharmaceuticals, Inc.), EMD-7200 (Merck AG), ABX-EGF (Amgen Inc. and Abgenix Inc.), HR3 (Cuban Government), IgA antibodies (University of Erlangen-Nuremberg), TP-38 (IVAX), EGFR fusion protein, EGF-vaccine, anti-EGFr immunoliposomes (Hermes Biosciences Inc.) and combinations thereof. Preferred EGFr inhibitors include Iressa, Erbitux, Tarceva and combinations thereof.

Other anti-tumor agents include those selected from pan erb receptor inhibitors or ErbB2 receptor inhibitors, such as CP-724,714 (Pfizer, Inc.), CI-1033 (canertinib, Pfizer, Inc.), Herceptin (trastuzumab, Genentech Inc.), Omitarg (2C4, pertuzumab, Genentech Inc.), TAK-165 (Takeda), GW-572016 (Ionafarnib, GlaxoSmithKline), GW-282974 (GlaxoSmithKline), EKB-569 (Wyeth), PKI-166 (Novartis), dHER2 (HER2 Vaccine, Corixa and GlaxoSmithKline), APC8024 (HER2 Vaccine, Dendreon), anti-HER2/neu bispecific antibody (Decof Cancer Center), B7.her2.IgG3 (Agensys), AS HER2 (Research Institute for Rad Biology & Medicine), trifunctional bispecific antibodies (University of Munich) and mAB AR-209 (Aronex Pharmaceuticals Inc) and mAB 2B-1 (Chiron) and combinations thereof.

Preferred erb selective anti-tumor agents include Herceptin, TAK-165, CP-724,714, ABX-EGF, HER3 and combinations thereof. Preferred pan erbb receptor inhibitors include GW572016, CI-1033, EKB-569, and Omitarg and combinations thereof.

Additional erbB2 inhibitors include those disclosed in WO 98/02434, WO 99/35146, WO 99/35132, WO 98/02437, WO 97/13760, WO 95/19970, U.S. Pat. No. 5,587,458, and U.S. Pat. No. 5,877,305, each of which is herein incorporated by reference in its entirety. ErbB2 receptor inhibitors useful in the present invention are also disclosed in U.S. Pat. Nos. 6,465,449, and 6,284,764, and in WO 2001/98277 each of which are herein incorporated by reference in their entirety.

Additionally, other anti-tumor agents may be selected from the following agents, BAY-43-9006 (Onyx Pharmaceuticals Inc.), Genasense (augmerosen, Genta), Panitumumab (Abgenix/Amgen), Zevalin (Schering), Bexxar (Corixa/GlaxoSmithKline), Abarelix, Alimta, EPO 906 (Novartis), discodermolide (XAA-296), ABT-510 (Abbott), Neovastat (Aeterna), enzastaurin (Eli Lilly), Combrestatin A4P (Oxigene), ZD-6126 (AstraZeneca), flavopiridol (Aventis), CYC-202 (Cyclacel), AVE-8062 (Aventis), DMXAA (Roche/Antisoma), Thymitaq (Eximias), Temodar (temozolomide, Schering Plough) and Revilimd (Celegene) and combinations thereof.

Other anti-tumor agents may be selected from the following agents, CyPat (cyproterone acetate), Histerelin (histrelin acetate), Plenaixis (abarelix depot), Atrasentan (ABT-627), Satraplatin (JM-216), thalomid (Thalidomide), Theratope, Temilifene (DPPE), ABI-007 (paclitaxel), Evista (raloxifene), Atamestane (Biomed-777), Xyotax (polyglutamate paclitaxel), Targetin (bexarotine) and combinations thereof.

Additionally, other anti-tumor agents may be selected from the following agents, Trizaone (tirapazamine), Aposyn (exisulind), Nevastat (AE-941), Ceplene (histamine dihydrochloride), Orathecin (rubitecan), Virulizin, Gastrimmune (G17DT), DX-8951f (exatecan mesylate), Onconase (ranpirnase), BEC2 (mitumoab), Xcytrin (motexafin gadolinium) and combinations thereof.

Further anti-tumor agents may be selected from the following agents, CeaVac (CEA), NeuTrexin (trimetresate glucuronate) and combinations thereof. Additional anti-tumor agents may be selected from the following agents, OvaRex (oregovomab), Osidem (IDM-1), and combinations thereof. Additional anti-tumor agents may be selected from the following agents, Advexin (ING 201), Tirazone (tirapazamine), and combinations thereof. Additional anti-tumor agents may be selected from the following agents, RSR13 (efaproxiral), Cotara (131I chTNT 1/b), NBI-3001 (IL-4) and combinations thereof. Additional anti-tumor agents may be selected from the following agents, Canvaxin, GMK vaccine, PEG Interon A, Taxoprexin (DHA/paclitaxel), and combinations thereof.

Other anti-tumor agents include Pfizer's MEK1/2 inhibitor PD325901, Array Biopharm's MEK inhibitor ARRY-142886, Bristol Myers'CDK2 inhibitor BMS-387,032, Pfizer's CDK inhibitor PD0332991 and AstraZeneca's AXD-5438, and combinations thereof.

Additionally, mTOR inhibitors may also be utilized such as CCI-779 (Wyeth) and rapamycin derivatives RAD001 (Novartis) and AP-23573 (Ariad), HDAC inhibitors, SAHA (Merck Inc./Aton Pharmaceuticals) and combinations thereof. Additional anti-tumor agents include aurora 2 inhibitor VX-680 (Vertex), and Chk1/2 inhibitor XL844 (Exilixis).

The following cytotoxic agents, e.g., one or more selected from the group consisting of epirubicin (Ellence), docetaxel (Taxotere), paclitaxel, Zinecard (dexrazoxane), rituximab (Rituxan) imatinib mesylate (Gleevec), and combinations thereof, may be used in combination with a compound of the present invention and pharmaceutical compositions disclosed herein.

The invention also contemplates the use of the compounds of the present invention together with hormonal therapy, including but not limited to, exemestane (Aromasin, Pfizer Inc.), leuprorelin (Lupron or Leuplin, TAP/Abbott/Takeda), anastrozole (Arimidex, Astrazeneca), gosrelin (Zoladex, AstraZeneca), doxercalciferol, fadrozole, formestane, tamoxifen citrate (tamoxifen, Nolvadex, AstraZeneca), Casodex (AstraZeneca), Abarelix (Praecis), Trelstar, and combinations thereof.

The invention also relates to the use of the compounds of the present invention together with hormonal therapy agents such as anti-estrogens including, but not limited to fulvestrant, toremifene, raloxifene, lasofoxifene, letrozole (Femara, Novartis), anti-androgens such as bicalutamide, flutamide, mifepristone, nilutamide, Casodex™ (4'-cyano-3-(4-fluorophenylsulphonyl)-2-hydroxy-2-methyl-3'-(trifluoromethyl) propionanilide, bicalutamide) and combinations thereof.

Further, the invention provides a compound of the present invention alone or in combination with one or more supportive care products, e.g., a product selected from the group consisting of Filgrastim (Neupogen), ondansetron (Zofran), Fragmin, Procrit, Aloxi, Emend, or combinations thereof.

Particularly preferred cytotoxic agents include Camptosar, Erbitux, Iressa, Gleevec, Taxotere and combinations thereof.

The following topoisomerase I inhibitors may be utilized as anti-tumor agents: camptothecin; irinotecan HCl (Camptosar); edotecarin; orathecin (Supergen); exatecan (Daiichi); BN-80915 (Roche); and combinations thereof. Particularly preferred toposimerase II inhibitors include epirubicin (Ellence).

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, Paraplatin (carboplatin), eptaplatin, lobaplatin, nedaplatin, Eloxatin (oxaliplatin, Sanofi) or satrplatin and combinations thereof. Particularly preferred alkylating agents include Eloxatin (oxaliplatin).

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, Alimta (premetrexed disodium, LY231514, MTA), Gemzar (gemcitabine, Eli Lilly), fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid and combinations thereof.

Antibiotics include intercalating antibiotics and include, but are not limited to: aclarubicin, actinomycin D, amrubicin, annamycin, adriamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin, zinostatin and combinations thereof.

Plant derived anti-tumor substances include for example those selected from mitotic inhibitors, for example vinblastine, docetaxel (Taxotere), paclitaxel and combinations thereof.

Cytotoxic topoisomerase inhibiting agents include one or more agents selected from the group consisting of aclarubcin, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, topotecan, and combinations thereof.

Preferred cytotoxic topoisomerase inhibiting agents include one or more agents selected from the group consisting of camptothecin, 10-hydroxycamptothecin, 9-aminocamptothecin, irinotecan HCl (Camptosar), edotecarin, epirubicin (Ellence), etoposide, SN-38, topotecan, and combinations thereof.

Immunologicals include interferons and numerous other immune enhancing agents. Interferons include interferon alpha, interferon alpha-2a, interferon, alpha-2b, interferon beta, interferon gamma-1a, interferon gamma-1b (Actimmune), or interferon gamma-n1 and combinations thereof. Other agents include filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab (Y-muHMFG1), Provenge (Dendreon) and combinations thereof.

Biological response modifiers are agents that modify defense mechanisms of living organisms or biological responses, such as survival, growth, or differentiation of tissue cells to direct them to have anti-tumor activity. Such agents include krestin, lentinan, sizofuran, picibanil, ubenimex and combinations thereof.

Other anticancer agents that can be used in combination with a compound of the present invention include alitretinoin, ampligen, atrasentan bexarotene, bortezomib. Bosentan, calcitriol, exisulind, finasteride, fotemustine, ibandronic acid, miltefosine, mitoxantrone, 1-asparaginase, procarbazine, dacarbazine, hydroxycarbamide, pegaspargase, pentostatin, tazarotne, Telcyta (TLK-286, Telik Inc.), Velcade (bortemazib, Millenium), tretinoin, and combinations thereof.

Platinum-coordinated compounds include but are not limited to, cisplatin, carboplatin, nedaplatin, oxaliplatin, and combinations thereof.

Camptothecin derivatives include but are not limited to camptothecin, 10-hydroxycamptothecin, 9-aminocamptothecin, irinotecan, SN-38, edotecarin, topotecan and combinations thereof.

Other antitumor agents include mitoxantrone, 1-asparaginase, procarbazine, dacarbazine, hydroxycarbamide, pentostatin, tretinoin and combinations thereof.

Anti-tumor agents capable of enhancing antitumor immune responses, such as CTLA4 (cytotoxic lymphocyte antigen 4) antibodies, and other agents capable of blocking CTLA4 may also be utilized, such as MDX-010 (Medarex) and CTLA4 compounds disclosed in U.S. Pat. No. 6,682,736; and anti-proliferative agents such as other farnesyl protein transferase inhibitors, for example the farnesyl protein transferase inhibitors. Additionally, specific CTLA4 antibodies that can be used in combination with compounds of the present invention include those disclosed in U.S. Pat. Nos. 6,682,736 and 6,682,736 both of which are herein incorporated by reference in their entirety.

Specific IGF1R antibodies that can be used in the combination methods of the present invention include those disclosed in WO 2002/053596, which is herein incorporated by reference in its entirety.

Specific CD40 antibodies that can be used in the present invention include those disclosed in WO 2003/040170 which is herein incorporated by reference in its entirety. Gene therapy agents may also be employed as anti-tumor agents such as TNFerade (GeneVec), which express TNFalpha in response to radiotherapy.

In one embodiment of the present invention statins may be used in combination with a compound of the present invention and pharmaceutical compositions thereof. Statins (HMG-CoA reductase inhibitors) may be selected from the group consisting of Atorvastatin (Lipitor™, Pfizer Inc.), Provastatin (Pravachol™, Bristol-Myers Squibb), Lovastatin (Mevacor™, Merck Inc.), Simvastatin (Zocor™, Merck Inc.), Fluvastatin (Lescol™, Novartis), Cerivastatin (Baycol™, Bayer), Rosuvastatin (Crestor™, AstraZeneca), Lovostatin and Niacin (Advicor™, Kos Pharmaceuticals), derivatives and combinations thereof.

In a preferred embodiment the statin is selected from the group consisting of Atovorstatin and Lovastatin, derivatives and combinations thereof. Other agents useful as anti-tumor agents include Caduet.

Methods of Preparation

Compounds of the present invention may be prepared using the reaction routes and synthetic schemes described below, employing the techniques available in the art using starting materials that are readily available. Those of skill in the art will understand that a variety of different reagents and protecting groups can be used to produce compounds of the invention according to the following general schemes. Accordingly, when terms such as "appropriate base", "appropriate catalyst", "appropriate oxidizing agent" and the like are used in the general schemes below, those of skill in the art will be able to recognize various alternatives that may be used.

The preparation of certain embodiments of the present invention is described in detail in the examples that follow the general schemes outlined herein. Those of ordinary skill in the art will recognize that the preparations described may be readily adapted to prepare other embodiments of the present invention. For example, the synthesis of non-exemplified compounds according to the invention may be performed by modifications apparent to those skilled in the art, e.g. by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

In one general synthetic process, reactive intermediate compounds of the general structure represented by A and B are prepared according to Method A.

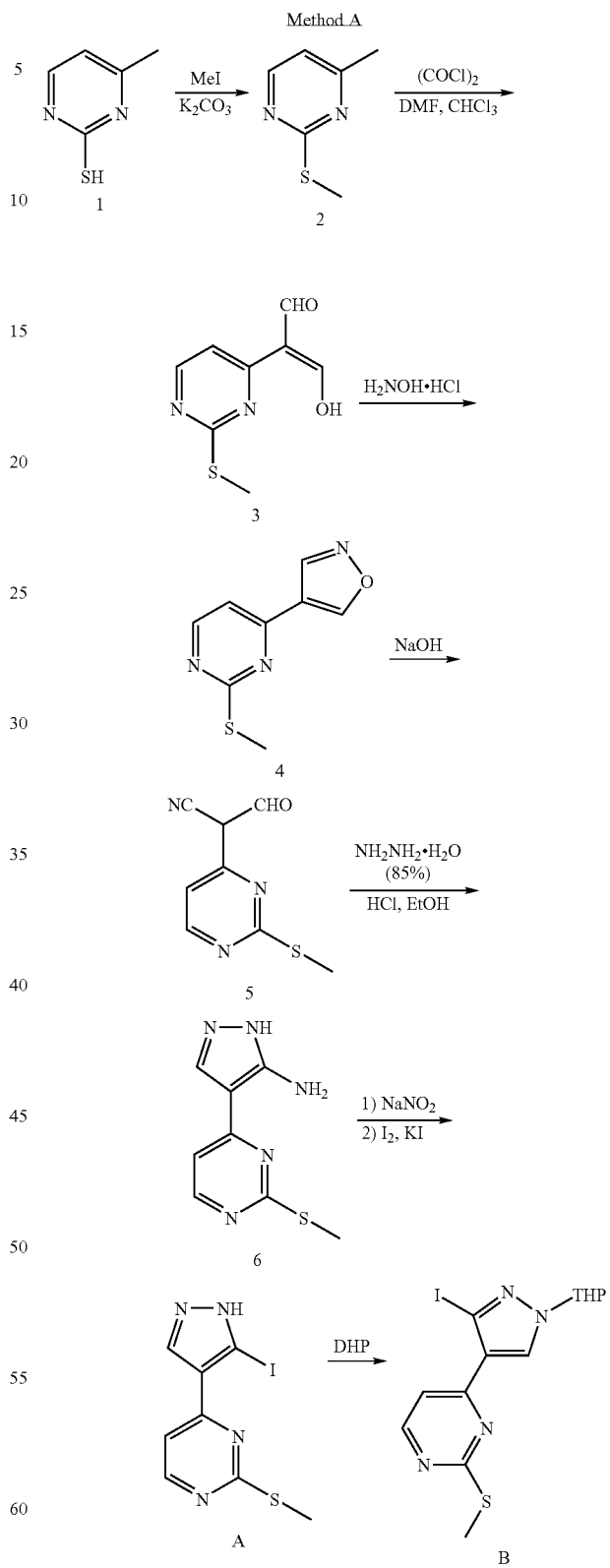

Reaction of thiol (1) with a methylating agent in the presence of an appropriate base provides a thio-methyl ether of the formula 2. Treatment of 2 with oxalyl chloride leads to formation of an aldehyde represented by formula 3. Aldehyde 3 can be further transformed to an isoxazole represented by the formula 4 by treatment with hydroxylamine. Isoxazole 4 can be cleaved to aldehyde 5 by treatment with an appropriate base. Isoxazole 5 can be further transformed to a pyrazoline of the type in formula 6 by reaction with hydrazine. Pyrazole 6 can be converted to A by a 2 step sequence involving reaction with NaNO$_2$ followed by reaction with iodide. Finally, A can be converted to B by reaction of the amine with dihydropyran.

In another general synthetic process, compounds of the general structure represented by 11 are prepared according to Method B.

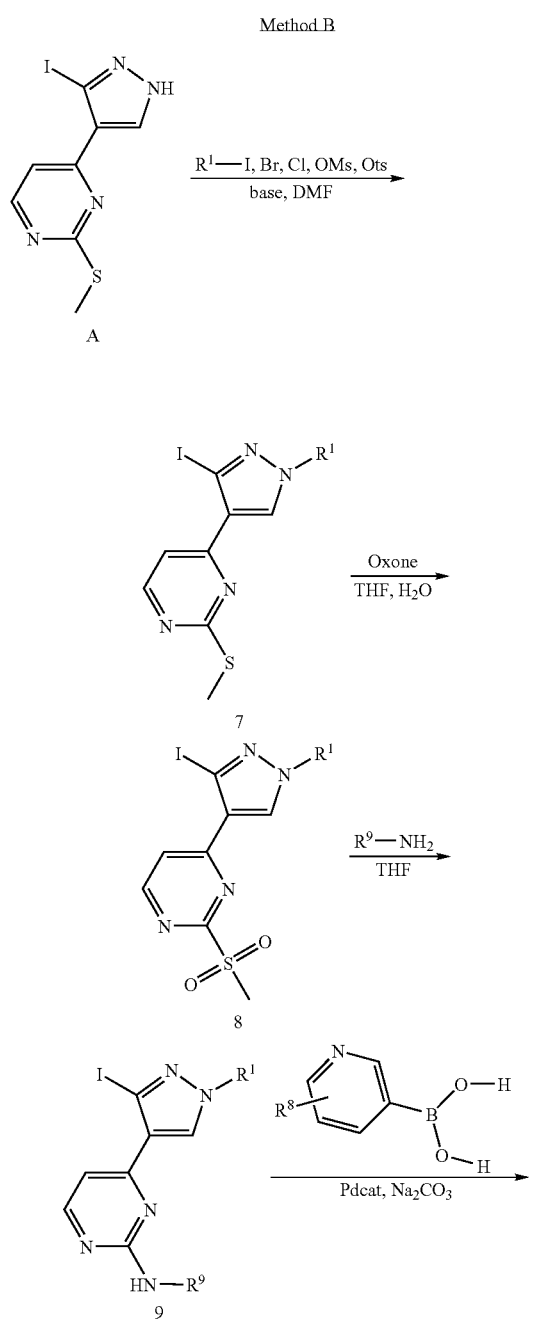

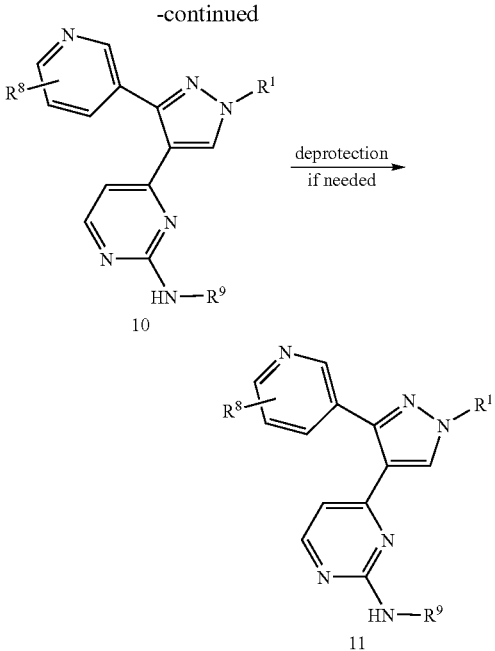

Reactive intermediate A can be prepared using Method A. The introduction of R$_1$ in 7 can be accomplished by alkylation of A under conditions appropriate to couple a reactive agent (e.g. R$^1$—I, R$^1$—Br, R$^1$—C$^1$, R$^1$—OMs, R$^1$—OTs, or the like) therewith. The sulfur in 7 can be oxidized to sulfones 8 by an appropriate oxidizing agent, such as oxone. Introduction of amines on the pyrimidine ring can be accomplished by displacement of the sulfur by an amine to yield 9. Suzuki coupling of 9 with a suitable boronic acid (or boronic ester) in the presence of an appropriate catalyst, such as a palladium catalyst, produces intermediates 10. Finally, if compounds 10 require deprotection of any remaining protecting groups, such deprotection can be accomplished by various methods to produce compounds 11. These methods are known to those skilled in the art (e.g. see T. Greene and P. Wuts, "Protective Groups in Organic Synthesis", 3$^{rd}$ Edition 1999, John Wiley & Sons).

In another general synthetic process, compounds of the general structure represented by 10 and 11 cab also be prepared according to Method C.

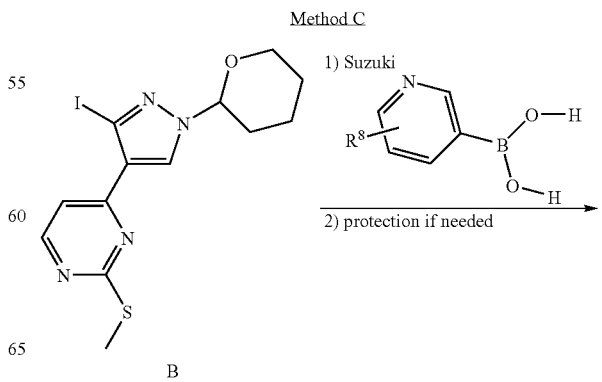

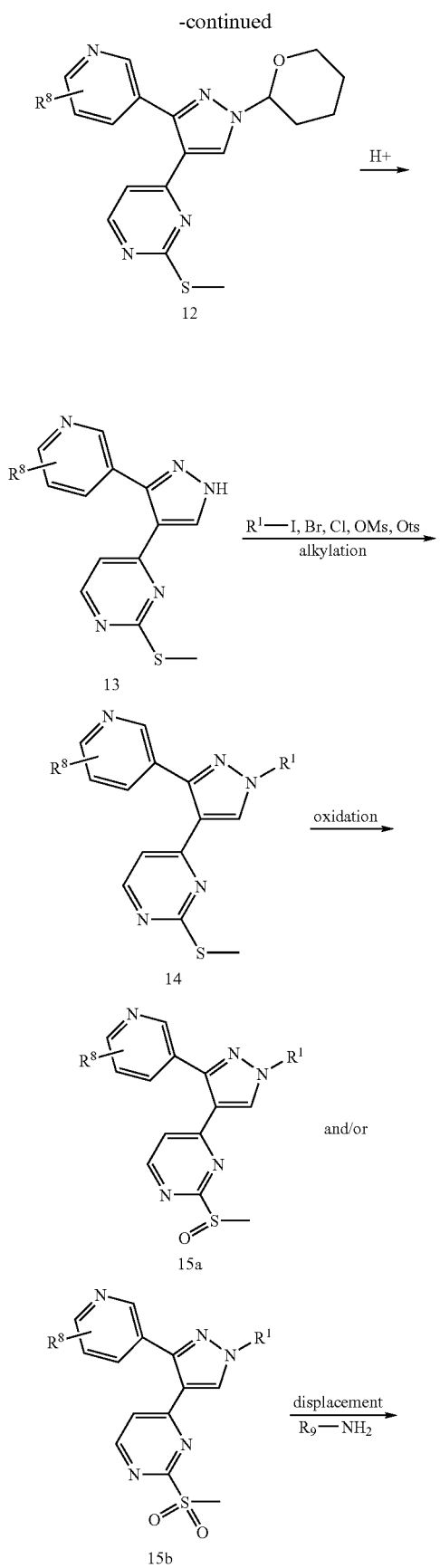

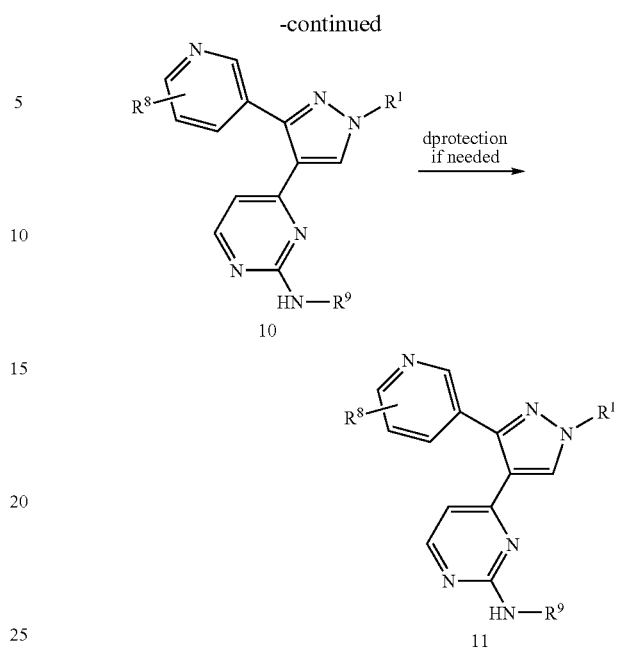

Reactive intermediate B can be prepared using Method A. Suzuki coupling of B with a suitable boronic acid (or boronic ester) in the presence of an appropriate catalyst, such as a palladium catalyst, produces intermediates 12. The THP protected amine can be revealed by deprotection using various methods to produce amine 13. Methods for removing a THP from an amine are known to those skilled in the art (e.g. see T. Greene and P. Wuts, "Protective Groups in Organic Synthesis", 3$^{rd}$ Edition 1999, John Wiley & Sons). The introduction of $R_1$ in 14 can be accomplished by alkylation of 13 under conditions appropriate to couple a reactive agent (e.g. $R^1$—I, $R^1$—Br, $R^1$—C$^1$, $R^1$—OMs, $R^1$—OTs, or the like) therewith. The sulfur in 14 can be oxidized to 15a and/or 15b by treatment with an appropriate oxidizing agent, such as ozone. Introduction of amines on the pyrimidine ring can be accomplished by displacement of the sulfur with an amine to yield 10. Finally, if compounds 10 require deprotection of any remaining protecting groups, such deprotection can be accomplished by various methods to produce compounds 11.

In another general synthetic process, compounds of the general structure represented by 20 and 22 are prepared according to Method D.

Method D

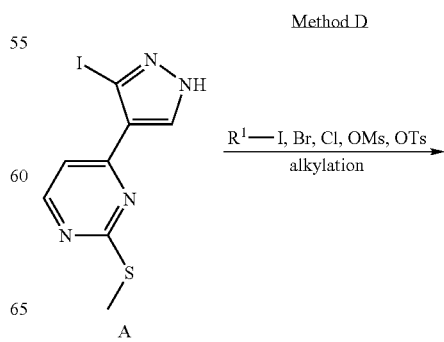

-continued

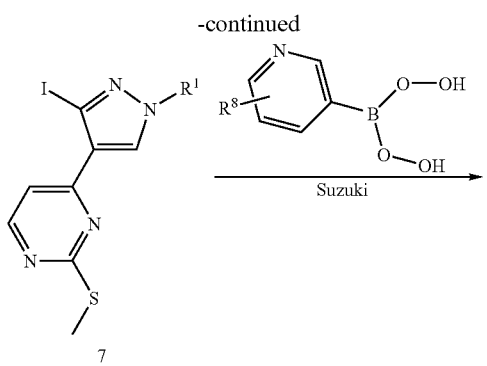

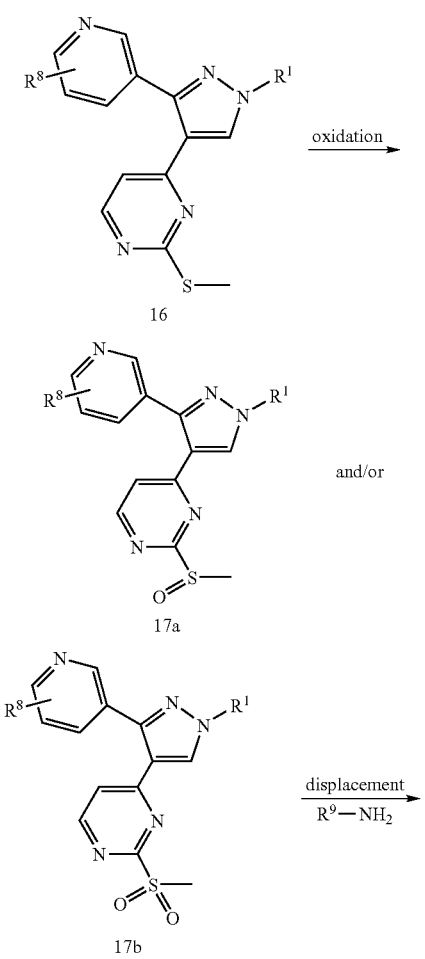

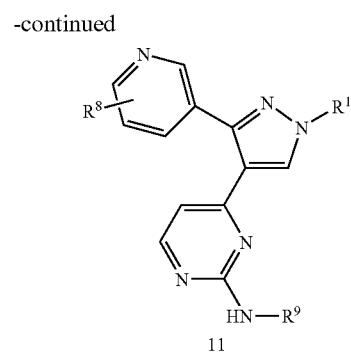

Reactive intermediate A can be prepared using Method A. The introduction of $R^1$ in 7 can be accomplished by alkylation of A under conditions appropriate to couple a reactive agent (e.g. $R^1$—I, $R^1$—Br, $R^1$—Cl, $R^1$—OMs, $R^1$—OTs, or the like) therewith. Suzuki coupling of 7 with a suitable boronic acid (or boronic ester) in the presence of an appropriate catalyst, such as a palladium catalyst, produces intermediates 16. The sulfur in 16 can be oxidized to 17a and/or 17b by treatment with an appropriate oxidizing agent, such as ozone. Introduction of amines on the pyrimidine ring can be accomplished by displacement of the sulfur with an amine to yield 10. Finally, if compounds 10 require deprotection of any remaining protecting groups, such deprotection can be accomplished by various methods to produce compounds 11.

In another general synthetic process, compounds represented by 20 are prepared according to Method E.

Method E

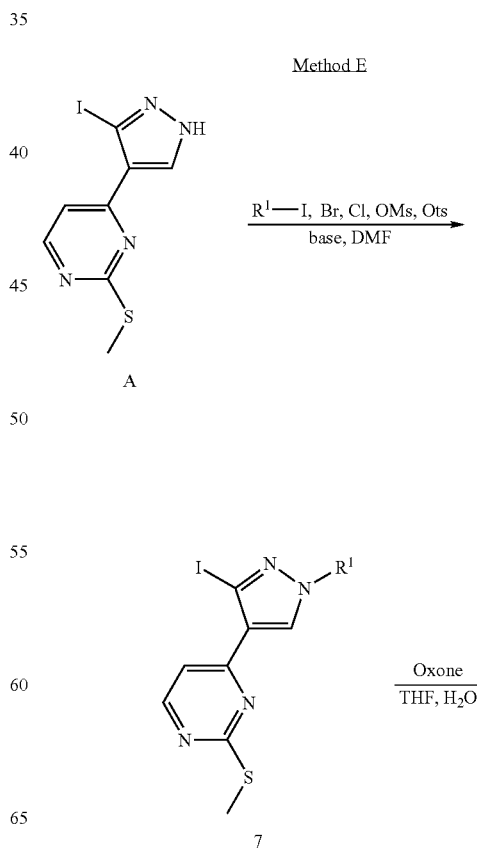

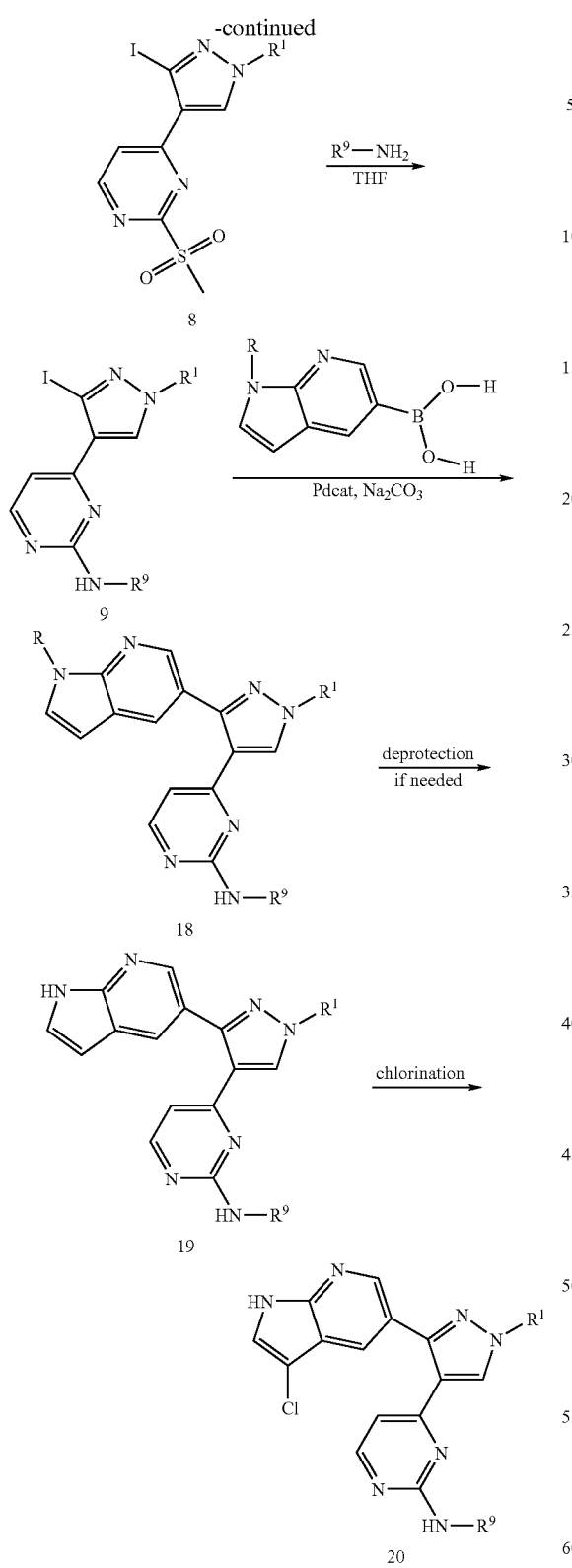

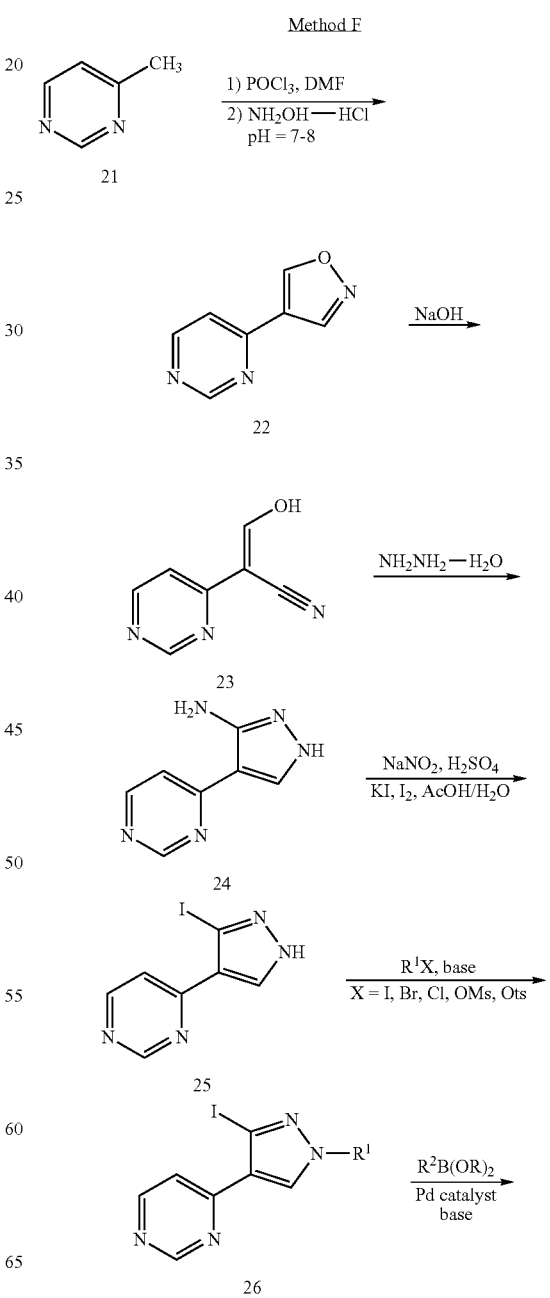

by an appropriate oxidizing agent, such as oxone. Introduction of amines on the pyrimidine ring can be accomplished by displacement of the sulfur by an amine to yield 9. Suzuki coupling of 9 with a suitable boronic acid or boronic ester (where R is hydrogen or a suitable nitrogen protecting group) in the presence of an appropriate catalyst, such as a palladium catalyst, produces intermediates 18. If compounds 18 require deprotection of any remaining protecting groups, such deprotection can be accomplished by various methods to produce compounds 19. Finally, compounds 19 can be chlorinated under appropriate chlorinating conditions to provide compounds 20.

In another general synthetic process, compounds represented by 29 can be prepared according to Method F.

Reactive intermediate A can be prepared using Method A. The introduction of $R_1$ in 7 can be accomplished by alkylation of A under conditions appropriate to couple a reactive agent (e.g. $R^1$—I, $R^1$—Br, $R^1$—C$^1$, $R^1$—OMs, $R^1$—OTs, or the like) therewith. The sulfur in 7 can be oxidized to sulfones 8

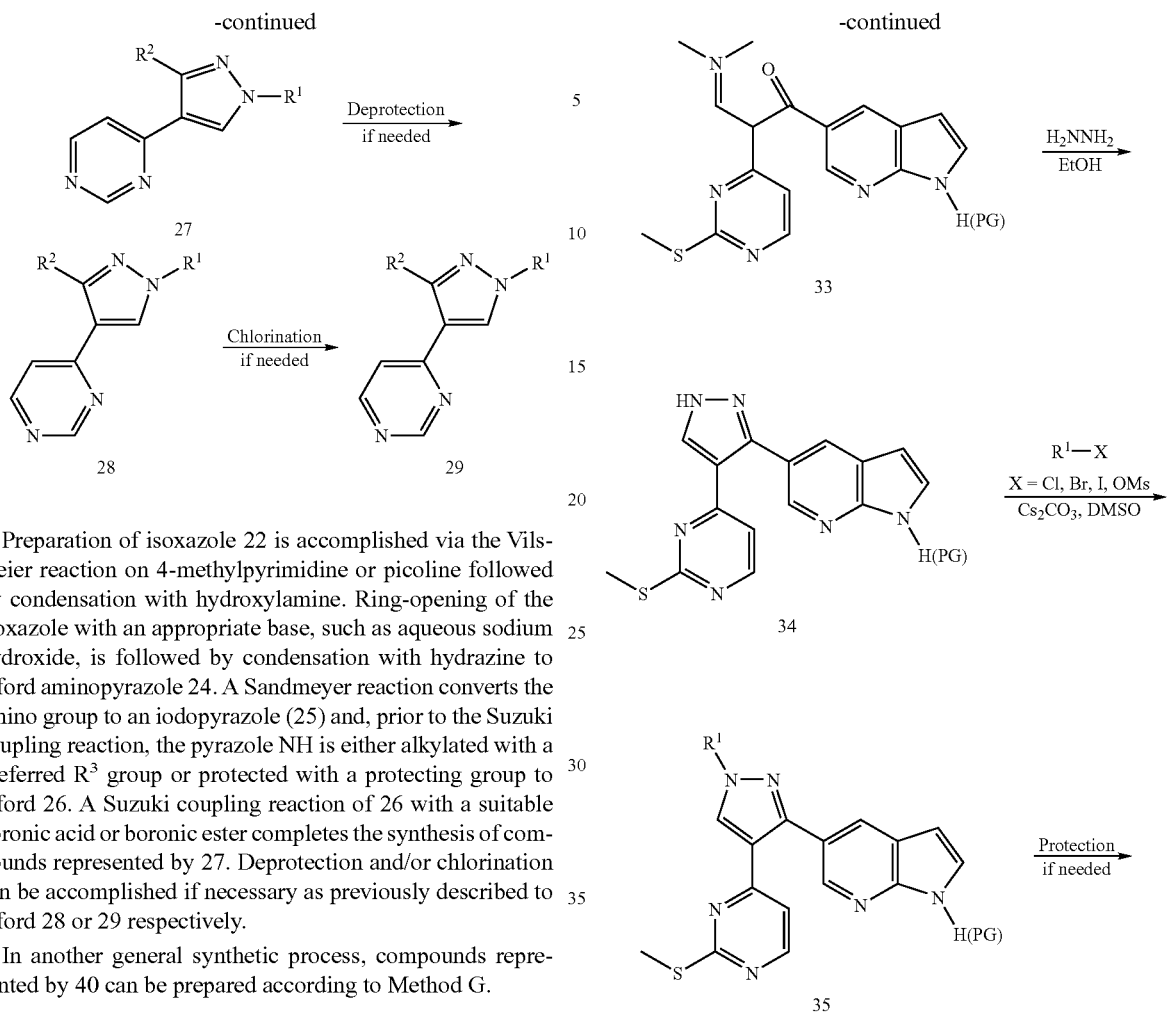

Preparation of isoxazole 22 is accomplished via the Vilsmeier reaction on 4-methylpyrimidine or picoline followed by condensation with hydroxylamine. Ring-opening of the isoxazole with an appropriate base, such as aqueous sodium hydroxide, is followed by condensation with hydrazine to afford aminopyrazole 24. A Sandmeyer reaction converts the amino group to an iodopyrazole (25) and, prior to the Suzuki coupling reaction, the pyrazole NH is either alkylated with a preferred $R^3$ group or protected with a protecting group to afford 26. A Suzuki coupling reaction of 26 with a suitable boronic acid or boronic ester completes the synthesis of compounds represented by 27. Deprotection and/or chlorination can be accomplished if necessary as previously described to afford 28 or 29 respectively.

In another general synthetic process, compounds represented by 40 can be prepared according to Method G.

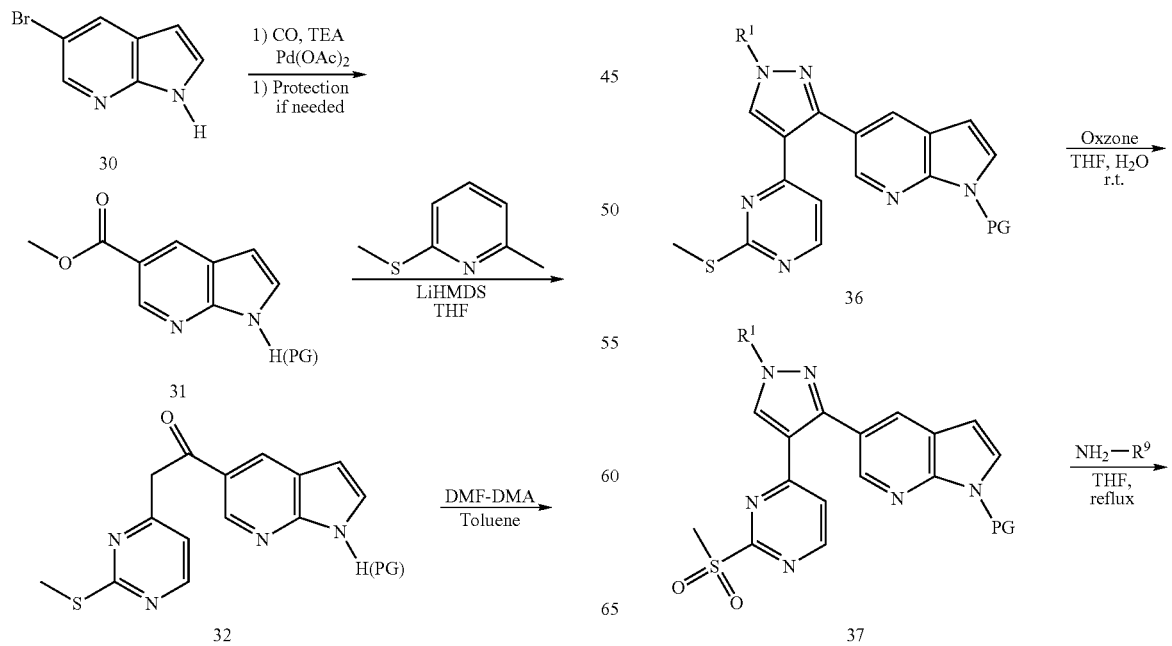

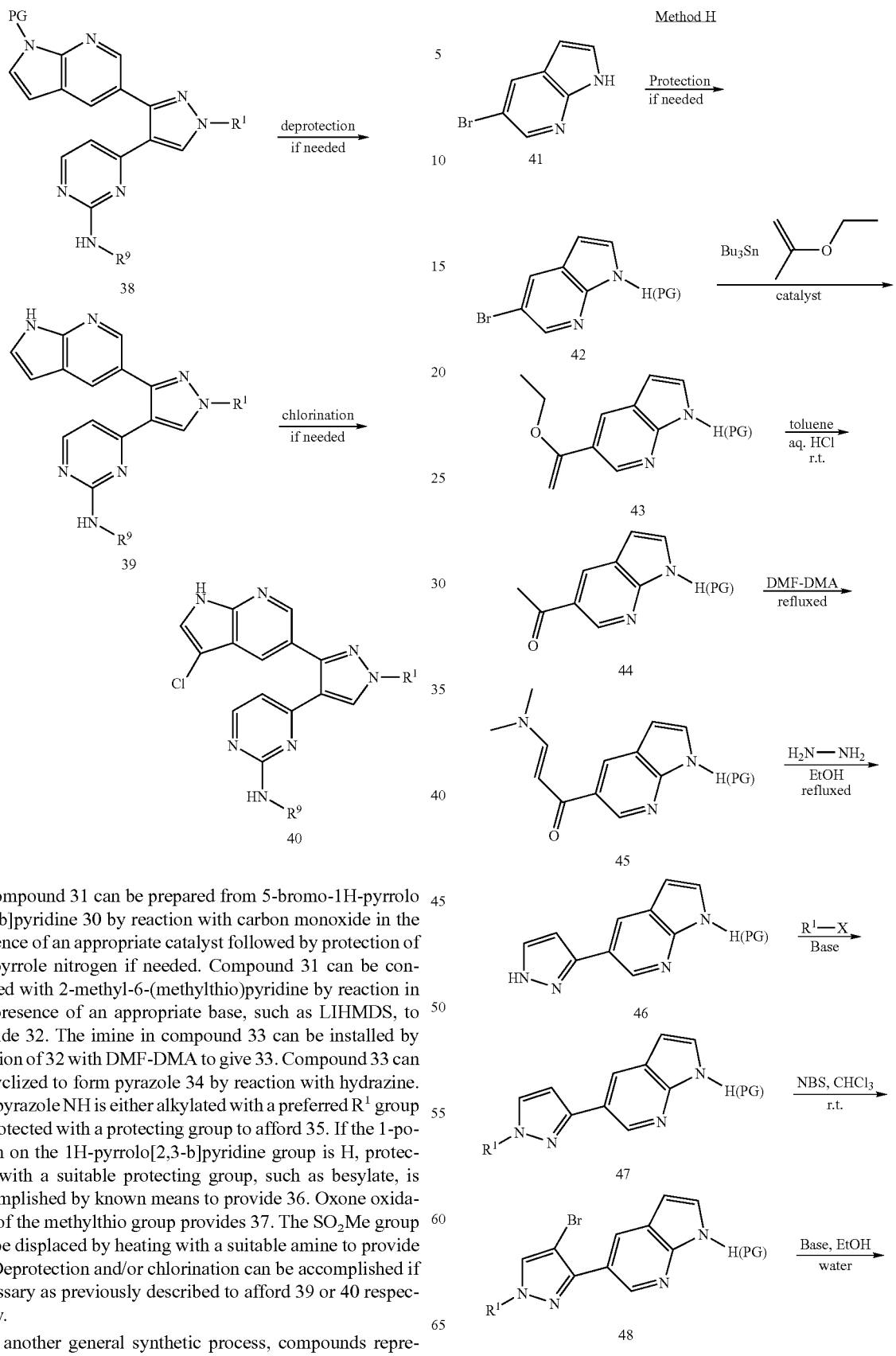

Compound 31 can be prepared from 5-bromo-1H-pyrrolo[2,3-b]pyridine 30 by reaction with carbon monoxide in the presence of an appropriate catalyst followed by protection of the pyrrole nitrogen if needed. Compound 31 can be condensed with 2-methyl-6-(methylthio)pyridine by reaction in the presence of an appropriate base, such as LIHMDS, to provide 32. The imine in compound 33 can be installed by reaction of 32 with DMF-DMA to give 33. Compound 33 can be cyclized to form pyrazole 34 by reaction with hydrazine. The pyrazole NH is either alkylated with a preferred $R^1$ group or protected with a protecting group to afford 35. If the 1-position on the 1H-pyrrolo[2,3-b]pyridine group is H, protection with a suitable protecting group, such as besylate, is accomplished by known means to provide 36. Oxone oxidation of the methylthio group provides 37. The $SO_2Me$ group can be displaced by heating with a suitable amine to provide 38. Deprotection and/or chlorination can be accomplished if necessary as previously described to afford 39 or 40 respectively.

In another general synthetic process, compounds represented by 51 can be prepared according to Method H.

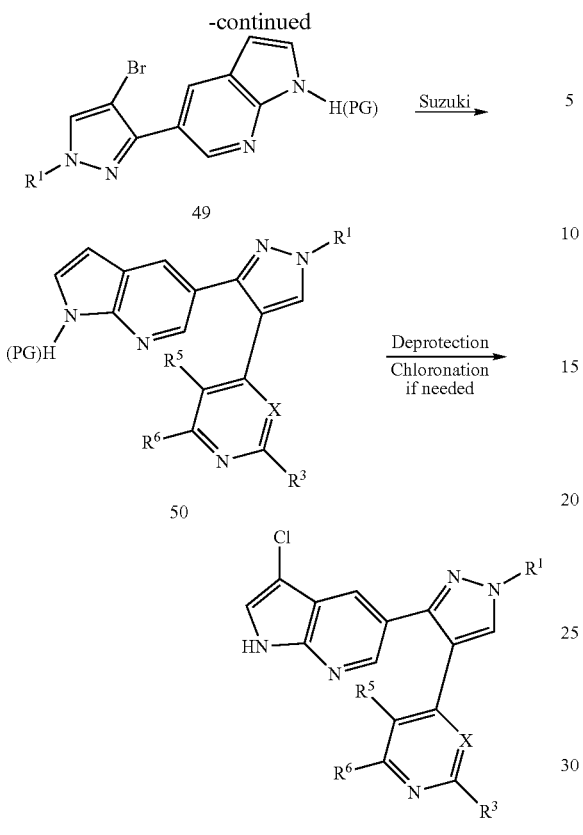

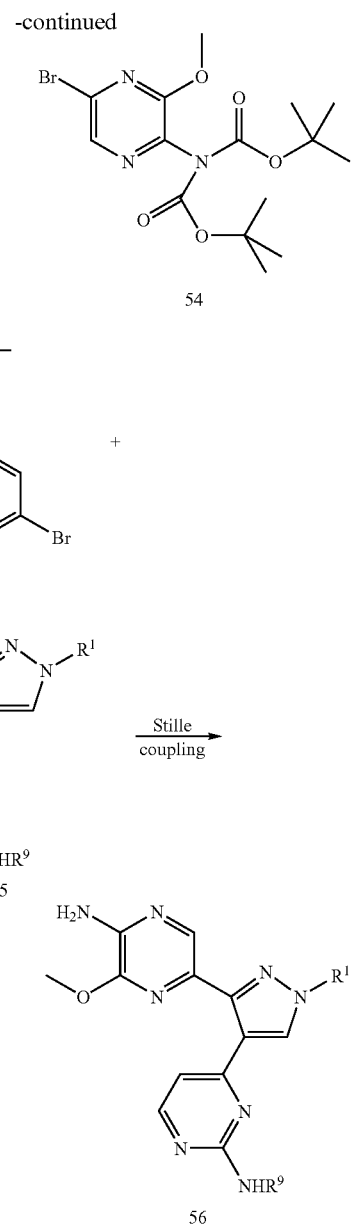

Compound 41 can be protected at the pyrrole nitrogen, if necessary, to provide compound 42. A coupling reaction in the presence of an appropriate tin reagent and an appropriate catalyst can provide a compound of the type 43. Compound 43 can then be converted into ketone 44 by heating with an appropriate acid, followed by condensation with DMF-DMA to form enone 45. Compound 45 can be cyclized to form pyrazole 46 by reaction with hydrazine. The pyrazole NH is either alkylated with a preferred $R^1$ group or protected with a protecting group to afford 47. A Suzuki coupling reaction of 49 with a suitable boronic acid or boronic ester completes the synthesis of compounds represented by 50. Deprotection and/or chlorination can be accomplished if necessary as previously described to afford compounds of the type 51.

In another general synthetic process, compounds represented by 56 can be prepared according to Method I.

Method I

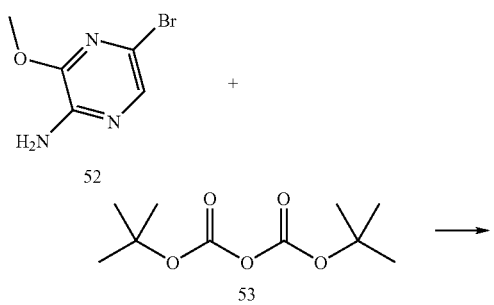

A halide of the type 52 can be reacted with an anhydride 53 to form compound 54. Compound 54 can be coupled, via Stille coupling, to an appropriate intermediate 55 to provide products of the type 56. intermediate 55 can be prepared by reacting a compound of the type 9 with an appropriate tin reagent.

EXAMPLES

The examples and preparations provided below further illustrate and exemplify the compounds of the present invention and methods of preparing such compounds. Examples B-1 to 1-1 provide detailed synthetic steps for preparing several specific compounds of the present invention. Table 1 shows analytical data for compounds that were prepared using the methods described herein. Table 2 and Table 3 show the biochemical and cellular data for the compounds of Examples B-1 to I-2. It is to be understood that the scope of the present invention is not limited in any way by the scope of the following examples and preparations. In the following examples molecules with a single chiral center, unless otherwise noted or indicated by the structural formula or chemical name, exist as a racemic mixture. Those molecules with two or more chiral centers, unless otherwise noted or indicated by the structural formula or chemical name, exist as a racemic mixture of diastereomers. Single enantiomers/diastereomers may be obtained by methods known to those skilled in the art.

Various starting materials and other reagents were purchased from commercial suppliers, such as Aldrich Chemical Company, and used without further purification, unless indicated otherwise. $^1$H-NMR spectra were recorded on a Bruker instrument operating either at 300 MHz, or 400 MHz and $^{13}$C-NMR spectra were recorded operating at 75 MHz. NMR spectra were obtained as CDCl$_3$ solutions (reported in ppm), using chloroform as the reference standard (7.25 ppm and 77.00 ppm) or DMSO-D$_6$ (2.50 ppm and 39.51 ppm) or CD$_3$OD (3.4 ppm and 4.8 ppm and 49.3 ppm), or internal tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz). The following abbreviations may be used herein: Et$_2$O (diethyl ether); DMF (N,N-dimethylformamide); THF (tetrahydrofuran); DHP (dihydropyran), DCM (dichloro-methane); DMA (dimethyl acetal); DBU (1,8-Diazabicyclo[5.4.0]undec-7-ene); LiHMDS or LHMDS (lithium hexamethyldisilazide); TBME (tert-butyl methyl ether); LDA (Lithium Diisopropylamide); DMSO (dimethylsulfoxide); MeOH (methanol); EtOH (ethanol); EtOAc (ethyl acetate); THF (tetrahydrofuran); Ac (acetyl); Me (methyl); Et (ethyl); and Ph (phenyl).

Boronic Acid and Boronic Ester Intermediates:

All boronic acids and esters are either commercially available, known in the literature or may be prepared according to the following methods. One of skill in the art would readily appreciate that the following are merely set forth as exemplary boronic acid and boronic ester intermediates, and that these exemplary intermediates can be modified according to known methods to provide a wide variety of possible boronic acids and borinic esters that could be used to prepare compounds within the scope of the claims.

Preparation of 1-(tert-butoxycarbonyl)-3-methyl-2,3-dihydro-1H-pyrrolo[2,3-b]pyridin-5-ylboronic acid (64)

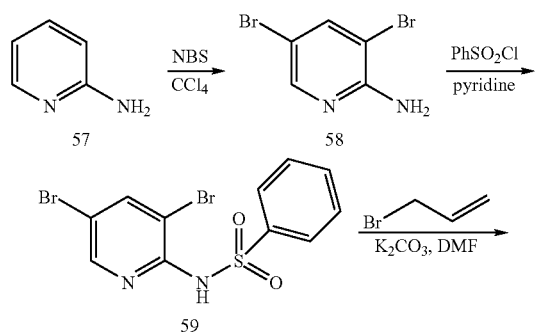

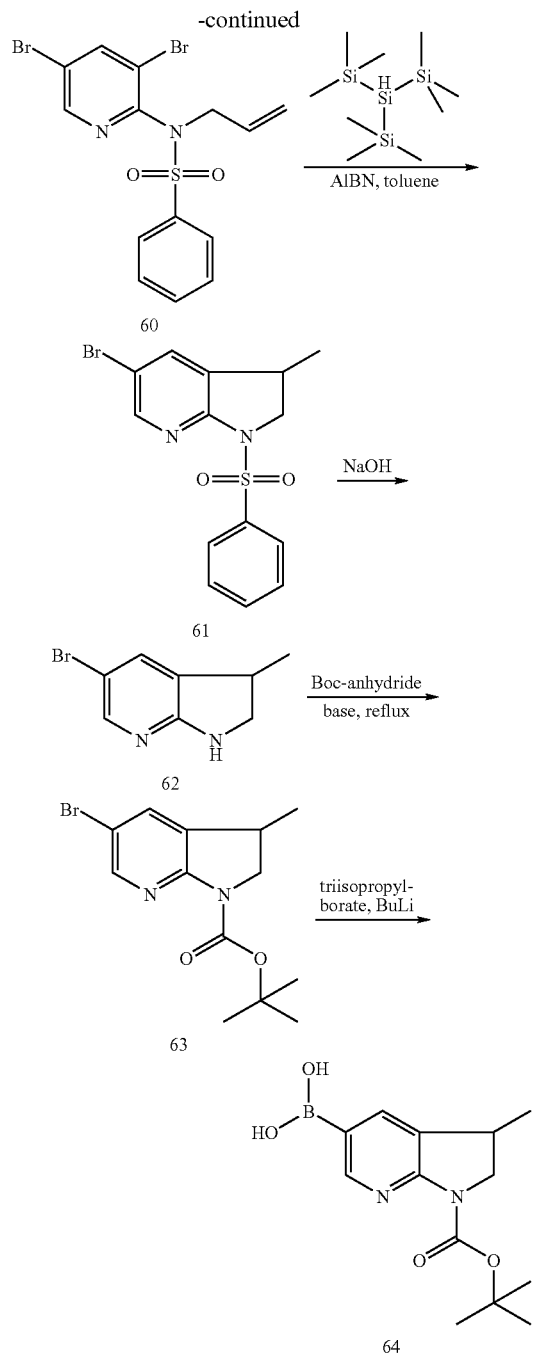

Step 1:

To a stirred suspension of compound 57 (74 g, 0.80 mol) in CCl$_4$ (2 L) was added NBS (296 g, 1.68 mol) portionwise at 20° C. After addition, the mixture was stirred at room temperature for 24 hours. TLC (EtOAc/Hexane 1:4) showed the material was consumed completely. The reaction mixture was filtered and the filtrate was concentrated in vacuum to give compound 58 (170 g, 83.7%) as a brown solid.

Step 2:

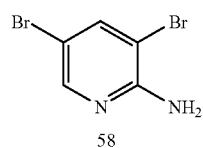

A mixture of compound 58 (172 g, 0.688 mol) and benzensulfonyl chloride (182.2 g, 1.032 mol) in pyridine (1000 mL) was heated to 85° C. with stirring for 72 hours. TLC (EtOAc/Hexane 1:4) showed most of material was consumed. Pyridine was removed in vacuum. The residue was suspended in EtOAc and filtered. The filtrate was concentrated in vacuum and the residue was purified by column chromatography (EtOAc/Petrol ether from 1:40 to 1:4) to give compound 59 (65 g, 24.2%) as a yellow solid.

Step 3:

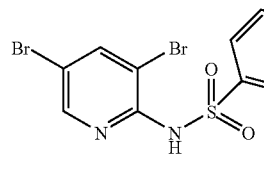

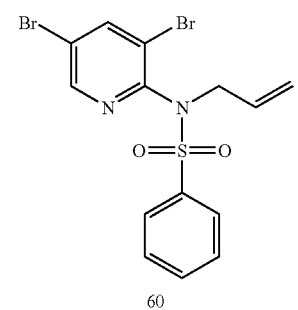

A mixture of compound 3 (45 g, 0.115 mol), 3-bromopropene (45.7 g, 0.38 mol) and K2CO3 (63.5 g, 0.46 mol) in dry DMF (900 mL) was heated to 110 ? with stirring for 16 h under N2 atmosphere. The mixture was cooled to room temperature, poured into water (1.5 L) and extracted with EtOAc (1 L) three times. The combined organic solvent was washed with water (1 L) three times, brine (1 L), dried over Na2SO4 and concentrated in vacuum. The residue was washed with petrol ether to give compound 60 (39 g, 78.9%) as a yellow solid.

Step 4:

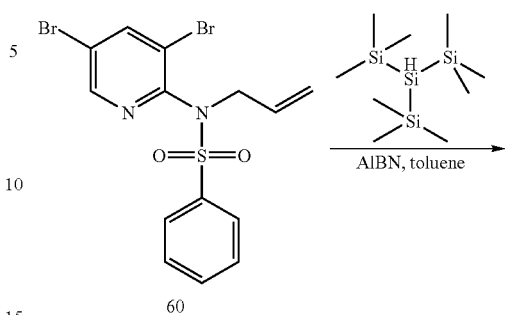

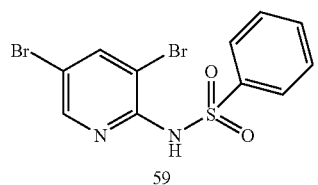

A mixture of compound 60 (47.4 g, 0.11 mol), tris(trimethylsilyl)silane (54.7 g, 0.22 mol) and azobisisobutyronitrile (AIBN, 18 g, 0.11 mol) in dry toluene (1000 mL) was heated to 80-83° C. for 3 hours under N$_2$. TLC (EtOAc/Hexane 1:4) showed the material was consumed completely. The mixture was concentrated in vacuum. The residue was purified by column chromatography (EtOAc/petroleum ether from 1:100 to 1:30) to give the product (10 g, 25.8%) as a white solid.

Step 5:

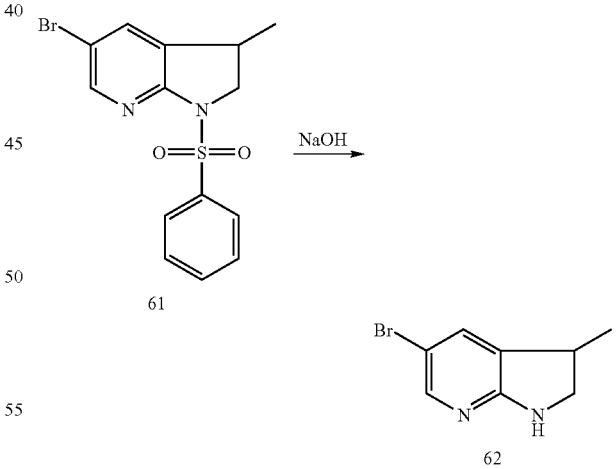

To a stirring solution of compound 61 (800 mg, 2.26 mmol) in 10 mL of boiling ethanol was added 2.0 mL aqueous solution of sodium hydroxide (127 mg, 2.26 mmol) dropwise. The reaction was sealed then heated in 100 degree oil bath and monitored with LCMS. Reaction stayed homogenous and 5 hours later, LCMS indicated reaction complete. Reaction was concentrated to dryness under high vacuum. The resulting residual was stirred in 100 mL DCM overnight and then filtered. LCMS indicated the solids contained no desired material while the filtrate was concentrated to give compound 62 (458 mg, 94.9%) as an off-white solid.

Step 6:

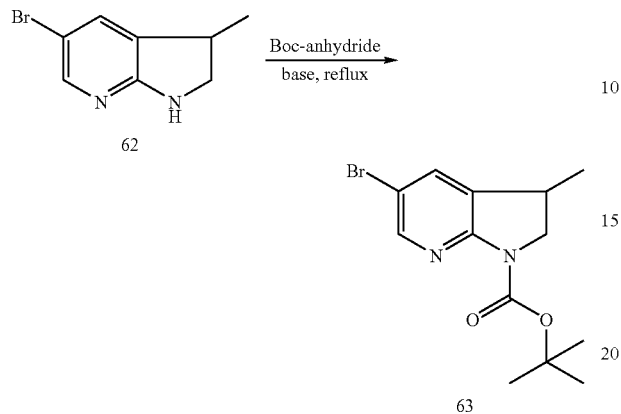

A mix of compound 62 (458 mg, 2.15 mmol), Boc-anhydride (563 mg, 2.58 mmol) and 1,1-diisopropyl ethylamine (305 mg, 2.37 mmol) in 50 mL of anhydrous THF was refluxed for 2 hrs under nitrogen. TLC indicated reaction complete. Reaction was concentrated to dryness under reduced pressure. The residual was partitioned between EtOAc (100 mL) and brine (50 mL). The organic layer was washed with brine, dried over sodium sulfate, filtered and concentrated and then loaded onto a 150 g silica gel column. Elution with 0~5% EtOAc in DCM gave compound 63 (460 mg, 68.4%) as an off-white solid.

Step 7:

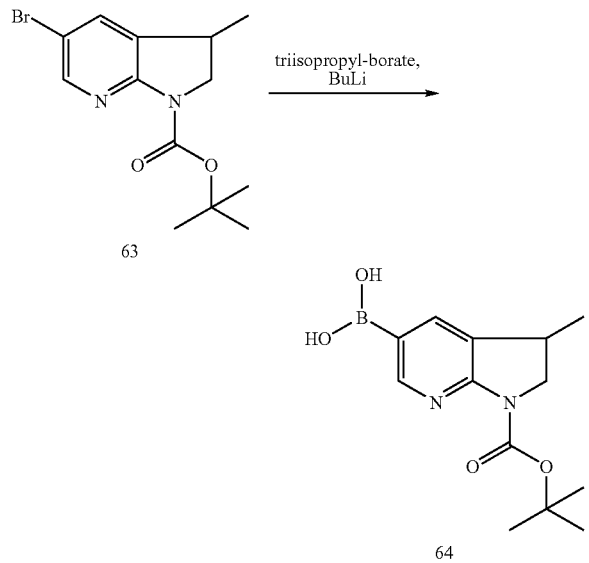

To a stirring solution of compound 63 (460 mg, 1.47 mmol) and triisopropylborate (691 mg, 3.67 mmol) in 25 mL dry THF at −78° C. was added Butyl lithium solution (2.5 M in hexanes, 1.47 mL, 3.67 mmol) dropwise under nitrogen. The reaction was stirred at −78° C. and monitored with LCMS. 2 hr later, LCMS indicated reaction complete. Reaction was quenched with 25 mL water and concentrated under reduced pressure to a total volume of about 15 mL. The residual was washed with ether (2×10 mL) and the aqueous later was placed in an ice-water bath. While stirring, 10 N HCl aqueous solution was carefully added dropwise until pH=7. Filtration and washing with ice-water (3×5 mL) gave compound 64 (208 mg, 51%) as a white solid.

Preparation of
3-fluoro-1H-pyrrolo[2,3-b]pyridin-5-ylboronic acid
(67)

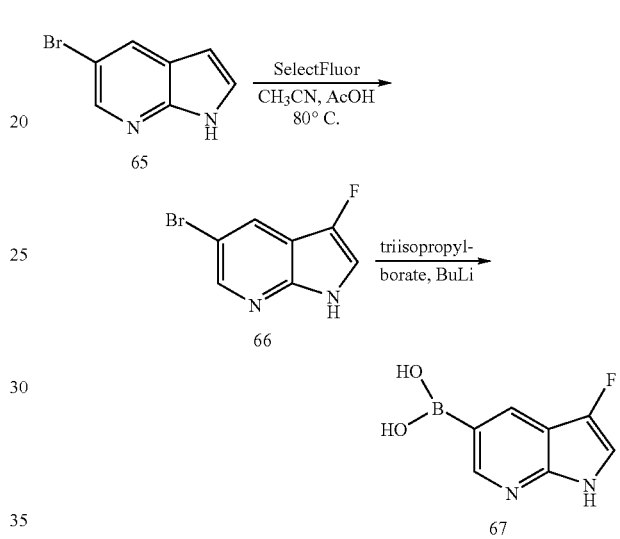

To a solution of compound 65 (4 g, 20 mmol) in MeCN (500 mL) and AcOH (100 mL) was added Select-Fluor (10 g, 30 mmol), the resulting mixture was heated at 80° C. overnight. TLC (Petroleum ether/EtOAc 5:1) indicated the complete consumption of compound 1. The reaction mixture was concentrated in vacuo, the residue was purified via flash chromatography on silica gel (Petroleum ether/EtOAc 10:1) to yield 66 (0.64 g, 13%) as an off-white solid. $^1$H NMR: (400 MHz, CDCl$_3$): δ 9.434 (brs, 1H), 8.311-8.280 (m, 1H), 8.056-8.023 (m, 1H), 7.191 (s, 1H), 7.086-7.053 (m, 1H).

To a stirring solution of compound 66 (250 mg, 1.16 mmol) and triisopropylborate (547 mg, 2.91 mmol) in 3 mL dry THF at −78° C. was added Butyl lithium solution (2.5 M in hexanes, 1.16 mL, 2.91 mmol) dropwise under nitrogen. The reaction was stirred at −78° C. and monitored with LCMS. 2 hr later, LCMS indicated 1:1:1 SM:desbromo-SM:desired product. Another 1.16 mL of n-butyl lithium was added. Reaction was stirred under nitrogen at −78° C. for another hour, quenched with 3 mL water and concentrated under reduced pressure to a total volume of about 3 mL. The residual was washed with ether (2×10 mL) and the aqueous later was placed in an ice-water bath. While stirring, 10 N HCl aqueous solution was carefully added dropwise until pH=7. A milky suspension was formed and filtration did not produce significant amount of solids. The mixture was concentrated on high vacuum to give compound 67 (200 mg, 95%) as an off-white solid.

Preparation of 2-oxo-2,3-dihydro-1H-pyrrolo[2,3-b]pyridin-5-ylboronic acid (69)

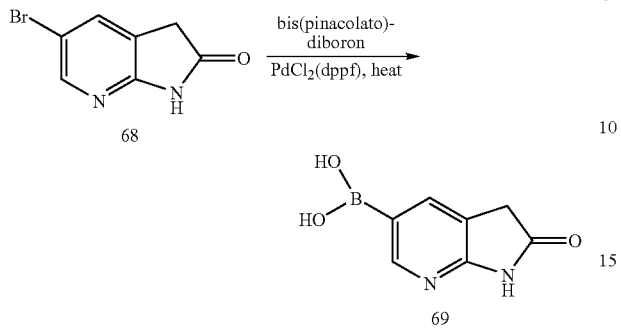

A mixture of compound 68 (1.0 g, 4.7 mmol), bis(pinacolato)diboron (1.79 g, 7.04 mmol), potassium acetate (1.38 g, 14.1 mmol), and catalyst PdCl$_2$(dppf) (68.7 mg, 0.094 mmol) in 20 ml DMF was heated in 100 degree microwave reactor for 60 min. LCMS indicated reaction was 20% complete. Reaction was heated in 100 degree oil bath overnight, LCMS indicated reaction complete. Reaction was concentrated to dryness under high vacuum. Then the residual was partitioned between EtOAc (50 mL) and brine (30 mL). The aqueous layer was extracted with EtOAc (3×25 mL)). The combined organic layers were dried over sodium sulfate and then concentrated to a residual. Flush chromatography on silica gel with 2-5% MeOH in DCM gave an off-white powder as desired product (803 mg, 66%). $^1$H NMR (400 MHz, CHLOROFORM-d) δ ppm 1.35 (s, 12H) 3.56 (s, 2H) 7.85 (s, 1H) 8.54 (s, 1H).

Preparation of 71

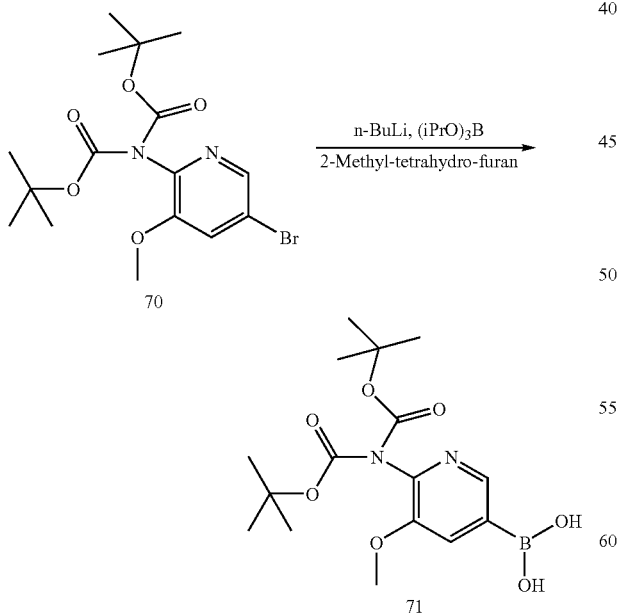

To a solution of compound 70 (40 g, 99.2 mmol) and (iPrO)$_3$B (59.2 mL, 258 mmol) in 2-methyl-tetrahydro-furan (496 mL) (496 mL) cooled to −60° C. was added n-BuLi (108 mL, 267 mmol). The reaction mixture was stirred at −60° C. for 2 hours. TLC (Petroleum ether: EtOAc=2:1) indicated the reaction was complete. The reaction mixture was quenched by the addition of water (500 mL), and concentrated under reduced pressure. The aqueous solution was acidified with conc. HCl to pH=5. The precipitate was filtered and the filter cake was washed with ice water to get the product (60 g, yield: 82.19%) as a white solid.

Preparation of 6-acetamido-4-methylpyridin-3-ylboronic acid (73)

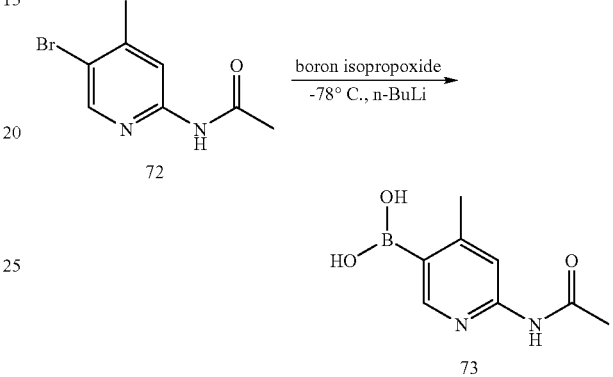

To a stirred solution of the 2-acetylamino-5-bromo-4-methylpyridine (1.858 g, 8.11 mmol) and boron isopropoxide (7.5 ml, 32.4 mmol) in THF cooled to −78° C. was added n-butyl lithium (4.1 ml, 41 mmol of 10 M soln in hexanes). After 1 hour at −78° C., the reaction was quenched with water and warmed to room temperature. THF was removed under reduced pressure. Added 2N HCl until a precipitate developed. Filtered and washed with a minimal amount of water and dried under vacuum. $^1$H NMR (400 MHz, DMSO-d6) d ppm 2.07 (s, 3H) 2.39 (s, 3H) 7.84 (s, 1H) 8.09 (s, 2H) 8.33 (s, 1H) 10.36 (s, 1H).

Preparation of 3-Methyl-5-(4,4,5,5-tetramethyl-[1,3,2]dioxaborolan-2-yl)-1H-pyrazolo[3,4-b]pyridine (79)

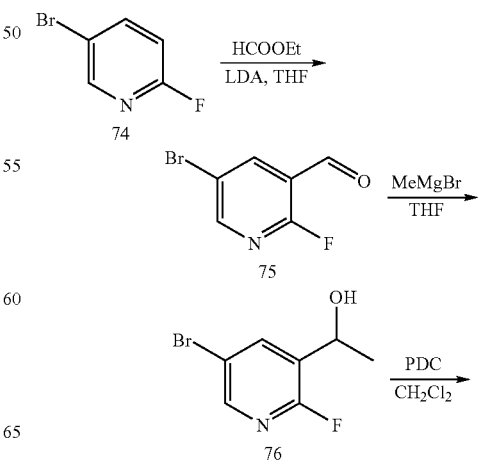

-continued

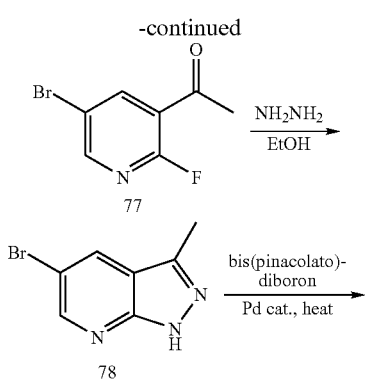

Step 1:

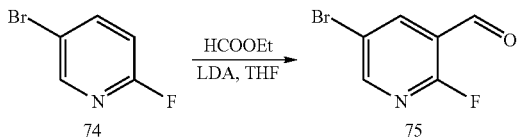

To a stirred solution of diisopropyl-amine (50 g, 0.5 mol) in dry THF (1000 mL) was added dropwise n-BuLi (200 mL, 0.5 mol) at −78° C. under N₂ atmosphere. After the addition, the resulting mixture was allowed to warm up to 0° C., maintained for 10 minutes and cooled to −78° C. again. A mixture of compound 74 (80 g, 0.455 mol) in THF (1000 mL) was added dropwise to the LDA solution at −78° C. under N₂ atmosphere. After the addition, the reaction mixture was stirred at −78° C. for 30 minutes. Then formic acid ethyl ester (50 g, 0.68 mol) was added portionwise to the mixture at −78° C. After 2 minutes, the resulting mixture was quenched with a solution of 10% citric acid in THF (400 mL) at −78° C. The mixture was allowed to warmed up to room temperature and poured into H₂O (500 mL), extracted with EtOAc (500 mL×3). The combined organic layers were washed with brine (500 mL), dried over Na₂SO₄ and concentrated in vacuo to give compound 75 (92 g, 99%) as a yellow solid.

Step 2:

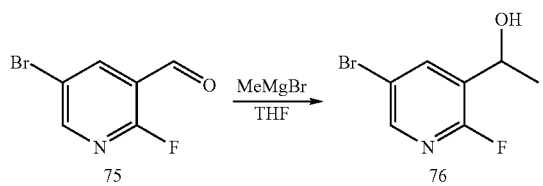

To a solution of compound 75 (92 g, 0.455 mol) in THF (2 L) was added MeMgBr (230 mL, 0.69 mol) portionwise at −78° C. under N₂ atmosphere. After the addition, the reaction mixture was warmed up to room temperature and stirred at room temperature overnight. TLC (petroleum ether/EtOAc 10:1) indicated the complete consumption of compound 2. The reaction mixture was quenched with saturated NH₄Cl (300 mL), extracted with EtOAc (1 L×3). The combined organic layers were washed with brine (1 L), dried over Na₂SO₄ and concentrated in vacuo to give crude compound 76, which was purified by column chromatography (silica gel, petroleum ether/EtOAc 10:1) to yield pure compound 76 (85 g, 85%) as yellow oil.

Step 3:

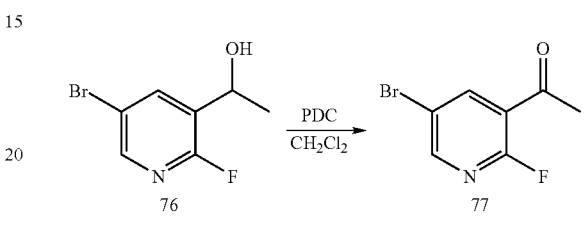

To a mixture of PDC (365 g, 0.97 mol) and CH₂Cl₂ (2000 mL) was added compound 76 (85 g, 0.39 mol) at 0° C. After the addition, the reaction mixture was warmed up to room temperature and stirred overnight. TLC (petroleum ether/EtOAc 10:1) indicated the reaction was complete. The resulting mixture was filtered and the filtrate was concentrated in vacuo to give crude compound 77, which was purified by column chromatography (silica gel, petroleum ether/EtOAc 50:1) to yield pure compound 77 (56 g, 63%) as a yellow solid.

Step 4:

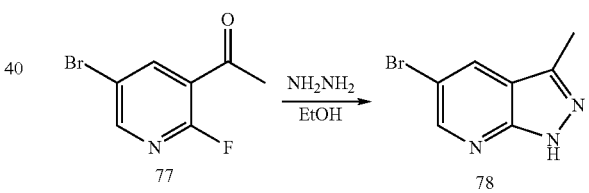

To a solution of compound 77 (40 g, 0.184 mol) in ethanol (300 mL) was added NH₂NH₂ (27.6 g, 0.553 mol) at room temperature. After the addition, the reaction mixture was refluxed overnight. TLC (petroleum ether/EtOAc 3:1) indicated the complete consumption of compound 77. The reaction mixture was allowed to cool to room temperature, and concentrated in vacuo to give crude product, which was purified by column chromatography (silica gel, petroleum ether/EtOAc from 10:1 to 3:1) to yield 78 (30 g, 76%) as a white solid.

Step 5:

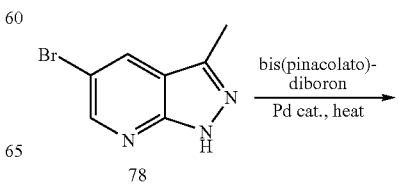

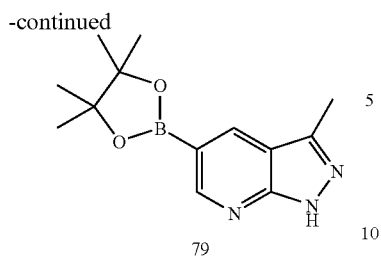

A suspension of 5-bromo-3-methyl-1H-pyrazolo[3,4-b]pyridine (1.04 g, 40.987 mmol), bis(pinacolato)diboron (1.93 g, 7.45 mmol, 1.5 Eq), potassium acetate (1.66 g, 16.9 mmol, 3.04 Eq) and [1,1'-Bis(diphenylphosphino)ferrocene]palladium(II) dichloride dichloromethane complex (1:1)(0.109 g, 0.149 mmol, 0.03 Eq) in 10 mL anhydrous DMSO was degassed by bubbling nitrogen via needle for 20 min. The reaction was then heated in a microwave reactor at 150° C. for 2 hours (high absorption). After this time, the reaction was cooled to room temperature and then poured in $H_2O$ (200 mL) and EtOAc (200 mL). The bi-layered mixture was filtered through compacted celite and the filtrate was dried over $Na_2SO_4$ and concentrated in vacuo to a dark oil which was purified by biotage column (Si 40+M); packed with hexanes; eluted with EtOAc/Hexanes (0-30%:900 mL, 30-30%:900 mL, 30-50%; 900 mL, 27 mL fractions) to afford the product as a white solid (1.19 g, 93.6%). $^1$H NMR (300 MHz, CHLOROFORM-d) δ ppm 8.88 (d, J=1.51 Hz, 1H) 8.51 (d, J=1.51 Hz, 1H) 2.60 (s, 3H) 1.30 (s, 6H) 1.25 (s, 6H); NH not seen in NMR.

Preparation of Compound 85

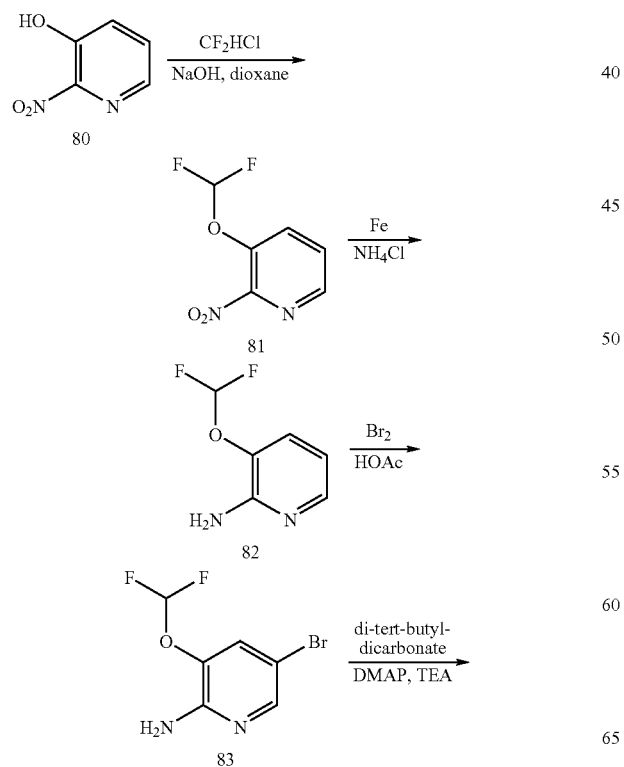

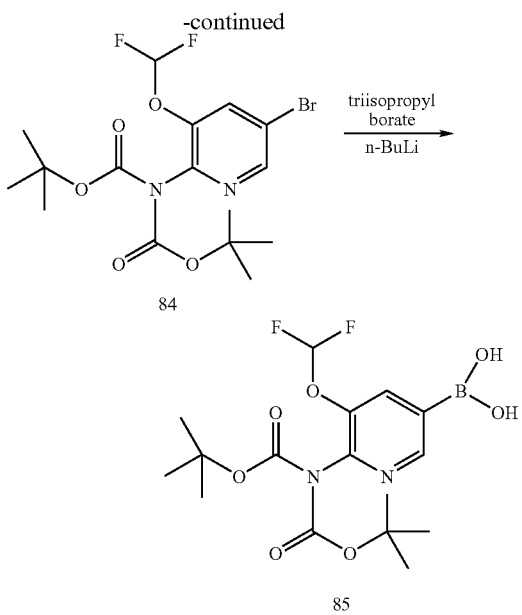

Step 1:

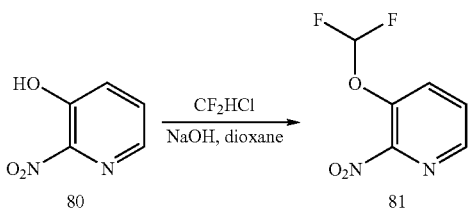

To a solution of compound 80 (28 g, 0.2 mol) and NaOH (40 g, 1 mol) in dioxane (450 mL) and $H_2O$ (150 mL) at 70° C. was bubbled through $CF_2HCl$ gas over 20 min and stirred at the same temperature overnight. TLC (Petroleum ether/EtOAc 2:1) indicated the reaction was done. The reaction mixture was extracted with $Et_2O$ (3×300 mL) and the combined organic layers were concentrated in vacuo to give crude product, which was purified via column chromatography (petroleum ether/EtOAc 30:1~3:1) to afford compound 81 (20 g, 52.6%) as yellow liquid.

Step 2:

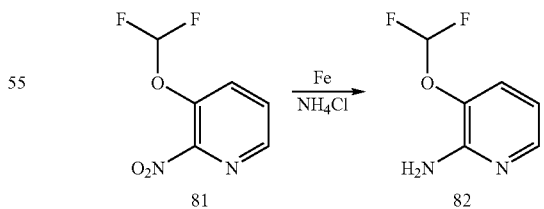

To a solution of compound 81 (10 g, 0.0526 mol) in EtOH/$H_2O$ (2:1, 450 mL) was added iron powder (15 g, 0.268 mol), followed by addition of $NH_4Cl$ (7.5 g, 0.14 mol) in one portion. After addition, the mixture was refluxed overnight. TLC (Petroleum ether/EtOAc 2:1) indicated the reaction was complete. EtOH was removed under reduced pressure and the residue was partitioned between saturated aq. NaHCO₃ (500 mL) and EtOAc (400 mL). The aqueous layer was extracted with EtOAc (2×300 mL) and the combined organic layers were washed with brine (2×300 mL), dried over anhydrous Na₂SO₄ and concentrated in vacuo to give compound 82 (8.0 g, 95%) as a yellow solid.

Step 3:

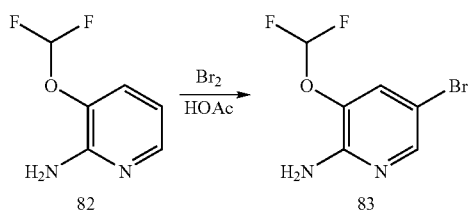

To a solution of compound 82 (8.0 g, 0.05 mol) in AcOH (100 mL) was added dropwise bromine (8.0 g, 0.05 mol) at room temperature. The mixture was stirred at ambient temperature for 2 h. TLC (Petroleum ether/EtOAc 2:1) indicated the reaction was complete. AcOH was removed under reduced pressure and the residue was partitioned between saturated aq. NaHCO₃ (200 mL) and EtOAc (200 mL). The aqueous layer was extracted with EtOAc (200 mL) and the combined organic layers were washed with brine (2×300 mL), dried over anhydrous Na₂SO₄ and concentrated in vacuo to give crude product, which was purified via column chromatography (petroleum ether/EtOAc 8:1~4:1) to afford the product 83 (10.9 g, 91.2%) as a yellow solid.

Step 4:

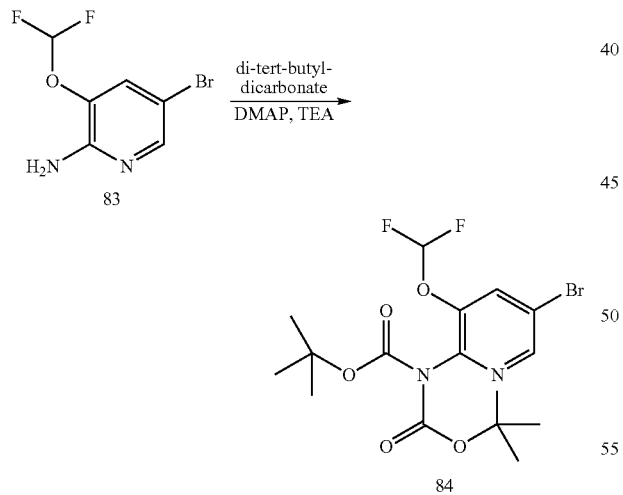

To a solution of compound 83 (5.61 g, 23.5 mmol) in acetonitrile (250 mL) was added di-tert-butyl-dicarbonate (15.65 g, 71.71 mmol), 4-(dimethylamino)pyridine (571 mg, 4.67 mmol), and triethyl amine (16.5 mL, 118 mmol). The mixture was stirred at room temperature for 1.5 hours, then concentrated to dryness and purified by silica gel chromatography (eluting with 10-25% ethyl acetate in hexanes gradient) to give compound 84 (9.53 g, 92.4%) as a white solid.

Step 5:

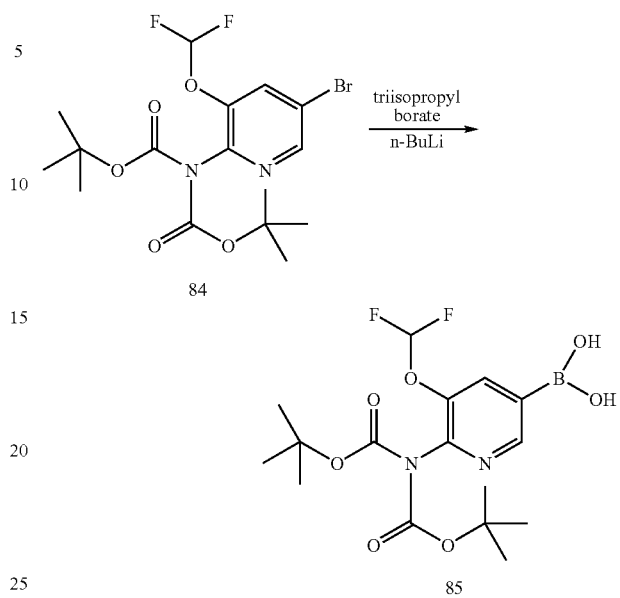

A solution of bromide 84 (3.30 g, 7.51 mmol) and triisopropyl borate (4.4 mL, 19 mmol) in 2-methyl-tetrahydrofuran (38 mL) was cooled to −65° C. (bath temperature) in a dry ice/isopropanol bath. A solution of 2.5 M n-butyllithium in hexanes (7.5 mL, 19 mmol) was added dropwise over 3 minutes. After stirring at −65° C. for 3 hours, deionized water (10 mL) was added, the cooling bath removed, and the solution allowed to warm to room temperature. Volatiles were removed in vacuo, and the aqueous residue extracted with diethyl ether (2×20 mL). These extracts were discarded. The aqueous layer was cooled to 0° C., acidified with 6N HCl to pH 3, and extracted with diethyl ether (20 mL), followed by ethyl acetate (20 mL). The combined organic extracts were dried over magnesium sulfate, filtered, and concentrated to give crude boronic acid 85 as a yellow foam (2.27 g, ~60% purity, 75% uncorrected yield). This crude boronic acid was used in Suzuki reactions without further purification.

Example A-1

Preparation of Reactive Intermediates A and B According to Method A

Preparation of 4-methyl-2-(methylthio)pyrimidine (2)

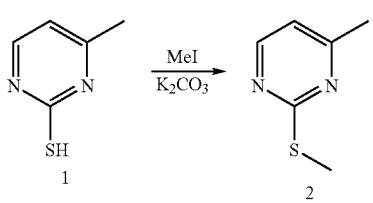

A mixture of compound 4-methylpyrimidine-2-thiol (500 g, 3.05 mol), iodomethane (611 g, 4.27 mol) and K₂CO₃ (915 g, 6.71 mol) in THF (4 L) was stirred at room temperature for 18 h. The suspension was filtered and the solid was washed with ether (500 mL×2). The filtrate was concentrated and dried in vacuum to give compound 2 (380 g, 89.2%) as a yellow oil.

Preparation of (E)-3-hydroxy-2-(2-(methylthio)pyrimidin-4-yl)acrylaldehyde (3)

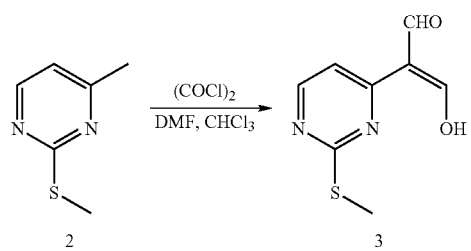

To a solution of DMF (114.9 g, 1.57 mol) in CHCl₃ (800 mL) was added dropwise oxalyl chloride (190.3 g, 1.50 mol) at 0° C. After the addition, the resulting mixture was warmed at 30° C. and stirred for 1 h. The mixture was allowed to cool to 0° C. and 4-methyl-2-(methylthio)pyrimidine (2) (100 g, 0.714 mol) was added to the mixture. The resulting mixture was warmed to 40° C. and stirred for 16 h. The reaction mixture was cooled to room temperature and filtered. The cake was washed with CHCl₃ (150 mL×3) and dried in vacuum to give (E)-3-hydroxy-2-(2-(methylthio)pyrimidin-4-yl)acrylaldehyde (3) (342.0 g, 100%) as a yellow solid.

Preparation of 4-(isoxazol-4-yl)-2-(methylthio)pyrimidine (4)

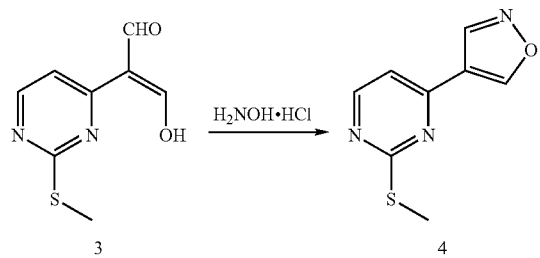

To a solution of hydroxylamine hydrochloride (60.0 g, 0.86 mol) in water (2 L) was added (E)-3-hydroxy-2-(2-(methylthio)pyrimidin-4-yl)acrylaldehyde (3) (342 g, 0.714 mol) in portions. After the addition, the mixture was heated at 60° C. and stirred for 2 h. The reaction mixture was allowed to cool to room temperature and the solution was adjusted to pH about 4 by addition of 10% aq. NaHCO₃. The resulting precipitate was filtered, washed with water (200 mL×2) and dried in vacuum to give 4-(isoxazol-4-yl)-2-(methylthio)pyrimidine (4) (112 g, 81.2%) as a yellow solid.

Preparation of 2-(2-(methylthio)pyrimidin-4-yl)-3-oxopropanenitrile (5)

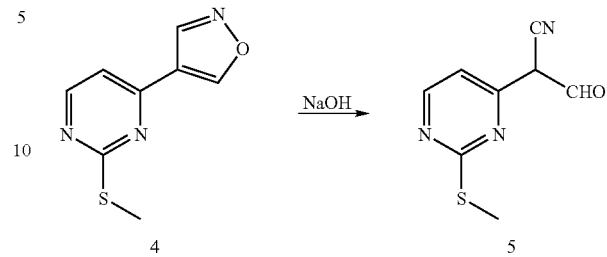

A mixture of 4-(isoxazol-4-yl)-2-(methylthio)pyrimidine (4) (112.0 g, 0.58 mol) and NaOH (23.2 g) in water/MeOH (350 mL/350 mL) was stirred at 70° C. for 6 h. The reaction mixture was allowed to cool to room temperature and adjusted to pH 3.5 with citric acid. The resulting precipitate was filtered, washed with water (500 mL×3) and ethyl ether (500 mL×3). Then the precipitate was dried in vacuum to give 2-(2-(methylthio)pyrimidin-4-yl)-3-oxopropanenitrile (5) (100 g, 89.3%) as a yellow solid.

Preparation of 4-(2-(methylthio)pyrimidin-4-yl)-1H-pyrazol-5-amine (6)

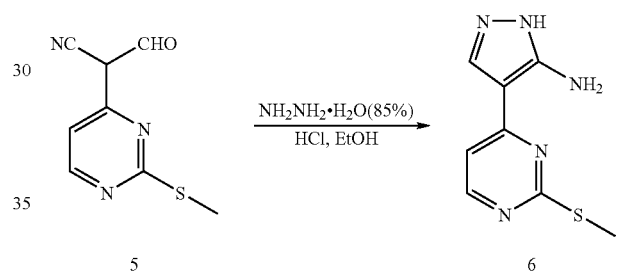

A suspension of 2-(2-(methylthio)pyrimidin-4-yl)-3-oxopropanenitrile (5) (100 g, 0.52 mol), NH₂NH₂—H₂O (85%, 31.2 g, 0.62 mol) and conc. HCl (60 mL) in ethanol (1 L) was stirred at reflux for 5 h. After cooled to room temperature, the mixture was concentrated in vacuum, and the residue was washed with ether (200 mL×3) and suspended in H₂O (200 mL). The mixture was basified with saturated aq. Na₂CO₃ to pH 9 and the precipitate was collected. The solid was washed with H₂O (100 mL×3) and ether (200 mL×3), then dried in vacuum to give 4-(2-(methylthio)pyrimidin-4-yl)-1H-pyrazol-5-amine (6) (56.8 g, 51.8%) as a yellow solid. ¹H NMR (400 MHz, CD₃CN): δ 8.295 (d, 1H), 7.826 (s, 1H), 7.101 (d, 2H), 5.800 (d, 1H), 2.586 (s, 3H).

Preparation of 4-(5-iodo-1H-pyrazol-4-yl)-2-(methylthio)pyrimidine (A)

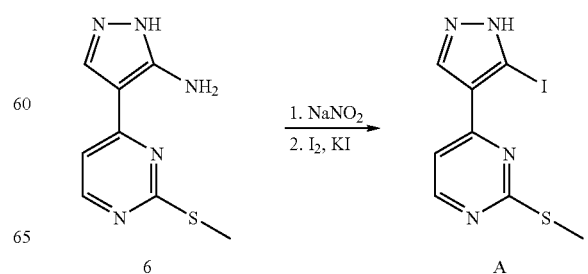

A solution of NaNO$_2$ (20.0 g, 0.29 mol) in water (150 mL) was poured into a solution of 4-(2-(methylthio)pyrimidin-4-yl)-1H-pyrazol-5-amine 6 (50.0 g, 0.24 mol) in a mixture of glacial acetic acid (400 mL) and water (100 mL) at –3° C. The temperature increased to –1° C. Concentrated H$_2$SO$_4$ (10 mL) was added to the obtained solution, and a solution of potassium iodide (120.0 g, 1.2 mol.) and 12 (123.0 g, 10.48 mol) in water (200 mL) was added dropwise. The obtained solution was heated to 50° C. for 2 h, and the mixture was neutralized with aqueous ammonia. Excess iodine was treated with Na$_2$S$_2$O$_3$. The precipitate was filtered, and the filtrate was extracted with ethyl acetate. The organic layer was evaporated, and the residue was purified by chromatography (THF: EtOAc=4:1) to give 4-(5-iodo-1H-pyrazol-4-yl)-2-(methylthio)pyrimidine (A) (42.2 g, 54.6%) as a yellow solid. $^1$H NMR (400 MHz, DMSO): δ 8.55 (d, 1H), 8.35 (s, 1H), 7.55 (d, 1H), 2.55 (s, 3H).

Example A-2
Procedure for Preparation of 4-(5-iodo-1-(tetrahydro-2H-pyran-2-yl)-1H-pyrazol-4-yl)-2-(methylthio)pyrimidine (B)

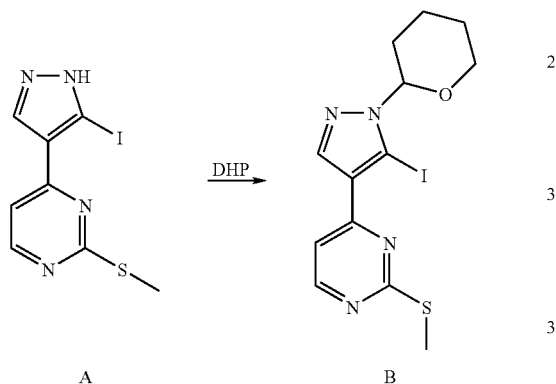

A mixture of compound A (75.0 g, 0.235 mmol), DHP (39.6 g, 0.471 mmol) and TsOH.H$_2$O (7.5 g) was stirred at 60° C. for 6 h. The mixture was cooled to room temperature and concentrated. The residue was purified by chromatography (EtOAc:petroleum ether=1:15) to give 4-(5-iodo-1-(tetrahydro-2H-pyran-2-yl)-1H-pyrazol-4-yl)-2-(methylthio)pyrimidine (B) (57.6 g, 60.8%). $^1$H NMR (400 MHz, CDCl$_3$): δ 8.495 (d, 1H), 8.400 (s, 1H), 7.638 (d, 1H), 5.398 (m, 1H), 4.070 (m, 1H), 3.732 (m, 1H), 2.796 (s, 3H), 2.110 (m, 3H), 1.900 (m, 3H).

Example B-1

Preparation of (2S)-1-(4-(1-isopropyl-3-(1H-pyrrolo[2,3-b]pyridin-5-yl)-1H-pyrazol-4-yl)pyrimidin-2-ylamino)propan-2-ol (B-1)

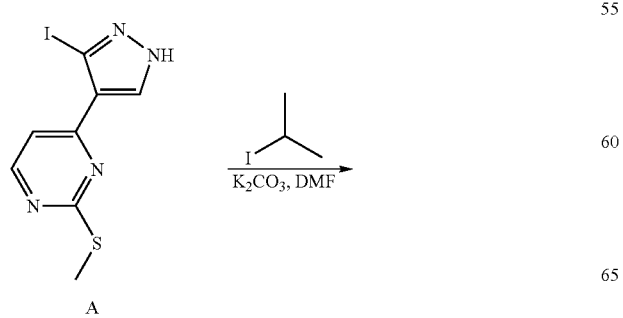

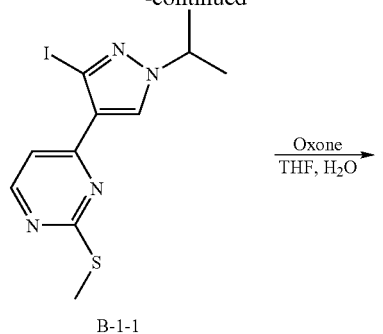

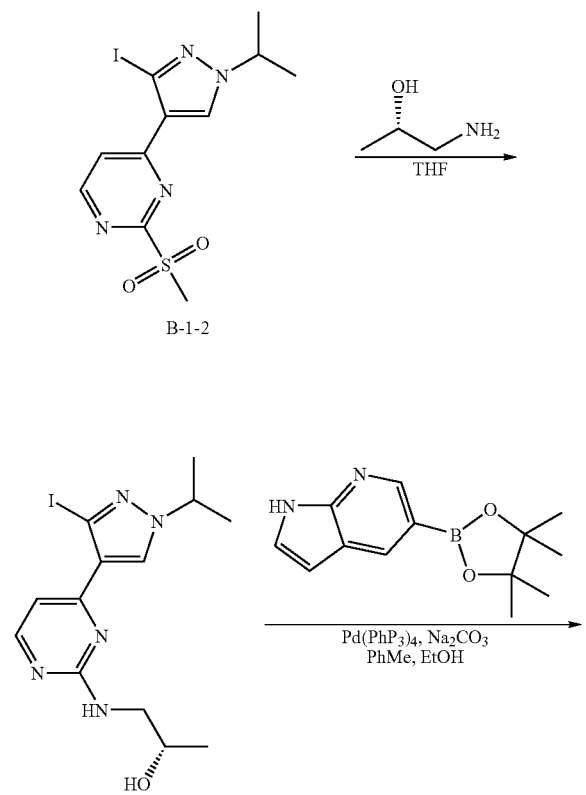

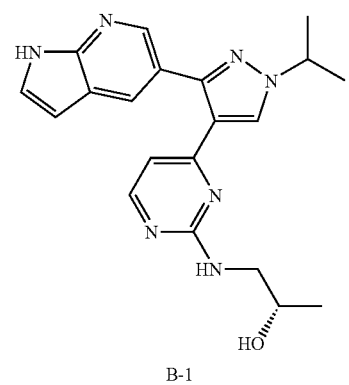

Preparation of 4-(3-iodo-1-isopropyl-1H-pyrazol-4-yl)-2-methylthio)pyrimidine (B-1-1)

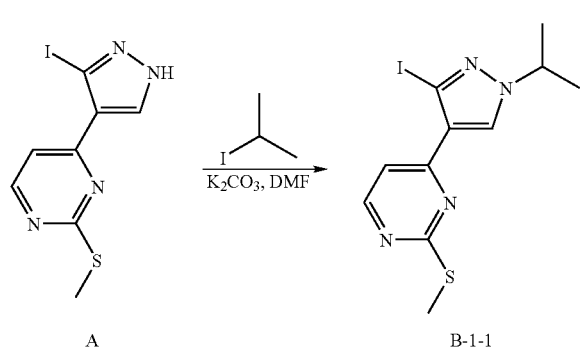

A mixture of 4-(5-iodo-1H-pyrazol-4-yl)-2-(methylthio)pyrimidine (A) (31.8 g, 0.1 mol), 2-iodo-propane (85 g, 50 mL, 0.5 mol) and K₂CO₃ (16.5 g, 0.12 mol) in DMF (500 mL) was heated at 40~50° C. overnight. When TLC (hexane: EtOAc=15:1) showed the reaction was complete, DMF was evaporated under reduced pressure. The residue was taken up with EtOAc (400 mL). The mixture was washed with saturated aqueous NaCl, dried over Na₂SO₄ and concentrated to give crude product, which was purified via prep. HPLC to give pure 4-(3-iodo-1-isopropyl-1H-pyrazol-4-yl)-2-(methylthio)pyrimidine B-1-1 (17 g, 47.2%) as a yellow oil.

Preparation of 4-(3-iodo-1-isopropyl-1H-pyrazol-4-yl)-2-(methylsulfonyl)pyrimidine (B-1-2)

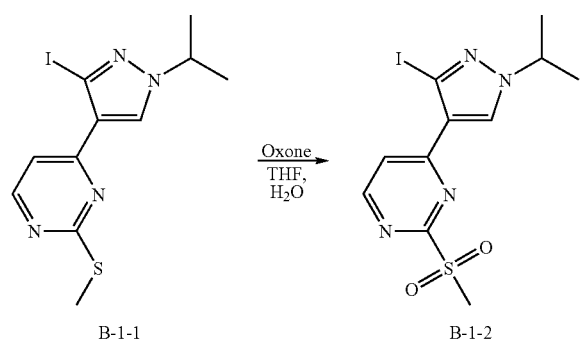

To a solution of 4-(3-iodo-1-isopropyl-1H-pyrazol-4-yl)-2-(methylthio)pyrimidine B-1-1 (15.5 g, 43 mmol) in THF (350 mL) and water (350 mL) was added oxone (39.6 g, 64.6 mmol) at 0-5° C. After the addition, the mixture was stirred at rt overnight. TLC (hexane:EtOAc=5:1) showed the reaction was complete, EtOAc (500 mL) was added. The organic layer was separated, washed with saturated aqueous NaCl, dried over Na₂SO₄ and concentrated to give 4-(3-iodo-1-isopropyl-1H-pyrazol-4-yl)-2-(methylsulfonyl)pyrimidine B-1-2 (16 g, 94.9%).

Preparation of (2S)-1-(4-(3-iodo-1-isopropyl-1H-pyrazol-4-yl)pyrimidin-2-ylamino)propan-2-ol (B-1-3)

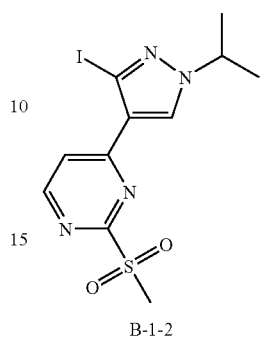

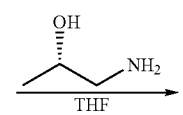

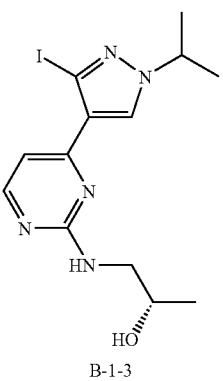

A mixture of 4-(3-iodo-1-isopropyl-1H-pyrazol-4-yl)-2-(methylsulfonyl)pyrimidine B-1-2 (16 g, 40 mmol) and (s)-1-amino-propan-2-ol (9 g, 122 mmol) in THF (160 mL) was heated to reflux overnight. TLC (hexane: EtOAc=2:1) showed the reaction was complete, EtOAc (80 mL) and saturated aqueous NaCl (80 mL) were added to the mixture, and the layers were separated. The organic layer was separated, washed with saturated aqueous NaCl (30 mL), dried over Na₂SO₄ and concentrated to give (2S)-1-(4-(3-iodo-1-isopropyl-1H-pyrazol-4-yl)pyrimidin-2-ylamino)propan-2-ol (B-1-3) (15 g, 96.9%) as a brown oil.

Preparation of (2S)-1-(4-(1-isopropyl-3-(1H-pyrrolo[2,3-b]pyridin-5-yl)-1H-pyrazol-4-yl)pyrimidin-2-ylamino)propan-2-ol (B-1)

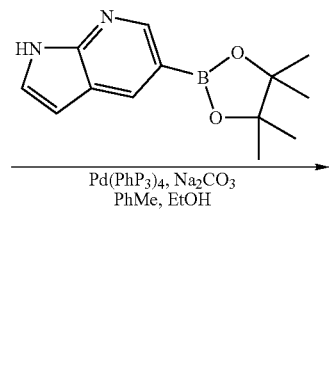

-continued

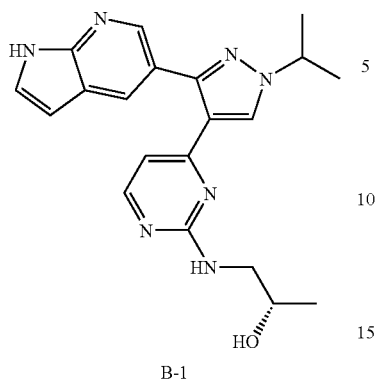

B-1

-continued

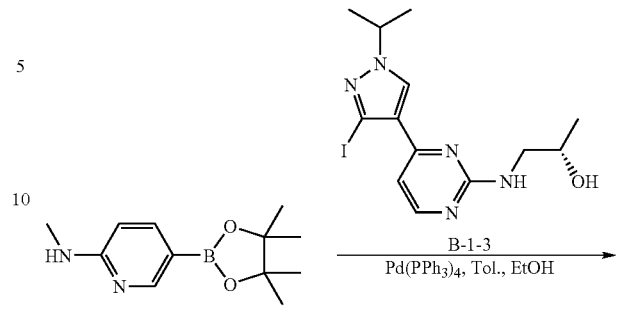

To a solution of (2S)-1-(4-(3-iodo-1-isopropyl-1H-pyrazol-4-yl)pyrimidin-2-ylamino)propan-2-ol B-1-3 (0.312 g, 0.8 mmol) in toluene (15 mL) and EtOH (5 mL) were added 1H-pyrrolo[2,3-b]pyridin-5-ylboronic acid (0.40 g, 1.6 mmol) and 2 N aq. $Na_2CO_3$ (1.24 mL), and the resulting mixture was degassed under $N_2$ for 2 minutes. Then $Pd(PPh_3)_4$ (0.23 g, 0.2 mmol) was added and the mixture was degassed again. The resulting mixture was heated to reflux and stirred overnight. The organic layer was separated and concentrated, the residue was purified via prep HPLC to afford (2S)-1-(4-(1-isopropyl-3-(1H-pyrrolo[2,3-b]pyridin-5-yl)-1H-pyrazol-4-yl)pyrimidin-2-ylamino)propan-2-ol (B-1) (0.260 g, 66.19%) as a yellow solid.

Example B-2

Preparation of (2S)-1-(4-(1-isopropyl-3-(6-(methylamino)pyridin-3-yl)-1H-pyrazol-4-yl)pyrimidin-2-ylamino)propan-2-ol (B-2)

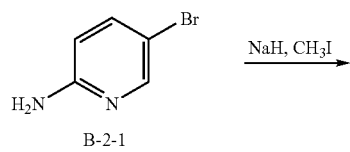

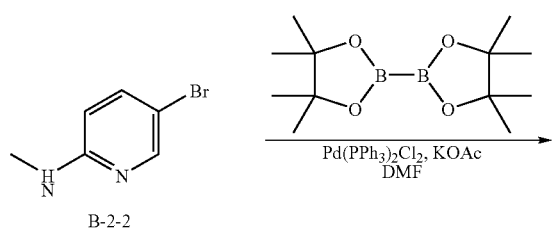

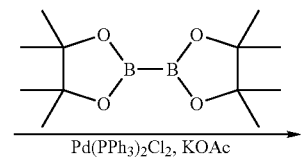

B-2

Preparation of N-methyl-5-(4,4,5,5-tetramethyl-1,3,2-dioxaborolan-2-yl)pyridin-2-amine B-2-3

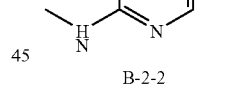

To a solution of 5-bromo-N-methylpyridin-2-amine B-2-2 (1 g, 5.37 mmol) in DMF (30 mL) were added KOAc (1.58 g, 16.1 mmol) and bis(pinacolato)diboron (2 g, 8.06 mmol). The resulting mixture was degassed under $N_2$ for 2 minutes. Then $Pd(PPh_3)_2Cl_2$ (0.5 g, 0.53 mmol) was added and the mixture was degassed again. The reaction was heated to 80~90° C. and stirred overnight. DMF was removed under reduced pressure. The residue was dissolved with EtOAc (40 mL), washed with saturated aqueous NaCl, dried over $Na_2SO_4$ and concentrated to give crude N-methyl-5-(4,4,5,5-tetramethyl-1,3,2-dioxaborolan-2-yl)pyridin-2-amine B-2-3 (2.3 g), which was used directly in next step.

Preparation of (2S)-1-(4-(1-isopropyl-3-(6-(methylamino)pyridin-3-yl)-1H-pyrazol-4-yl)pyrimidin-2-ylamino)propan-2-ol (B-2)

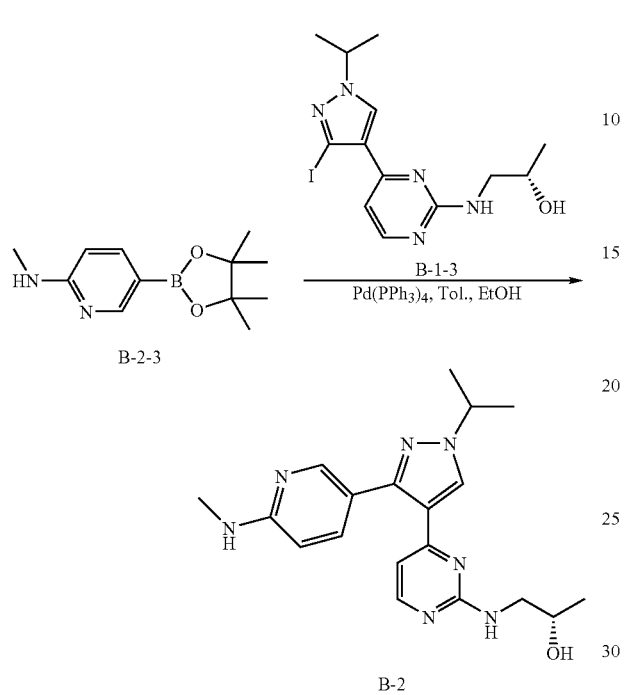

To a solution of (2S)-1-(4-(3-iodo-1-isopropyl-1H-pyrazol-4-yl)pyrimidin-2-ylamino)propan-2-ol (9) (0.65 g, 1.68 mmol) in toluene (20 mL) and EtOH (7 mL) were added N-methyl-5-(4,4,5,5-tetramethyl-1,3,2-dioxaborolan-2-yl)pyridin-2-amine 12 (1.44 g, 3.36 mmol in theory) and 2 N $Na_2CO_3$ aq. (2.5 mL). The resulting mixture was degassed under $N_2$ for 2 minutes. Then $Pd(PPh_3)_4$ (0.2 g, 0.168 mmol) was added and the mixture was degassed again. The reaction was heated to 80-90° C. and stirred overnight. The mixture was cooled. The organic layer was separated and concentrated. The residue was purified by prep. HPLC to afford (2S)-1-(4-(1-isopropyl-3-(6-(methylamino)pyridin-3-yl)-1H-pyrazol-4-yl)pyrimidin-2-ylamino)propan-2-ol (B-2) (0.020 g, 3.2%) as a light yellow solid.

Example B-3

Preparation of (2S)-1-(4-(3-(6-amino-5-methylpyridin-3-yl)-1-isopropyl-1H-pyrazol-4-yl)pyrimidin-2-ylamino)propan-2-ol (B-3)

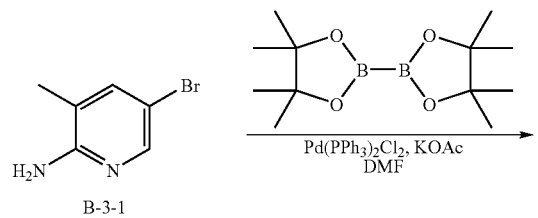

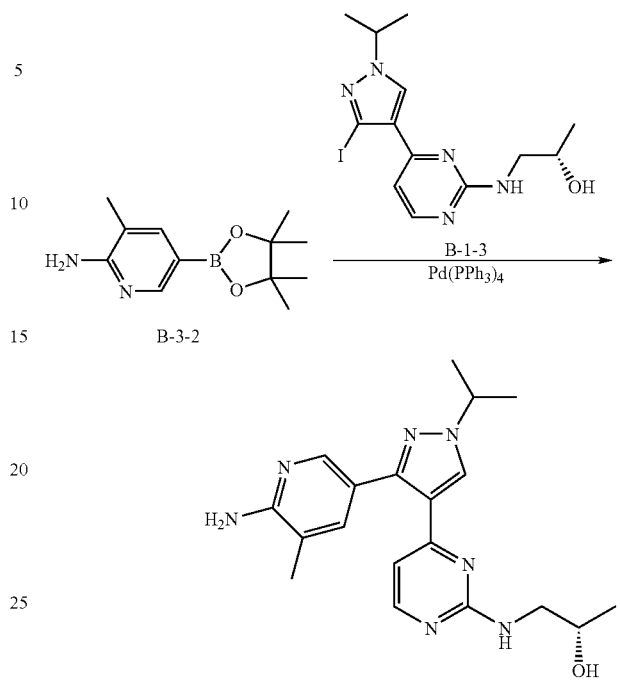

Preparation of 3-methyl-5-(4,4,5,5-tetramethyl-1,3,2-dioxaborolan-2-yl)pyridin-2-amine (B-3-2)

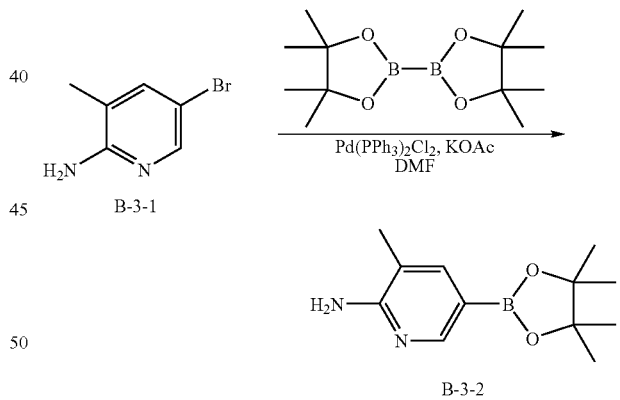

To a solution of 5-bromo-3-methylpyridin-2-amine B-3-1 (2 g, 11 mmol) in DMF (70 mL) were added KOAc (3.2 g, 33 mmol) and bis(pinacolato)diboron (4.1 g, 16 mmol). The resulting mixture was degassed under $N_2$ for 2 minutes. Then $Pd(PPh_3)_2Cl_2$ (1 g, 1.1 mmol) was added and the mixture was degassed again. The reaction was heated to 80-90° C. and stirred overnight. The mixture was poured into water (100 mL). The mixture was extracted with EtOAc (50 mL×3), the organic layer was washed with saturated aqueous NaCl, dried over $Na_2SO_4$ and concentrated to give crude 3-methyl-5-(4,4,5,5-tetramethyl-1,3,2-dioxaborolan-2-yl)pyridin-2-amine (B-3-2) (3.5 g), which was used directly in next step.

Preparation of (2S)-1-(4-(3-(6-amino-5-methylpyridin-3-yl)-1-isopropyl-1H-pyrazol-4-yl)pyrimidin-2-ylamino)propan-2-ol (B-3)

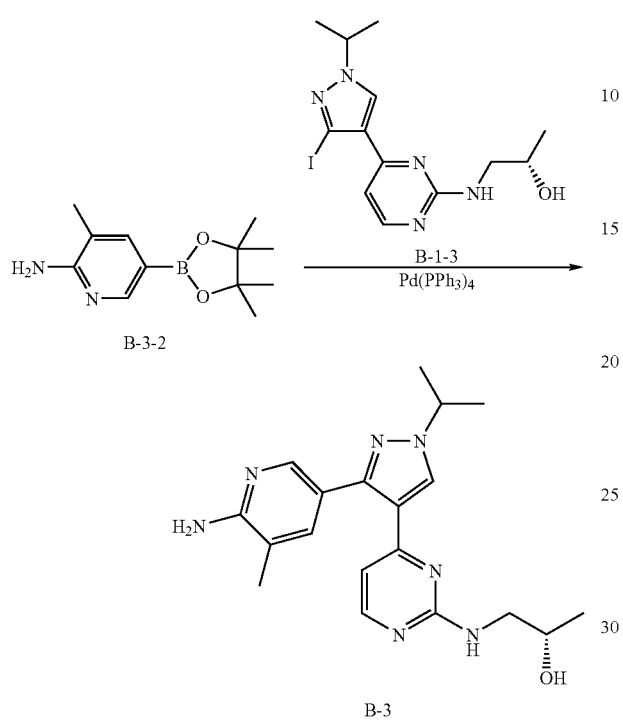

To a solution of (2S)-1-(4-(3-iodo-1-isopropyl-1H-pyrazol-4-yl)pyrimidin-2-ylamino)propan-2-ol (B-1-3) (0.52 g, 1.34 mmol) in toluene (21 mL) and EtOH (7 mL) were added 3-methyl-5-(4,4,5,5-tetramethyl-1,3,2-dioxaborolan-2-yl)pyridin-2-amine (B-3-2) (1 g, 2.68 mmol in theory) and 2 N aq. $Na_2CO_3$ (2 mL). The resulting mixture was degassed under $N_2$ for 2 minutes. Then $Pd(PPh_3)_4$ (0.15 g, 0.134 mmol) was added and the mixture was degassed again. The reaction was heated to 80-90° C. and stirred overnight. The mixture was cooled. The organic layer was separated and concentrated. The residue was purified by prep. HPLC to afford (2S)-1-(4-(3-(6-amino-5-methylpyridin-3-yl)-1-isopropyl-1H-pyrazol-4-yl)pyrimidin-2-ylamino)propan-2-ol (B-3) (0.057 g, 11.6%) as a light yellow solid.

Example B-4

Preparation of (2S)-1-(4-(1-isopropyl-3-(5-methyl-6-(methylamino)pyridin-3-yl)-1H-pyrazol-4-yl)pyrimidin-2-ylamino)propan-2-ol (B-4)

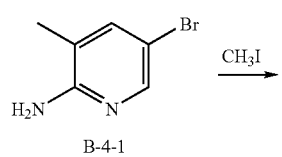

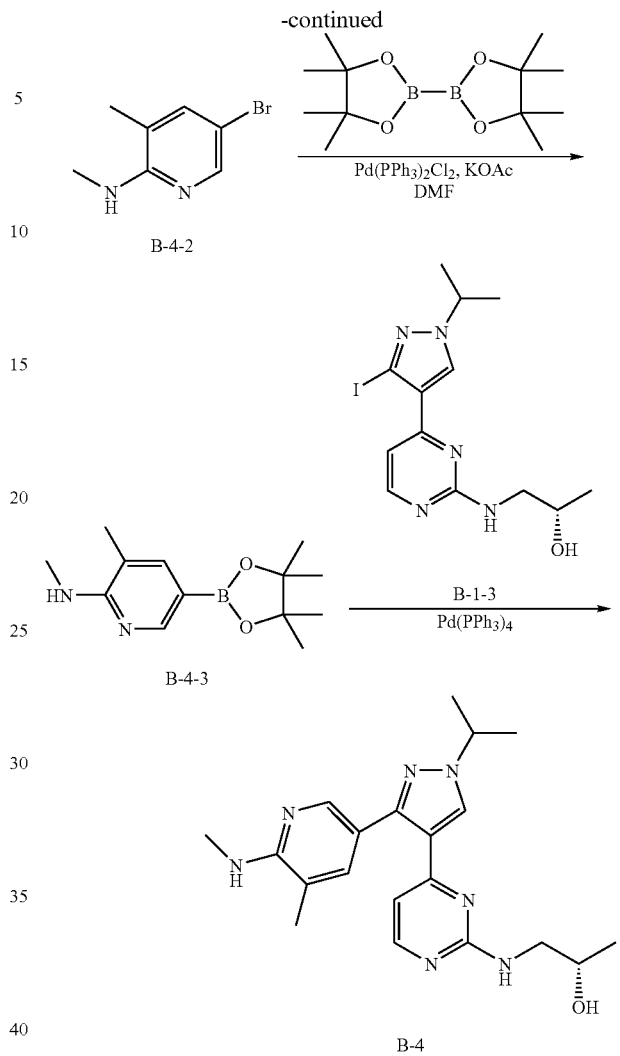

Preparation of 5-bromo-N,3-dimethylpyridin-2-amine (B-4-2)

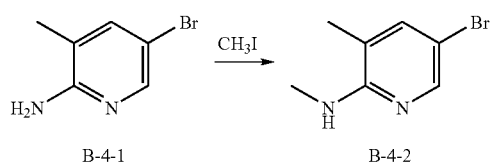

To a solution of 5-bromo-3-methylpyridin-2-amine (B-4-1) (3.7 g, 0.02 mol) in THF (50 mL) was added portionwise NaH (0.8 g, 0.02 mol) at 0° C. After the addition, the mixture was stirred at room temperature for about 0.5 hr, and cooled to 0° C. again. Iodomethane (2.8 g, 0.02 mol) was added slowly. The resulting mixture was allowed to rise to room temperature and stirred for 1 hr. TLC (EtOAc: Petroleum ether=1:4) showed that the reaction was complete. Saturated aqueous NaCl (10 mL) and EtOAc (10 mL) were added. The organic layer was concentrated and the residue was purified via a silica gel column eluted with EtOAc/Petroleum ether (1:8) to give 5-bromo-N,3-dimethylpyridin-2-amine (B-4-2) (2.3 g, 57.8%) as a white solid.

Preparation of N,3-dimethyl-5-(4,4,5,5-tetramethyl-1,3,2-dioxaborolan-2-yl)pyridin-2-amine (B-4-3)

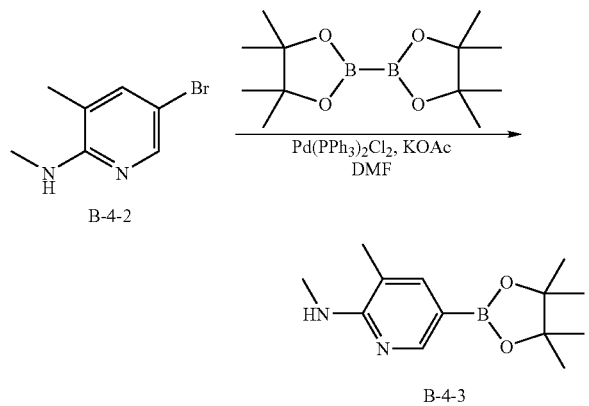

To a solution of give 5-bromo-N,3-dimethylpyridin-2-amine (B-4-2) (2.3 g, 11.4 mmol) in DMF (70 mL) were added KOAc (3.35 g, 34.2 mmol) and bis(pinacolato)diboron (4.34 g, 17.1 mmol). The resulting mixture was degassed under $N_2$ for 2 minutes. Then $Pd(PPh_3)_2Cl_2$ (1 g, 1.1 mmol) was added and the mixture was degassed again. The reaction was heated to 80-90° C. and stirred overnight. The mixture was poured into saturated aqueous NaCl (80 mL). The mixture was extracted with EtOAc (50 mL×3). The organic layer was washed with saturated aqueous NaCl, dried over $Na_2SO_4$ and concentrated to give crude N,3-dimethyl-5-(4,4,5,5-tetramethyl-1,3,2-dioxaborolan-2-yl)pyridin-2-amine (B-4-3) (3.5 g), which was not purified and used directly in next step.

Preparation of (2S)-1-(4-(1-isopropyl-3-(5-methyl-6-(methylamino)pyridin-3-yl)-1H-pyrazol-4-yl)pyrimidin-2-ylamino)propan-2-ol (B-4)

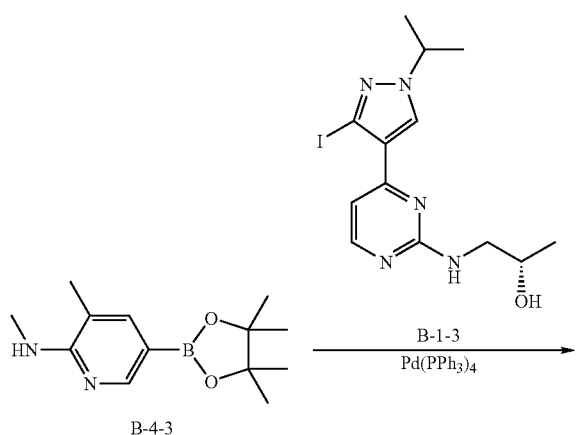

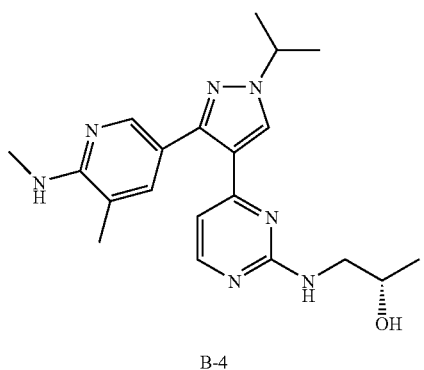

To a solution of (2S)-1-(4-(3-iodo-1-isopropyl-1H-pyrazol-4-yl)pyrimidin-2-ylamino)propan-2-ol (B-1-3) (1 g, 2.58 mmol) in toluene (30 mL) and EtOH (10 mL) were added N,3-dimethyl-5-(4,4,5,5-tetramethyl-1,3,2-dioxaborolan-2-yl)pyridin-2-amine (B-4-3) (2 g, 6.3 mmol in theory) and 2 N aq. $Na_2CO_3$ (4 mL). The resulting mixture was degassed under $N_2$ for 2 minutes. Then $Pd(PPh_3)_4$ (0.3 g, 0.26 mmol) was added and the mixture was degassed again. The reaction was heated to 80-90° C. and stirred overnight. MS showed the reaction was complete and the mixture was cooled. The organic layer was separated and concentrated. The residue was purified by prep. HPLC to afford (2S)-1-(4-(1-isopropyl-3-(5-methyl-6-(methylamino)pyridin-3-yl)-1H-pyrazol-4-yl)pyrimidin-2-ylamino)propan-2-ol (B-4) (0.167 g, 16.98%) as a light yellow solid.

Example B-5

Preparation of (2S)-1-(4-(1-isopropyl-3-(3-methyl-1H-pyrrolo[2,3-b]pyridin-5-yl)-1H-pyrazol-4-yl)pyrimidin-2-ylamino)propan-2-ol (B-5)

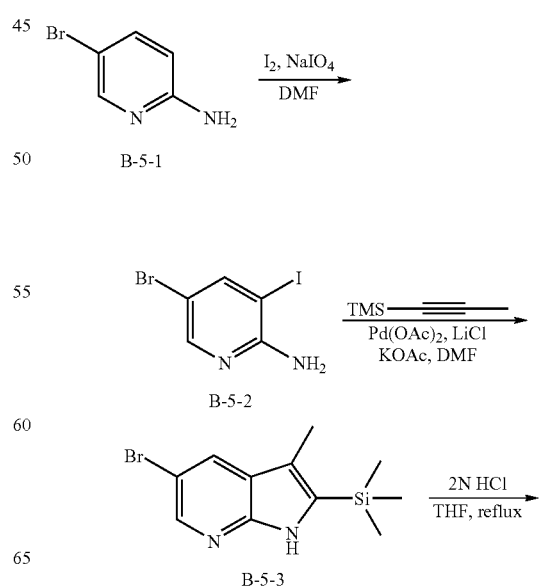

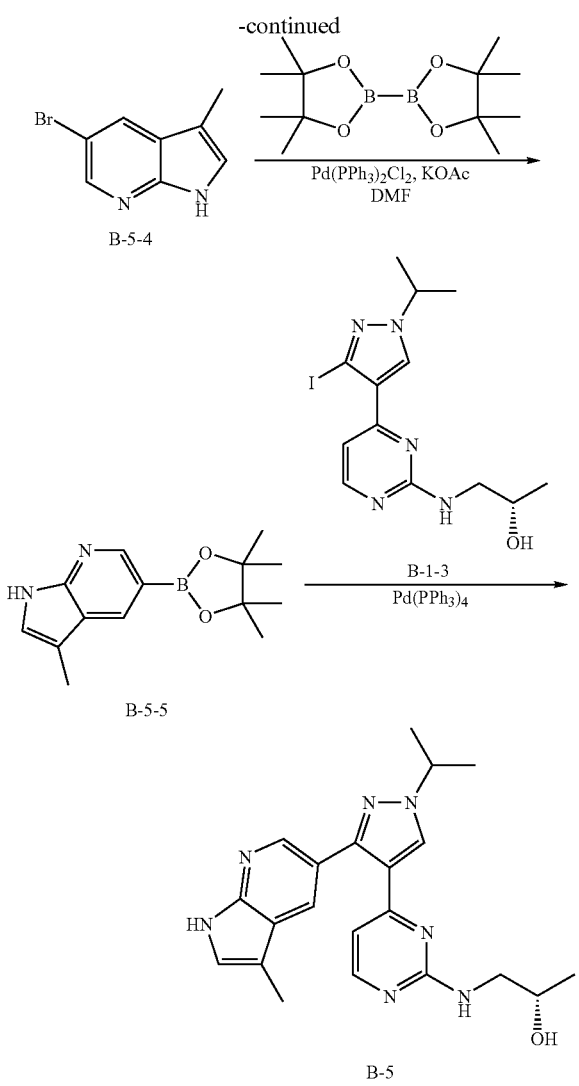

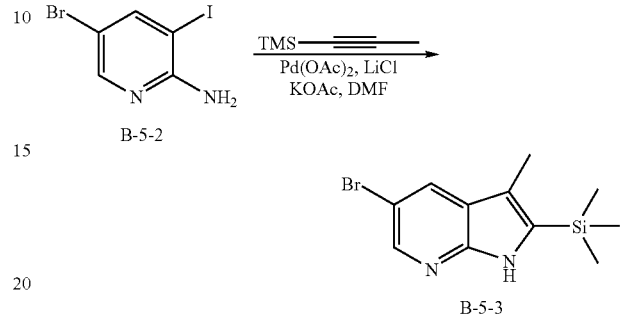

gel column eluted with EtOAc/Petroleum ether (12:1) to afford pure 5-bromo-3-iodopyridin-2-amine (B-5-2) (35 g, 40.5%) as an orange solid.

Preparation of 5-bromo-3-methyl-2-(trimethylsilyl)-1H-pyrrolo[2,3-b]pyridine (B-5-3)

To a solution of 5-bromo-3-iodopyridin-2-amine (B-5-2) (30 g, 0.1 mol) in DMF (600 mL) were added KOAc (29.4 g, 0.3 mol) and LiCl (4.25 g, 0.1 mol). After the mixture was degassed under $N_2$ for 3 times, Pd(OAc)$_2$ (2.24 g, 0.01 mol) was added, and the mixture was degassed again. Then trimethyl-prop-1-ynyl-silane (56 g, 0.5 mol) was added. The resulting mixture was heated to 80-100° C. for 2 days. TLC (EtOAc: Petroleum ether=1:5) showed that the reaction was complete. Excess DMF was removed under reduced pressure. The residue was dissolved in EtOAc (500 mL), washed with saturated aqueous NaCl, dried over Na$_2$SO$_4$ and concentrated to give crude product, which was purified via a silica gel column chromatography (100-200) (Petroleum ether, then EtOAc:Petroleum ether=1:10) to give 5-bromo-3-methyl-2-(trimethylsilyl)-1H-pyrrolo[2,3-b]pyridine (B-5-3) (not pure, 5 g, 17.7%) as a brown oil.

Preparation of 5-bromo-3-methyl-1H-pyrrolo[2,3-b]pyridine (B-5-4)

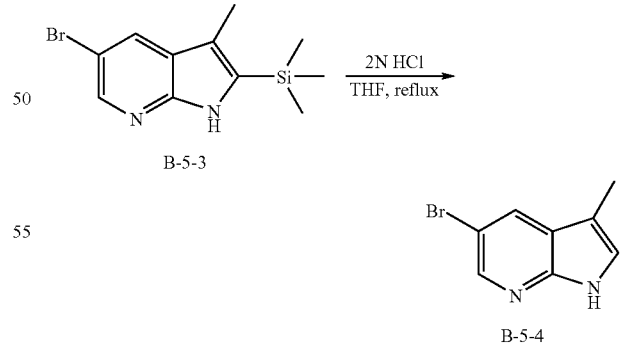

Preparation of 5-bromo-3-iodopyridin-2-amine (B-5-2)

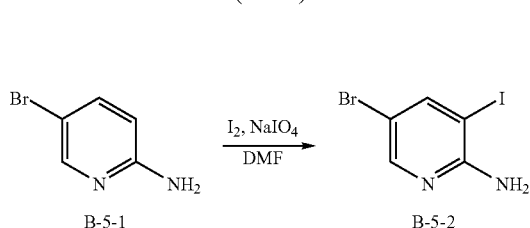

A mixture of 5-bromopyridin-2-amine (B-5-1) (50 g, 0.29 mol), I$_2$ (59 g, 0.233 mol) and NaIO$_4$ (24.8 g, 0.116 mol) in DMF 600 mL) was stirred at 80-90° C. overnight. TLC (EtOAc: Petroleum ether=1:5) showed that the reaction was complete. The mixture was concentrated under reduced pressure to remove the solvent. The residue was dissolved in EtOAc (500 mL), washed with water (100 mL) and saturated aqueous NaCl (100 mL), dried over Na$_2$SO$_4$ and concentrated to give crude compound B-5-2, which was purified via a silica To a solution of 5-bromo-3-methyl-2-(trimethylsilyl)-1H-pyrrolo[2,3-b]pyridin (B-5-3) (5 g, 17.8 mmol) in THF (50 mL) was added 2 N HCl (20 mL). The mixture was stirred at reflux overnight. HPLC showed the reaction was complete. After the mixture was concentrated under reduced pressure, the residue was dissolved in aqueous NaHCO$_3$ (20 mL) and extracted with EtOAc (10 mL×3). The organic layer was washed with saturated aqueous NaCl, dried over Na₂SO₄ and concentrated to give crude product, which was purified via prep. HPLC to give 5-bromo-3-methyl-1H-pyrrolo[2,3-b]pyridine (B-5-4) (2 g, 53.2%) as a pale solid.

Preparation of 3-methyl-5-(4,4,5,5-tetramethyl-1,3,2-dioxaborolan-2-yl)-1H-pyrrolo[2,3-b]pyridine (B-5-5)

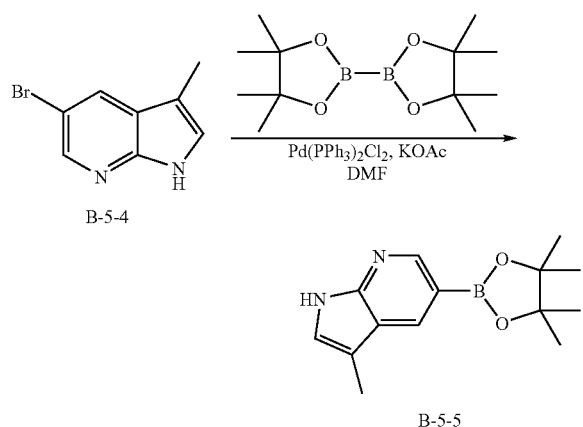

To a solution of 5-bromo-3-methyl-1H-pyrrolo[2,3-b]pyridine (B-5-4) (0.5 g, 2.37 mmol) in DMF (150 mL) were added KOAc (0.7 g, 7.11 mmol) and bis(pinacolato)diboron (0.72 g, 2.84 mmol). The resulting mixture was degassed under N₂ for 2 minutes. Then Pd(PPh₃)₂Cl₂ (0.2 g, 0.237 mmol) was added and the mixture was degassed again. The reaction was heated to 80-90° C. and stirred overnight. The mixture was poured into water (30 mL), extracted with EtOAc (15 mL×3). The organic layer was washed with saturated aqueous NaCl, dried over Na₂SO₄ and concentrated to give crude 3-methyl-5-(4,4,5,5-tetramethyl-1,3,2-dioxaborolan-2-yl)-1H-pyrrolo[2,3-b]pyridine (B-5-5) (0.7 g), which was used directly in next step.

Preparation of (2S)-1-(4-(1-isopropyl-3-(3-methyl-1H-pyrrolo[2,3-b]pyridin-5-yl)-1H-pyrazol-4-yl)pyrimidin-2-ylamino)propan-2-ol (B-5)

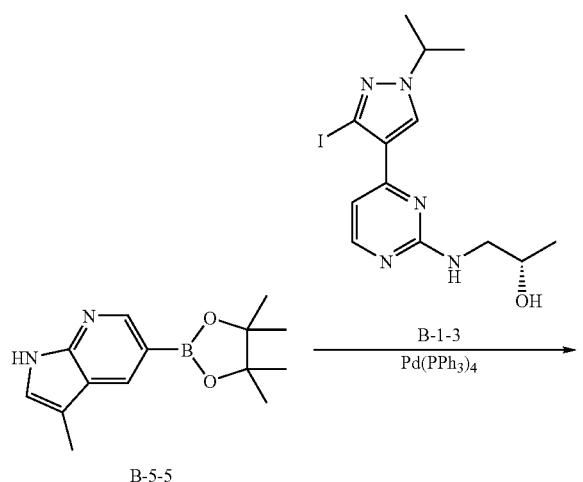

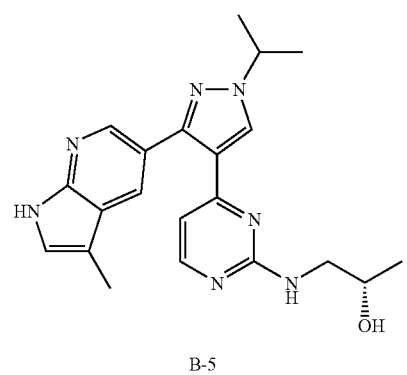

To a solution of (2S)-1-(4-(3-iodo-1-isopropyl-1H-pyrazol-4-yl)pyrimidin-2-ylamino)propan-2-ol (9) (0.65 g, 1.7 mmol) in toluene (21 mL) and EtOH (7 mL) were added 3-methyl-5-(4,4,5,5-tetramethyl-1,3,2-dioxaborolan-2-yl)-1H-pyrrolo[2,3-b]pyridine 21 (0.7 g, 2.37 mmol in theory) and 2 N aq. Na₂CO₃ (2.5 mL). The resulting mixture was degassed under N₂ for 2 minutes. Then Pd(PPh₃)₄ (0.19 g, 0.17 mmol) was added and the mixture was degassed again. The reaction was heated to 80-90° C. and stirred overnight. The mixture was cooled. The organic layer was separated and concentrated. The residue was purified by prep. HPLC to afford (2S)-1-(4-(1-isopropyl-3-(3-methyl-1H-pyrrolo[2,3-b]pyridin-5-yl)-1H-pyrazol-4-yl)pyrimidin-2-ylamino)propan-2-ol (B-5) (0.150 mg, 16.2%) as a white solid.

Example B-6

Preparation of (2S)-1-(4-(3-(2,3-dimethyl-1H-pyrrolo[2,3-b]pyridin-5-yl)-1-isopropyl-1H-pyrazol-4-yl)pyrimidin-2-ylamino)propan-2-ol (B-6)

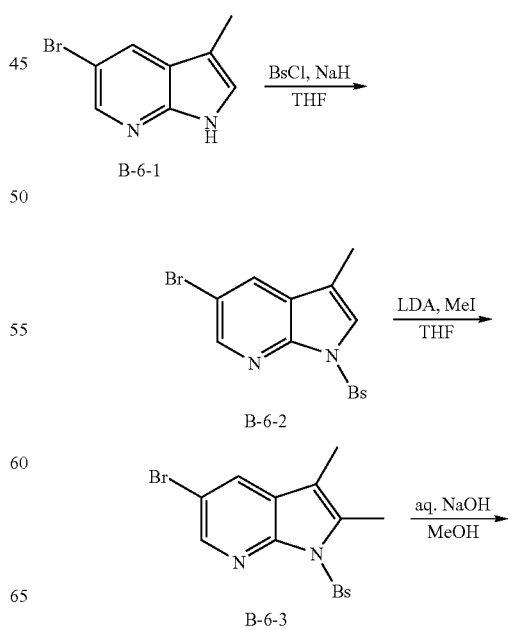

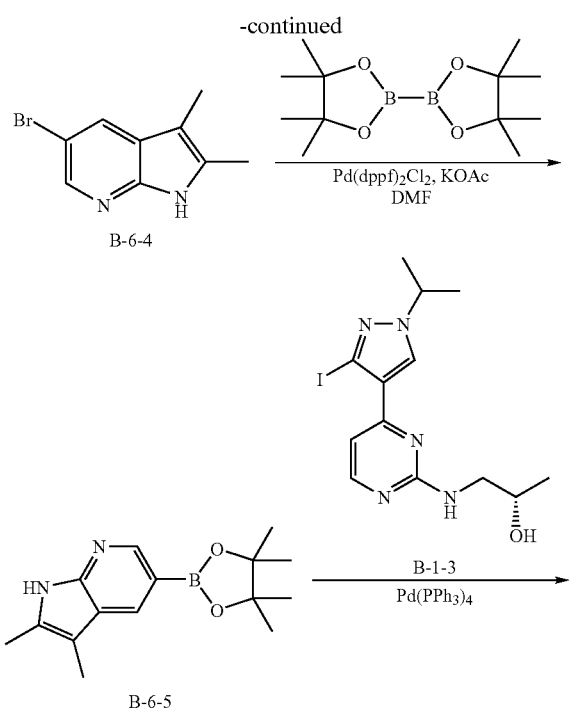

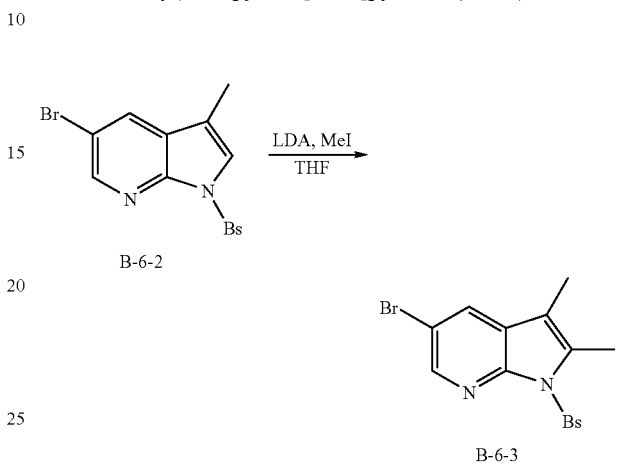

as a white solid. The organic layer was separated from the filtrate, concentrated to 8 mL, then filtered to give 5-bromo-1-(4-bromophenylsulfonyl)-3-methyl-1H-pyrrolo[2,3-b]pyridine (0.5 g). Two batches were combined to give 5-bromo-3-methyl-1-(phenylsulfonyl)-1H-pyrrolo[2,3-b]pyridine (B-6-2) (1.3 g, 65.2%) as a white solid.

Preparation of 5-bromo-2,3-dimethyl-1-(phenylsulfonyl)-1H-pyrrolo[2,3-b]pyridine (B-6-3)

To a suspension of 5-bromo-1-(4-bromophenylsulfonyl)-3-methyl-1H-pyrrolo[2,3-b]pyridine (B-6-2) (0.9 g, 2.56 mmol) in THF (20 mL) was added dropwise LDA (15 mL, 0.2 M in THF) at −40° C. The mixture was stirred at −10~−20° C. for 0.5 hour. Methyl iodide (0.55 g 3.84 mmol) was added dropwise at −40~−30° C. The reaction was stirred at room temperature overnight. LC-MS showed that the reaction was complete. Saturated aqueous NaCl (10 mL) and EtOAc (10 mL) were added into the mixture. The organic layer was separated, dried over anhydrous Na$_2$SO$_4$ and concentrated to give 5-bromo-2,3-dimethyl-1-(phenylsulfonyl)-1H-pyrrolo[2,3-b]pyridine (B-6-3) (0.9 g, 96.3%, containing some starting material (B-6-2) as a light yellow solid.

Preparation of 5-bromo-2,3-dimethyl-1H-pyrrolo[2,3-b]pyridine (B-6-4)

Preparation of 5-bromo-3-methyl-1-(phenylsulfonyl)-1H-pyrrolo[2,3-b]pyridine (B-6-2)

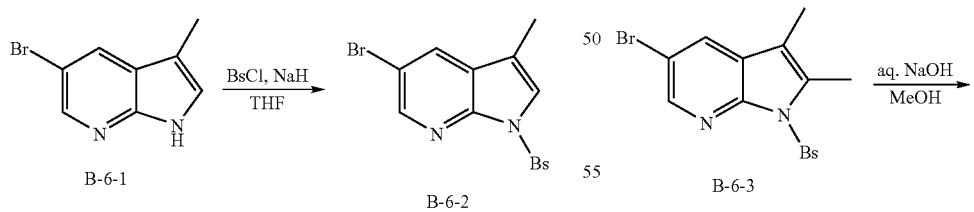

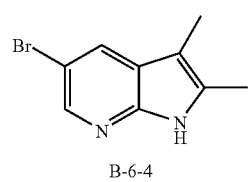

To a solution of 5-bromo-3-methyl-1H-pyrrolo[2,3-b]pyridine (B-6-1) (1.2 g, 5.68 mmol) in THF (30 mL) was added NaH (0.34 g, 8.5 mmol) under N$_2$ at 0° C., 4-bromophenylsulfonyl chloride (1.2 g, 6.8 mmol) was added 30 minutes later. The mixture was stirred at room temperature for 1.5 h. TLC (Petroleum ether: EtOAc=5:1) showed that the reaction was complete. Saturated aqueous NaCl (10 mL) was added, and the mixture was filtered to give 5-bromo-3-methyl-1-(phenylsulfonyl)-1H-pyrrolo[2,3-b]pyridine (B-6-2) (0.8 g)

To a suspension of 5-bromo-2,3-dimethyl-1-(phenylsulfonyl)-1H-pyrrolo[2,3-b]pyridine (B-6-3) (0.9 g, 2.5 mmol) in THF (30 mL) and MeOH (30 mL) was added aq. NaOH (20%, 19 mL) at room temperature. The mixture was heated to reflux overnight. TLC (Petroleum ether: EtOAc=5:1) showed the reaction was complete. After the solvent was removed under reduced pressure, water (20 mL) and CH$_2$Cl$_2$ (20 mL) were added into the mixture. The organic layer was separated, dried over anhydrous Na$_2$SO$_4$. The mixture was concentrated to give crude mixture which was purified via prep. HPLC to afford 5-bromo-2,3-dimethyl-1H-pyrrolo[2,3-b]pyridine (B-6-4) (0.4 g, 72.4%) as a white solid.

Preparation of 2,3-dimethyl-5-(4,4,5,5-tetramethyl-1,3,2-dioxaborolan-2-yl)-1H-pyrrolo[2,3-b]pyridine (B-6-5)

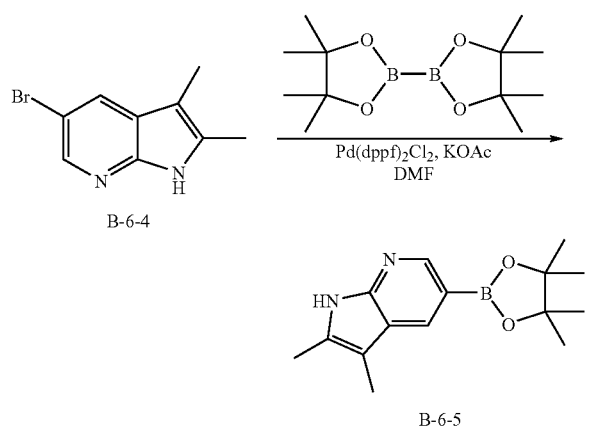

To a solution of 5-bromo-2,3-dimethyl-1H-pyrrolo[2,3-b]pyridine (B-6-4) (0.4 g, 1.77 mmol) in DMF (30 mL) were added KOAc (0.52 g, 5.3 mmol) and bis(pinacolato)diboron (0.68 g, 2.65 mmol), and the resulting mixture was degassed under N$_2$ for 2 minutes. Then Pd(dppf)$_2$Cl$_2$ (40 mg, 0.049 mmol) was added and the mixture was degassed again. The reaction was heated to 80-90° C. and stirred overnight. The mixture was poured into water (100 mL), extracted with EtOAc (40 mL×3). The organic layer was washed with saturated aqueous NaCl, dried over Na$_2$SO$_4$ and concentrated to give crude 2,3-dimethyl-5-(4,4,5,5-tetramethyl-1,3,2-dioxaborolan-2-yl)-1H-pyrrolo[2,3-b]pyridine (B-6-5) (0.7 g), which was not purified and used directly in next step.

Preparation of (2S)-1-(4-(3-(2,3-dimethyl-1H-pyrrolo[2,3-b]pyridin-5-yl)-1-isopropyl-1H-pyrazol-4-yl)pyrimidin-2-ylamino)propan-2-ol (B-6)

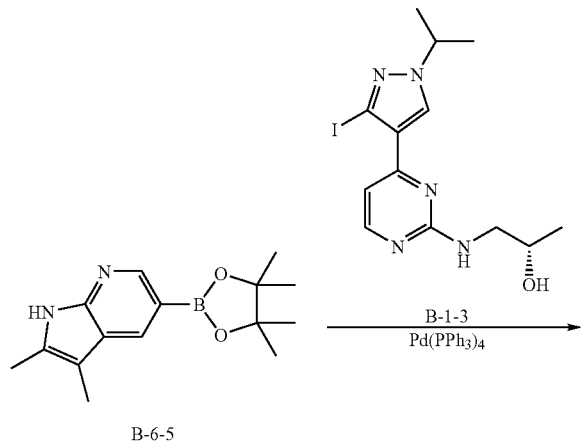

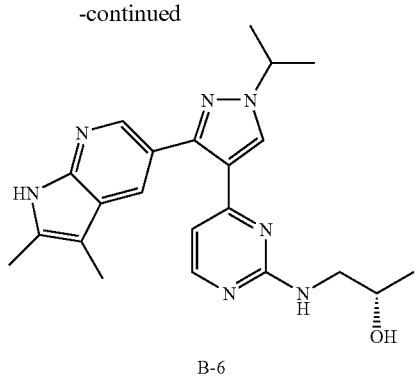

To a solution of (2S)-1-(4-(3-iodo-1-isopropyl-1H-pyrazol-4-yl)pyrimidin-2-ylamino)propan-2-ol (B-1-3) (0.34 g, 0.885 mmol) in toluene (30 mL) and EtOH (10 mL) were added 2,3-dimethyl-5-(4,4,5,5-tetramethyl-1,3,2-dioxaborolan-2-yl)-1H-pyrrolo[2,3-b]pyridine (B-6-5) (0.7 g, 1.77 mmol in theory) and 2 N aq. Na$_2$CO$_3$ (1.3 mL). The resulting mixture was degassed under N$_2$ for 2 minutes. Then Pd(PPh$_3$)$_4$ (68 mg, 0.058 mmol) was added and the mixture was degassed again. The reaction was heated to 80-90° C. and stirred overnight. The mixture was cooled. The organic layer was separated and concentrated. The residue was purified by prep. HPLC to afford (2S)-1-(4-(3-(2,3-dimethyl-1H-pyrrolo[2,3-b]pyridin-5-yl)-1-isopropyl-1H-pyrazol-4-yl)pyrimidin-2-ylamino)propan-2-ol (B-6) (0.170 mg, 23.6%) as a light yellow solid.

Example B-7

Preparation of (2S)-1-(4-(1-isopropyl-3-(2-methyl-1H-pyrrolo[2,3-b]pyridin-5-yl)-1H-pyrazol-4-yl)pyrimidin-2-ylamino)propan-2-ol (B-7)

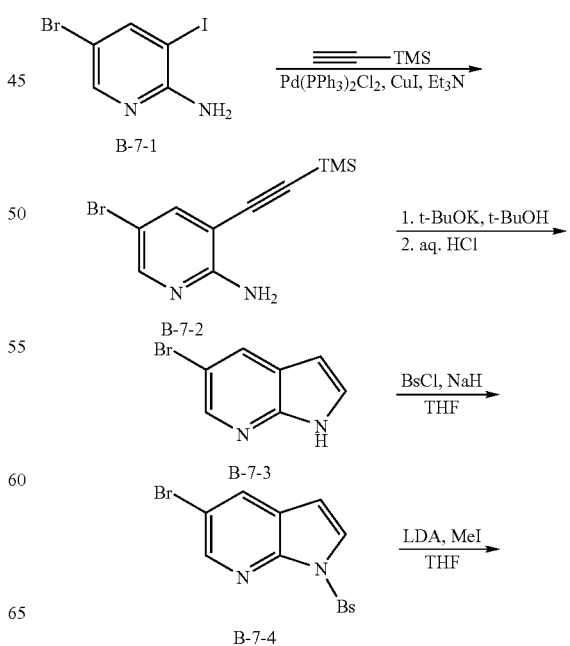

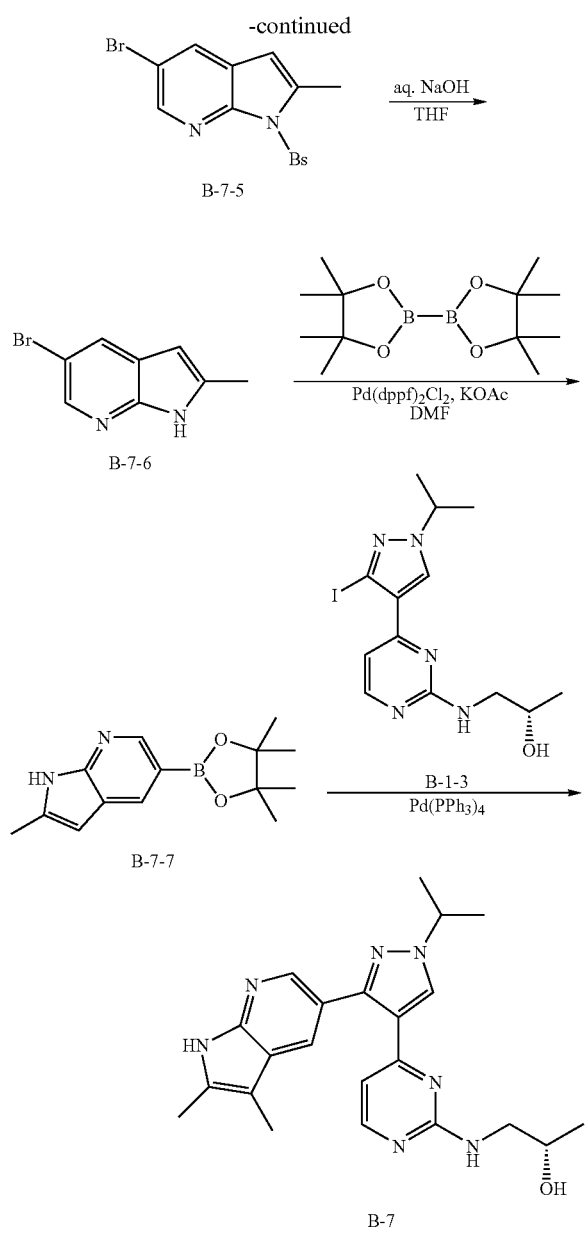

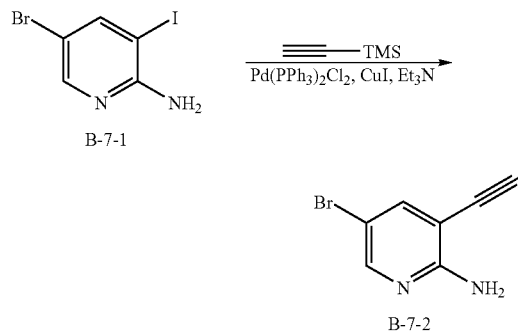

Preparation of 5-bromo-3-(2-(trimethylsilyl)ethynyl)pyridin-2-amine (B-7-2)

To a solution of 5-bromo-3-iodopyridin-2-amine (B-7-1) (20 g, 66.9 mmol) in Et₃N (200 mL) was added CuI (1.27 g, 6.69 mmol), and the resulting mixture was degassed with N₂ for 2 minutes. Then Pd(PPh₃)₂Cl₂ (1.4 g, 20.1 mmol) was added and the mixture was degassed again. Then ethynyl-trimethylsilane (7.2 g, 73.6 mmol) was added dropwise into the mixture at 0° C. The mixture was stirred at room temperature for 4 hours. TLC (Petroleum ether: EtOAc=5:1) showed that the reaction was complete. The mixture was evaporated under reduced pressure to give crude mixture which was purified via a silica gel column eluted with petroleum ether/EtOAc (20:1) to afford 5-bromo-3-(2-(trimethylsilyl)ethynyl)pyridin-2-amine (B-7-2) (10 g, 55.6%) as a white solid.

Preparation of 5-bromo-1H-pyrrolo[2,3-b]pyridine (B-7-3)

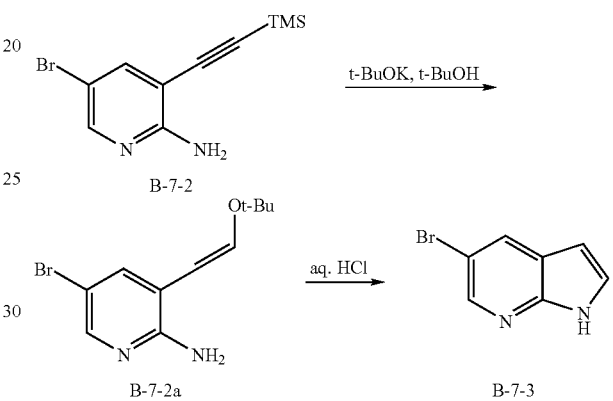

To a solution of 5-bromo-3-(2-(trimethylsilyl)ethynyl)pyridin-2-amine (B-7-2) (9.5 g, 35.3 mmol) in t-BuOH (100 mL) was added t-BuOK (10.5 g, 141.3 mmol). The mixture was stirred at 80° C. for 20 hours. TLC (Petroleum ether: EtOAc=5:1) showed that the reaction was complete. Then the mixture was cooled to room temperature. Concentrated hydrochoric acid (50 mL) was added to the mixture. Then the mixture was heated to reflux for 8 hours. TLC (Petroleum ether: EtOAc=5:1) showed that the reaction was complete. The mixture was cooled to room temperature and poured into water (100 mL). The mixture was filtered through a bed of Celite. The filtrate was diluted with water (100 mL) and made basic by the addition of 50% sodium hydroxide. The mixture was extracted with EtOAc (150 mL×3). The organic layers were washed with water (100 mL) and saturated sodium chloride (100 mL), dried over sodium sulfate and concentrated under reduced pressure to afford 5-bromo-1H-pyrrolo[2,3-b]pyridine (B-7-3) (6.2 g, 88.6%) as a light yellow solid.

Preparation of 5-bromo-1-(phenylsulfonyl)-1H-pyrrolo[2,3-b]pyridine (B-7-4)

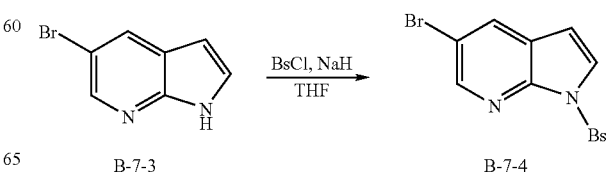

To a suspension of 5-bromo-1H-pyrrolo[2,3-b]pyridine (B-7-3) (6.2 g, 0.031 mol) in THF (100 mL) was added NaH (1.51 g, 0.037 mol) under N$_2$. BsCl (3.58 g, 0.035 mol) was added 30 minutes later. The mixture was stirred at room temperature overnight. TLC (Petroleum ether: EtOAc=5:1) showed that the reaction was complete. Water (200 mL) and EtOAc (50 mL×3) were added into the mixture. The organic layer was separated and concentrated to give 5-bromo-1-(phenylsulfonyl)-1H-pyrrolo[2,3-b]pyridine (B-7-4) (10 g, 94.3%) as a light yellow solid. $^1$HNMR (400 MHz, CDCl$_3$): δ 8.465 (s, 1H), 8.141-8.114 (d, 2H), 7.905 (s, 1H), 7.679-7.669 (d, 1H), 7.586-7.529 (m, 1H), 7.430-7.351 (2, 1H), 6.458-6.475 (d, 1H).

Preparation of 5-bromo-1-(4-bromophenylsulfonyl)-2-methyl-1H-pyrrolo[2,3-b]pyridine (B-7-5)

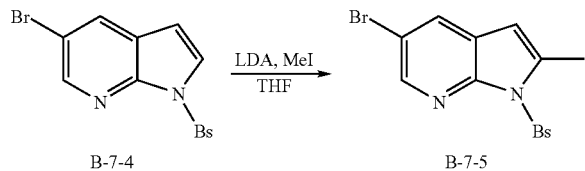

To a suspension of 5-bromo-1-(phenylsulfonyl)-1H-pyrrolo[2,3-b]pyridine (B-7-4) (10 g, 0.03 mol) in THF (50 mL) was added dropwise LDA (200 mL, 0.21 M in THF) at –78° C. The mixture was stirred at –78° C. for one hour. Then MeI (5.2 g 0.038 mol) was added dropwise at –78° C. The reaction was stirred at –70° C. for 3 hours, and then stirred at room temperature overnight. LC-MS showed the reaction was complete. Water (200 mL) and EtOAc (100 mL×3) were added into the mixture. The organic layer was separated, dried over anhydrous Na$_2$SO$_4$ and concentrated to give 5-bromo-1-(4-bromophenylsulfonyl)-2-methyl-1H-pyrrolo[2,3-b]pyridine (B-7-5) (6 g, 57.7%) as a light yellow solid. $^1$HNMR (400 MHz, CDCl$_3$): δ 8.390-8.385 (d, 1H), 8.176-8.145 (d, 2H), 7.828-7.823 (d, 1H), 7.613-7.576 (t, 1H), 7.517-7.479 (t, 2H), 6.254 (s, 1H), 2.748 (s, 3H).

Preparation of 5-bromo-2-methyl-1H-pyrrolo[2,3-b]pyridine (B-7-6)

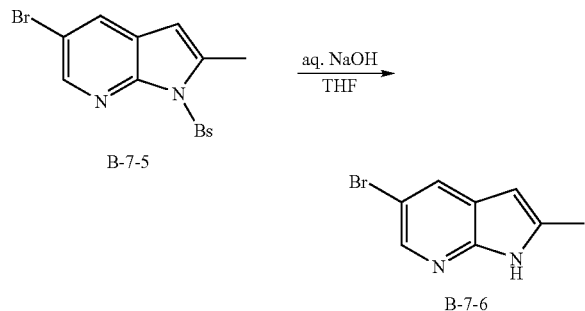

To a suspension of 5-bromo-1-(4-bromophenylsulfonyl)-2-methyl-1H-pyrrolo[2,3-b]pyridine (B-7-5) (4 g, 11.4 mmol) in THF (20 mL) was added aq. NaOH (20 mL) at room temperature. The mixture was heated to reflux overnight. LC-MS showed the reaction was complete. Water (100 mL) and EtOAc (50 mL×3) were added into the mixture. The organic layer was separated, dried over anhydrous Na$_2$SO$_4$ and concentrated to give crude mixture which was purified via prep. HPLC to afford 5-bromo-2-methyl-1H-pyrrolo[2,3-b]pyridine (B-7-6) (1.2 g, 50.2%) as a white solid.

Preparation of 2-methyl-5-(4,4,5,5-tetramethyl-1,3,2-dioxaborolan-2-yl)-1H-pyrrolo[2,3-b]pyridine (B-7-7)

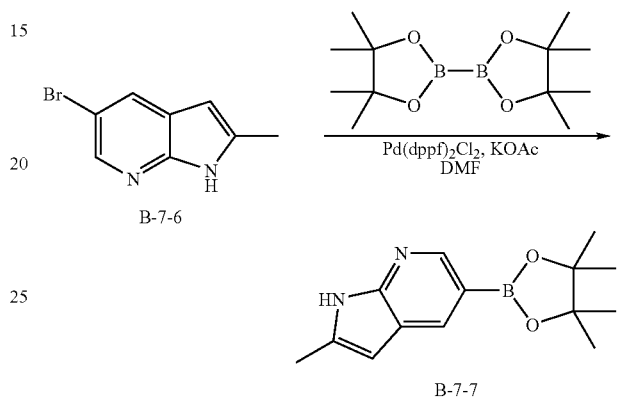

To a mixture of 5-bromo-2-methyl-1H-pyrrolo[2,3-b]pyridine (B-7-6) (0.5 g, 2.4 mmol), bis(pinacolato)diboron (1.2 g, 4.7 mmol) and KOAc (0.7 g, 7.1 mmol) in DMF (50 mL) was added Pd(dppf)$_2$Cl$_2$ (0.05 g, 0.06 mmol). The mixture was degassed under N$_2$ for 2 minutes. Then the mixture was stirred at 80° C. overnight. TLC (CH$_2$Cl$_2$: MeOH=20:1) showed that the reaction was complete. Water (50 mL) and EtOAc (50 mL×3) were added into the mixture. The organic layer was separated, dried over anhydrous Na$_2$SO$_4$ and concentrated to give crude 2-methyl-5-(4,4,5,5-tetramethyl-1,3,2-dioxaborolan-2-yl)-1H-pyrrolo[2,3-b]pyridine (B-7-7) (1.8 g) as a brown solid.

Preparation of (2S)-1-(4-(1-isopropyl-3-(2-methyl-1H-pyrrolo[2,3-b]pyridin-5-yl)-1H-pyrazol-4-yl)pyrimidin-2-ylamino)propan-2-ol (B-7)

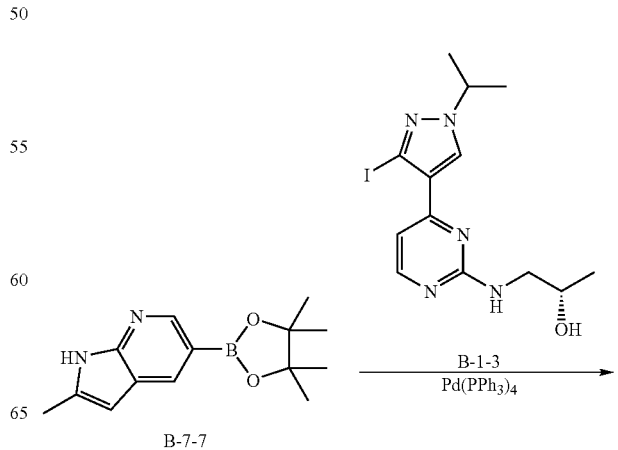

-continued

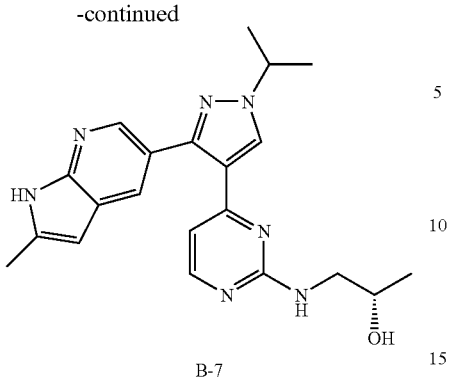

B-7

To a suspension of 2-methyl-5-(4,4,5,5-tetramethyl-1,3,2-dioxaborolan-2-yl)-1H-pyrrolo[2,3-b]pyridine (B-7-7) (1.8 g, 2.3 mmol in the theory) and (2S)-1-(4-(3-iodo-1-isopropyl-1H-pyrazol-4-yl)pyrimidin-2-ylamino)propan-2-ol (B-1-3) (0.45 g, 1.2 mmol) in toluene/EtOH (3:1, 50 mL) was added aq. $Na_2CO_3$ (1.7 mL, 2 M). The mixture was degassed under $N_2$ for 2 minutes, $Pd(PPh_3)_4$ (0.05 g, 0.042 mmol) was added into the mixture and degassed again. The mixture was stirred at 80° C. for 30 hours. TLC ($CH_2Cl_2$: MeOH=20:1) showed that the reaction was complete. Water (50 mL) and EtOAc (50 mL×3) were added into the mixture. The organic layer was separated, dried over anhydrous $Na_2SO_4$ and concentrated to give crude product which was purified via prep. HPLC to afford (2S)-1-(4-(1-isopropyl-3-(2-methyl-1H-pyrrolo[2,3-b]pyridin-5-yl)-1H-pyrazol-4-yl)pyrimidin-2-ylamino)propan-2-ol (B-7) (0.169 g, 18.6%) as a white solid.

Example B-8

Preparation of (2S)-1-(4-(1-isopropyl-3-(2-methylimidazo[1,2-a]pyrimidin-6-yl)-1H-pyrazol-4-yl)pyrimidin-2-ylamino)propan-2-ol (B-8)

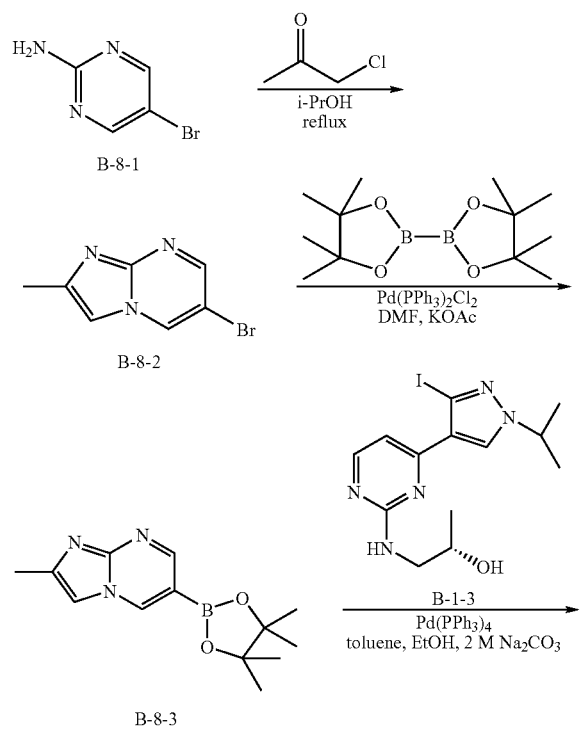

-continued

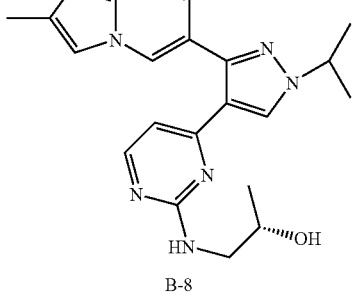

B-8

Preparation of 6-bromo-2-methylimidazo[1,2-a]pyrimidine (B-8-2)

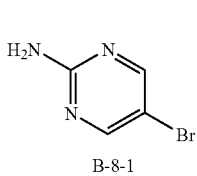

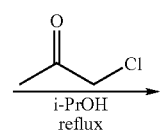

B-8-2

To a solution of 5-bromopyrimidin-2-amine (170.0 g, 0.98 mol) in i-PrOH (2 L) and DMF (500 mL) was added 1-chloropropan-2-one (606 g, 6.53 mol), then the mixture was stirred at 10° C. for 16 h. TLC (petroleum ether:ethyl acetate=1:2) showed the reaction was complete. The reaction mixture was quenched by $Na_2CO_3$ and filtered. The filtrate was concentrated in vacuo and the residue was purified by column chromatography (petroleum ether:ethyl acetate=5:1) to afford compound B-8-2 (10.0 g, 4.8%) as a yellow solid.

Preparation of 2-methyl-6-(4,4,5,5-tetramethyl-1,3,2-dioxaborolan-2-yl)imidazo[1,2-a]pyrimidine (B-8-3)

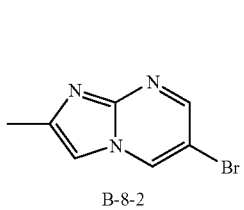
B-8-2

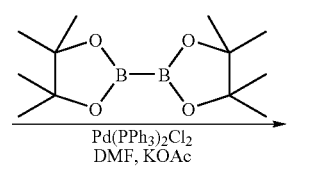

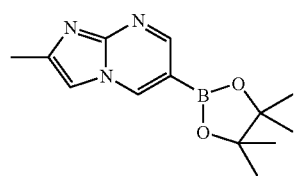
B-8-3

To a solution of compound B-8-3 (3.0 g, 14.1 mmol) in DMF (60 mL) were added bis(pinacolato)diboron (3.95 g, 15.5 mmol) and KOAc (4.58 g, 42.4 mmol). The resulting mixture was degassed under N₂ for 2 minutes. Then Pd(PPh₃)₂Cl₂ (0.20 g, 0.23 mmol) was added and the mixture was degassed again. The resulting mixture was heated to 90° C. and stirred overnight. TLC (petroleum ether:ethyl acetate=1:2) showed the reaction was complete. The mixture was then cooled and filtered. The filtrate was concentrated to give crude compound B-8-3 (2.5 g) as a brown solid, which was used for the next step without purification.

Preparation of (2S)-1-(4-(1-isopropyl-3-(2-methylimidazo[1,2-a]pyrimidin-6-yl)-1H-pyrazol-4-yl)pyrimidin-2-ylamino)propan-2-ol (B-8)

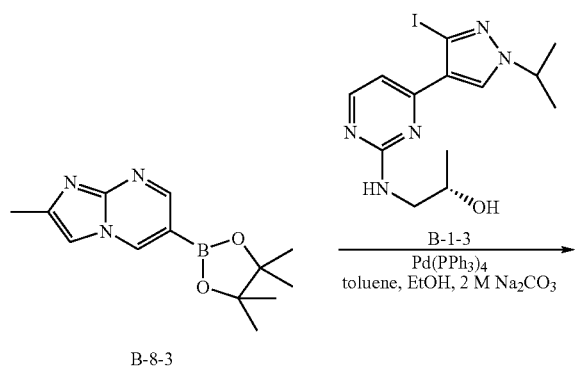

To a solution of compound B-1-3 (2.0 g, 5.16 mmol) in toluene (48 mL) and EtOH (16 mL) were added crude compound B-8-3 (2.5 g, 9.26 mmol) and 2 N aqueous Na₂CO₃ (7.5 mL). The resulting mixture was degassed under N₂ for 2 minutes. Then Pd(PPh₃)₄ (0.41 g, 0.36 mmol) was added and the mixture was degassed again. The resulting mixture was heated to 80° C. and stirred overnight. TLC(CH₂CL₂:MeOH=20:1) showed the reaction was complete, the mixture was cooled. The organic layer was separated and concentrated, and the residue was purified by prep. HPLC to give compound (B-8) (60 mg, 1.6%) as a yellow solid.

Example B-9

Preparation of (2S)-1-(4-(3-(2,3-dimethylimidazo[1,2-a]pyrimidin-6-yl)-1-isopropyl-1H-pyrazol-4-yl)pyrimidin-2-ylamino)propan-2-ol PF-04597926. (B-9)

Preparation of 3-bromobutan-2-one (B-9-2)

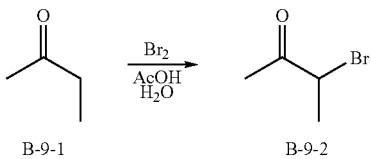

To a solution of butan-2-one (600 g, 8.3 mol) in AcOH (500 mL) and H₂O (2 L) was added dropwise bromine (360 g, 8.5 mol) at 70° C. for 3 h, then the resulting mixture was stirred at room temperature for 14 hrs. TLC (petroleum ether:ethyl acetate=5:1) showed the reaction was complete. Water (1 L) was added, and the organic layer was separated. The aqueous layer was extracted with EtOAc (400 mL×3). The combined organic layers were dried over Na₂SO₄ and concentrated. The residue was distilled to yield compound B-9-2 (400 g, 70%) as a yellow oil.

Preparation of 6-bromo-2,3-dimethylimidazo[1,2-a]pyrimidine (B-9-4)

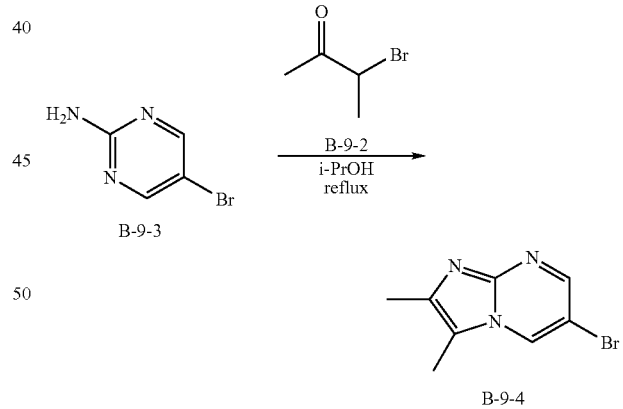

To a solution of 5-bromopyrimidin-2-amine (400 g, 2.2 mol) in i-PrOH (2 L) and DMF (500 mL) was added compound B-9-2 (400 g, 2.6 mol), the resulting mixture was stirred at 100° C. for 20 hrs. TLC (petroleum ether:ethyl acetate=1:1) showed the reaction was complete, the reaction mixture was quenched by addition of aqueous Na₂CO₃ and filtered. The filtrate was concentrated in vacuo and the residue was purified by column chromatography (petroleum ether:ethyl acetate=1:1) to afford compound B-9-4 (12.0 g, 2.4%) as a yellow solid.

Preparation of 2,3-dimethyl-6-(4,4,5,5-tetramethyl-1,3,2-dioxaborolan-2-yl)imidazo[1,2-a]pyrimidine (B-9-5)

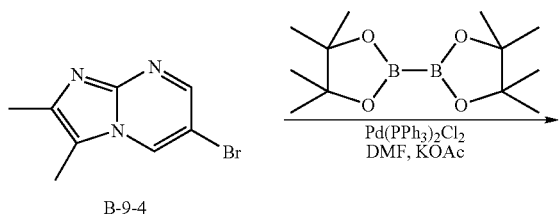

To a solution of compound B-9-4 (2.0 g, 8.92 mmol) in DMF (60 mL) were added bis(pinacolato)diboron (2.79 g, 11 mmol) and KOAc (2.74 g, 30 mmol), and the resulting mixture was degassed under $N_2$ for 2 minutes. Then $Pd(PPh_3)_2Cl_2$ (0.20 g, 0.23 mmol) was added and the mixture was degassed again. The resulting mixture was heated to 90° C. and stirred overnight. The mixture was cooled, filtered and the filtrate was concentrated to give crude compound B-9-5 (2.4 g) as a brown solid, which was used for the next step without purification.

Preparation of (2S)-1-(4-(3-(2,3-dimethylimidazo[1,2-a]pyrimidin-6-yl)-1-isopropyl-1H-pyrazol-4-yl)pyrimidin-2-ylamino)propan-2-ol (B-9)

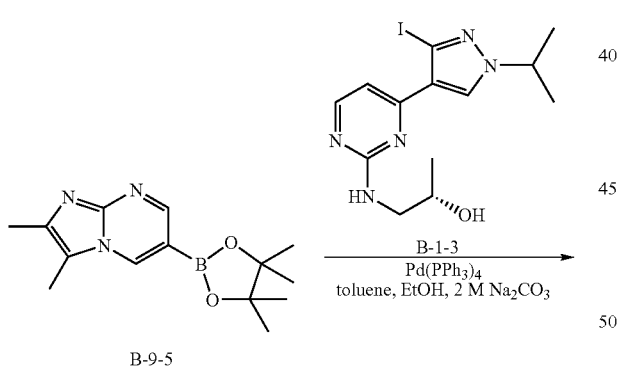

To a solution of compound B-1-3 (2.0 g, 5.16 mmol) in toluene (48 mL) and EtOH (16 mL) were added compound B-9-5 (2.4 g) and 2 N aqueous $Na_2CO_3$ (7.5 mL), and the resulting mixture was degassed under $N_2$ for 2 minutes. Then $Pd(PPh_3)_4$ (0.41 g, 0.36 mmol) was added and the mixture was degassed again. The resulting mixture was heated to 80° C. and stirred overnight. When the mixture was cooled, the organic layer was separated and concentrated. The residue was purified by prep. HPLC to give compound B-9 (220 mg, 1.6%) as a yellow solid.

Example B-10

Preparation of (2S)-1-(4-(1-isopropyl-3-(5-methyl-5H-pyrrolo[3,2-b]pyrazin-2-yl)-1H-pyrazol-4-yl)pyrimidin-2-ylamino)propan-2-ol (B-10)

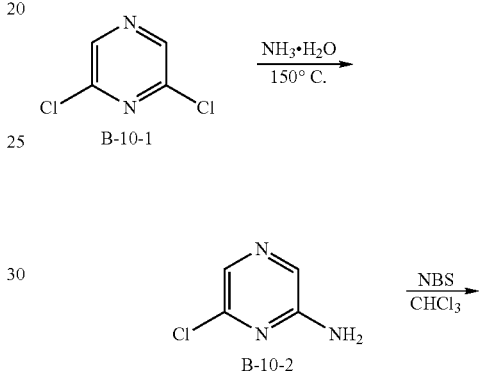

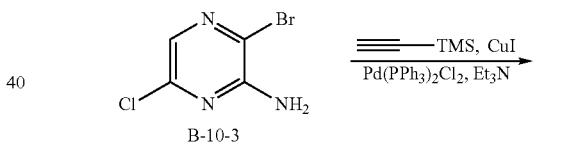

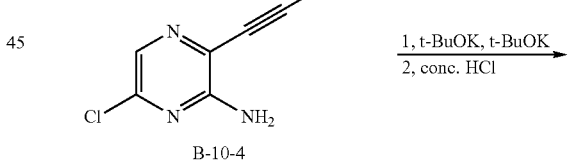

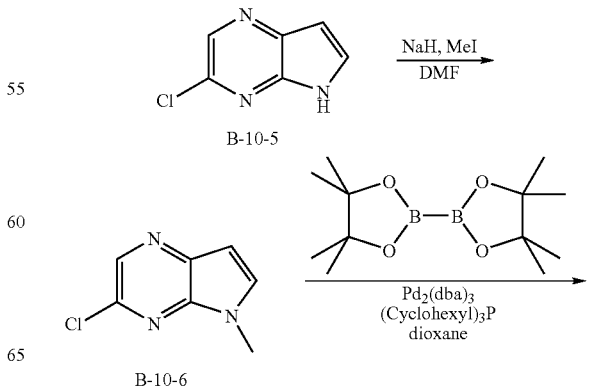

-continued

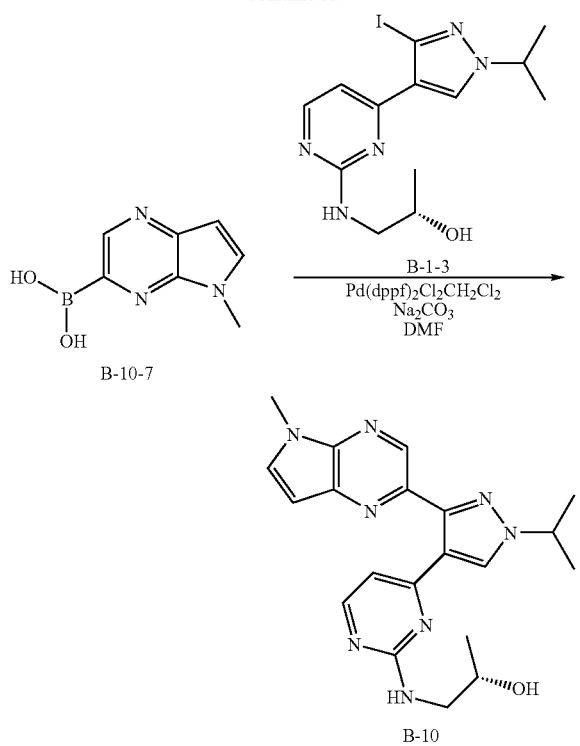

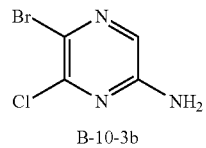

To a solution of compound B-10-2 (110 g, 0.85 mol) in CHCl₃ (1.5 L) was added N-bromo-succinimide (151.3 g, 0.85 mol) portionwise at 0° C. under N₂ atmosphere. After the addition, the reaction mixture was warmed to room temperature and stirred overnight. TLC (petroleum ether/EtOAc 3:1) indicated most of compound B-10-2 was consumed. The reaction mixture was washed with saturated Na₂CO₃ (1 L×3), H₂O (1 L×3) and saturated aqueous NaCl (1 L) in sequence, dried over Na₂SO₄ and concentrated in vacuo. The residue was purified via column chromatography (silica gel, EtOAc/hexane 1:20) to yield pure B-10-3b (35 g) and pure compound B-10-3 (45 g, 28%) as a yellow solid.

Preparation of 6-chloro-3-(2-(trimethylsilyl)ethynyl)pyrazin-2-amine (B-10-4)

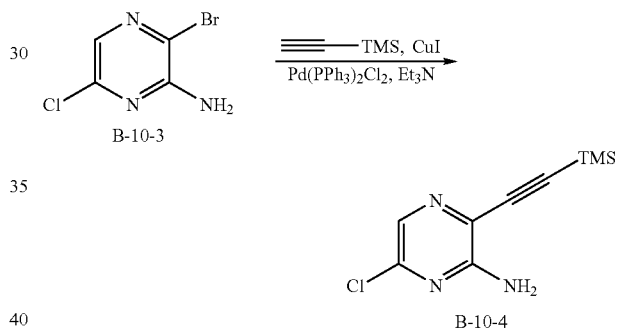

Preparation of 6-chloropyrazin-2-amine (B-10-2)

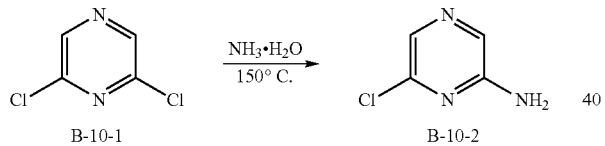

A mixture of 2,6-dichloropyrazine (300 g, 2 mol) and 28% aq. NH₃ (8 L) was stirred at 140° C. in a sealed system for 14 hours. TLC (petroleum ether/EtOAc 3:1) indicated complete consumption of starting material. The reaction mixture was extracted with EtOAc (3 L×3). The combined organic layers were washed with saturated aqueous NaCl (3 L), dried over Na₂SO₄ and concentrated in vacuo to give crude compound B-10-2, which was purified by column chromatography (silica gel, petroleum ether/EtOAc 2:1) to yield pure compound B-10-2 (410 g, yield: 59.7%) as a white solid.

Preparation of 3-bromo-6-chloropyrazin-2-amine (B-10-3)

To a mixture of compound B-10-3 (70 g, 0.336 mol), CuI (6.3 g, 0.0336 mol) and Pd(PPh₃)₂Cl₂ (7 g) in Et₃N (1 L) was added ethynyl-trimethyl-silane (35.6 g, 0.352 mol) dropwise at 0° C. under N₂ atmosphere. After the addition, the reaction mixture was warmed to room temperature and stirred for 1.5 hours. TLC (petroleum ether/EtOAc 5:1) indicated complete consumption of starting material. The mixture was concentrated in vacuo to give crude compound B-10-4, which was purified by column chromatography (silica gel, petroleum ether/EtOAc 20:1) to yield pure compound B-10-4 (36.5 g, yield 42%) as a yellow solid.

Preparation of 3-chloro-5H-pyrrolo[2,3-b]pyrazine (B-10-5)

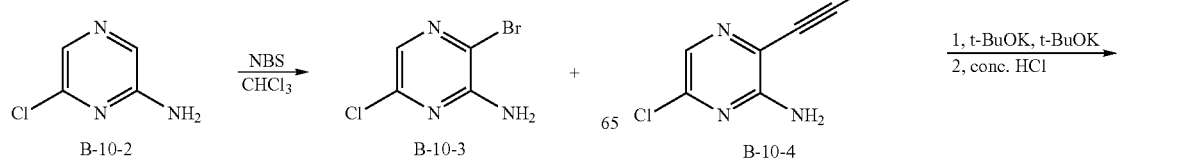

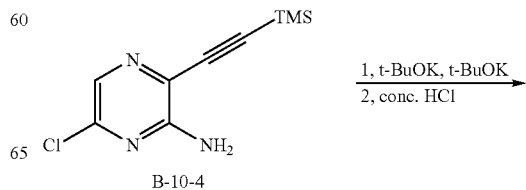

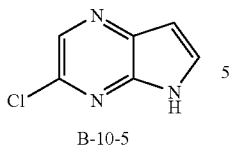

B-10-5

A solution of compound B-10-4 (32 g, 0.14 mol) and t-BuOK (63.5 g, 0.57 mol) in t-BuOH (1 L) was stirred at 80° C. overnight. TLC (petroleum ether/EtOAc 5:1) indicated complete consumption of starting material. The reaction mixture was allowed to cool to room temperature. Then conc. HCl (200 mL) was added to the mixture. The resulting mixture was heated to 80° C. and refluxed overnight. TLC (petroleum ether/EtOAc 5:1) indicated the reaction was complete. The reaction mixture was allowed to cool to room temperature, poured into water (1 L) and extracted with EtOAc (1 L×3). The combined organic layers were washed with 50% $Na_2CO_3$ (300 mL), $H_2O$ (500 mL) and saturated aqueous NaCl (1 L) in sequence, dried over $Na_2SO_4$ and concentrated in vacuo to give crude B-10-5 which was purified by column chromatography (silica gel, petroleum ether/EtOAc 10:1) to yield pure B-10-5 (15 g, yield: 63%) as a yellow solid.

Preparation of
3-chloro-5-methyl-5H-pyrrolo[2,3-b]pyrazine
(B-10-6)

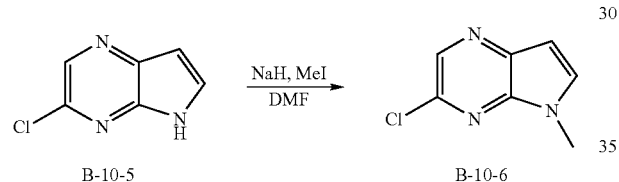

A solution was made of 310 mg (1.95 mmol) of compound B-10-5 in 3 ml of anhydrous DMF. This mixture was added to a solution of 125 mg (3.05 mmol) of 60% NaH dispersion in mineral oil in 3 ml of anhydrous DMF. Another 6 ml of DMF was used to rinse the container. Let stir reaction mixture stir for 15 min at room temperature. Added another 150 µl (2.40 mmol) of MeI. Let stir for 2 hr. LCMS shows one peak M+H=168 with Cl isotope pattern. The reaction mixture was poured into saturated $NH_4Cl$ solution (100 ml) slowly, then extracted with EtOAc (3×50 ml). The organics were combined, dried over $MgSO_4$ and filtered. Silicia gel chromoatography using EtOAc/Hexane gave 257 mg (76% yield) of compound B-10-6 as a yellow solid.

Preparation of
5-methyl-5H-pyrrolo[2,3-b]pyrazin-3-ylboronic acid
(B-10-7)

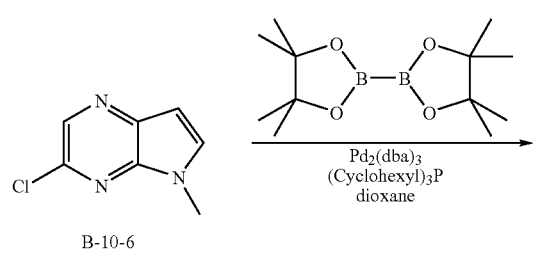

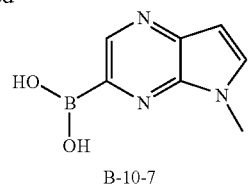

B-10-7

In a flask, dissolved 36 mg (0.128 mmol) of tricyclohexylphosphine and 48 mg (0.052 mmol) of $Pd_2(dba)_3$ in 5 ml of anhydrous dioxane. Bubbled in Argon for 10 minutes and let stir at room temperature for another 20 minutes. To this was added 429 mg (1.69 mmol) of bis(pinacolato)diboron. Finally, added a suspension of 257 mg (1.53 mmol) of compound B-10-6 and 226 mg (2.30 mmol) of KOAc in 5 ml of dioxane. Fitted reaction flask with air condensor and heated to 80° C. overnight. After 24 h, poured reaction mixture into saturated aqueous NaCl, extracted with EtOAc (3×75 ml) and washed with water. The organics were combined, dried over $MgSO_4$, filtered, and the solvents were removed in vacuo. A gradient column on Biotage was run with $CHCl_3$ to 15% (5% $NH_4OH$ in EtOH) in $CHCl_3$ to isolate compound B-10-7 as a brown solid (73 mg, 27% yield).

Preparation of (2S)-1-(4-(1-isopropyl-3-(5-methyl-5H-pyrrolo[3,2-b]pyrazin-2-yl)-1H-pyrazol-4-yl)pyrimidin-2-ylamino)propan-2-ol (B-10)

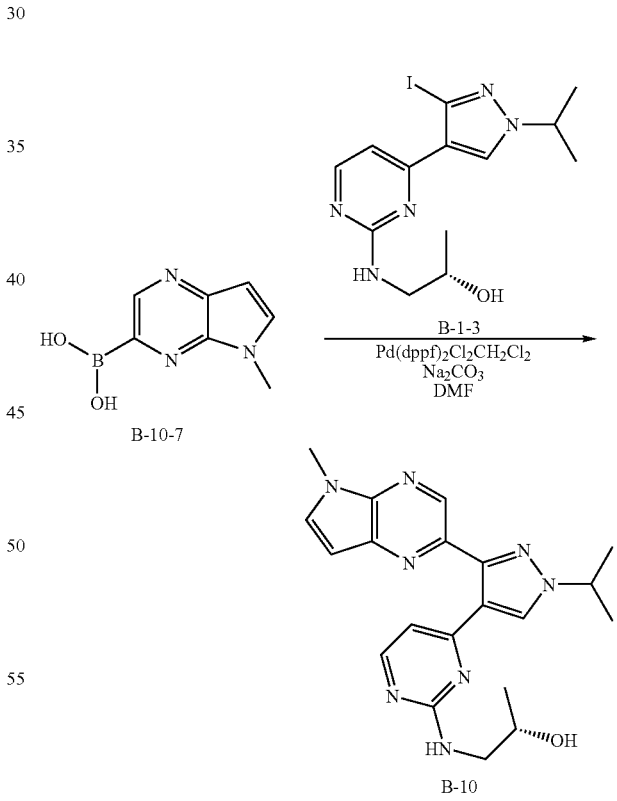

In a flask was dissolved 155 mg (0.40 mmol) of compound B-1-3 and 73 mg (0.41 mmol) of boronic acid B-10-7 in 6 ml of anhydrous DMF. To this mixture was added 600 µl of 2.0 M $Na_2CO_3$ solution. Argon gas was bubbled into the reaction mixture for 10 minutes. Finally, 17 mg (0.052 mmol) of $Pd(dppf)_2CH_2Cl_2$ catalyst was added and the reaction was heated to 80° C. overnight. After 20 h, the reaction mixture was poured into 40 ml of saturated aqueous NaCl and extracted with EtOAc (3×50 ml). The organic extracts were combined, dried over magnesium sulfate, filtered, and the solvent removed in vacuo. Compound (B-10) was isolated by HPLC as a glassy solid in 20% yield (34 mg).

Example B-12

Preparation of (2S)-1-(4-(3-(2,3-dihydro-1H-pyrrolo[2,3-b]pyridin-5-yl)-1-isopropyl-1H-pyrazol-4-yl)pyrimidin-2-ylamino)propan-2-ol (B-12)

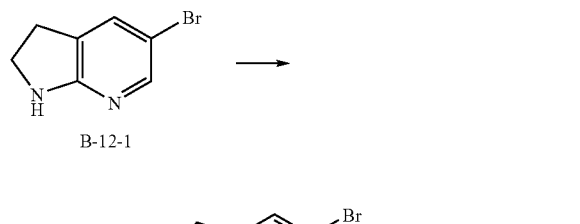

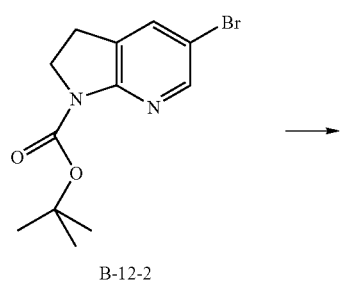

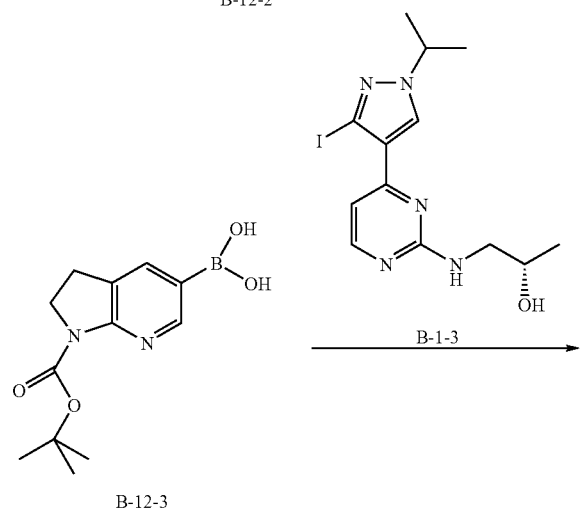

Preparation of tert-butyl 5-bromo-2,3-dihydropyrrolo[2,3-b]pyridine-1-carboxylate (B-12-2)

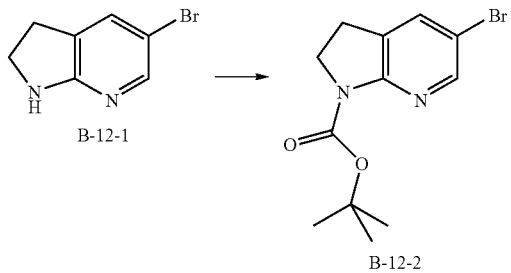

To a stirred solution of 5-bromo-2,3-dihydro-1H-pyrrolo[2,3-b]pyridine (500 mg, 2.51 mMoles) and Boc-anhydride (658 mg, 3.01 mMoles) in 10 mL of DMF was added diisopropyl ethylamine (357 mg, 2.76 mMoles). The mixture was refluxed for one hour under nitrogen. TLC indicated reaction complete. Reaction was concentrated to dryness (under high vacuum). The residual was partitioned between EtOAc and saturated aqueous NaCl. The organic layer was washed with saturated aqueous NaCl, dried over sodium sulfate, filtered and concentrated under reduced pressure. The residue was chromatographed on a 15 g pre-packed silica gel cartridge. Elution with 0~5% EtOAc in DCM gave tert-butyl 5-bromo-2,3-dihydropyrrolo[2,3-b]pyridine-1-carboxylate (B-12-2) as an off-white solid (725 mg). $^1$H NMR (400 MHz, CHLOROFORM-d) δ ppm 1.56 (s, 9H) 3.05 (t, J=8.59 Hz, 2H) 4.03 (t, 2H) 7.50 (d, J=2.02 Hz, 1H) 8.26 (d, J=2.02 Hz, 1H).

Preparation of 1-(tert-butoxycarbonyl)-2,3-dihydro-1H-pyrrolo[2,3-b]pyridin-5-ylboronic acid (B-12-3)

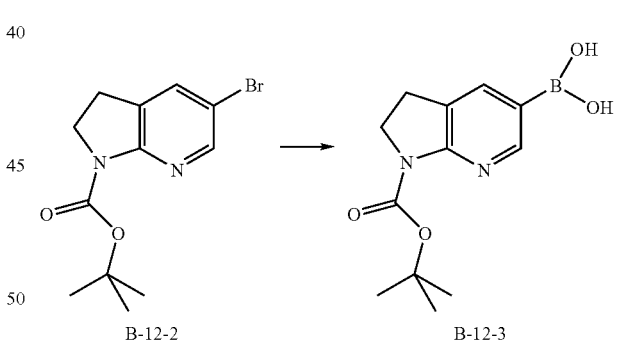

To a mixture of tert-butyl 5-bromo-2,3-dihydropyrrolo[2,3-b]pyridine-1-carboxylate (B-12-2) (725 mg, 2.42 mMoles) and bis(pinacolato) diboron (894 mg, 3.52 mMoles) in 20 ml DMF were added potassium acetate (691 mg, 7.04 mMoles) and [1,1-Bis(diphenylphosphino)-ferrocene]dichloropalladium (II) dichloromethane (1:1) complex (34.3 mg, 0.0469 mMoles). The mixture was heated in 100° C. microwave reactor for 60 min. LCMS indicated reaction was complete. RXN was filtered and the filtrate was concentrated to dryness under high vacuum. The residual was partitioned between EtOAc and saturated aqueous NaCl. The aqueous layer was extracted with EtOAc (3×40 mL). The combined organic layers were dried over sodium sulfate, filtered and concentrated under reduced pressure. The residue was chromatographed on a 25 g silica gel cartridge with 1~4% MeOH in DCM as solvent. The crude product and was used as is in the next step.

Preparation of (2S)-1-(4-(3-(2,3-dihydro-1H-pyrrolo [2,3-b]pyridin-5-yl)-1-isopropyl-1H-pyrazol-4-yl) pyrimidin-2-ylamino)propan-2-ol (B-12)

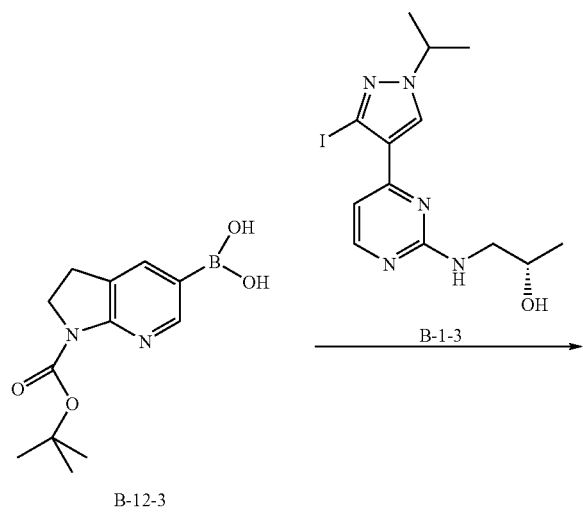

B-12

To a solution of 1-(tert-butoxy carbonyl)-2,3-dihydro-1H-pyrrolo[2,3-b]pyridine-5-ylboronic acid (B-12-3) (546 mg, 2.07 mMoles) and (2S)-1-(4-(3-iodo-1-isopropyl-1H-pyrazol-4-yl)pyrimidin-2-ylamino)propan-2-ol (400 mg, 1.03 mMoles) in 10 mL of DMF were added [1,1-Bis(diphenylphosphino)-ferrocene]dichloropalladium (II) dichloromethane (1:1) complex (22.7 mg, 0.031 mMoles) and 2N aqueous solution of sodium carbonate (1.55 mL, 3.10 mMoles). The mixture was flushed with nitrogen for 5 min and then heated in microwave for 1 hour at 100° C. LCMS indicated reaction complete. RXN was filtered and the filtrate was concentrated to a residual under high vacuum. The residual was partitioned between EtOAc and water. The organic layer was washed once with saturated aqueous NaCl and dried over sodium sulfate, filtered and concentrated to a residue. The residue was then loaded onto a 25 g silica-gel cartridge. Elution first with 50% EtOAc in DCM and then 2-5% MeOH in 1:3 MTBE:DCM gave the Boc-protected product as a white solid. Treating it with 4N HCl in dioxane in DCM overnight at room temperature under nitrogen followed by solvent removal gave a brownish residual. This residual was dissolved in DCM, washed with saturated sodium bicarbonate, dried over sodium sulfate, concentrated and then loaded onto a 15 g silica gel cartridge. Elution with 2~5% MeOH in DCM gave (2S)-1-(4-(3-(2,3-dihydro-1H-pyrrolo [2,3-b]pyridin-5-yl)-1-isopropyl-1H-pyrazol-4-yl)pyrimidin-2-ylamino)propan-2-ol (B-12) as a white foam (125 mg).

Example B-33

Preparation of 3-({4-[1-(2,2-difluoroethyl)-3-(1H-pyrrolo[2,3-b]pyridin-5-yl)-1H-pyrazol-4-yl]pyrimidin-2-yl}amino)propanenitrile Preparation of 4-(1-(2,2-difluoroethyl)-3-iodo-1H-pyrazol-4-yl)-2-(methylthio)pyrimidine (B-33-1)

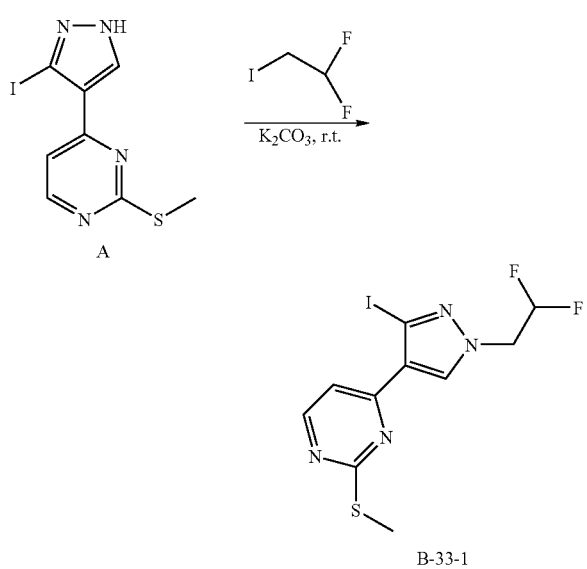

B-33-1

To a solution of Intermediate A (83 g, 0.26 mol) in DMF (600 mL) were K$_2$CO$_3$ (58 g, 0.417 mol) and 1,1-difluoro-2-iodo-ethane (60 g, 0.313 mol). Then the mixture was stirred at room temperature overnight. TLC (CH$_2$Cl$_2$: MeOH=20:1) showed the reaction was complete. The mixture was concentrated and the solid was diluted with CH$_2$Cl$_2$ (500 mL). The slurry was filtered and the filtrate was concentrated to give crude product, which was purified via prep. SFC to give compound B-33-1 (41.1 g, 41.3%) as a white solid.

Preparation of 4-(1-(2,2-difluoroethyl)-3-iodo-1H-pyrazol-4-yl)-2-(methylsulfonyl)pyrimidine and/or 4-(1-(2,2-difluoroethyl)-3-iodo-1H-pyrazol-4-yl)-2-(methylsulfinyl)pyrimidine

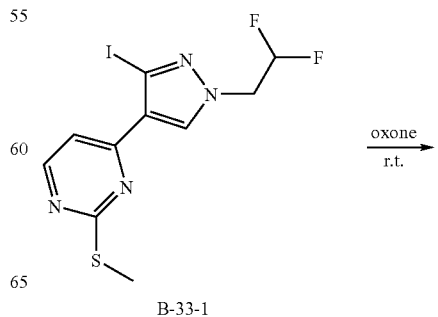

B-33-1

-continued

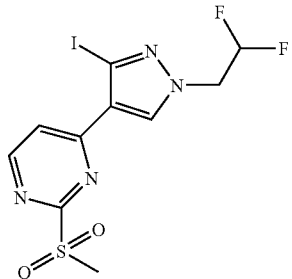
B-33-2a

+

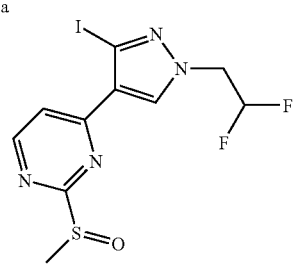
B-33-2b

To a solution of compound B-33-1 (41.1 g, 0.107 mol) in THF (360 mL) was added a solution of Oxone (81.2 g, 0.132 mol) in H₂O (200 mL). Then the mixture was stirred at room temperature overnight. TLC (CH₂Cl₂: MeOH=10:1) showed the reaction was complete. The mixture was concentrated to about one second. The mixture was extracted with CH₂Cl₂ (600 mL). The organic layer was washed with water (100 mL×2), dried over Na₂SO₄ and concentrated to give a mixture of sulfone and sulfoxide (7:3 determined by HPLC) (38.6 g, 88.2%) as a yellow solid.

Preparation of 3-(4-(1-(2,2-difluoroethyl)-3-iodo-1H-pyrazol-4-yl)pyrimidin-2-ylamino)propanenitrile (B-33-3)

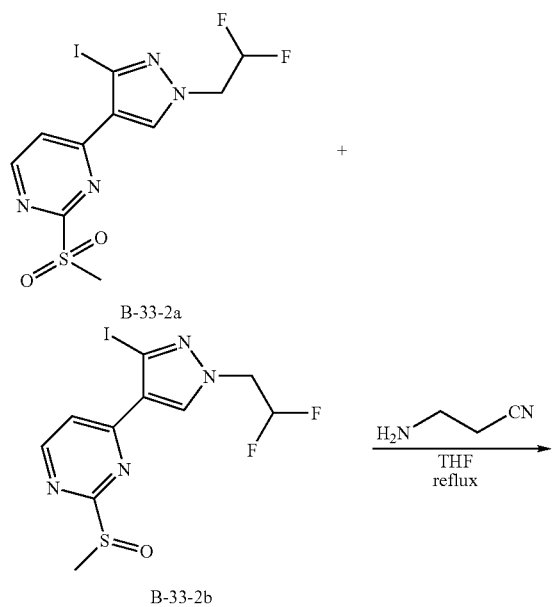

-continued

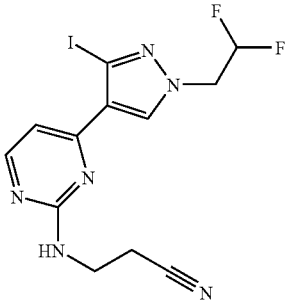
B-33-3

To a mixture of sulfone and sulfonxide (16 g, 0.039 mol) in THF (250 mL) was added 3-amino-propionitrile (16 g, 0.23 mol). Then the mixture was stirred at 80° C. for two days. TLC (CH₂Cl₂:MeOH=10:1) showed the reaction was not complete. The mixture was stirred at this temperature for another one day. The mixture was concentrated to dryness. The residue was purified by silica gel chromatography (CH₂Cl₂:MeOH=80:1) to give B-33-3 (9.8 g, 61.5%) as a white solid.

Preparation of 3-({4-[1-(2,2-difluoroethyl)-3-(1H-pyrrolo[2,3-b]pyridin-5-yl)-1H-pyrazol-4-yl]pyrimidin-2-yl}amino)propanenitrile (B-33)

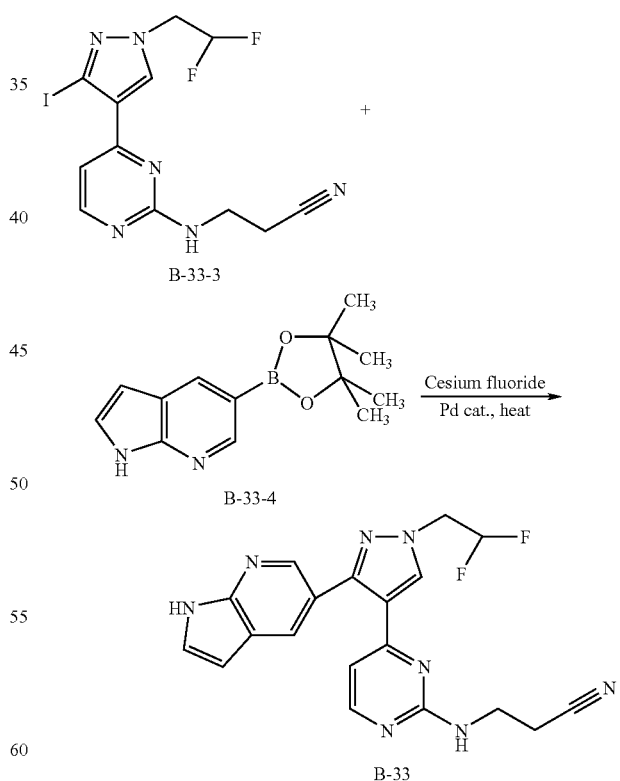

A mixture of the 5-(4,4,5,5-tetramethyl-1,3,2-dioxaborolan-2-yl)-1H-pyrrolo[2,3-b]pyridine B-33-4, which was prepared from 5-bromo-1H-pyrrolo[2,3-b]pyridine according to known literature methods, (145 mg, 0.594 mmol), 3-({4-[1-

(2,2-difluoroethyl)-3-iodo-1H-pyrazol-4-yl]pyrimidin-2-yl}amino)propanenitrile (200 mg, 0.495 mmol), and cesium fluoride (1.48 mL of a 1M aqueous solution) in 3 mL of DME was deoxygenated with a nitrogen bubbler for 5 min and then [1,1'-bis(diphenylphosphino)ferrocene]dichloropalladium (II) 1:1 complex with dichloromethane (41 mg, 0.05 mmol) was added. The mixture was then heated in a microwave reactor at 80° C. for 2.5 hours. The reaction was degassed and fresh catalyst (20 mg) was added. The mixture was heated in the microwave at 80° C. for 4 more hours. The resulting dark mixture was partitioned between ethyl acetate and brine. The aqueous layer was extracted twice with ethyl acetate. The combined organics were washed with brine, dried over Magnesium sulfate and reduced to minimum volume. The residue was purified on silica gel using a gradient of 0-8% methanol (containing 10% ammonium hydroxide) in a mixture of tert-butyl methyl ether and dichloromethane (1:1) to give the desired product as a pale orange solid. This material was triturated twice with tert-butyl methyl ether to give 82 mg (42%) of analytically pure 3-({4-[1-(2,2-difluoroethyl)-3-(1H-pyrrolo[2,3-b]pyridin-5-yl)-1H-pyrazol-4-yl]pyrimidin-2-yl}amino)propanenitrile as an off white solid. $^1$H NMR (400 MHz, ACETONITRILE-d$_3$) δ ppm 9.73 (br. s., 1H), 8.37 (d, J=2.02 Hz, 1H), 8.22 (s, 1H), 8.10 (d, J=5.31 Hz, 1H), 8.08 (d, J=1.52 Hz, 1H), 7.35-7.46 (m, 1H), 6.54 (d, J=3.79 Hz, 1H), 6.51 (dd, J=3.54, 2.02 Hz, 1H), 6.30 (tt, J=55.04, 3.82 Hz, 1H), 5.91 (br. t, J=6.82 Hz, 1H), 4.62 (td, J=14.65, 3.79 Hz, 2H), 3.39 (br. s., 2H), 2.40 (br. s., 2H).

Example B-49

Preparation of 3-(4-(1-(1-hydroxy-2-methylpropan-2-yl)-3-(5-methoxypyridin-3-yl)-1H-pyrazol-4-yl)pyrimidin-2-ylamino)propanenitrile

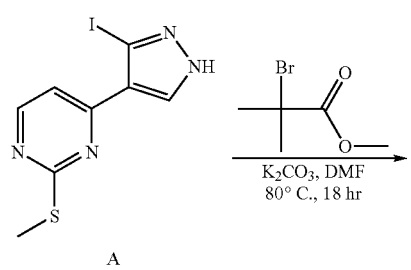

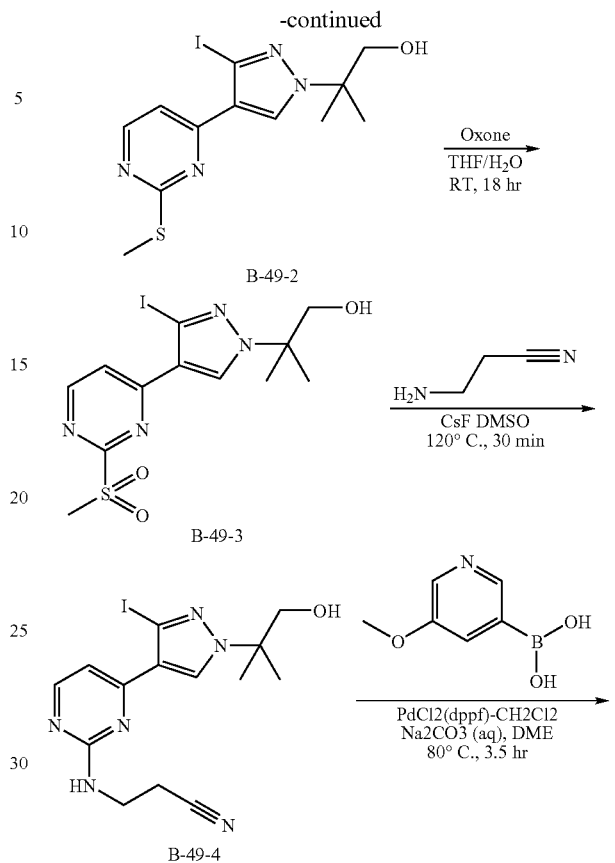

Preparation of methyl 2-(3-iodo-4-(2-(methylthio)pyrimidin-4-yl)-1H-pyrazol-1-yl)-2-methylpropanoate (B-49-1)

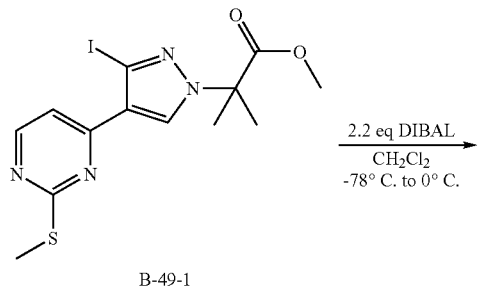

-continued

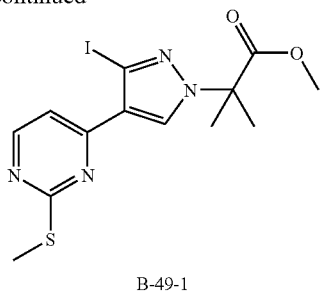

B-49-1

To a mixture compound A (60 g, 0.19 mol) and methyl 2-bromo-2-methylpropanoate (102 g, 0.57 mol) in DMF (400 mL) was added freshly ground potassium carbonate (65 g, 0.47 mol) in one portion. The reaction mixture was stirred at 80° C. for 18 hours. LC-MS indicated the reaction was complete. The reaction mixture was filtered and the filtrate was partitioned between ethyl acetate (1200 mL) and brine (300 mL). The aqueous layer was extracted with EtOAc (2×500 mL). The combined organic layers were washed with brine, dried over anhydrous $Na_2SO_4$ and concentrated. The residue was purified by silica gel chromatography using 5-30% EtOAc in petroleum ether as eluent to give compound B-49-1 (62 g, 78%) as syrup, which solidified on standing.

Preparation of 2-(3-iodo-4-(2-(methylthio)pyrimidin-4-yl)-1H-pyrazol-1-yl)-2-methylpropan-1-ol (B-49-2)

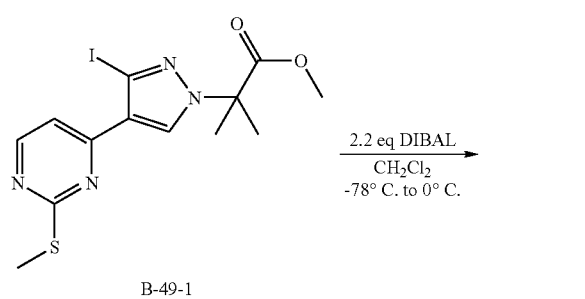

To a solution of compound B-49-1 (48 g, 0.11 mol) in dry $CH_2Cl_2$ (1800 mL) at −78° C. was added dropwise DIBAL solution (256 mL, 1 M) via syringe. The mixture was stirred from −78° C. to 0° C. for 1 hour. The reaction mixture was quenched by the addition of MeOH (80 mL), and then the mixture was diluted with saturated aq. Rochelle salt and $CH_2Cl_2$. The resulting suspension was stirred vigorously until layers were separated. The aqueous layer was extracted with dichloromethane (2×500 mL). The combined organic layers were dried over sodium sulfate and concentrated to 70 g of yellow oil. The oil was purified by chromatography on silica gel using 0-40% ether in DCM as eluent to give compound B-49-2 (20 g, 45%) as a white solid.

Preparation of 2-(3-iodo-4-(2-(methylsulfonyl)pyrimidin-4-yl)-1H-pyrazol-1-yl)-2-methylpropan-1-ol (B-49-3)

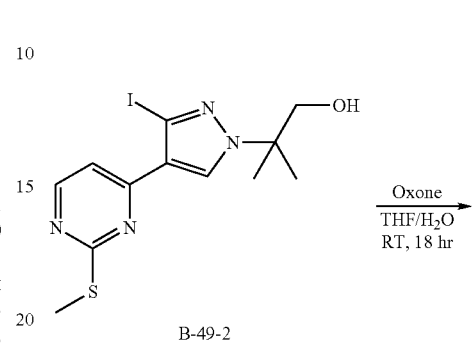

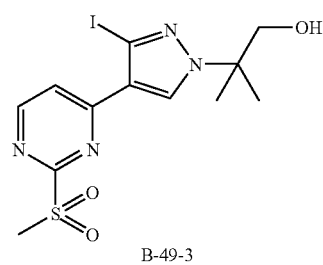

A mixture of compound B-49-3 (20 g, 51 mmol) and Oxone (61.5 g, 0.10 mol) in THF (300 mL) and water (300 mL) was stirred at room temperature overnight. The reaction mixture was partitioned between EtOAc (2 L) and brine (600 mL). The aqueous layer was extracted with EtOAc (1 L×2). The combined organic layers were washed with brine, dried over sodium sulfate and concentrated. The residue was purified by a short column chromatography using 0-50% ether/DCM as eluent to afford the product B-49-3 (15 g, 74%) as a white solid.

Preparation of 3-(4-(1-(1-hydroxy-2-methylpropan-2-yl)-3-iodo-1H-pyrazol-4-yl)pyrimidin-2-ylamino) propanenitrile (B-49-4)

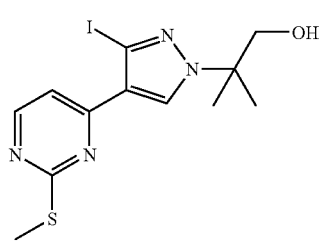

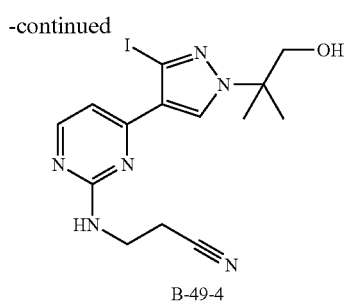

B-49-4

A microwave reaction vessel was charged with sulfone B-49-3 (6 g, 14.3 mmol, in five batches), 3-aminopropanenitrile (3.0 g, 42.9 mmol) and CsF (2.39 g, 15.7 mmol) in DMSO (60 mL). The resulting solution was subjected to microwave irradiation at 120° C. for 30 minutes. The reaction mixture was cooled to room temperature. The mixture was partitioned between EtOAc (600 mL) and brine (100 mL×3). The layers were separated and the aqueous layer extracted with EtOAc (2×200 mL). The combined organic phases were dried over anhydrous $Na_2SO_4$, filtered and concentrated in vacuo. The residue was purified by a short column chromatography using 0-50% EtOAc in petroleum ether as eluent and further purified by prep-HPLC to afford product B-49-4 (3.055 g, 55%) as a brown foamlike solid.

Preparation of 3-(4-(1-(1-hydroxy-2-methylpropan-2-yl)-3-(5-methoxypyridin-3-yl)-1H-pyrazol-4-yl)pyrimidin-2-ylamino)propanenitrile (B-49)

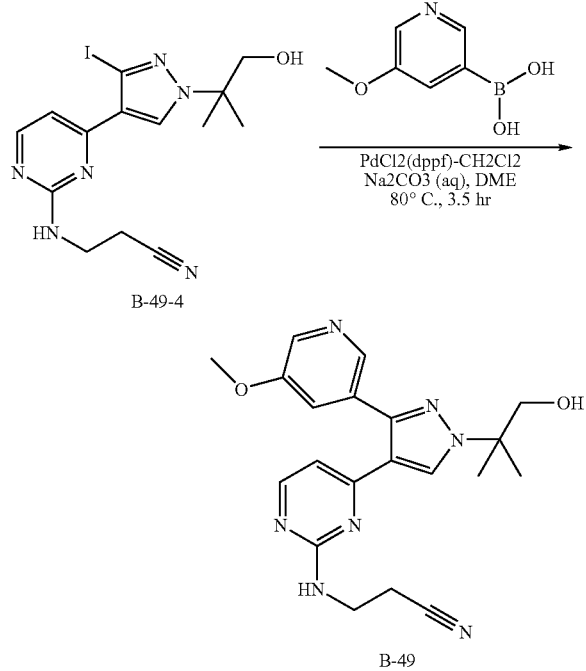

A solution of iodide B-49-4 (156.2 mg, 0.374 mmol) and 5-methoxypyridine-3-boronic acid (122.1 mg, 0.798 mmol) dissolved in DME (3.7 mL) was degassed by evacuation until the solvent just begins to boil, followed by argon purge, 3 cycles. Added 1.5 mL of 2.0 M aqueous sodium carbonate solution and 25.5 mg [1,1'-bis(diphenylphosphino)ferrocene]palladium(II) dichloride dichloromethane complex (0.035 mmol) and degassed 3 more cycles. Heated in 80° C. oil bath for 3.5 hour, then let cool to room temperature overnight. The reaction mixture was partitioned between 25 mL ethyl acetate and 10 mL deionized water. The aqueous layer was back-extracted with 15 mL ethyl acetate. The combined organic extracts were dried over magnesium sulfate, filtered, concentrated, and purified by silica gel chromatography, eluting with 0-20% [ethanol+5% conc. ammonium hydroxide] in ethyl acetate. The product was lyophilized to give B-49 (128.4 mg, 84%) as a pale pink solid.

Preparation of 3-(4-(3-(5-acetyl-6-aminopyridin-3-yl)-1-(2,2-difluoroethyl)-1H-pyrazol-4-yl)pyrimidin-2-ylamino)propanenitrile (B-78)

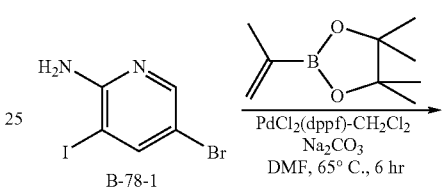

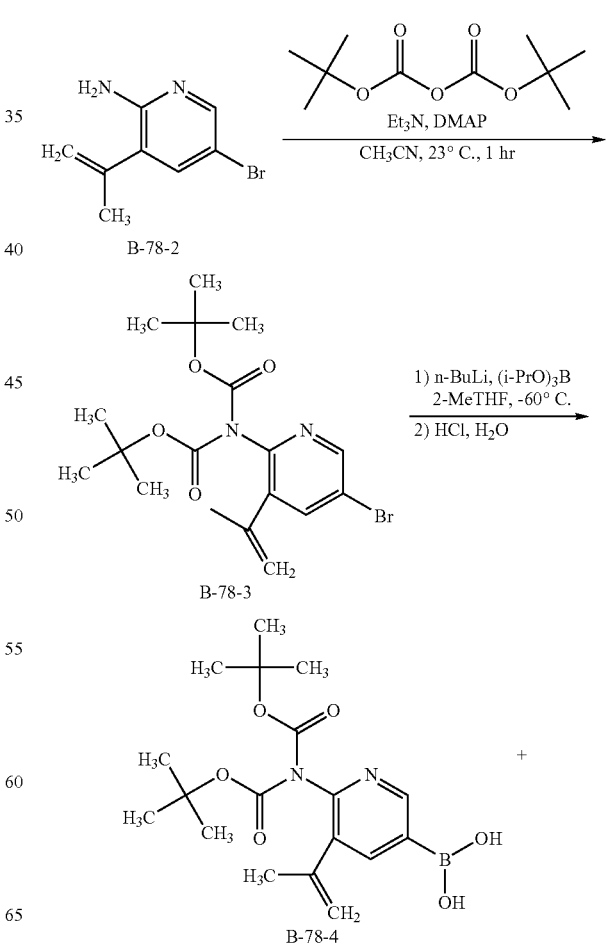

-continued

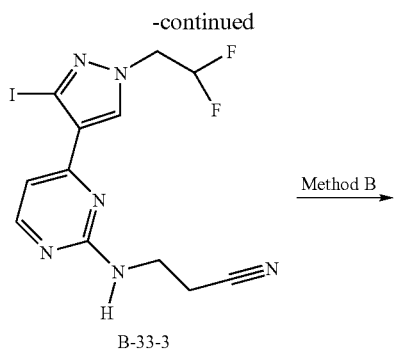
B-33-3

Method B →

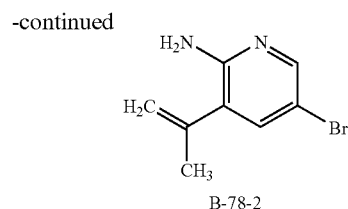
B-78-2

A solution of 2-amino-5-bromo-3-iodopyridine B-78-1 (4.75 g, 15.9 mmol), isopropenylboronic acid pinacol ester (3.28 mL, 2.94 g, 17.5 mmol), and [1,1'-bis(diphenylphosphino)ferrocene]-palladium(II) dichloride dichloromethane complex (1:1) (295 mg, 0.403 mmol) in dimethylformamide (48 mL) was treated with 24 mL of 2.0 M aqueous sodium carbonate solution. The resulting biphasic mixture was stirred under argon in a 65° C. oil bath for 6 hours. After cooling to room temperature, the mixture was diluted with 200 mL ethyl acetate and 75 mL deionized water, then suction-filtered to remove some insoluble black precipitate. After separation, the aqueous layer was back-extracted with 100 mL ethyl acetate. The combined organic extracts were dried over magnesium sulfate, filtered, and concentrated to 5.87 g brown oil. The crude product was purified by silica gel chromatography (eluting with a 10-50% ethyl acetate in hexanes gradient), to give B-78-2 (2.5501 g, 75.3%) as a tan solid.

Preparation of B-78-3

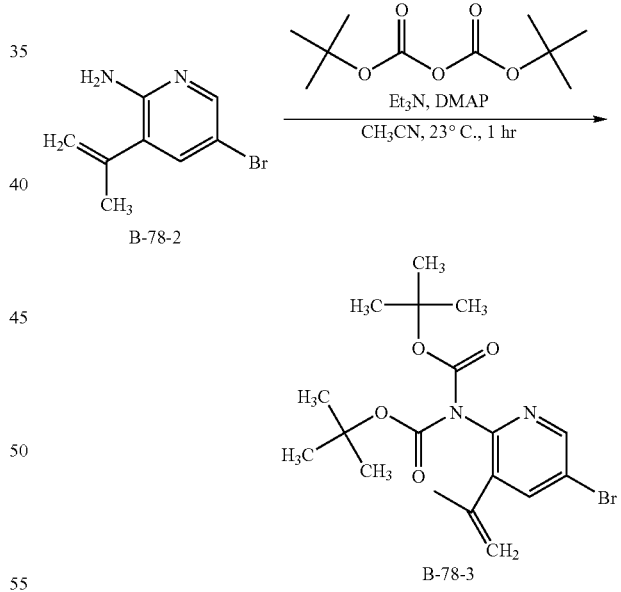

A solution of compound B-78-2 (2.50 g, 11.7 mmol), di-tert-butyldicarbonate (7.75 g, 35.5 mmol), triethylamine (8.3 mL, 60 mmol), and 4-(dimethylamino)pyridine (391 mg, 3.1 mmol) in acetonitrile (59 mL) was stirred at room temperature for 1 hour. The solvents were removed under reduced pressure, then the residue partitioned between 100 mL ethyl acetate and 25 mL saturated aqueous sodium bicarbonate solution. The aqueous layer was back-extracted with 30 mL ethyl acetate, and the combined organic extracts dried over magnesium sulfate, filtered, and concentrated to 5.38 g orange gel. The crude product was purified by silica gel 1) O₃, CH₂Cl₂ -70° C.
2) DMS
30%

B-78-5

B-78

Preparation of 5-bromo-3-(prop-1-en-2-yl)pyridin-2-amine (B-78-2)

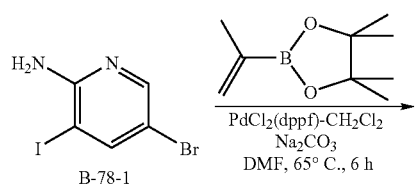
B-78-1

PdCl₂(dppf)-CH₂Cl₂
Na₂CO₃
DMF, 65° C., 6 h chromatography (eluting with 0-40% ethyl acetate in hexanes gradient), affording compound B-78-3 (4.22 g, 87%) as a colorless oil.

Preparation of B-78-4

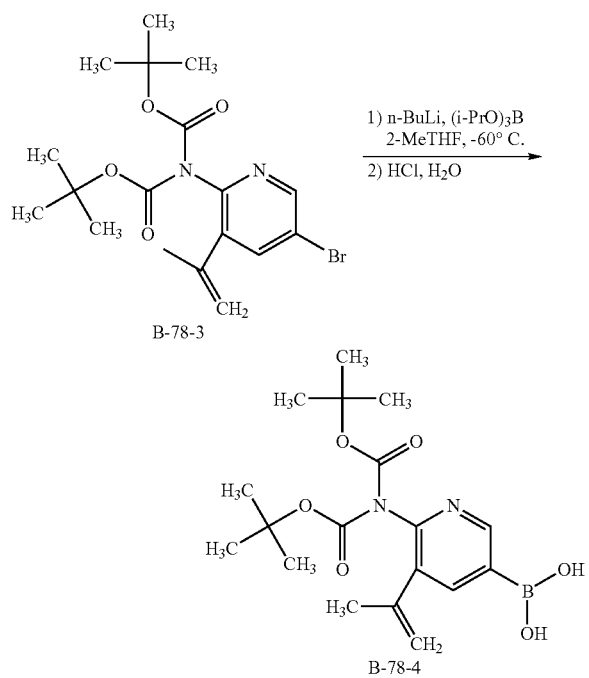

A solution of B-78-3 (4.15 g, 10.0 mmol) and triisopropyl borate (5.8 mL, 4.8 g, 25 mmol) in 2-methyl tetrahydrofuran (67 mL) was cooled to −70° C. (internal temperature). To this was added 16 mL (25.6 mmol) of 1.6 M n-butyllithium in hexanes solution, dropwise over 4 minutes. After stirring at −70° C. for 30 minutes, 25 mL deionized water was added, and the mixture allowed to warm to room temperature. Volatiles were removed in vacuo, and the aqueous residue extracted with diethyl ether (2×30 mL). These extracts were discarded. The aqueous layer was acidified to pH 2 with 6N HCl, and stirred at room temperature overnight, causing a granular white precipitate to form. The precipitate was collected by suction filtration and dried in a 50° C. vacuum oven for 6 hours, to give boronic acid B-78-4 (2.9348 g, 62.2%) as a white powder.

Preparation of 3-(4-(3-(6-amino-5-(prop-1-en-2-yl)pyridin-3-yl)-1-(2,2-difluoroethyl)-1H-pyrazol-4-yl)pyrimidin-2-ylamino)propanenitrile (B-78-5)

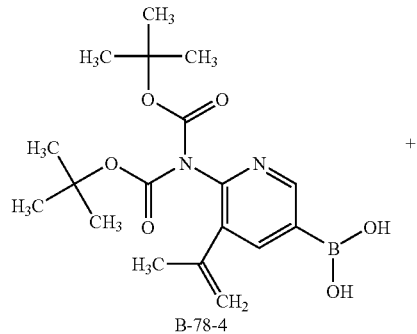

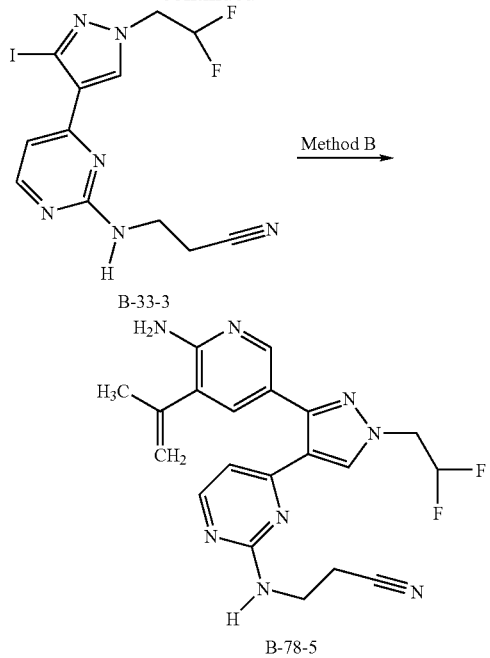

A solution of boronic acid B-78-4 (721.4 mg, 1.88 mmol), iodide B-33-3 (576.0 mg, 1.425 mmol), and [1,1'-bis(diphenylphosphino)ferrocene]palladium(II) dichloride-dichloromethane complex (66.5 mg, 0.091 mmol) in DME (14.2 mL) was treated with 2.0 M aqueous sodium carbonate solution (2.4 mL), and the resulting biphasic mixture heated in an 80° C. oilbath for 15 hours. After cooling to room temperature, the mixture was partitioned between ethyl acetate (50 mL) and deionized water (25 mL). The aqueous layer was back-extracted with 25 mL ethyl acetate. The combined organic extracts were dried over magnesium sulfate, filtered, and concentrated to dryness. The residue was dissolved in dichloromethane (27 mL), trifluoroacetic acid (3 mL) was added, and the mixture stirred at room temperature for 6.5 hr. Then the solvent was evaporated, and the residue partitioned between ethyl acetate (50 mL) and saturated aqueous sodium bicarbonate solution (25 mL). The organic layer was dried over magnesium sulfate, filtered, and concentrated to a brown tar. The crude product was purified by silica gel chromatography, eluting with 0-20% [ethanol+5% conc. ammonium hydroxide] in ethyl acetate, affording B-78-5 (325.7 mg, 56%) as a light brown foam.

Preparation of 3-(4-(3-(5-acetyl-6-aminopyridin-3-yl)-1-(2,2-difluoroethyl)-1H-pyrazol-4-yl)pyrimidin-2-ylamino)propanenitrile (B-78)

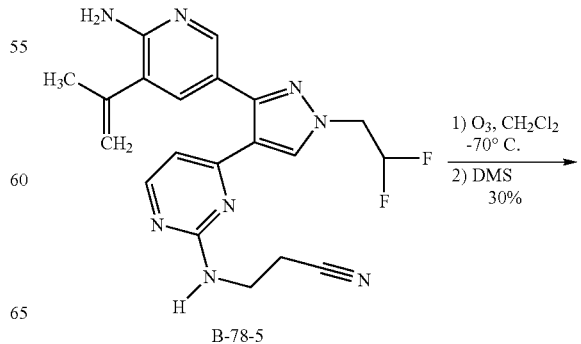

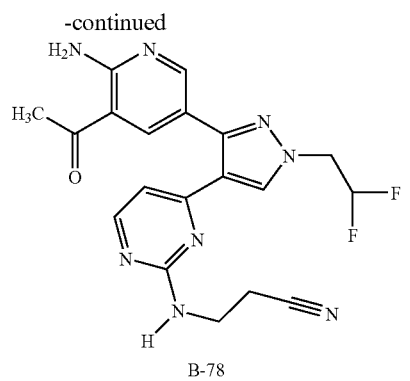

B-78

A solution of alkene 6 (227.8 mg, 0.555 mmol) in dichloromethane (28 mL) was cooled to −70° C. and treated with ozone for 30 seconds, long enough for solution color to change from brown to bright yellow. The solution was purged with nitrogen for 2 minutes, then quenched with dimethyl sulfide (0.50 ml, 6.8 mmol). The cooling bath was removed, and the mixture stirred at room temperature for 3 hours. The solution was concentrated to dryness, and purified by silica gel chromatography, eluting with 0-20% [EtOH+5% NH4OH] in ethyl acetate. Ketone B-78 (63.4 mg, 28%) was obtained as a yellow solid. $^1$H NMR $^1$H NMR (400 MHz, CHLOROFORM-d) δ ppm 2.57 (s, 3H) 2.60-2.71 (m, 2H) 3.56-3.74 (m, 2H) 4.55 (td, J=13.45, 4.17 Hz, 2H) 5.54 (t, J=5.05 Hz, 1H) 6.21 (tt, J=55.29, 4.20 Hz, 1H) 6.61 (d, J=5.31 Hz, 1H) 8.03 (s, 1H) 8.21 (d, J=5.05 Hz, 1H) 8.23 (d, J=2.02 Hz, 1H) 8.45 (d, J=2.27 Hz, 1H).

Example B-79

Preparation of 3-{4-[3-(5-Amino-6-methoxy-pyrazin-2-yl)-1-(2,2-difluoro-ethyl)-1H-pyrazol-4-yl]-pyrimidin-2-ylamino}-propionitrile

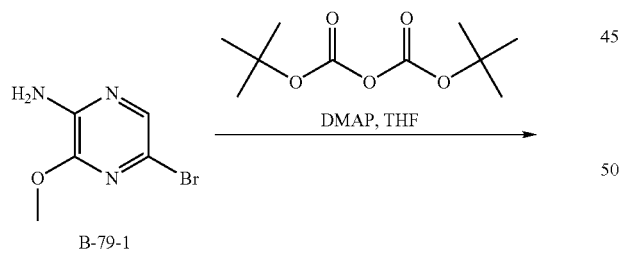

B-79-1

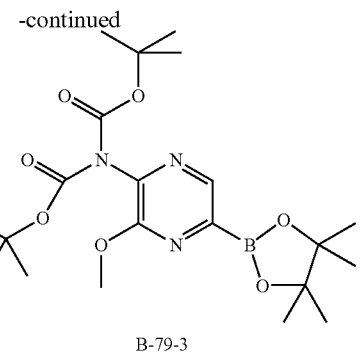

B-79-3

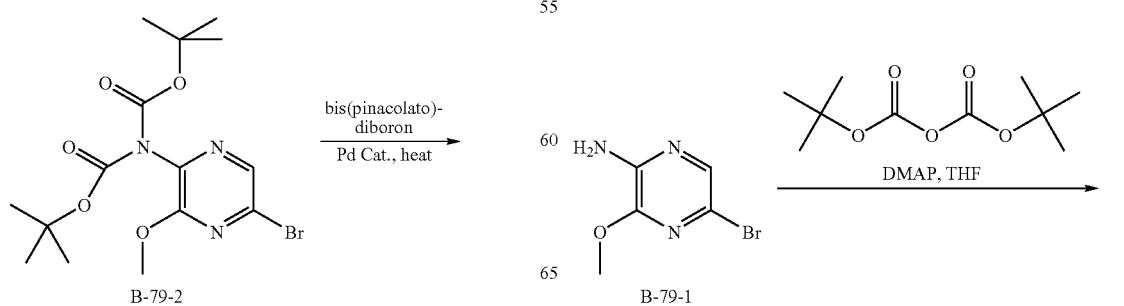

Preparation of B-79-2

124

Preparation of 3-{4-[3-(5-Amino-6-methoxy-pyrazin-2-yl)-1-(2,2-difluoro-ethyl)-1H-pyrazol-4-yl]-pyrimidin-2-ylamino}-propionitrile (B-79)

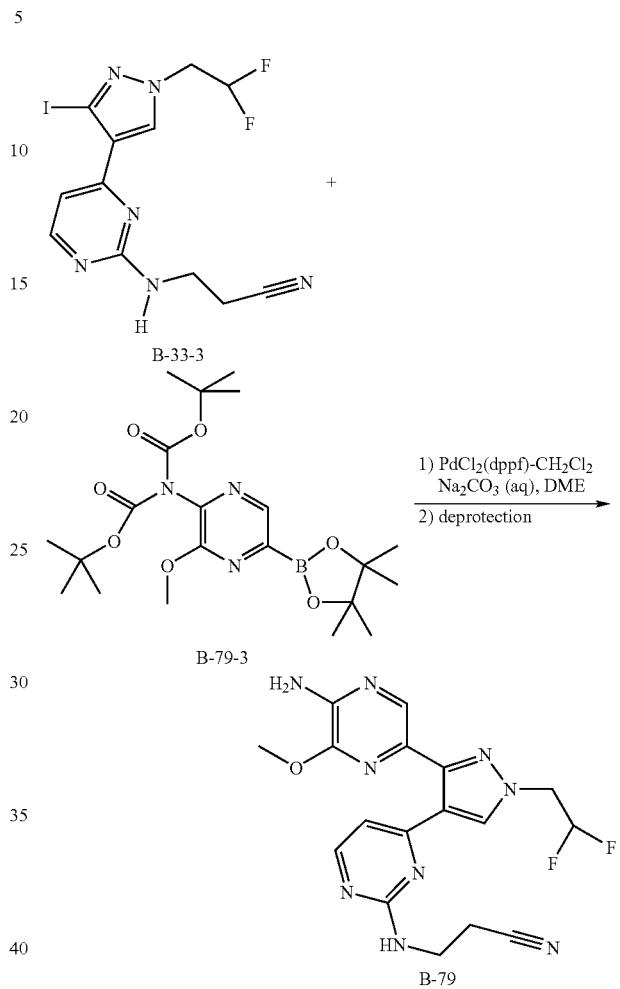

To a solution of the crude di-tert-butyl[3-methoxy-5-(4,4,5,5-tetramethyl-1,3,2-dioxaborolan-2-yl)pyrazin-2-yl]imidodicarbonate B-79-3 (0.6 mmol) in dimethoxyethane (2.5 mL) was added 3-{4-[1-(2,2-Difluoro-ethyl)-3-iodo-1H-pyrazol-4-yl]-pyrimidin-2-ylamino}-propionitrile B-33-3 (150 mg, 0.37 mmol) and Cesium Fluoride (1.1 mL of a 1M aqueous solution, 1.1 mmol). The resulting mixture was deoxygenated with a nitrogen bubbler for 5 min and then 1,1'-Bis(diphenylphosphino)ferrocene-palladium(II) dichloride dichloromethane complex (15 mg, 0.019 mmol) was added. The mixture was then heated in an 80° C. oil bath for 20 hours. LCMS indicated the iodide had been completely consumed. The mixture was partitioned between ethyl acetate and water. The aqueous layer was extracted with ethyl acetate. The combined organics were dried over magnesium sulfate and reduced to minimum volume. The residue was taken up in dimethoxyethane (3 mL) and then heated at 170° C. in the microwave for 25 minutes to thermolyze the tert-butoxycarbonyl groups. The resulting dark mixture was filtered through a 0.45µ filter and the filtrate reduced to minimum volume. The residue was purified by HPLC to give 59 mg (37%) of B-79 as a fluffy white solid after lyophilization of the desired fractions. $^1$H NMR (400 MHz, ACETONITRILE-$d_3$) δ ppm 8.17 (s, 1H), 8.15 (d, J=5.05 Hz, 1H), 7.83 (s, 1H), 6.72 (d, J=5.31

123

-continued

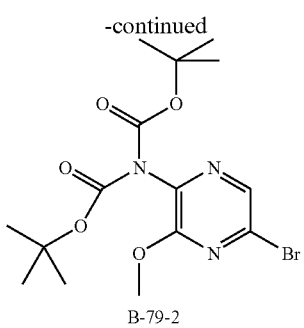

B-79-2

To a solution of 5-bromo-3-methoxypyrazin-2-amine (4.50 g, 19.8 mmol) and 4-(dimethylamino)pyridine (1.24 g, 10.1 mmol) in 70 ml THF was added di-tert-butyldicarbonate (10.4 g, 47.6 mmol) and the reaction mixture was stirred at room temperature for 5.5 hour. The solvents were removed under reduced pressure and the residue was flash chromed on silica gel eluting 3:1 Hexanes/EtOAc to give B-79-2 as a white solid (5.403 g, 67%).

Preparation of Di-tert-butyl[3-methoxy-5-(4,4,5,5-tetramethyl-1,3,2-dioxaborolan-2-yl)pyrazin-2-yl]imidodicarbonate (B-79-3)

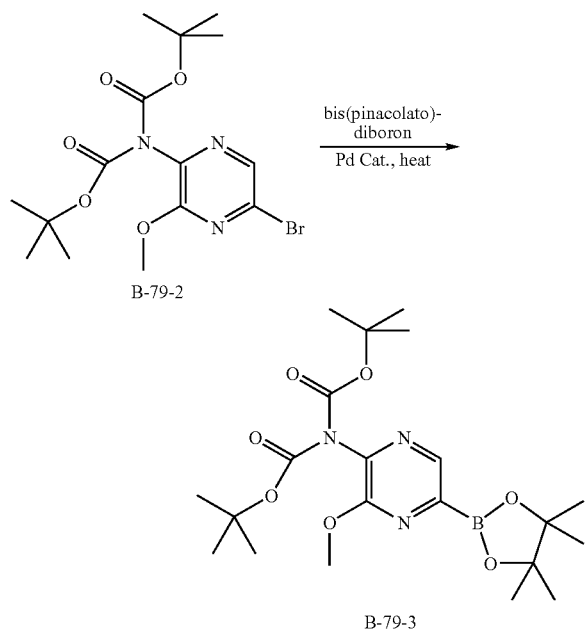

A mixture of the bis(pinacolato)diboron (1.12 g, 4.4 mmol), di-tert-butyl (5-bromo-3-methoxypyrazin-2-yl)imidodicarbonate B-79-2 (1.62 g, 4 mmol) and potassium acetate (1.2 g, 12 mmol) in toluene (40 mL) was deoxygenated with a nitrogen bubbler for a few minutes before the addition of 1,1'-Bis(diphenylphosphino)ferrocene-palladium(II) dichloride dichloromethane complex (78 mg, 0.096 mmol). The mixture was then heated in a 50 degree oil bath for 4 days. LCMS indicated that the reaction was complete. The mixture was filtered and the filtrate reduced to minimum volume. The residue B-79-3 was carried straight into the next step without purification, assuming a quantitative yield.

Hz, 1H), 6.27 (tt, J=54.98, 3.76 Hz, 1H), 5.91 (br.t, J=5.18 Hz, 1H), 5.34 (br. s., 2H), 4.59 (td, J=14.65, 3.79 Hz, 2H), 3.76 (s, 3H), 3.55 (q, J=6.23 Hz, 2H), 2.64 (t, J=6.44 Hz, 2H)

Example C-1

Preparation of [4-[2-((S)-2-Hydroxy-propylamino)-pyrimidin-4-yl]-3-(1H-pyrrolo[2,3-b]pyridin-5-yl)-pyrazol-1-yl]-acetonitrile Preparation of 5-[4-(2-Methylsulfanyl-pyrimidin-4-yl)-1-(tetrahydro-pyran-2-yl)-1H-pyrazol-3-yl]-1H-pyrrolo[2,3-b]pyridine (C-1-1)

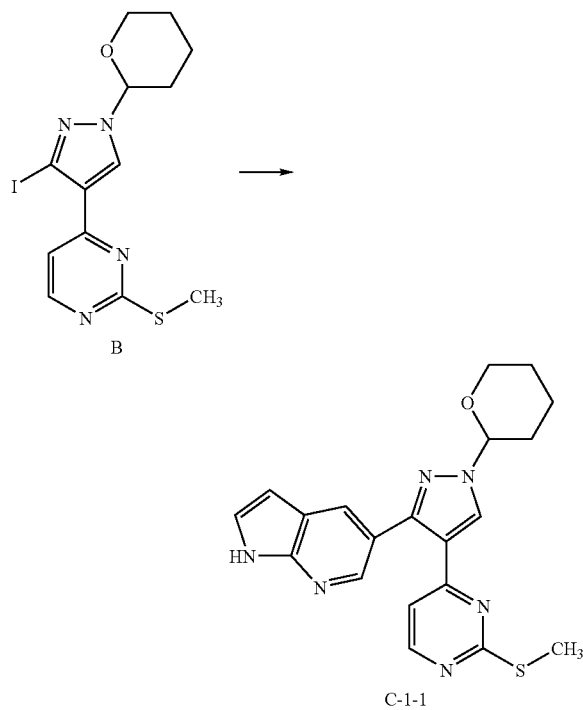

B

C-1-1

To a solution of 4-[3-Iodo-1-(tetrahydro-pyran-2-yl)-1H-pyrazol-4-yl]-2-methylsulfanyl-pyrimidine B (1.33 g, 3.3 mmol) and 5-(4,4,5,5-Tetramethyl-[1,3,2]dioxaborolan-2-yl)-1H-pyrrolo[2,3-b]pyridine (1 g, 4.1 mmol) in DMF (30 mL) was added a 2M solution of sodium carbonate (2 mL). The sodium carbonate appeared to come out of solution upon addition. The mixture was deoxygenated with a nitrogen bubbler for a few minutes. The palladium catalyst was added and nitrogen bubbling continued for a few minutes before the bubbler was removed. The mixture was heated at 85° C. for 18 hr. LCMS shows complete conversion to product. The mixture was dropped into saturated aqueous NaCl and the resulting solids collected by filtration and rinsed with water. The solids were dissolved in methanol/dichloromethane (1:9), dried over MgSO₄ and reduced to minimum volume. The residue was purified on a short column of silica gel using a gradient of 0-50% ethyl acetate in dichloromethane as eluent to give 5-[4-(2-Methylsulfanyl-pyrimidin-4-yl)-1-(tetrahydro-pyran-2-yl)-1H-pyrazol-3-yl]-1H-pyrrolo[2,3-b]pyridine (C-1-1) (0.89 g, 69%) as a yellow solid. ¹H NMR (400 MHz, DMSO-d6) δ ppm 11.73 (br. s., 1H), 8.69 (s, 1H), 8.43 (d, J=5.31 Hz, 1H), 8.29 (d, J=2.02 Hz, 1H), 8.07 (d, J=2.02 Hz, 1H), 7.51 (t, J=3.03 Hz, 1H), 7.11 (d, J=5.31 Hz, 1H), 6.48 (dd, J=3.28, 1.77 Hz, 1H), 5.53 (dd, J=9.85, 2.27 Hz, 1H), 4.00 (br. d, J=13.39 Hz, 1H), 3.61-3.76 (br. m, 1H), 2.10-2.24 (br. m, 4H), 1.91-2.06 (br. m, 2H), 1.65-1.80 (br. m, 1H), 1.50-1.63 (br. m, 2H).

Preparation of 1-Benzenesulfonyl-5-[4-(2-methylsulfanyl-pyrimidin-4-yl)-1-(tetrahydro-pyran-2-yl)-1H-pyrazol-3-yl]-1H-pyrrolo[2,3-b]pyridine (C-1-2)

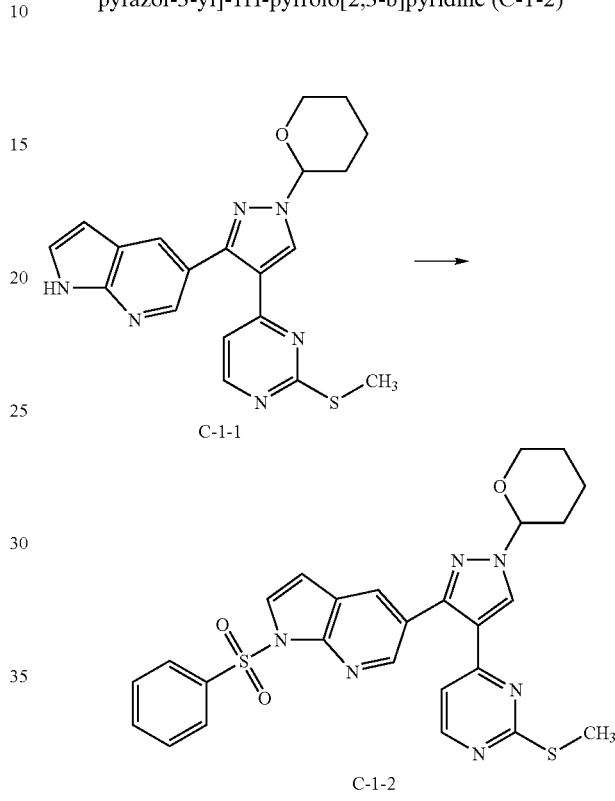

C-1-1

C-1-2

To a solution of the 5-[4-(2-Methylsulfanyl-pyrimidin-4-yl)-1-(tetrahydro-pyran-2-yl)-1H-pyrazol-3-yl]-1H-pyrrolo[2,3-b]pyridine (C-1-1) (870 mg, 2.22 mmol) in DMF (10 mL) at 25° C. was added Sodium Hydride (60% dispersion in oil, 133 mg, 3.32 mmol). The resulting suspension was stirred at ambient temperature for a few minutes until gas evolution ceased. Benzenesulfonyl chloride (0.4 mL, 3.13 mmol) was added and the mixture became cloudy. After stirring at ambient temperature for 15 minutes, LCMS showed complete conversion to desired product. The mixture was added slowly to 150 ml of saturated aqueous NaCl. The resulting precipitate was filtered, washed with water, and air dried. The solids were dissolved in dichloromethane, dried over MgSO₄ and reduced to minimum volume. The residue was purified on a short column of silica gel using a gradient of 0-20% ethyl acetate in dichloromethane as eluent to give 1-Benzenesulfonyl-5-[4-(2-methylsulfanyl-pyrimidin-4-yl)-1-(tetrahydro-pyran-2-yl)-1H-pyrazol-3-yl]-1H-pyrrolo[2,3-b]pyridine (C-1-2) (0.83 g, 70%) as a yellow foam. ¹H NMR (400 MHz, DMSO-d₆) δ ppm 8.77 (s, 1H), 8.47 (d, J=5.31 Hz, 1H), 8.43 (d, J=2.02 Hz, 1H), 8.16 (d, J=2.02 Hz, 1H), 8.09-8.15 (m, 2H), 7.95 (d, J=4.04 Hz, 1H), 7.68-7.77 (m, 1H), 7.57-7.67 (m, 2H), 7.29 (d, J=5.05 Hz, 1H), 6.86 (d, J=4.04 Hz, 1H), 5.52 (dd, J=9.85, 2.27 Hz, 1H), 3.98 (br. d, J=11.87 Hz, 1H), 3.62-3.74 (m, 1H), 2.07-2.23 (br. m, 1H), 1.90-2.05 (br. m, 2H), 1.66-1.77 (br. m, 1H), 1.65 (s, 3H), 1.50-1.61 (br. m, 2H).

Preparation of 5-{4-[2-(methylthio)pyrimidin-4-yl]-1H-pyrazol-3-yl}-1-(phenylsulfonyl)-1H-pyrrolo[2,3-b]pyridine (C-1-3)

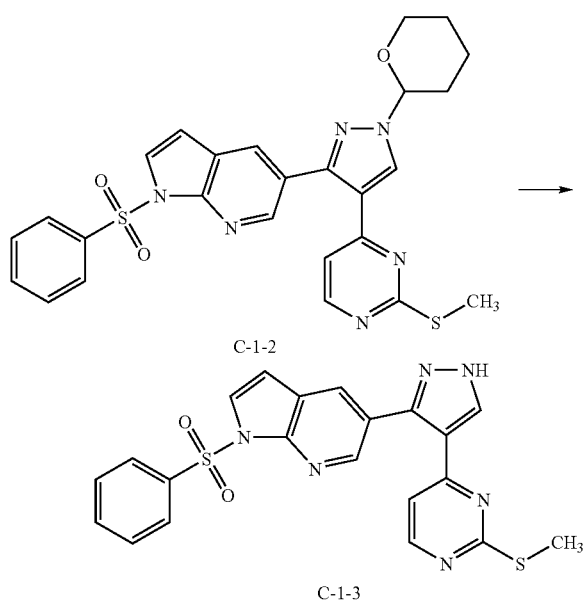

To a solution of the 1-Benzenesulfonyl-5-[4-(2-methylsulfanyl-pyrimidin-4-yl)-1-(tetrahydro-pyran-2-yl)-1H-pyrazol-3-yl]-1H-pyrrolo[2,3-b]pyridine (C-1-2) (750 mg, 1.41 mmol) in MeOH (1 mL) was added a solution of HCl in Dioxane (~4N, 0.1 mL). After stirring at ambient temperature for 45 minutes, the solution was dropped into phosphate buffer (pH 7, 15 mL). The resulting precipitate was collected by filtration, rinsed with water and air dried to give 5-{4-[2-(methylthio)pyrimidin-4-yl]-1H-pyrazol-3-yl}-1-(phenylsulfonyl)-1H-pyrrolo[2,3-b]pyridine (C-1-3) (622 mg, 98%) which was carried on without further purification. $^1$H NMR (400 MHz, ACETONITRILE-d$_3$) δ ppm 11.51 (br. s., 1H), 8.47 (d, J=2.02 Hz, 1H), 8.34 (d, J=5.05 Hz, 1H), 8.23 (br. s., 1H), 8.14 (d, J=7.58 Hz, 2H), 8.10 (d, J=1.77 Hz, 1H), 7.84 (d, J=2.78 Hz, 1H), 7.68 (t, J=7.45 Hz, 1H), 7.57 (t, J=7.71 Hz, 2H), 7.07 (d, J=4.80 Hz, 1H), 6.75 (d, J=3.79 Hz, 1H), 1.81 (s, 3H).

Preparation of [3-(1-Benzenesulfonyl-1H-pyrrolo[2,3-b]pyridin-5-yl)-4-(2-methylsulfanyl-pyrimidin-4-yl)-pyrazol-1-yl]-acetonitrile (C-1-4)

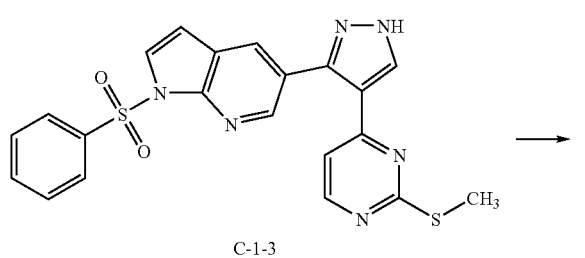

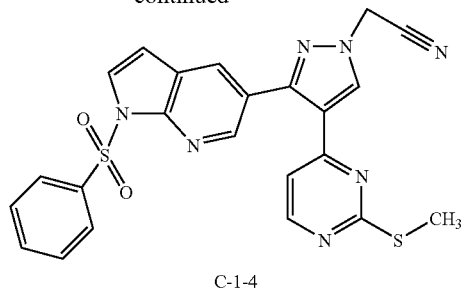

To a solution of the 5-{4-[2-(methylthio)pyrimidin-4-yl]-1H-pyrazol-3-yl}-1-(phenylsulfonyl)-1H-pyrrolo[2,3-b]pyridine (C-1-3) (638 mg, 1.42 mmol) and bromoacetonitrile (0.5 mL, 7 mmol) in DMF was added freshly ground Potassium Carbonate (254 mg, 1.84 mmol). The resulting suspension was stirred at 75° C. for 18 hr. LCMS showed complete consumption of starting material. The mixture was partitioned between ethyl acetate and saturated aqueous NaCl. The aqueous layer was extracted with ethyl acetate twice. The combined organics were washed with water twice, saturated aqueous NaCl, dried over MgSO$_4$ and reduced to minimum volume. The residue was purified on silica gel using a gradient of 25 to 100% methyl tert-butyl ether in hexanes as eluent to give [3-(1-Benzenesulfonyl-1H-pyrrolo[2,3-b]pyridin-5-yl)-4-(2-methylsulfanyl-pyrimidin-4-yl)-pyrazol-1-yl]-acetonitrile (C-1-4) (440 mg, 63%) as a crisp foam. $^1$H NMR (400 MHz, ACETONITRILE-d$_3$) δ ppm 8.46 (d, J=2.02 Hz, 1H), 8.36 (d, J=5.31 Hz, 1H), 8.31 (s, 1H), 8.11-8.16 (m, 2H), 8.09 (d, J=2.02 Hz, 1H), 7.83 (d, J=4.04 Hz, 1H), 7.64-7.71 (m, 1H), 7.57 (t, J=7.71 Hz, 2H), 7.01 (d, J=5.31 Hz, 1H), 6.75 (d, J=4.04 Hz, 1H), 5.26 (s, 2H), 1.88 (s, 3H).

Preparation of [3-(1-Benzenesulfonyl-1H-pyrrolo[2,3-b]pyridin-5-yl)-4-(2-methanesulfonyl-pyrimidin-4-yl)-pyrazol-1-yl]-acetonitrile (C-1-5)

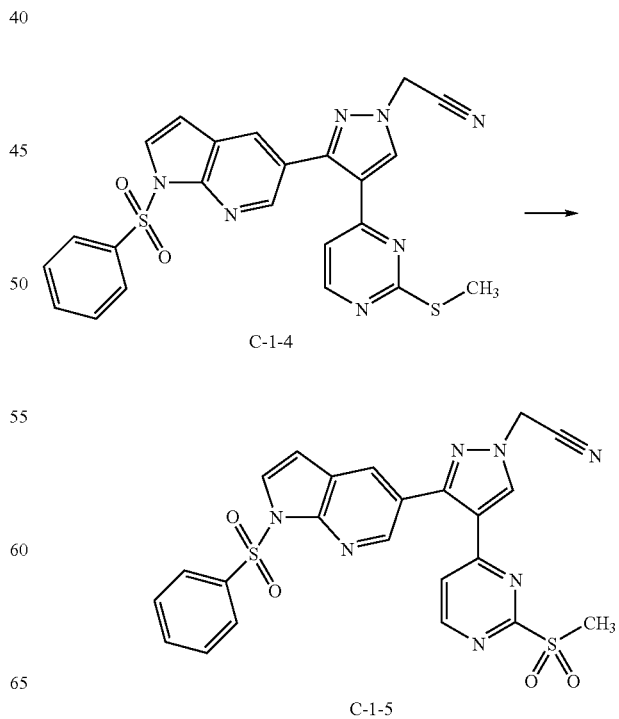

A solution of the [3-(1-Benzenesulfonyl-1H-pyrrolo[2,3-b]pyridin-5-yl)-4-(2-methylsulfanyl-pyrimidin-4-yl)-pyrazol-1-yl]-acetonitrile (C-1-4) (175 mg, 0.36 mmol) in THF (2 mL) and H$_2$O (2 mL) was cooled to 0° C. and OXONE (330 mg, 0.54 mmol, 1.5 eq) was added in one portion. The resulting yellow slurry was stirred at 0° C. for 10 min and was then stirred at ambient temperature overnight. The resulting mixture was filtered and the solids rinsed with ethyl acetate and water. The filtrate was partitioned between ethyl acetate and water. The aqueous layer was extracted with ethyl acetate and the combined organics dried over MgSO$_4$ and reduced to minimum volume. The residue was triturated with methyl tert-butyl ether and the solids collected by filtration to give [3-(1-Benzenesulfonyl-1H-pyrrolo[2,3-b]pyridin-5-yl)-4-(2-methanesulfonyl-pyrimidin-4-yl)-pyrazol-1-yl]-acetonitrile (C-1-5) (158 mg, 85%) which was carried forward without further purification. $^1$H NMR (400 MHz, ACETONITRILE-d$_3$) δ ppm 8.74 (d, J=5.56 Hz, 1H), 8.53 (d, J=2.02 Hz, 1H), 8.45 (s, 1H), 8.18 (d, J=2.27 Hz, 1H), 8.12-8.17 (m, 2H), 7.84 (d, J=4.04 Hz, 1H), 7.63-7.73 (m, 1H), 7.55-7.62 (m, 2H), 7.53 (d, J=5.31 Hz, 1H), 6.75 (d, J=4.04 Hz, 1H), 5.29 (s, 2H), 2.78 (s, 3H).

Preparation of {3-(1-Benzenesulfonyl-1H-pyrrolo[2,3-b]pyridin-5-yl)-4-[2-((S)-2-hydroxy-propylamino)-pyrimidin-4-yl]-pyrazol-1-yl}-acetonitrile (C-1-6)

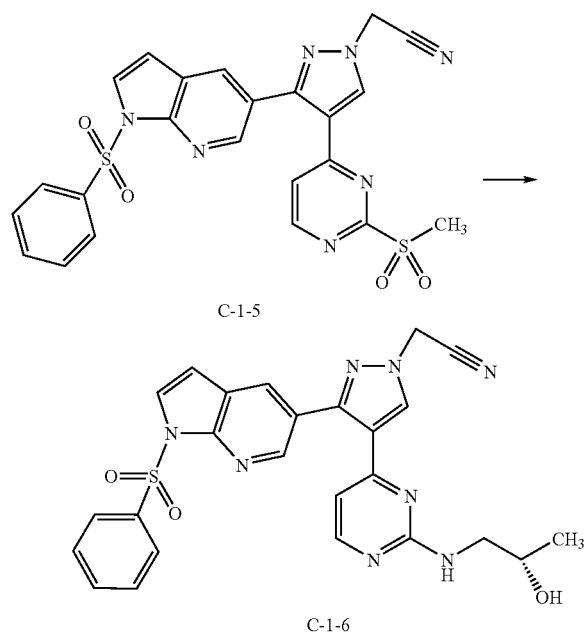

C-1-5

C-1-6

A Mixture of the [3-(1-Benzenesulfonyl-1H-pyrrolo[2,3-b]pyridin-5-yl)-4-(2-methanesulfonyl-pyrimidin-4-yl)-pyrazol-1-yl]-acetonitrile (C-1-5) (310 mg, 0.6 mmol) and (S)-(+)-1-amino-2-propanol (134 mg, 1.8 mmol) in THF (5 mL) was heated at 80° C. for 18 hr. The mixture was concentrated onto silica gel then purified on silica gel using a gradient of 0-6% methanol in a mixture of dichloromethane and ethyl acetate (1:1) as eluent to yield 220 mg (72%) of {3-(1-Benzenesulfonyl-1H-pyrrolo[2,3-b]pyridin-5-yl)-4-[2-((S)-2-hydroxy-propylamino)-pyrimidin-4-yl]-pyrazol-1-yl}-acetonitrile (C-1-6) as a foam from methyl tert-butyl ether. $^1$H NMR (400 MHz, ACETONITRILE-d$_3$) δ ppm 8.52 (d, J=2.02 Hz, 1H), 8.20 (s, 1H), 8.07-8.17 (m, 4H), 7.81 (d, J=4.04 Hz, 1H), 7.63-7.73 (m, 1H), 7.52-7.60 (m, 2H), 6.75 (d, J=4.04 Hz, 1H), 6.53 (br. s., 1H), 5.67 (br. t, J=4.93 Hz, 1H), 5.24 (s, 2H), 3.56 (br. s., 1H), 2.64-3.28 (br. m, 3H), 0.74 (br. s., 3H).

Preparation of [4-[2-((S)-2-Hydroxy-propylamino)-pyrimidin-4-yl]-3-(1H-pyrrolo[2,3-b]pyridin-5-yl)-pyrazol-1-yl]-acetonitrile (C-1)

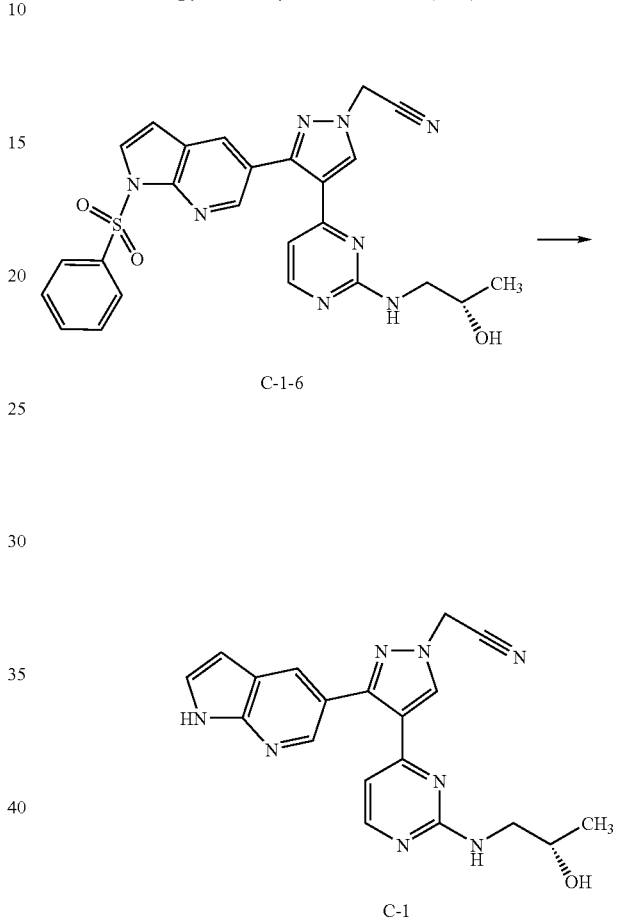

C-1-6

C-1

To solution of the {3-(1-Benzenesulfonyl-1H-pyrrolo[2,3-b]pyridin-5-yl)-4-[2-((S)-2-hydroxy-propylamino)-pyrimidin-4-yl]-pyrazol-1-yl}-acetonitrile (C-1-6) (145 mg, 0.28 mmol) in THF (5 mL) at −40° C. was added sodium hydroxide (1.1 mL of a 10 mg/mL solution in MeOH, 0.28 mmol). The mixture was allowed to slowly warm to 0° C. After 2 hr the mixture was diluted with 10 mL THF and stirring continued at 0° C. for 2 hr. Mixture was partitioned between pH 7 phosphate buffer and ethyl acetate. The aqueous layer was extracted twice with ethyl acetate. The combined organics were washed with saturated aqueous NaCl, dried over MgSO$_4$ and reduced to minimum volume. The residue was purified by HPLC to give the [4-[2-((S)-2-Hydroxy-propylamino)-pyrimidin-4-yl]-3-(1H-pyrrolo[2,3-b]pyridin-5-yl)-pyrazol-1-yl]-acetonitrile (C-1) in 23% yield. $^1$H NMR (400 MHz, ACETONITRILE-d$_3$) δ ppm 9.78 (br. s., 1H), 8.42 (d, J=2.02 Hz, 1H), 8.22 (s, 1H), 8.05-8.14 (m, 2H), 7.38-7.45 (m, 1H), 6.42-6.56 (m, 2H), 5.74 (br. s., 1H), 5.25 (s, 2H), 3.72 (br. s., 1H), 3.19 (br. s., 1H), 3.04 (br. s., 1H), 0.95 (br. s., 3H).

Example D-1

Preparation of (2S)-1-(4-(1-isopropyl-3-(1H-pyrazolo[3,4-b]pyridin-5-yl)-1H-pyrazol-4-yl)pyrimidin-2-ylamino)propan-2-ol

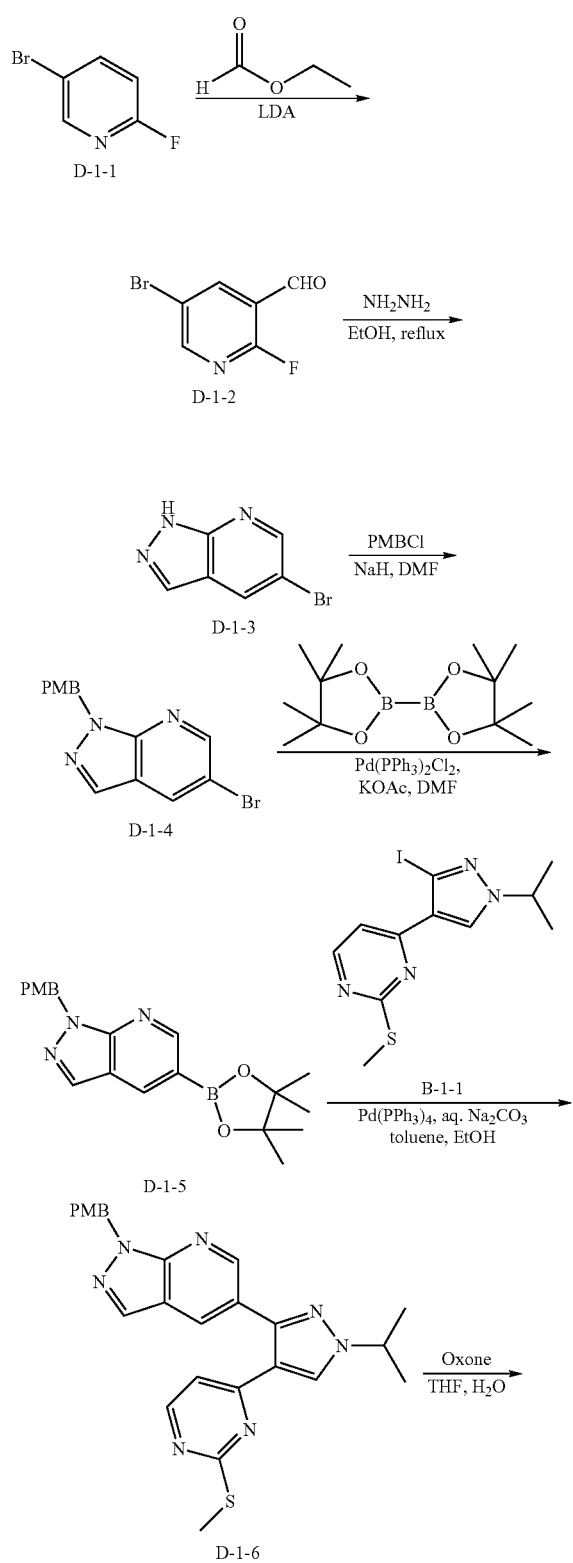

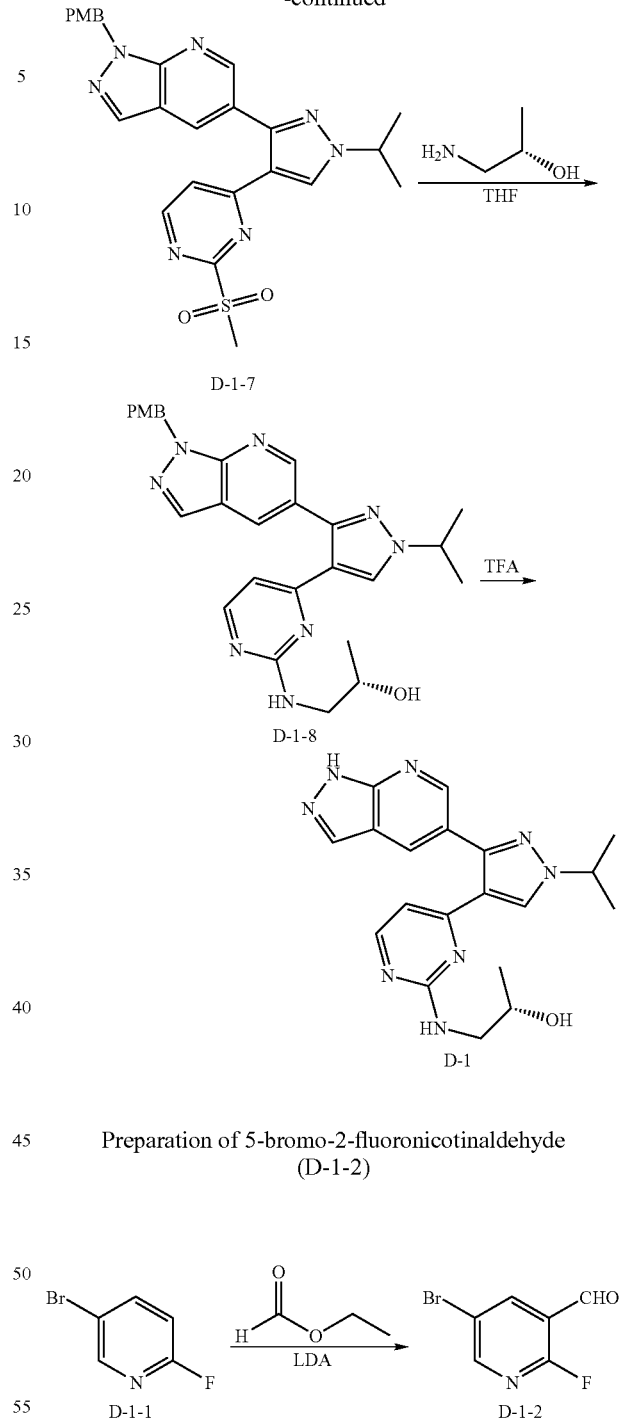

Preparation of 5-bromo-2-fluoronicotinaldehyde (D-1-2)

To a solution of diisopropylamine (17 mL, 0.17 mol) in dry THF (200 mL) was added 2.5 M n-BuLi in hexane (68 mL, 0.17 mol) dropwise at 0° C. under $N_2$ atmosphere. After the addition, the resulting mixture was cooled to −65° C. A solution of 5-bromo-2-fluoropyridine (25 g, 0.14 mol) in dry THF (100 mL) was then added dropwise. The resulting mixture was stirred at −65° C. for 90 minutes. Then ethyl formate (15.6 g, 0.21 mol) was added dropwise to the mixture. After stirred for 10 minutes, the reaction mixture was quenched with a solution of 10% citric acid in THF (100 mL) at −65° C.

The resulting mixture was warmed up to room temperature, poured into water (100 mL) and extracted with EtOAc (200 mL). The organic layer was separated and washed with saturated aqueous NaCl (100 mL×2), dried over $Na_2SO_4$ and concentrated in vacuo to yield compound D-1-2 (25 g, 85%) as a yellow solid.

Preparation of 5-bromo-1H-pyrazolo[3,4-b]pyridine (D-1-3)

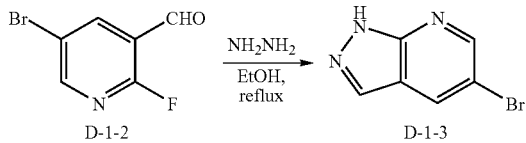

A solution of compound D-1-2 (20 g, 0.1 mol) and anhydrous hydrazine (18 g, 0.56 mol) in ethanol was heated to reflux overnight. TLC (petroleum ether/EtOAc 2:1) indicated complete consumption of starting material. The reaction mixture was concentrated in vacuo to a volume of about 50 mL and poured into water (500 mL), the resulting mixture was filtered. The cake was washed with water (50 mL×3) and ether (20 mL×3), then dried in vacuo to yield compound D-1-3 (9.0 g, 46%) as a yellow solid.

Preparation of 1-(4-methoxybenzyl)-5-bromo-1H-pyrazolo[3,4-b]pyridine (D-1-4)

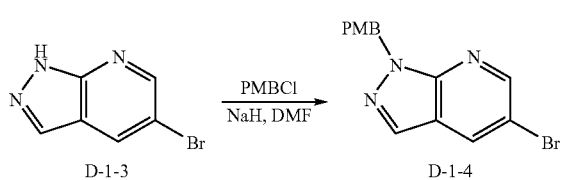

To a solution of compound D-1-3 (3.47 g, 17.5 mmol) in dry DMF (50 mL) was added NaH (77 mg, 19.25 mmol) portion-wise at 0° C. After the addition, the resulting mixture was stirred at 0° C. for 30 minutes. PMBCl (3.29 g, 21 mmol) was then added dropwise at 0° C. The resulting mixture was stirred at room temperature overnight. TLC (petroleum ether/EtOAc 1:1) indicated complete consumption starting material. The reaction mixture was poured into $H_2O$ (100 mL) and extracted with EtOAc (100 mL×3). The combined organic layers were washed with $H_2O$ (100 mL×2) and saturated aqueous NaCl (100 mL), dried over $Na_2SO_4$ and concentrated in vacuo. The crude product was purified by column chromatography (silica gel, petroleum ether/EtOAc from 50:1 to 4:1) to yield pure compound D-1-4 (4.3 g, yield: 77.2%) as a yellow solid.

Preparation of 1-(4-methoxybenzyl)-5-(4,4,5,5-tetramethyl-1,3,2-dioxaborolan-2-yl)-1H-pyrazolo[3,4-b]pyridine (D-1-5)

To a stirred solution of compound D-1-4 (4.3 g, 13.5 mmol) in dry DMF (80 mL) were added 4,4,5,5,4',4',5',5'-octamethyl-[2,2']bi[[1,3,2]dioxaborolanyl] (6.9 g, 27 mmol), KOAc (3.9 g, 40.5 mmol) and $Pd(PPh_3)_2Cl_2$ (0.43 g, 0.5 mmol) under $N_2$ atmosphere. The resulting mixture was heated at 80~90° C. overnight. TLC (petroleum ether/EtOAc 4:1) indicated complete consumption of compound 39. The reaction mixture was poured into $H_2O$ (300 mL) and extracted with EtOAc (300 mL×3). The combined organic layers were washed with $H_2O$ (300 mL×2) and saturated aqueous NaCl (300 mL), dried over $Na_2SO_4$ and concentrated in vacuo to yield crude D-1-5 (8 g, yield: 100%) as a black oil, which was directly used to next step without any purification.

Preparation of 1-(4-methoxybenzyl)-5-(1-isopropyl-4-(2-(methylthio)pyrimidin-4-yl)-1H-pyrazol-3-yl)-1H-pyrazolo[3,4-b]pyridine (D-1-6)

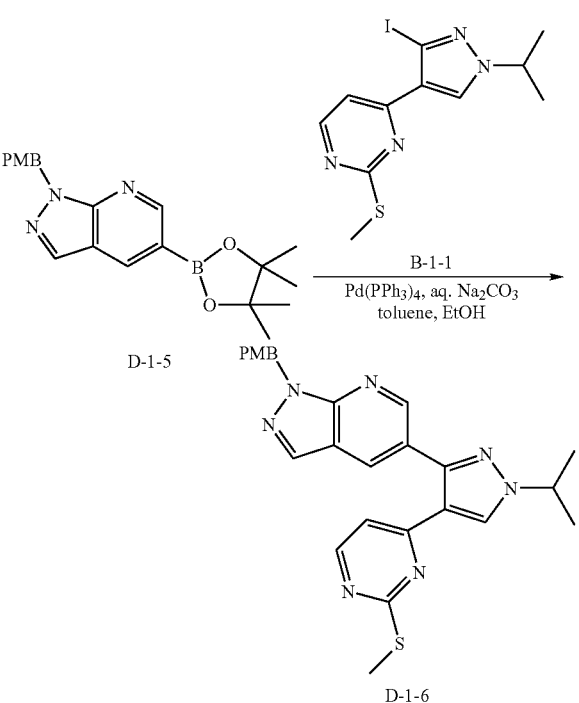

To a stirred solution of compound B-1-1 (1.8 g, 5 mmol) in toluene (60 mL) and EtOH (20 mL) was added the crude mixture of compound D-1-5 (8 g, 13.5 mmol), 2 N aqueous $Na_2CO_3$ (7.5 mL) and $Pd(PPh_3)_4$ (0.18 g, 0.11 mmol) under $N_2$ atmosphere. The resulting mixture was heated at reflux overnight. TLC (petroleum ether/EtOAc 2:1) indicated complete consumption of compound 7. The reaction mixture was washed with $H_2O$ (50 mL) and saturated aqueous NaCl (100 mL), dried over $Na_2SO_4$ and concentrated in vacuo. The residue was purified via column chromatography (silica gel, petroleum ether/EtOAc 2:1) to yield crude compound D-1-6, which was purified via preparative HPLC to yield pure compound D-1-6 (560 mg, yield: 23.8%) as a yellow oil.

Preparation of 1-(4-methoxybenzyl)-5-(1-isopropyl-4-(2-(methylsulfonyl)pyrimidin-4-yl)-1H-pyrazol-3-yl)-1H-pyrazolo[3,4-b]pyridine (D-1-7)

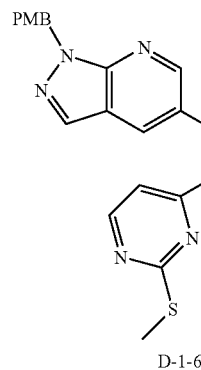

D-1-6

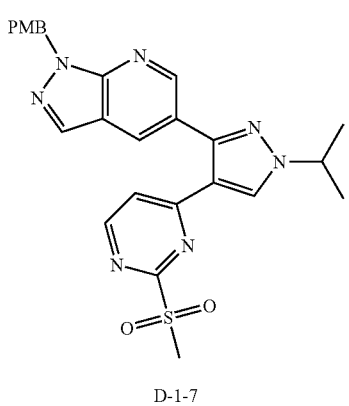

D-1-7

A mixture of compound D-1-6 (560 mg, 1.19 mmol) and Oxone (1.1 g, 1.79 mmol) in THF (10 mL) and $H_2O$ (10 mL) was stirred at room temperature for 2 hours. TLC (petroleum ether/EtOAc 2:1) indicated complete consumption of starting material. The reaction mixture was concentrated in vacuo. $H_2O$ (30 mL) was added to the residue and the mixture was extracted with EtOAc (50 mL×3). The combined organic layers were washed with saturated aqueous NaCl (50 mL), dried over $Na_2SO_4$ and concentrated in vacuo to yield compound D-1-7 (600 mg, yield: 100%) as a red oil.

Preparation of (2S)-1-(4-(3-(1-(4-methoxybenzyl)-1H-pyrazolo[3,4-b]pyridin-5-yl)-1-isopropyl-1H-pyrazol-4-yl)pyrimidin-2-ylamino)propan-2-ol (D-1-8)

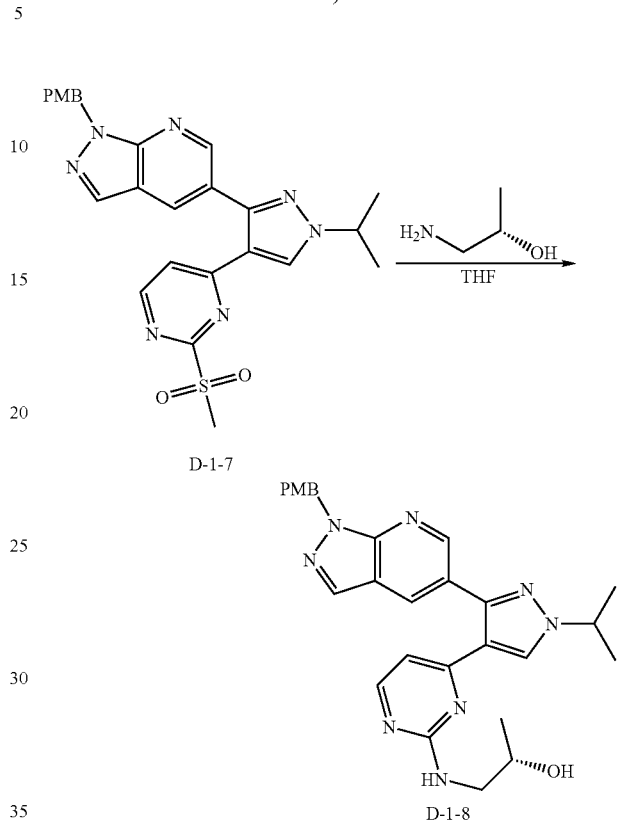

A mixture of compound D-1-7 (600 mg, 1.2 mmol) and (S)-1-aminopropan-2-ol (528 mg, 7.15 mmol) in THF (30 mL) was heated at reflux for two days. TLC ($CH_2Cl_2$/MeOH 15:1) indicated complete consumption of starting material. The mixture was concentrated in vacuo and the residue was purified via column chromatography (silica gel, EtOAc) to yield compound D-1-8 (460 mg, yield: 77.4%) as a yellowish oil.

Preparation of (2S)-1-(4-(1-isopropyl-3-(1H-pyrazolo[3,4-b]pyridin-5-yl)-1H-pyrazol-4-yl)pyrimidin-2-ylamino)propan-2-ol (D-1)

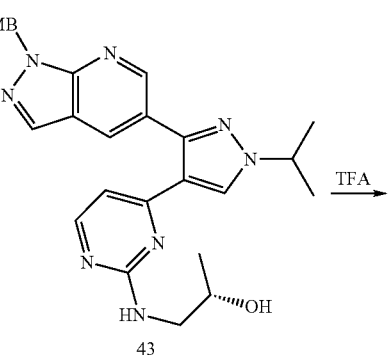

43

-continued

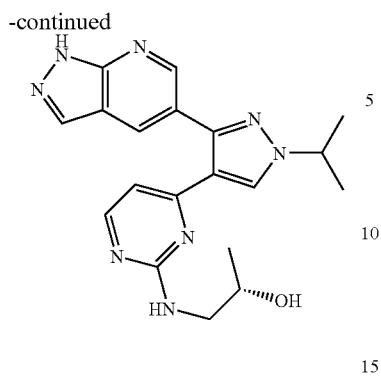

A solution of compound D-1-8 (460 mg, 0.92 mmol) in TFA (20 mL) was stirred at room temperature for 3 days. TLC (CH$_2$Cl$_2$/MeOH 15:1) indicated about half of compound D-1-8 was consumed. The reaction mixture was concentrated in vacuo. The residue was basified to pH~8 by saturated NaHCO$_3$ (10 mL) and extracted with EtOAc (50 mL×3). The combined organic layers were washed with saturated aqueous NaCl (100 mL), dried over Na$_2$SO$_4$ and concentrated in vacuo. The residue was purified via preparative HPLC to yield D-1 (130 mg, yield: 21.5%) as a yellow solid.

Example D-2

Preparation of (2S)-1-(4-(1-isopropyl-3-(3-methyl-1H-pyrazolo[3,4-b]pyridin-5-yl)-1H-pyrazol-4-yl)pyrimidin-2-ylamino)propan-2-ol

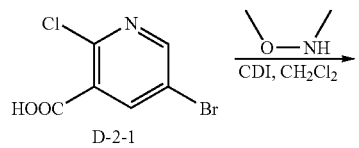

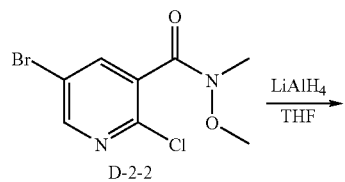

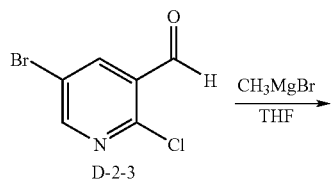

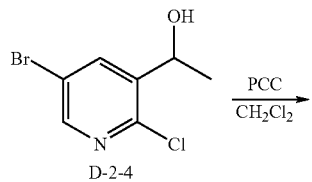

-continued

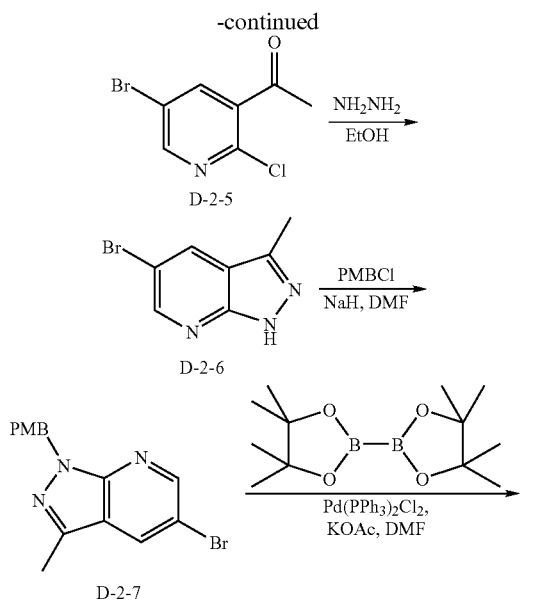

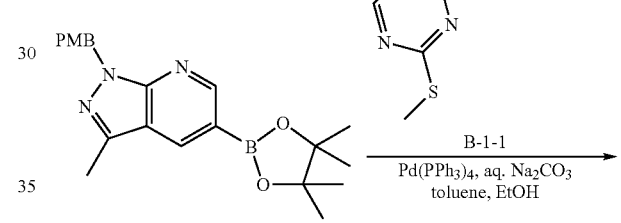

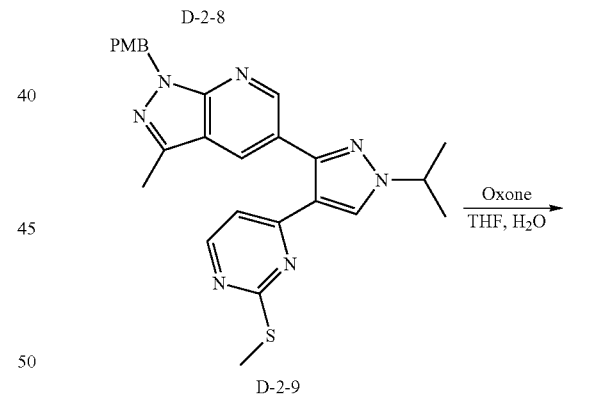

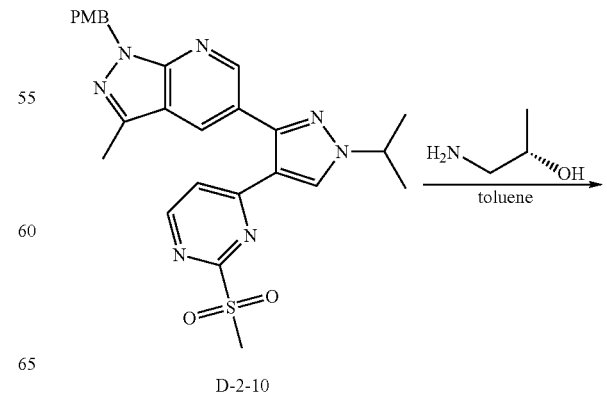

-continued

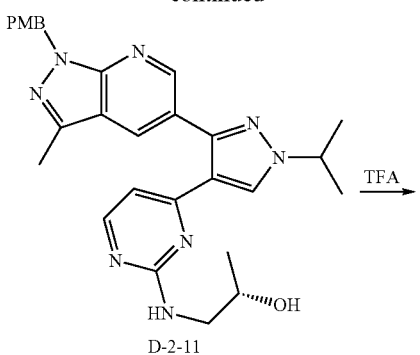

D-2-11

↓ TFA

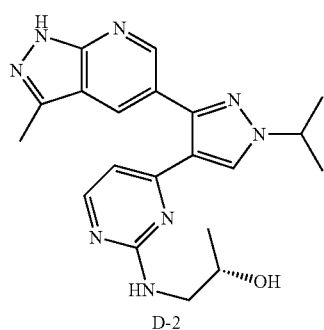

D-2

Preparation of 5-bromo-2-chloro-N-methoxy-N-methylnicotinamide (D-2-2)

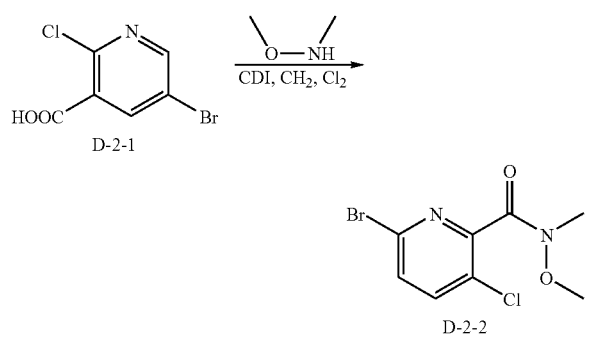

To a solution of compound D-2-1 (23.5 g, 0.1 mol) in dry CH$_2$Cl$_2$ (400 mL) was added CDI (19.5 g, 0.12 mol) portionwise at room temperature under N$_2$ atmosphere. After the addition, the mixture was stirred for 1 hour. O,N-dimethylhydroxylamine (11.5 g, 0.12 mol) was then added portionwise at room temperature. After the addition, the resulting mixture was stirred at room temperature overnight. TLC (petroleum ether/EtOAc 8:1) indicated complete consumption of starting material. H$_2$O (200 mL) was added and the organic layer was separated, washed with 1 N HCl (100 mL), 1 N Na$_2$CO$_3$ (100 mL) and saturated aqueous NaCl (200 mL) in sequence, dried over Na$_2$SO$_4$ and concentrated in vacuo to give compound D-2-2 (25 g, 90%) as a yellow solid.

Preparation of 5-bromo-2-chloronicotinaldehyde (D-2-3)

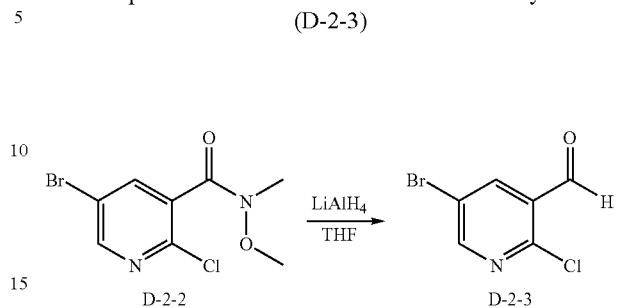

To a stirred solution of compound D-2-2 (25 g, 89.4 mmol) in dry THF (200 mL) was added LiAlH$_4$ (1.7 g, 27 mmol) at −10° C. under N$_2$ atmosphere. After the addition, the reaction mixture was allowed to warm up to room temperature and stirred overnight. TLC (petroleum ether/EtOAc 5:1) indicated complete consumption of starting material. To the reaction mixture was added 1 N KHSO$_4$ (200 mL) and extracted with EtOAc (300 mL×3). The combined organic layers were washed with saturated aqueous NaCl (200 mL), dried over Na$_2$SO$_4$ and concentrated in vacuo to yield crude compound D-2-3, which was purified by column chromatography (silica gel, petroleum ether/EtOAc 30:1) to yield pure compound D-2-3 (8.0 g, 45%) as a white solid.

Preparation of 1-(5-bromo-2-chloropyridin-3-yl)ethanol (D-2-4)

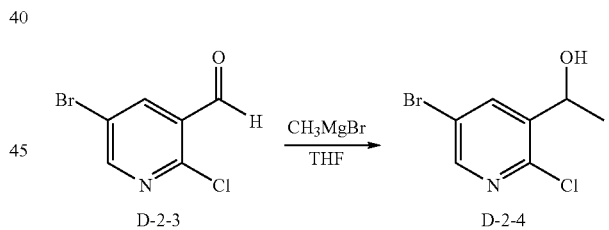

To a stirred solution of compound D-2-3 (8.0 g, 36.3 mmol) in dry THF (100 mL) was added a solution of 3 M CH$_3$MgBr in THF (18.14 mL, 54.4 mmol) dropwise at −78° C. under N$_2$ atmosphere. After the addition, the resulting mixture was allowed to warmed up to room temperature and stirred overnight. TLC (petroleum ether/EtOAc 8:1) indicated most of compound D-2-3 was consumed. H$_2$O (200 mL) was added to the reaction mixture and the mixture was extracted with EtOAc (100 mL×3). The combined organic layers were washed with saturated aqueous NaCl (200 mL), dried over Na$_2$SO$_4$ and concentrated in vacuo to give crude compound D-2-4, which was purified by column chromatography (silica gel, petroleum ether/EtOAc 50:1) to yield pure compound D-2-4 (6.3 g, 73.6%) as a yellow oil.

Preparation of 1-(5-bromo-2-chloropyridin-3-yl)ethanone (D-2-5)

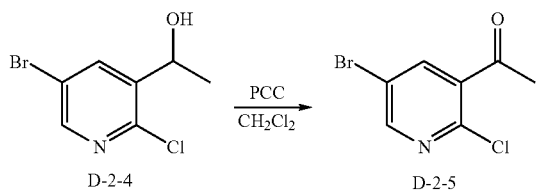

To a stirred solution of pyridine (13 g, 0.165 mol) in CH$_2$Cl$_2$ (200 mL) was added CrO$_3$ (8.25 g, 0.083 mol) and silica gel (20 mL) portionwise at 0° C. After the addition, the reaction mixture was stirred for 10 minutes. Compound D-2-4 (6.5 g, 27.5 mmol) was then added and the resulting mixture was stirred at room temperature overnight. TLC (petroleum ether/EtOAc 8:1) indicated most of compound D-2-4 was consumed. The reaction mixture was filtered and the filtrate was concentrated in vacuo to give crude compound D-2-5, which was purified by column chromatography (silica gel petroleum ether/EtOAc 20:1) to give pure compound D-2-5 (5 g, yield: 77%) as a yellow oil.

Preparation of 5-bromo-3-methyl-1H-pyrazolo[3,4-b]pyridine (D-2-6)

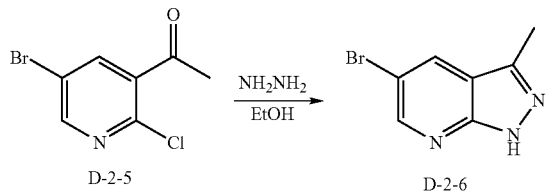

A mixture of compound D-2-5 (4 g, 16 mmol) and hydrazine (30 mL) in ethanol (300 mL) was stirred at room temperature overnight. TLC (petroleum ether/EtOAc 5:1) indicated complete consumption of starting material. The reaction mixture was concentrated in vacuo and the residue was purified via column chromatography (silica gel, petroleum ether/EtOAc 15:1) to yield crude compound D-2-6, which was further purified by preparative HPLC to yield pure compound D-2-6 (800 mg, yield: 20%) as a white solid.

Preparation of 1-(4-methoxybenzyl)-5-bromo-3-methyl-1H-pyrazolo[3,4-b]pyridine (D-2-7)

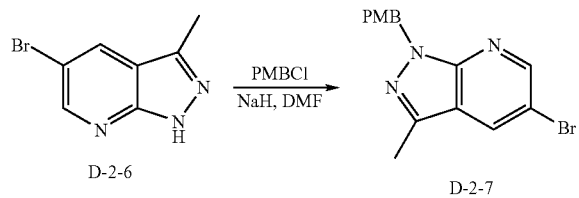

To a stirred solution of compound D-2-6 (0.6 g, 3 mmol) in dry DMF (50 mL) was added NaH (0.24 g, 6 mmol) portionwise at 0° C. under N$_2$ atmosphere. The resulting mixture was stirred at room temperature for 1 hour. PMBCl (0.52 g, 3.3 mmol) was then added dropwise at 0° C. The resulting mixture was stirred at room temperature overnight. TLC (petroleum ether/EtOAc 3:1) indicated complete consumption of starting material. The reaction mixture was quenched with H$_2$O (50 mL) and extracted with EtOAc (50 mL×3). The combined organic layers were washed with saturated aqueous NaCl (100 mL), dried over Na$_2$SO$_4$ and concentrated in vacuo. The residue was purified via column chromatography (silica gel, petroleum ether/EtOAc from 8:1 to 5:1) to yield compound D-2-7 (0.7 g, yield: 71%) as a white solid.

Preparation of 1-(4-methoxybenzyl)-3-methyl-5-(4,4,5,5-tetramethyl-1,3,2-dioxaborolan-2-yl)-1H-pyrazolo[3,4-b]pyridine (D-2-8)

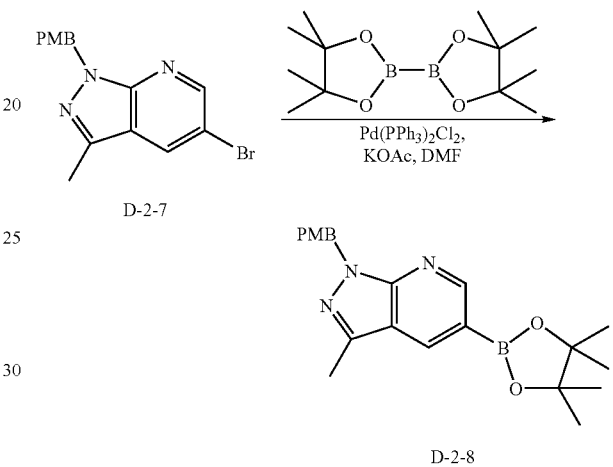

A solution of compound D-2-7 (0.7 g, 2.1 mmol), 4,4,5,5,4',4',5',5'-octamethyl-[2,2']bi[[1,3,2]dioxaborolanyl] (1.05 g, 4.2 mmol), KOAc (0.63 g, 6.3 mmol) and a catalytic amount of Pd(PPh$_3$)$_2$Cl$_2$ in dry DMF (80 mL) was stirred at 80-90° C. under N$_2$ atmosphere overnight. TLC (petroleum ether/EtOAc 3:1) indicated complete consumption of starting material. H$_2$O (100 mL) was added and the reaction mixture was extracted with EtOAc (100 mL×3). The combined organic layers were washed with saturated aqueous NaCl (100 mL), dried over Na$_2$SO$_4$ and concentrated in vacuo to yield crude D-2-8 (0.8 g, yield: 100%) as a brown oil, which was used directly without any further purification.

Preparation of 1-(4-methoxybenzyl)-5-(1-isopropyl-4-(2-(methylthio)pyrimidin-4-yl)-1H-pyrazol-3-yl)-3-methyl-1H-pyrazolo[3,4-b]pyridine (D-2-9)

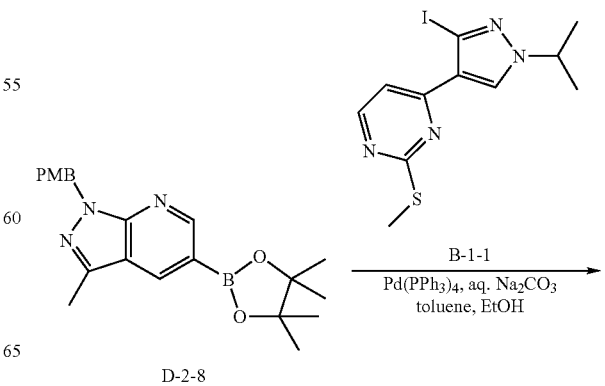

-continued

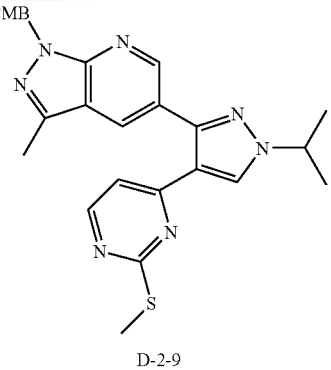

D-2-9

To a stirred solution of compound B-1-1 (0.38 g, 1.05 mmol) in toluene (60 mL) and EtOH (20 mL) were added crude material of compound D-2-8 (0.8 g, 2.1 mmol) and 2 N aq. Na₂CO₃ (1.6 mL) under N₂ atmosphere. After 10 minutes, a catalytic amount of Pd(PPh₃)₄ was added. The resulting mixture was refluxed overnight. TLC (petroleum ether/EtOAc 2:1) indicated complete consumption of D-2-8. Water (30 mL) was added to the reaction mixture and the mixture was extracted with EtOAc (100 mL×3). The combined organic layers were washed with saturated aqueous NaCl (100 mL), dried over Na₂SO₄ and concentrated in vacuo. The residue was purified via column chromatography (silica gel, petroleum ether/EtOAc 5:1) to yield compound D-2-9 (0.9 g, 30.1%) as a white solid.

Preparation of 1-(4-methoxybenzyl)-5-(1-isopropyl-4-(2-(methylsulfonyl)pyrimidin-4-yl)-1H-pyrazol-3-yl)-3-methyl-1H-pyrazolo[3,4-b]pyridine (D-2-10)

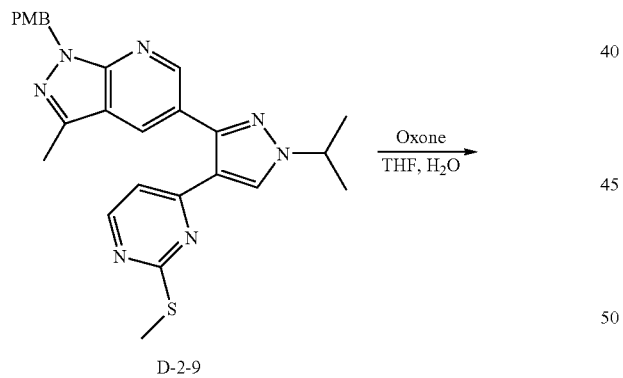

D-2-10

A mixture of compound D-2-9 (0.4 g, 0.82 mmol) and Oxone (0.76 g, 1.2 mmol) in THF (10 mL) and H₂O (10 mL) was stirred at room temperature for 2 hours. TLC (EtOAc) indicated complete consumption of starting material. The reaction mixture was concentrated in vacuo. H₂O (30 mL) was added to the residue and the mixture was extracted with EtOAc (50 mL×3). The combined organic layers were washed with saturated aqueous NaCl (50 mL), dried over Na₂SO₄ and concentrated in vacuo to yield compound D-2-10 (0.42 g, yield: 100%) as a yellow solid.

Preparation of (2S)-1-(4-(3-(1-(4-methoxybenzyl)-3-methyl-1H-pyrazolo[3,4-b]pyridin-5-yl)-1-isopropyl-1H-pyrazol-4-yl)pyrimidin-2-ylamino)propan-2-ol (D-2-11)

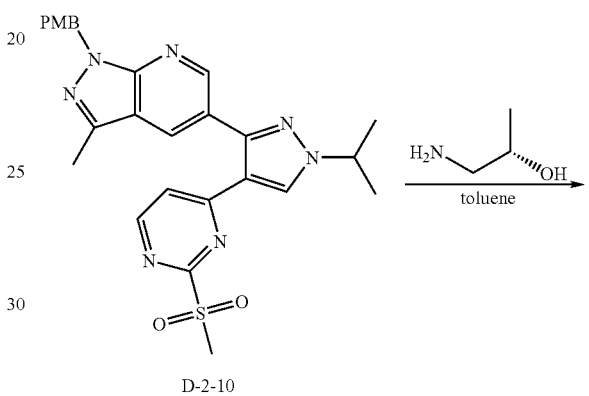

D-2-10

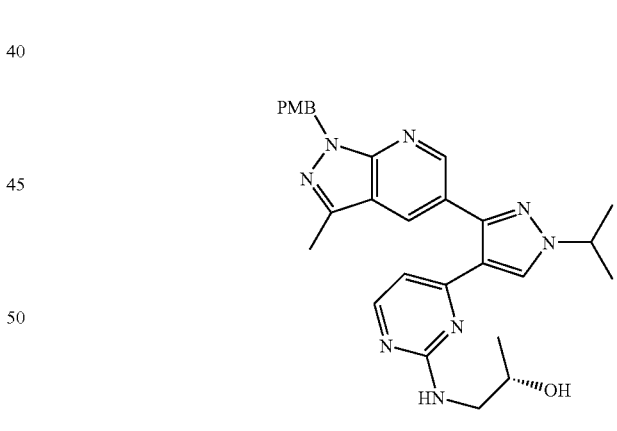

D-2-11

A mixture of compound D-2-10 (0.42 g, 0.82 mmol) and (S)-1-aminopropan-2-ol (0.6 g, 8.2 mmol) in toluene (25 mL) was refluxed overnight. TLC (EtOAc) indicated complete consumption of starting material. The mixture was concentrated in vacuo and the residue was purified via column chromatography (silica gel, EtOAc) to yield compound D-2-11 (0.4 g, yield: 100%) as a yellow solid.

Preparation of (2S)-1-(4-(1-isopropyl-3-(3-methyl-1H-pyrazolo[3,4-b]pyridin-5-yl)-1H-pyrazol-4-yl)pyrimidin-2-ylamino)propan-2-ol (D-2)

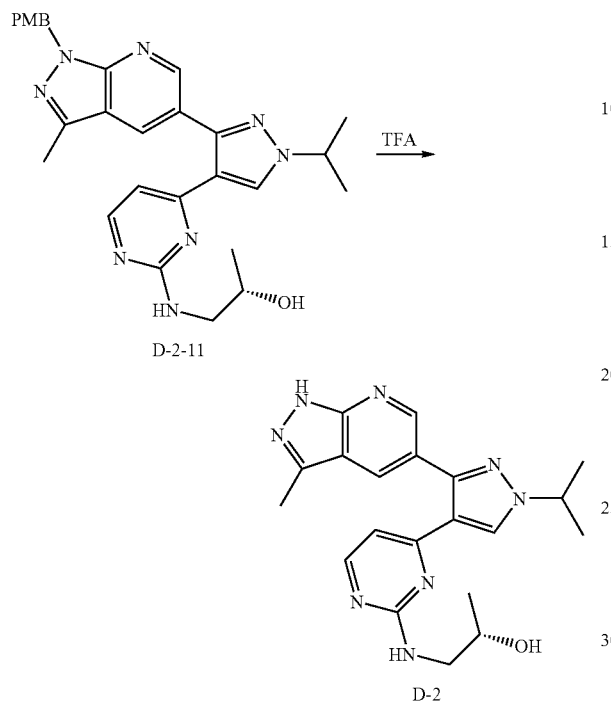

A solution of compound D-2-11 (400 mg, 0.82 mmol) in TFA (5 mL) was stirred at room temperature for 48 hours. TLC (petroleum ether/EtOAc 1:2) indicated about half of compound D-2-11 was consumed. Et$_3$N (10 mL) was added to the mixture and the resulting mixture was concentrated in vacuo. The residue was purified by column chromatography (silica gel, petroleum ether/EtOAc 1:1) to yield crude product, which was further purified by preparative HPLC to give pure D-2 (141.1 mg, yield: 47%) as a white solid.

Example F-1

Preparation of 3-chloro-5-(1-isopropyl-4-(pyrimidin-4-yl)-1H-pyrazol-3-yl)-1H-pyrrolo[2,3-b]pyridine

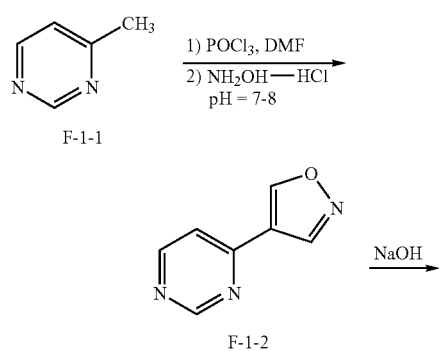

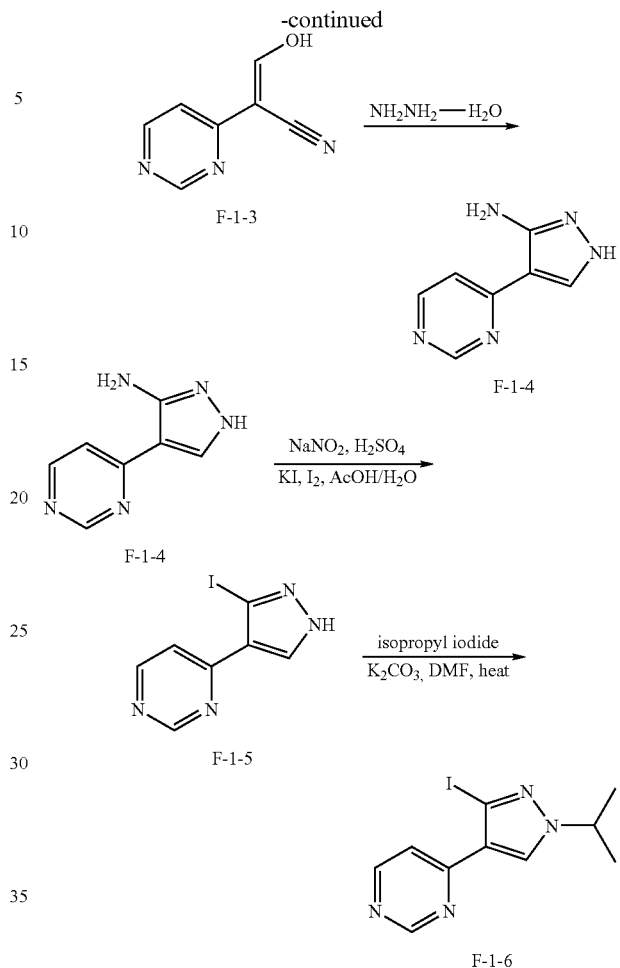

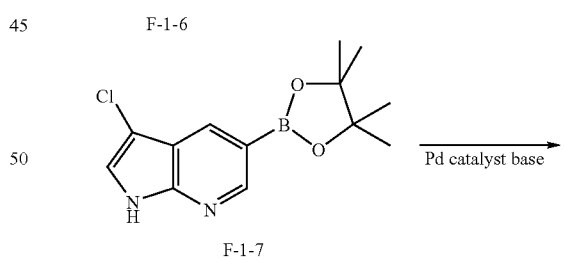

Preparation of 4-Isoxazol-4-ylpyrimidine (F-1-2)

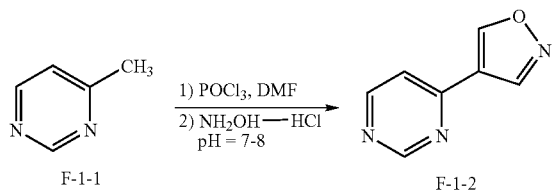

Crystalline triphosgene (44.3 g, 0.447 mol, 2.1 eq.) was started to be added to a solution of 4-methylpyrimidine (20.3 g, 0.213 mol) and dimethyl formamide (32.7 g, 0.447 mol, 2.1 eq.) at −10° C. This was accompanied by severe heating and densification of the reaction mass. It was necessary to change the cooling mixture several times and to add chloroform into the reaction mixture (totally 60 mL). After 3 h, when the addition of triphosgene was finished, the cooling mixture was removed, and the reaction mixture was allowed to heat to 35° C. When the reaction mixture started to cool, chloroform was evaporated, and red a oily residue was triturated with ethyl acetate to give crude compound F-1-1a (yield 78 g).

Compound F-1-1a was carefully sprinkled to a solution of hydroxylamine hydrochloride (17.8 g, 0.258 mol, 1.2 eq) and NaHCO$_3$ (17.9 g, 0.213 mol) in water (300 mL) at 10° C. under stirring. NaHCO$_3$ (36 g, 2 eq.) was additionally added (caution, foaming) to the obtained mixture, which was accompanied by formation of light crystalline precipitate. The precipitate was subjected to extraction with ethyl acetate. Next day, the extraction was repeated. The combined extracts were evaporated to give compound F-1-2 as a crystalline product (yield 94% calculated for 4 methylpyrimidine, 29.6 g).

Preparation of 3-Oxo-2-pyrimidin-4-ylpropanenitrile (F-1-3)

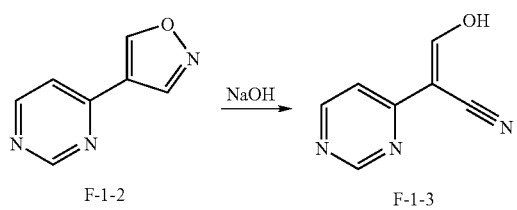

Compound F-1-2 was sprinkled to a solution of NaOH (8.06 g, 0.201 mol) in the mixture water/ethanol (30 mL/30 mL) under stirring. The mixture spontaneously heated to 70° C., a brownish-red solution formed, and a light precipitate formed. On densification, water was added. After spontaneous heating ceased, the mixture was stirred at room temperature for 1 h. Ethanol was added, and the solution was rotary evaporated. This operation was repeated twice, and the residue was washed on a filter with ethyl acetate and ether to give compound F-1-3 as beige crystals (yield 100%, 34 g).

Preparation of 4-Pyrimidin-4-yl-1H-pyrazol-3-amine (F-1-4)

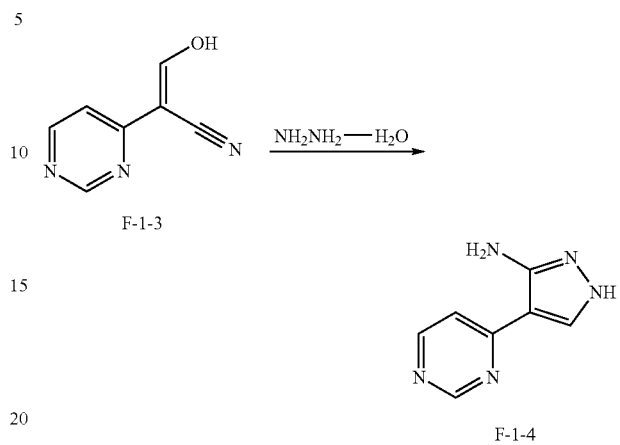

Compound F-1-3 (30 g, 0.178 mol) was sprinkled to a solution of hydrazine hydrate (20 mL) in glacial acetic acid (300 mL), which was accompanied by the formation of a dense orange precipitate. The obtained mixture was kept under stirring at 70-80° C. for 1 h. The precipitate disappeared, and the solution became less intense colored. The reaction mass was evaporated to half-volume and neutralized with excess aqueous ammonia to give compound F-1-4 as a light precipitate (yield 66%, 18.9 g).

Preparation of 3-[5-(Methoxycarbonyl)-1-(tetrahydro-2H-pyran-2-yl)-1H-indazol-3-yl]benzoic Acid (F-1-5)

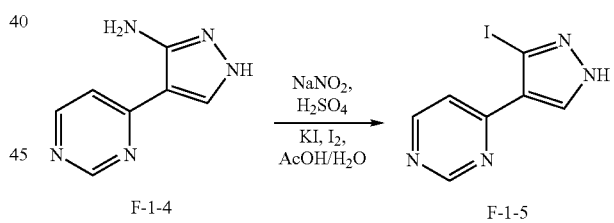

A solution of NaNO$_2$ (4.7 g, 0.068 mol) in water (20 mL) was poured at −3° C. in a thin jet to a solution of compound F-1-4 (10.9 g, 0.068 mol) in a mixture of glacial acetic acid (200 mL) and water (50 mL). The temperature increased to −1° C., and the solution became orange and transparent. Concentrated H$_2$SO$_4$ (1.85 mL, 0.0338 mol) was poured to the obtained solution, and a solution of KI (33.7 g, 0.2 mol, 3 eq.) and 12 (35 g, 138 mmol, 2 eq.) was added. The obtained solution was heated to 55° C. for 1 h, and acetic acid was neutralized with a large excess of aqueous ammonia. Iodine was neutralized with excess Na$_2$S$_2$O$_3$, and a light precipitate (16.5 g) formed. The precipitate was separated by filtration, and the mother solution was extracted with ethyl acetate. Ethyl acetate was evaporated, and the residue was dissolved in THF. The solution was passed through silica gel washing out with ethyl acetate and evaporated to give compound F-1-5 (total yield 93%, 17.1 g).

Preparation of 4-(3-Iodo-1-isopropyl-1H-pyrazol-4-yl)-pyrimidine (F-1-6)

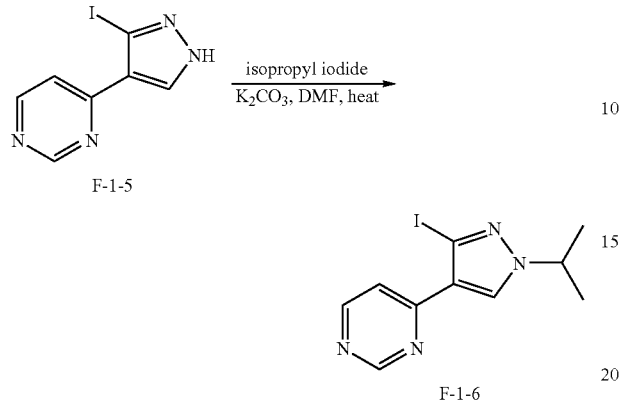

To a solution of the pyrazole F-1-5 (3.0 g, 11 mmol) and K₂CO₃ (1.98 g, 14.3 mmol) in DMF was added isopropyl iodide (5.51 ml, 55.1 mmol). The reaction mixture was heated at 55 C. After 25 hr, more of isopropyl iodide (1 ml 10 mmol), and of K₂CO₃ (457 mg, 3.3 mmol) was added. Stirred for 2 hr more. Cooled. Poured into 300 ml sat NaCl soln and extracted with TBME (2×). Combined organic layers were washed with saturated aqueous NaCl, dried over MgSO₄ and conc under reduced pressure to a yellow/orange solid. Recrystallized from TBME. TLC analysis showed the crystalline product to be enriched in one isomer of the isopropyl product F-1-6. Triturated the solid with TBME (3×) to give 680 mg of lt. yellow powder which shows pure isomer F-1-6.

Preparation of 3-chloro-5-(1-isopropyl-4-(pyrimidin-4-yl)-1H-pyrazol-3-yl)-1H-pyrrolo[2,3-b]pyridine

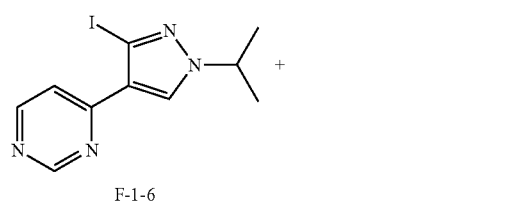

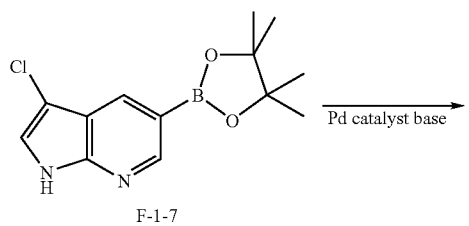

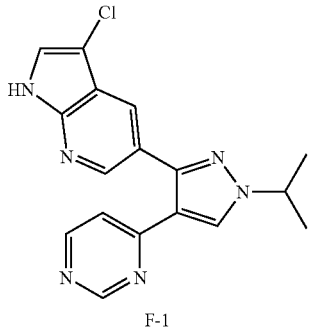

A mixture of 4-(3-Iodo-1-isopropyl-1H-pyrazol-4-yl)-pyrimidine (0.05 g, 0.2 mmol), 3-chloro-5-(4,4,5,5-tetramethyl-[1,3,2]dioxaborolan-2-yl)-1H-pyrrolo[2,3-b]pyridine (0.089 g, 0.318 mmol) and 2 M aq Na₂CO₃ (0.067 g, 0.636 mmol, 0.318 mL 3.0 Eq) in DMF (4 mL) was bubbled with Nitrogen for 15 min and DPPF PdCl₂ (0.0140 g, 0.019 mmol, 0.06 Eq) was added and then heated in biotage microwave initiator for 2.0 hour at 100° C. and under a high absorption. The resultant black reaction was cooled to room temperature. The reaction was poured into H₂O (100 mL) and extracted (3×50 mL EtOAC). The combined organics were dried over Na₂SO₄ and concentrated in vacuo to a black oil which was purified by Biotage column (Si 25+M) packed with hexanes and eluted with (5% MeOH/EtOAc)/Hexanes (0-50%:700 mL, 50-100%:700 mL, 100%; 700 mL, 27 mL fractions) to yield the product F-1 as an off-white solid (0.025, 50%).

Example G-1

Preparation of (2S)-1-(4-(3-(3-chloro-1H-pyrrolo[2,3-b]pyridin-5-yl)-1-(tetrahydrofuran-3-yl)-1H-pyrazol-4-yl)pyrimidin-2-ylamino)propan-2-ol

Preparation of methyl 1H-pyrrolo[2,3-b]pyridine-5-carboxylate (G-1-1a)

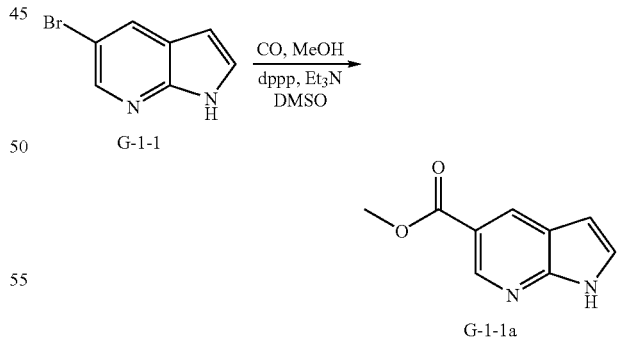

A mixture of 5-bromo-1H-pyrrolo[2,3-b]pyridine (90 g, 0.4 mol) and dppp (3 g, 0.072 mol) in DMSO (300 mL) and MeOH (300 mL) was added Pd(OAc)₂ (16.5 g, 0.072 mol). The resulting mixture was degassed under N₂ for 2 min and then heated to 100° C. under 2 MPa of CO gas for two days. TLC (Petroleum ether: EtOAc=4:1) showed the reaction was complete. The mixture was cooled and filtered then concentrated. The obtained residue was poured into ice-water. The formed solid was collected and dried in vacuum to give crude compound 5 (86.1 g, crude), which was directly used to the next reaction without further purification.

Preparation of methyl 1-(phenylsulfonyl)-1H-pyrrolo[2,3-b]pyridine-5-carboxylate (G-1-2)

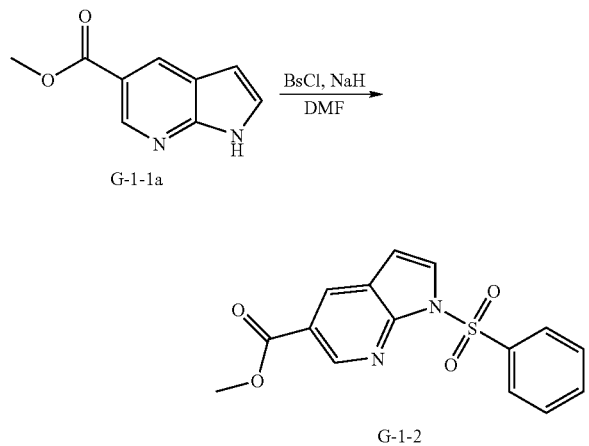

To a solution of G-1-1a (58 g, 0.33 mol) in dry THF (800 mL) was added NaH (20 g, 0.495 mol) at 0-10° C. in small portions. The resulting mixture was stirred at 10° C. for 1 h. BsCl (70.1 g, 0.397 mol) was added drop-wise. The resulting mixture was allowed to warm to room temperature and stirred overnight. TLC (Petroleum ether: EtOAc=2:1) indicated the reaction was complete. The reaction mixture was cooled and quenched with water. The mixture was extracted with EtOAc (400 mL×3). The combined organic layers were washed with saturated aqueous NaCl, dried with $Na_2SO_4$, filtered and concentrated to give crude product, which was purified by recrystallization with petroleum ether: EtOAc=3:1 to give compound G-1-2 (60 g, 57.6%) as a grey yellow solid.

Preparation of 2-(2-(methylthio)pyrimidin-4-yl)-1-(1-(phenylsulfonyl)-1H-pyrrolo[2,3-b]pyridin-5-yl)ethanone (G-1-3)

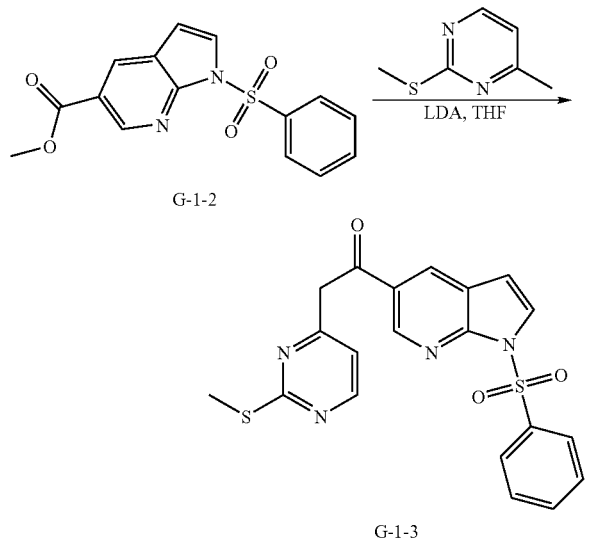

n-BuL₁ (2.5 M, 93 mL, 0.233 mol) was added drop-wise to a solution of i-Pr2NH (32.5 mL, 0.233 mol) in dry THF (420 mL) at −78° C. and the resulting solution was stirred at −78° C. for 30 min. Then, a solution of 4-methyl-2-(methylthio)pyrimidine (22.33 g, 0.16 mol) in dry THF (110 mL) was added drop-wise and the resulting mixture was stirred at −78° C. for another 30 min. A solution of compound G-1-2 (50.0 g, 0.145 mol) in dry THF (250 mL) was then added drop-wise at −110° C. After the addition, the resulting mixture was stirred at −110° C. for 10 min. TLC (hexane:EtOAc 1:1) indicated the reaction was complete. EtOAc (300 mL) and $H_2O$ (300 mL) were added to the reaction mixture to quench the reaction. The organic layer was separated and the aq. layer was extracted with EtOAc (300 mL×3). The combined organic layers were washed with saturated aqueous NaCl (500 mL), dried over $Na_2SO_4$ and concentrated in vacuo. The residue was purified by column chromatography ($CH_2Cl_2$) to give compound 7 (36.0 g, 58.5%) as a yellow solid.

Preparation of (Z)-3-(dimethylamino)-2-(2-(methylthio)pyrimidin-4-yl)-1-(1-(phenylsulfonyl)-1H-pyrrolo[2,3-b]pyridin-5-yl)prop-2-en-1-one (G-1-4)

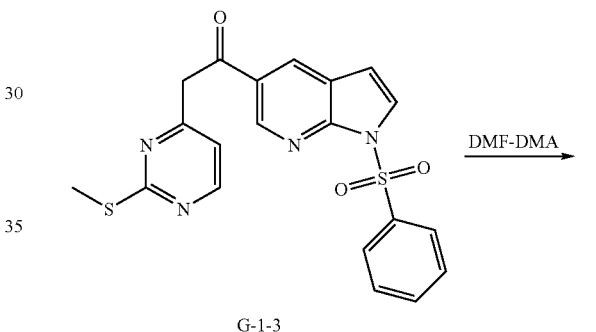

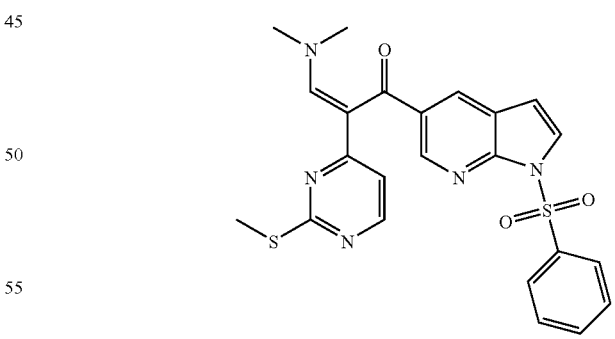

A solution of compound G-1-3 (30 g, 70.7 mmol) in DMF-DMA (300 mL) was heated to 80° C. for 3.5 h. TLC ($CH_2Cl_2$: MeOH=20:1) indicated the reaction was complete. The solvent was concentrated under reduced pressure to give crude compound G-1-4 (36 g) as a dark red oil, which was directly used to the next reaction without purification.

Preparation of 5-(4-(2-(methylthio)pyrimidin-4-yl)-1H-pyrazol-5-yl)-1-(phenylsulfonyl)-1H-pyrrolo[2,3-b]pyridine (G-1-5)

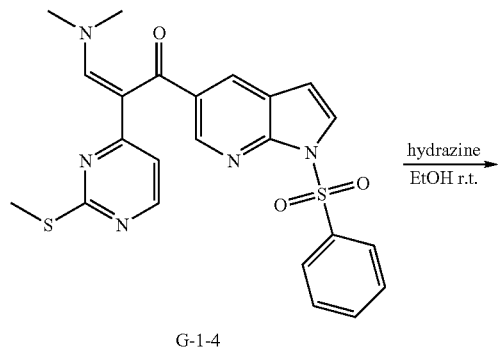

G-1-4

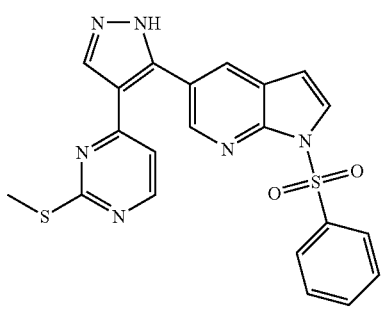

G-1-5

A solution of compound G-1-4 (36 g, crude) in EtOH (360 mL) was added NH$_2$NH$_2$.H$_2$O (30 mL). The mixture was stirred at room temperature for 5 h. The product was deposited from the reaction mixture. The mixture was filtered and the solid was washed with EtOH (50 mL×3) to give the product (19.6 g, 62.1% in two steps) as a orange solid.

Preparation of 5-(4-(2-(methylthio)pyrimidin-4-yl)-1-(tetrahydrofuran-3-yl)-1H-pyrazol-3-yl)-1H-pyrrolo[2,3-b]pyridine (G-1-6)

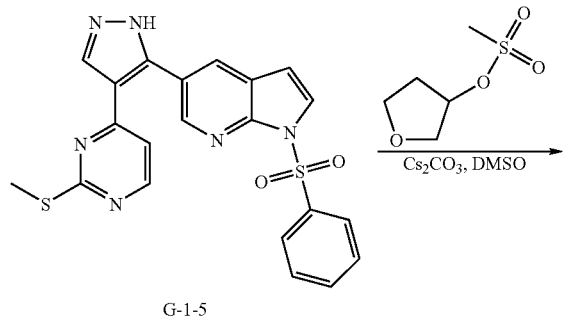

G-1-5

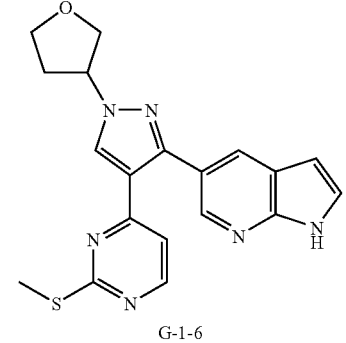

G-1-6

A mixture of compound G-1-5 (1.9 g, 4.24 mmol),

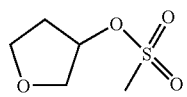

(1.02 g, 5.088 mmol), Cs$_2$CO$_3$ (4.13 g, 12.72 mol) in DMSO (20 mL) was heated to 80° C. and stirred overnight. The mixture was allowed to cool to room temperature and diluted with water (100 mL) and CH$_2$Cl$_2$ (100 mL). The organic layer was separated and the aqueous was extracted with CH$_2$Cl$_2$ for three times. The combined organic layer was washed with saturated aqueous NaCl (300 mL×3), dried over anhydrous Na$_2$SO$_4$, evap. to give the crude compound, which was purified by column chromatography and then via prep. HPLC to afford compound G-1-6 (700 mg, 43.75%) as a yellow solid.

Preparation of 5-(4-(2-(methylthio)pyrimidin-4-yl)-1-(tetrahydrofuran-3-yl)-1H-pyrazol-3-yl)-1-(phenylsulfonyl)-1H-pyrrolo[2,3-b]pyridine (G-1-7)

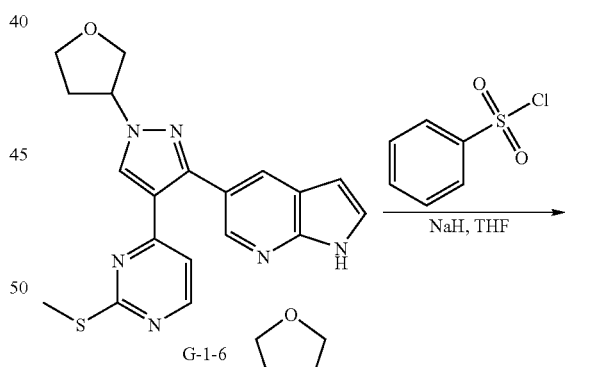

G-1-6

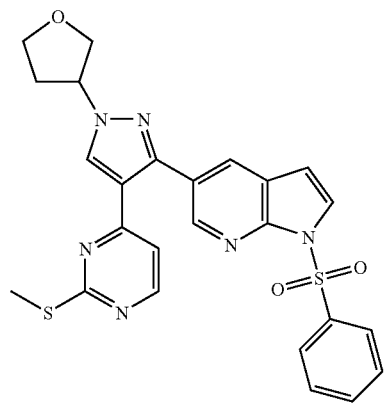

G-1-7

To a cooled mixture of compound G-1-6 (370 mg, 0.98 mmol) in THF (30 mL) was added NaH (47.0 mg, 1.176 mmol, 60% in oil) slowly. After the addition, the mixture was stirred for 1 hour, followed by adding BsCl (207.56 mg, 1.176 mmol) and stirred at room temperature for two hours until TLC analysis (MeOH/CH$_2$Cl$_2$=1/10) showed the starting material was consumed. The resultant mixture was then quenched with saturated aq. NH$_4$Cl and concentrated. The residue was extracted with EtOAc (50 m×3). The combined organic layer was washed with saturated aqueous NaCl (300 mL×3), dried over anhydrous Na$_2$SO$_4$, and evaporated to give the crude compound G-1-7 (600 mg, 100%), which was used for next step directly without further purification.

Preparation of 5-(4-(2-(methylsulfonyl)pyrimidin-4-yl)-1-(tetrahydrofuran-3-yl)-1H-pyrazol-3-yl)-1-(phenylsulfonyl)-1H-pyrrolo[2,3-b]pyridine (G-1-8)

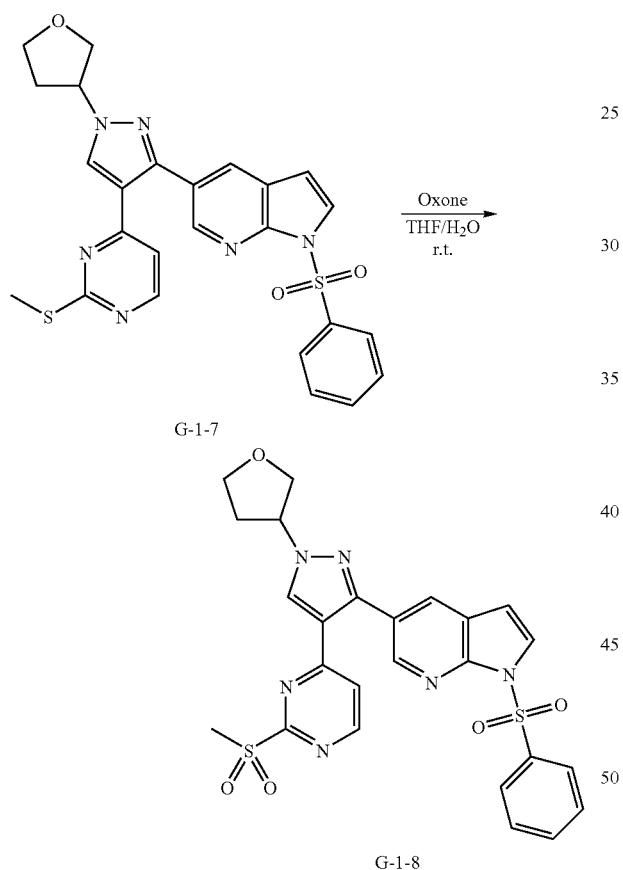

The crude compound G-1-7 (600 mg, 0.98 mmol) was combined with Oxone (0.90 g, 1.47 mmol) in THF/H$_2$O (1/1, 15 mL) and stirred at room temperature for 5 hours until TLC analysis (EtOAc/Petroleum=1/2) showed the starting material was consumed. The resulting mixture was diluted with EtOAc (100 mL) and water (50 mL). The organic layer was separated and the aqueous was extracted with EtOAc for three times. The combined organic layer was then washed with water (100 mL×1), saturated aq. NaHCO$_3$ (100 mL×2), saturated aqueous NaCl (100 mL), separately. The resultant organic layer was dried over anhydrous Na$_2$SO$_4$, evap. to give compound G-1-8 (600 mg, 100%), which was used for next step directly without further purification.

Preparation of (2S)-1-(4-(3-(1-(phenylsulfonyl)-1H-pyrrolo[2,3-b]pyridin-5-yl)-1-(tetrahydrofuran-3-yl)-1H-pyrazol-4-yl)pyrimidin-2-ylamino)propan-2-ol (G-1-9)

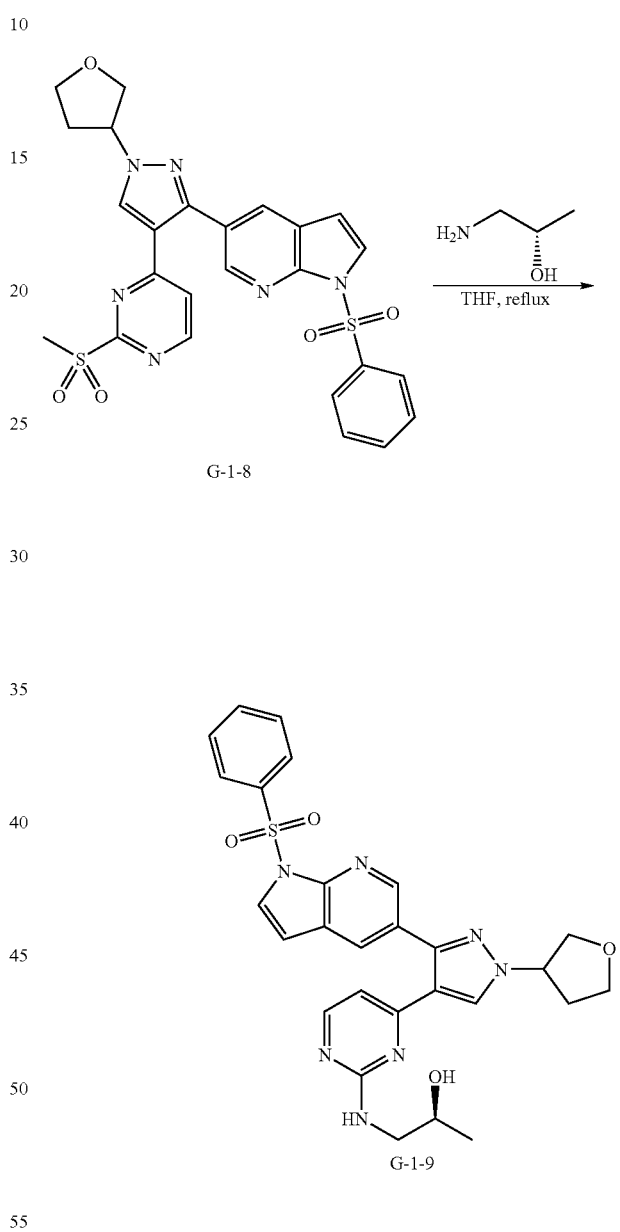

A mixture of compound G-1-8 (600 mg, 0.98 mmol), S-1-aminopropan-2-ol (367.5 mg, 4.9 mmol) in THF (25 mL) was heated to reflux and stirred for 24 hours until TLC analysis (MeOH/CH$_2$Cl$_2$=1/10) showed the starting material was consumed. The resulting mixture was then concentrated to dryness and the residue was dissolved in CH$_2$Cl$_2$ (200 mL), washed with water (100 mL×2) and saturated aqueous NaCl (100 mL×1), dried over anhydrous Na$_2$SO$_4$, followed by evaporation to give Compound G-1-9 (500 mg, 100%) as yellow oil.

157

Preparation of (2S)-1-(4-(3-(1H-pyrrolo[2,3-b]pyridin-5-yl)-1-(tetrahydrofuran-3-yl)-1H-pyrazol-4-yl)pyrimidin-2-ylamino)propan-2-ol (G-1-10)

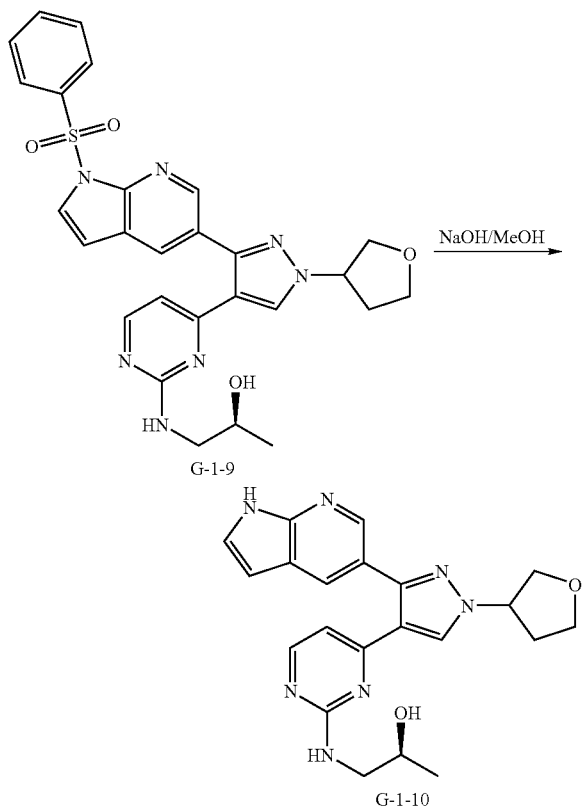

To the solution of crude compound G-1-9 (500 mg, 0.98 mmol) in MeOH (15 mL) was added the solution of NaOH (78.4 mg, 1.96 mmol) in H₂O (3 mL). The mixture was then gently heated and stirred overnight. TLC analysis (MeOH/CH₂Cl₂=1/10) showed the completely consumption of the starting material and formation of new product. Thus, the resulting mixture was diluted with EtOAc (250 mL) and the organic layer was separated and washed with saturated aqueous NaCl (100 mL×2), dried over anhydrous Na₂SO₄, evap. to give the crude product G-1-10 (400 mg, 100%), which was used for next step directly.

Preparation of (2S)-1-(4-(3-(3-chloro-1H-pyrrolo[2,3-b]pyridin-5-yl)-1-(tetrahydrofuran-3-yl)-1H-pyrazol-4-yl)pyrimidin-2-ylamino)propan-2-ol (G-1)

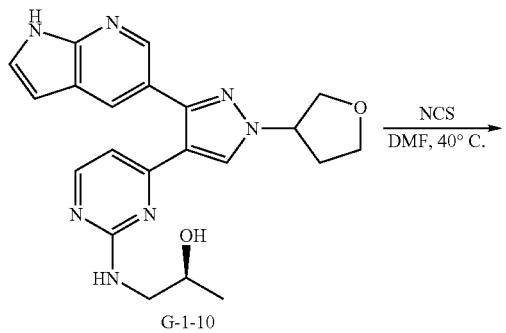

158

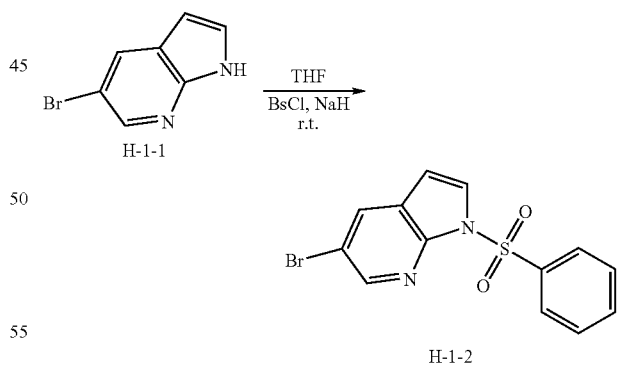

The crude azaindole G-1-10 (400 mg, 0.98 mmol), N-chlorosuccinimide (NCS, 130.83 mg, 0.98 mmol) in DMF (50 mL) under N₂ atmosphere was heated to 40° C. and stirred overnight. LC-MS showed the starting material was completely consumption. The resultant mixture was then diluted with EtOAc (500 mL). The organic layer was separated and washed with water and saturated aqueous NaCl for several times, dried over anhydrous Na₂SO₄, evap. to give the crude product (380 mg). The crude product was purified by prep. HPLC to afford the product G-1 (170 mg, 39.53%) as green solid. $^1$H NMR (400 MHz, CDCl₃): δ 11.281 (s, 1H), 9.809 (s, 1H), 8.508 (s, 1H), 8.284 (s, 1H), 8.2166 (m, 1H), 7.811 (s, 1H), 7.353 (s, 1H), 7.194 (s, 1H), 6.604 (s, 1H), 5.044 (s, 1H), 4.190-4.122 (m, 2H), 4.061-4.022 (m, 1H), 3.966-3.908 (m, 1H), 2.940 (s, 2H), 2.583-2.510 (m, 1H), 2.490-2.364 (m, 1H), 0.917 (s, 3H).

Example H-1

4-(3-(3-chloro-1H-pyrrolo[2,3-b]pyridin-5-yl)-1-isopropyl-1H-pyrazol-4-yl)pyridin-2-amine Preparation of 5-bromo-1-(phenylsulfonyl)-1H-pyrrolo[2,3-b]pyridine (H-1-2)

To a suspension of NaH (87 g, 2.18 mol, 60% in oil) in dry THF (1 L) was added dropwise a solution of 5-bromo-1H-pyrrolo[2,3-b]pyridine H-1-1 (120 g, 0.62 mol) in dry THF (1 L) at 0° C. After addition, the mixture was stirred at 0° C. under N₂ for 0.5 h. To the mixture was added dropwise BsCl (219.5 g, 1.24 mol) at 5° C. After the addition, the mixture was stirred at room temperature overnight. TLC (Petroleum ether/EtOAc 5:1) showed the reaction was complete. The reaction mixture was poured slowly into ice-cold saturated NH₄Cl (500 mL). The mixture was extracted with EtOAc (600 mL×2). The combined organic layers were washed with saturated aqueous NaCl (700 mL), dried over Na₂SO₄ and concentrated in vacuo. The residue was washed with Petroleum ether/EtOAc (15:1, 1.5 L) to give compound H-1-2 (198 g, 94.8%) as an off-white solid.

Preparation of 5-(1-ethoxyvinyl)-1-(phenylsulfonyl)-1H-pyrrolo[2,3-b]pyridine (H-1-3)

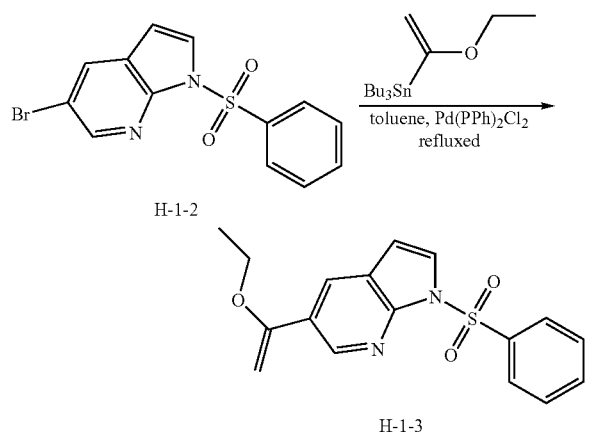

To a solution of compound H-1-2 (110 g, 0.33 mol) and 2-ethoxyprop-1-ene (141.3 g, 0.39 mol) in toluene (2 L) was added Pd(PPh₃)₂Cl₂ (11.4 g, 16.3 mmol) under N₂. The mixture was refluxed overnight. TLC (petroleum ether/EtOAc 5:1) showed the reaction was complete. The reaction mixture was directly used in next step.

Preparation of 1-(1-(phenylsulfonyl)-1H-pyrrolo[2,3-b]pyridin-5-yl)ethanone (H-1-4)

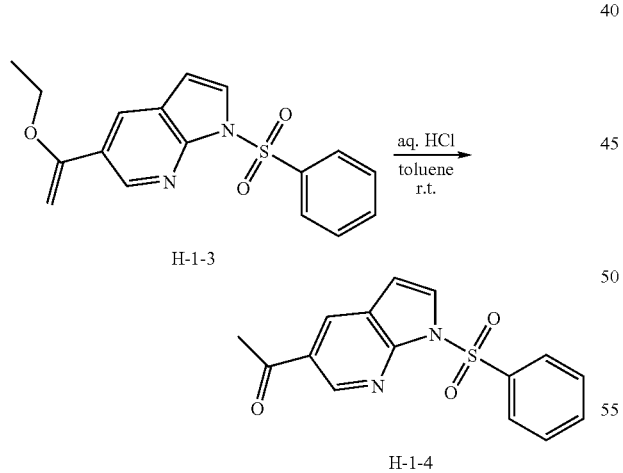

To a mixture of compound H-1-3 (216 g, 0.66 mol) in toluene (2 L) was added HCl (3 N, 440 mL, 1.32 mol). The mixture was stirred at room temperature for 2 h. TLC (petroleum ether/EtOAc 3:1) showed the reaction was complete. The mixture was concentrated in vacuo. The residue was purified via column chromatography (silica gel, petroleum ether/EtOAc 5:1~3:1) to give compound H-1-4 (188 g, 95.0%) as an off-white solid.

Preparation of (E)-3-(dimethylamino)-1-(1-(phenylsulfonyl)-1H-pyrrolo[2,3-b]pyridin-5-yl)prop-2-en-1-one (H-1-5)

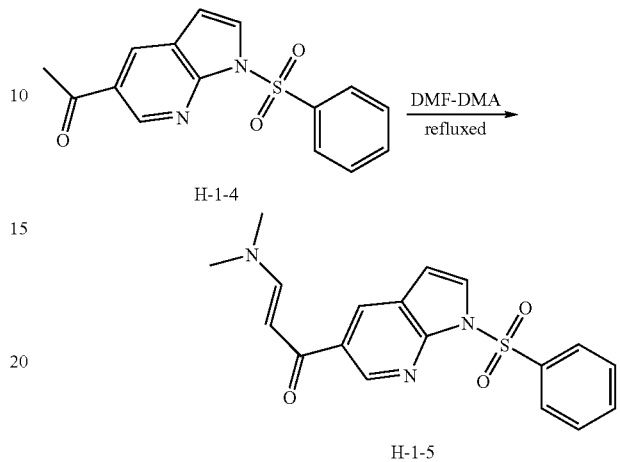

A mixture of compound H-1-4 (97.5 g, 0.325 mol) in DMF-DMA (500 mL) was refluxed under N₂ overnight. TLC (petroleum ether/EtOAc 1:1) showed the reaction was complete. The reaction mixture was concentrated in vacuo. The residue was washed with EtOAc to give compound H-1-5 (35 g, 30.3%) as a yellow solid and crude compound H-1-5 (90 g) as brown oil.

Preparation of 1-(phenylsulfonyl)-5-(1H-pyrazol-3-yl)-1H-pyrrolo[2,3-b]pyridine (H-1-6)

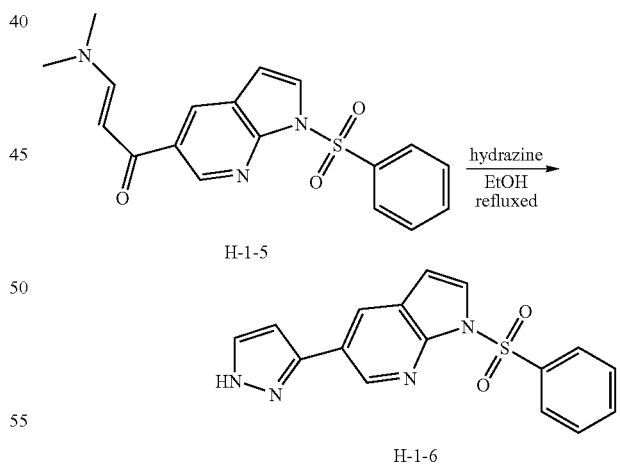

To a mixture of compound H-1-5 (50 g, 0.14 mol) in EtOH (200 mL) was added compound 5B (6.8 g, 0.21 mol) under N₂. After the addition, the mixture was refluxed overnight. TLC (petroleum ether/EtOAc 1:1) showed the reaction was complete. About half of the solvent of EtOH was removed in vacuum and the resulting mixture was filtered. The cake was dried in vacuum to give compound H-1-6 (34 g, 75%) as a gray solid.

Preparation of 5-(1-isopropyl-1H-pyrazol-3-yl)-1-(phenylsulfonyl)-1H-pyrrolo[2,3-b]pyridine (H-1-7)

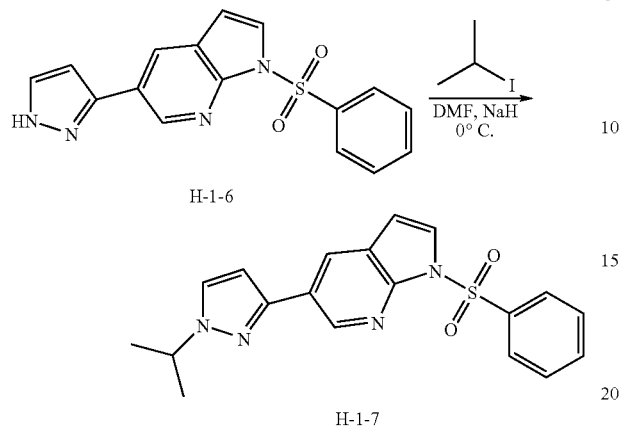

To a mixture of NaH (2.96 g, 74.1 mmol, 60% in oil) in DMF (200 mL) was added portionwise compound H-1-6 (20 g, 61.7 mmol) at 0° C. under $N_2$. After stirring at 0° C. for 0.5 h, isopropyl iodide (31.5 g, 185.2 mmol) was added dropwise to the mixture at 0° C. The resulting mixture was stirred at 0° C. for 0.5 h. TLC (petroleum ether/EtOAc 1:1) showed most of compound H-1-6 was consumed. The reaction mixture was poured into ice-cold saturated $NH_4Cl$ (1000 mL). The mixture was extracted with EtOAc (400 mL). The aq. layer was basified with $K_2CO_3$ to a pH~8, saturated with NaCl and extracted with EtOAc (400 mL). The combined organic layers were washed with saturated aqueous NaCl (400 mL×5), dried over $Na_2SO_4$ and concentrated in vacuo. The residue was purified via column chromagraphy (silica gel, petroleum ether/EtOAc 10:1) to give compound H-1-7 (9 g, 38.1%) as a white solid and crude compound H-1-7 (3 g) as brown oil.

Preparation of 5-(4-bromo-1-isopropyl-1H-pyrazol-3-yl)-1-(phenylsulfonyl)-1H-pyrrolo[2,3-b]pyridine (H-1-8)

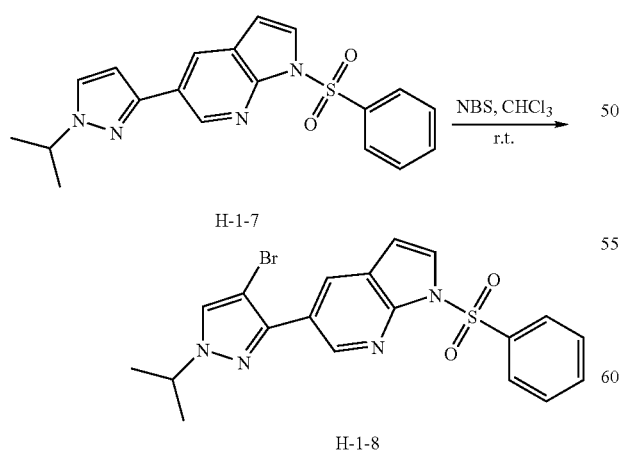

To a solution of compound H-1-7 (5 g, 14 mmol) in $CHCl_3$ (100 mL) was added NBS (2.8 g, 16 mmol) under $N_2$. After the addition, the mixture was stirred at room temperature for 3 h. TLC (petroleum ether/EtOAc 3:1) showed the reaction was complete. The reaction mixture was concentrated in vacuo. To the residue was added EtOAc (200 mL). The mixture was washed with water (200 mL) and saturated aqueous NaCl (200 mL), dried over $Na_2SO_4$ and concentrated in vacuo. The residue was washed with petroleum ether/EtOAc (3:1, 15 mL) to give crude compound H-1-8 (4.5 g, 72%) as a yellow solid. The crude solids were re-crystallized from $CH_2Cl_2$/petroleum ether (1:20, 50 mL) to give pure compound H-1-8 (4.35 g, 70%) as an off-white solid.

Preparation of 5-(4-bromo-1-isopropyl-1H-pyrazol-3-yl)-1H-pyrrolo[2,3-b]pyridine (H-1-9)

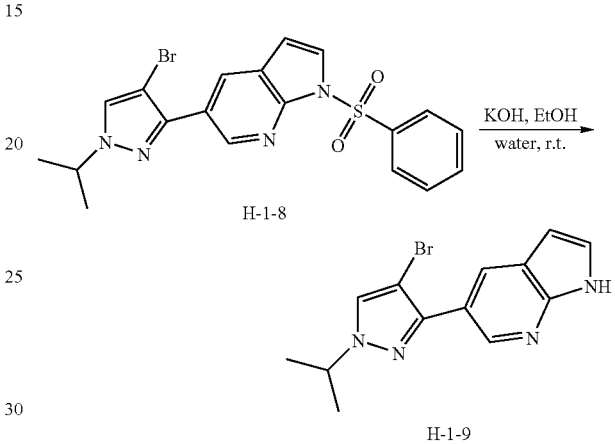

A solution of KOH in 8 ml water was added to a suspension of the Bs protected azaindole (H-1-8) in 50 ml EtOH. Stirred at room temperature overnight. The reaction was concentrated by rotary evaporation. The concentrated reaction mixture was diluted with EtOAc and saturated aqueous NaCl, and the layers were separated. The aqueous layer was re-extracted with EtOAc. The combined organic layers were washed with saturated aqueous NaCl, and dried over $MgSO_4$. The solution was filtered and concentrated under reduced pressure to give a yellow solid. Trituration with TBME (2×) gave 3.37 g of H-1-9 as a yellow solid. The product was used in the next step without further purification. $^1$H NMR (400 MHz, DMSO-d6) δ ppm 1.47 (d, J=6.82 Hz, 6H) 4.36-4.66 (m, 1H) 6.53 (d, J=2.53 Hz, 1H) 7.40-7.60 (m, 1H) 8.15 (s, 1H) 8.30 (d, J=2.02 Hz, 1H) 8.61 (d, J=2.02 Hz, 1H) 11.76 (br. s., 1H).

Preparation of 4-(1-isopropyl-3-(1H-pyrrolo[2,3-b]pyridin-5-yl)-1H-pyrazol-4-yl)pyridin-2-amine (H-1-10)

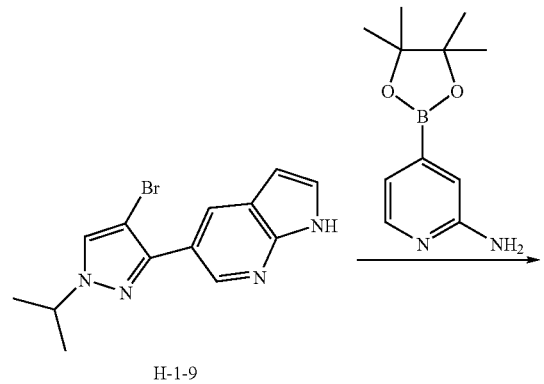

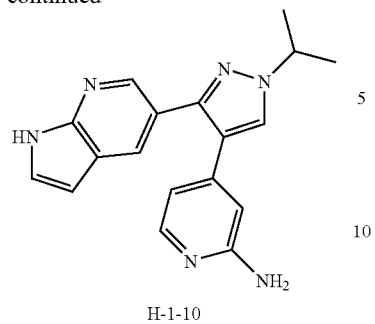

H-1-10

A mixture of the pyrazole H-1-9 (400 mg, 1.31 mmol), 4-(4,4,5,5-tetramethyl-1,3,2-dioxaborolan-2-yl)pyridin-2-amine (375 mg, 1.70 mmol), and 1N sodium carbonate (4 ml, 4 mmol) in 5 mL of DME was flushed with nitrogen for 5 min. 1,1'-Bis(diphenylphospino)ferrocene palladium (II) chloride (96 mg, 0.131 mmol) was then added and the mixture was heated in an oil bath. Reaction turned dark within 5 min. Heating at 80° C. was continued for an additional 18 hours at which time 150 mg more of 4-(4,4,5,5-tetramethyl-1,3,2-dioxaborolan-2-yl)pyridin-2-amine and 25 mg more 1,1'-bis(diphenylphospino)ferrocene palladium (II) chloride were added. After degassing, the reaction was sealed and placed in microwave for 60 min at 80° C. The mixture was filtered and the solids rinsed with water and MeOH. The filtrate was partitioned between ethyl acetate and saturated aqueous NaCl. The aqueous layer was extracted with ethyl acetate (2×). The combined organics were washed with water, saturated aqueous NaCl, and dried over MgSO$_4$, and concentrated under vacuum to a crude brown oil (570 mg) which was purified by reverse phase HPLC to give 51 mg (12% yield) of H-1-10 as a white solid. $^1$H NMR (400 MHz, DMSO-d6) δ ppm 1.50 (d, J=6.57 Hz, 6H) 4.45-4.65 (s, 1H) 5.79 (s, 2H) 6.25-6.38 (m, 2H) 6.45 (dd, J=3.41, 1.89 Hz, 1H) 7.40-7.55 (m, 1H) 7.71-7.86 (m, 1H) 7.95 (d, J=2.02 Hz, 1H) 8.09 (s, 1H) 8.22 (d, J=1.77 Hz, 1H) 11.68 (br. s., 1H).

Preparation of 4-(3-(3-chloro-1H-pyrrolo[2,3-b]pyridin-5-yl)-1-isopropyl-1H-pyrazol-4-yl)pyridin-2-amine (H-1)

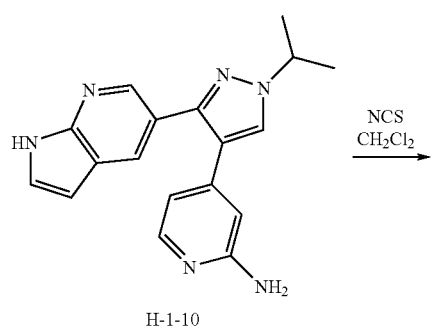

H-1-10

NCS
CH$_2$Cl$_2$

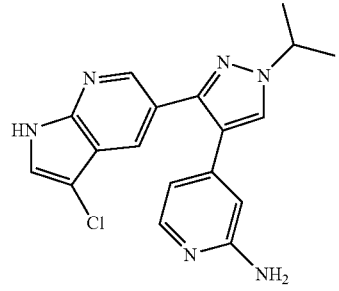

H-1

A mixture 4-(1-isopropyl-3-(1H-pyrrolo[2,3-b]pyridin-5-yl)-1H-pyrazol-4-yl)pyridin-2-amine (H-1-10) (40 mg, 0.13 mmol) and N-chlorosuccinimide (19.3 mg, 0.14 mmol) in CH$_2$Cl$_2$ (2 ml) was stirred at room temperature for 18 hours. Another portion of N-chlorosuccinimide (5 mg, 0.04 mmol) was added and stirring continued at room temperature for an additional 4 hours. The reaction was concentrated under reduced pressure and the residue was purified by reverse phase HPLC to give 14 mg (31% yield) 4-(3-(3-chloro-1H-pyrrolo[2,3-b]pyridin-5-yl)-1-isopropyl-1H-pyrazol-4-yl)pyridin-2-amine (H-1) as a white solid. 1H NMR (400 MHz, DMSO-d6) δ ppm 1.51 (d, J=6.82 Hz, 6H) 4.43-4.69 (m, 1H) 6.22-6.63 (m, 4H) 7.72 (d, J=2.78 Hz, 1H) 7.82 (d, J=5.81 Hz, 1H) 7.92 (d, J=1.77 Hz, 1H) 8.23 (s, 1H) 8.30 (d, J=2.02 Hz, 1H) 12.08 (d, J=1.77 Hz, 1H).

Example 1-1

Preparation of (2S)-1-({4-[3-(5-amino-6-methoxy-pyrazin-2-yl)-1-(2,2-difluoroethyl)-1H-pyrazol-4-yl]pyrimidin-2-yl}amino)propan-2-ol Preparation of I-1-1

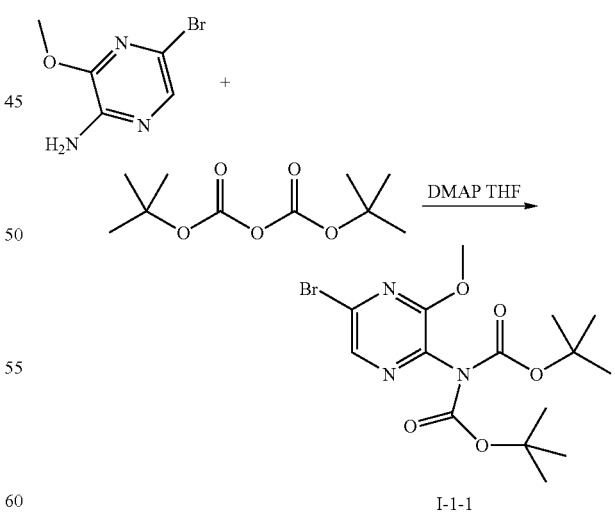

I-1-1

To a solution of 5-bromo-3-methoxypyrazin-2-amine (4.05 g, 19.8 mmol) in 70 mL dry THF was added DMAP (1.24 g, 10.1 mmol) followed by boc anhydride (10.4 g, 47.6 mmol) in one portion at room temperature. The resulting mixture was allowed to stir at room temperature. When the starting mate- Preparation of (2S)-1-({4-[1-(2,2-difluoroethyl)-3-(trimethylstannyl)-1H-pyrazol-4-yl]pyrimidin-2-yl}amino)propan-2-ol (I-1-2)

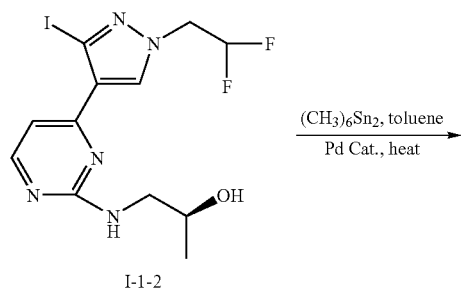

I-1-2

A solution of (2S)-1-({4-[1-(2,2-difluoroethyl)-3-iodo-1H-pyrazol-4-yl]pyrimidin-2-yl}amino)propan-2-ol (2.0 g, 4.9 mmol) and hexamethylditin (1.9 g, 5.9 mmol) in toluene (15 mL) was degassed with a Nitrogen bubbler for 5 minutes prior to the addition of Tetrakis(triphenylphoshine)palladium (0) (566 mg, 0.489 mmol). The resulting mixture was sealed in a 20 mL microwave reaction vial and heated in an oil bath at 90° C. for 18 hrs then at 110° C. for 2 hrs. The mixture was removed from the oil bath and allowed to cool to room temperature. The mixture was loaded directly onto silica gel and purified using a gradient of 0-35% ethyl acetate in dichloromethane as eluent to give 1.26 g (58%) of I-1-3 as an oil. $^1$H NMR (400 MHz, CHLOROFORM-d) δ ppm 8.17 (d, J=5.31 Hz, 1H), 7.99 (s, 1H), 6.68 (d, J=5.31 Hz, 1H), 6.15 (tt, J=55.52, 4.55, 4.42 Hz, 1H), 5.23 (br. t, J=5.31 Hz, 1H), 4.56 (td, J=13.52, 4.29 Hz, 2H), 3.91-4.17 (m, 1H), 3.51-3.75 (m, 1H), 3.28-3.48 (m, 1H), 1.25 (d, J=6.32 Hz, 3H), 0.36 (t, J=28.55 Hz, 9H)

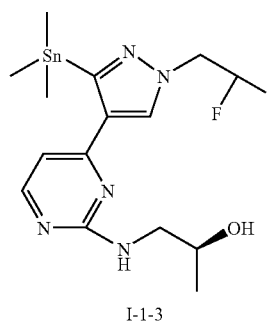

I-1-3

Preparation of (2S)-1-({4-[3-(5-amino-6-methoxypyrazin-2-yl)-1-(2,2-difluoroethyl)-1H-pyrazol-4-yl]pyrimidin-2-yl}amino)propan-2-ol (I-1)

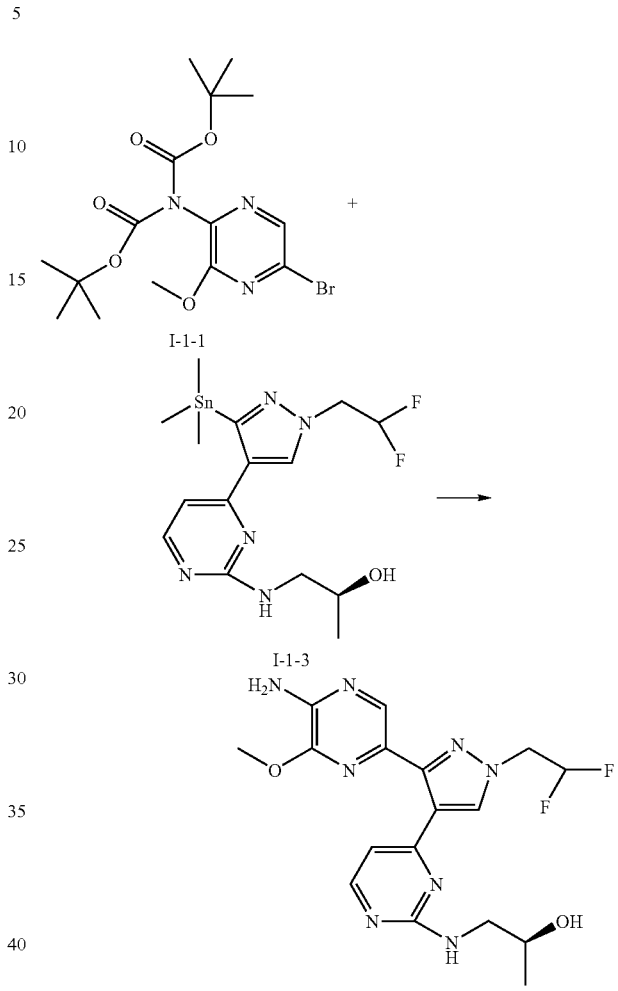

A mixture of di-tert-butyl (5-bromo-3-methoxypyrazin-2-yl) imidodicarbonate (517 mg, 1.28 mmol), (2S)-1-({4-[1-(2,2-difluoroethyl)-3-(trimethylstannyl)-1H-pyrazol-4-yl]pyrimidin-2-yl}amino)propan-2-ol (570 mg, 1.28 mmol), Copper iodide (5 mg, 0.026 mmol) in DMF (13 mL) was deoxygenated with a $N_2$ bubbler for a few minutes before adding Tetrakis(triphenylphoshine)palladium (0) (74 mg, 0.064 mmol). The mixture was sealed in a microwave vial and heated in an oil bath at 10° C. for 18 hrs. This mixture was then heated in the microwave at 170° C. for 20 minutes to themolyze the tert-butoxycarbonyl groups. The mixture was partitioned between ethyl acetate and saturated aqueous NaCl. Some dark insoluble solids did not go into either phase and were removed by filtration. The layers were separated and the aqueous layer was extracted twice with ethyl acetate. The combined organics were washed once each with water and saturated aqueous NaCl, dried over Magnesium sulfate and reduced to minimum volume. The residue was then purified on silica gel using a gradient of 0-8% methanol (containing 10% ammonium hydroxide) in a mixture of tert-butyl methyl ether and dichloromethane (1:1) as eluent. A small amount of the product still containing the tert-butoxycarbonyl groups was recovered from the column. This material was treated with 10% hydrochloric acid in methanol at 70° C. for 2 hours to complete the deprotection. The mixture was partitioned between aqueous Sodium bicarbonate and ethyl acetate. The aqueous layer was extracted twice with ethyl acetate. The combined organics were washed with water (1×), saturated aqueous NaCl (1×), dried over MgSO$_4$ and reduced to minimum volume. The residue was then purified on silica gel in a similar fashion to obtain a second batch of product. The batched were combined and dissolved in a mixture of methanol and water then lyophilized to give 180 mg (33%) (2S)-1-({4-[3-(5-amino-6-methoxypyrazin-2-yl)-1-(2,2-difluoroethyl)-1H-pyrazol-4-yl]pyrimidin-2-yl}amino)propan-2-ol (I-1) as a fluffy white solid. $^1$H NMR (400 MHz, ACETONITRILE-d$_3$) δ ppm 8.05-8.15 (m, 2H), 7.83 (s, 1H), 6.65 (d, J=5.31 Hz, 1H), 6.27 (tt, J=54.95, 3.79 Hz, 1H), 5.73 (br. t, J=4.93 Hz, 1H), 5.34 (br. s., 2H), 4.58 (td, J=14.72, 3.66 Hz, 2H), 3.81 (br. s., 1H), 3.76 (s, 3H), 3.54 (br. s., 1H), 3.27-3.41 (br. m, 1H), 3.06-3.23 (br. m, 1H), 1.08 (d, J=6.32 Hz, 3H).

Preparation of (2S)-1-(4-(1-(2,2-difluoroethyl)-3-iodo-1H-pyrazol-4-yl)pyrimidin-2-ylamino)propan-2-ol (I-1-2)

Step 1:

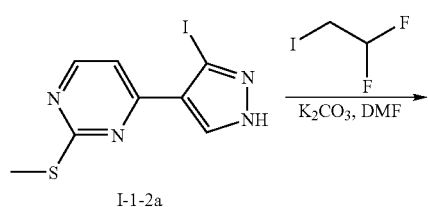

I-1-2a

Step 2:

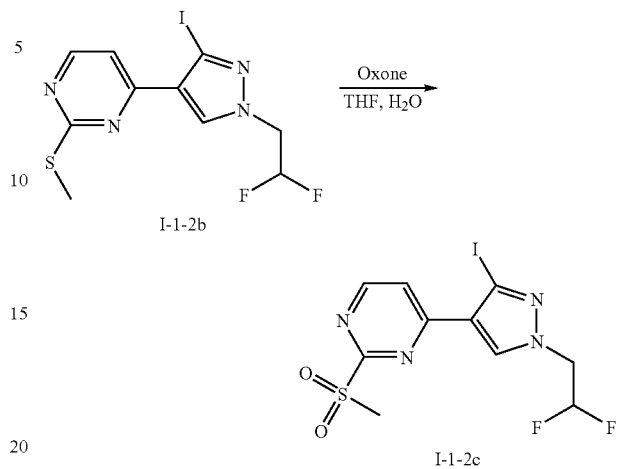

To a solution of I-1-2b (10 g, 26.2 mmol) in THF (100 mL) and water (100 mL) was added oxone (24 g, 39.1 mmol) at 0~5° C. After the addition, the mixture was stirred at room temperature overnight. TLC (EtOAc/Petroleum ether=1:2) showed the reaction was complete, the mixture was concentrated to ½ volume, then EtOAc (200 mL) was added and the organic layer was separated, washed with brine, dried over Na$_2$SO$_4$ and concentrated to give I-1-2c (10.9 g, 100%) as a yellow solid.

Step 3:

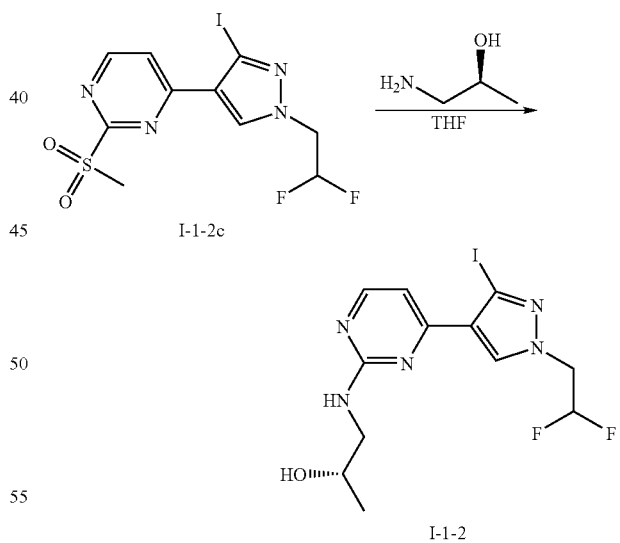

A mixture of compound I-1-2a (22 g, 69.2 mmol), 1,1-difluoro-2-iodoethane (16 g, 83.3 mmol) and K$_2$CO$_3$ (19.2 g, 0.138 mol) in DMF (80 mL) was stirred at 30° C. overnight. When TLC (EtOAc/Petroleum ether=1:4) showed the reaction was complete, DMF was evaporated under reduced pressure. The residue was taken up with EtOAc (500 mL). The mixture was washed with brine, dried over Na$_2$SO$_4$ and concentrated to give crude product, which was purified via SFC to give the product (12.1 g, 45.8%) as a yellow solid.

A mixture of I-1-2c (10.9 g, 26.3 mmol) and (S)-1-aminopropan-2-ol (7.9 g, 0.105 mol) in THF (100 mL) was heated to reflux overnight. When TLC (CH$_2$Cl$_2$: MeOH=10:1) showed the reaction was complete, EtOAc (300 mL) and brine (100 mL) were added to the mixture, and the layers were separated. The organic layer was washed with brine (80 mL×5), dried over Na$_2$SO$_4$, filtered and concentrated to give the product I-1-2 (10.1 g, 93.9%) as a pale solid.

TABLE 1

| Ex. No./ Method | Structure | Structure Name | ¹H NMR/MS (m/z + 1) M + H |
|---|---|---|---|
| B-1/B | 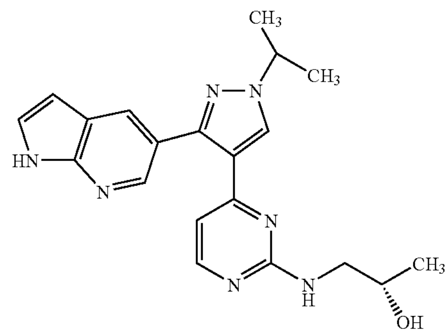 | (2S)-1-(4-(1-isopropyl-3-(1H-pyrrolo[2,3-b]pyridin-5-yl)-1H-pyrazol-4-yl)pyrimidin-2-ylamino)propan-2-ol | 1 H NMR (400 MHz, ACETONITRILE-d3) δ ppm 9.71 (br. s., 1 H), 8.46 (br. s., 1 H), 8.01-8.23 (m, 3 H), 7.39 (d, J = 3.03 Hz, 1 H), 6.51 (d, J = 3.28 Hz, 2 H), 5.71 (br. s., 1 H), 4.45-4.73 (m, 1 H), 3.70 (br. s., 1 H), 3.16 (br. s., 1 H), 3.03 (br. s., 1 H), 1.55 (d, J = 6.57 Hz, 6 H), 0.92 (br. s., 3 H). M + H: 378.2 |
| B-2/B | 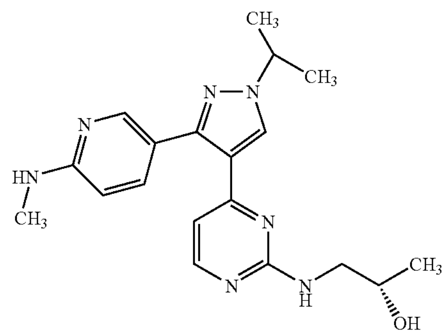 | (2S)-1-(4-(1-isopropyl-3-(6-(methylamino)pyridin-3-yl)-1H-pyrazol-4-yl)pyrimidin-2-ylamino)propan-2-ol | 1 H NMR (400 MHz, MeOD): δ 8.172 (s, 1 H), 8.062 (s, 1 H), 8.014-8.002 (d, 1 H), 7.528-7.506 (d, 1 H), 6.538-6.487 (m, 2 H), 4.528-4.497 (m, 2 H), 3.782 (s, 1 H), 3.100 (s, 1 H), 2.835 (s, 3 H), 1.504-1.429 (d, 6 H), 1.058-1.045 (d, 3 H). M + H: 368.4 |
| B-3/B | 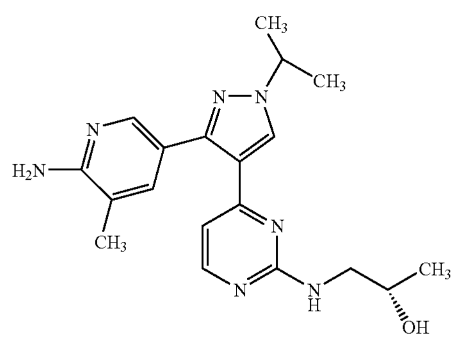 | (2S)-1-(4-(3-(6-amino-5-methylpyridin-3-yl)-1-isopropyl-1H-pyrazol-4-yl)pyrimidin-2-ylamino)propan-2-ol | 1 H NMR (400 MHz, MeOD): δ 8.121 (s, 1 H), 7.959-7.947 (d, 1 H), 7.824 (s, 1 H), 7.374 (s, 1 H), 6.477 (s, 1 H), 4.474-4.429 (m, 2 H), 3.710 (s, 1 H), 3.026 (s, 1 H), 2.049 (s, 3 H), 1.449-1.433 (d, 6 H), 0.992-0.978 (d, 3 H). M + H: 368.4 |
| B-4/B | 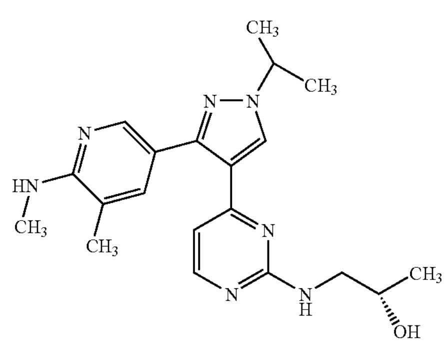 | (2S)-1-(4-(1-isopropyl-3-(5-methyl-6-(methylamino)pyridin-3-yl)-1H-pyrazol-4-yl)pyrimidin-2-ylamino)propan-2-ol | 1 H NMR (400 MHz, MeOD): δ 8.159 (s, 1 H), 8.000-7.966 (m, 2 H), 7.338 (s, 1 H), 6.515 (s, 1 H), 4.537-4.470 (m, 1 H), 3.761 (s, 1 H), 3.246-3.234 (s, 1 H), 3.087-3.077 (s, 1 H), 2.908-2.901 (s, 3 H), 2.086-2.055 (s, 3 H), 1.498-1.482 (d, 6 H), 1.018 (s, 3 H). M + H: 382.6 |

TABLE 1-continued

| Ex. No./ Method | Structure | Structure Name | $^1$H NMR/MS (m/z + 1) M + H |
|---|---|---|---|
| B-5/B | 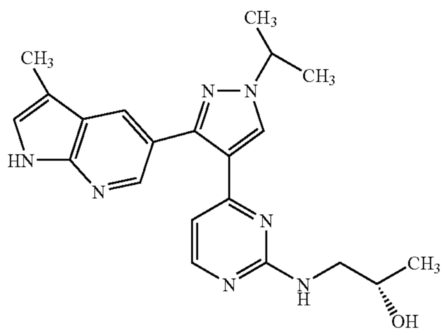 | (2S)-1-(4-(1-isopropyl-3-(3-methyl-1H-pyrrolo[2,3-b]pyridin-5-yl)-1H-pyrazol-4-yl)pyrimidin-2-ylamino)propan-2-ol | 1 H NMR (400 MHz, MeOD): δ 8.227 (s, 1 H), 8.185-8.180 (d, 1 H), 7.981-7.976 (d, 1 H), 7.954-7.940 (d, 1 H), 7.097 (s, 1 H), 6.479 (s, 1 H), 4.567-4.500 (m, 1 H), 3.591 (s, 1 H), 3.035 (m, 1 H), 2.840 (m, 1 H), 2.219 (s, 3 H), 1.511-1.494 (d, 6 H), 0.798 (d, 3 H). M + H: 392.2 |
| B-6/B | 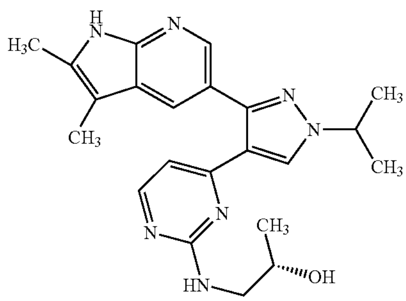 | (2S)-1-(4-(3-(2,3-dimethyl-1H-pyrrolo[2,3-b]pyridin-5-yl)-1-isopropyl-1H-pyrazol-4-yl)pyrimidin-2-ylamino)propan-2-ol | 1 H NMR (400 MHz, MeOD): δ 8.203 (s, 1 H), 8.065-8.060 (d, 1 H), 7.929-7.916 (d, 1 H), 7.816-7.813 (d, 1 H), 6.442 (s, 1 H), 4.564-4.464 (m, 1 H), 3.599 (s, 1 H), 3.039-2.866 (m, 2 H), 2.293 (s, 3 H), 2.193 (s, 3 H), 1.562-1.494 (d, 6 H), 0.814 (s, 3 H). M + H: 406.1 |
| B-7/B | 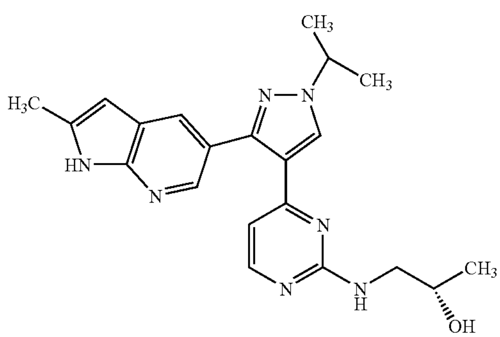 | (2S)-1-(4-(1-isopropyl-3-(2-methyl-1H-pyrrolo[2,3-b]pyridin-5-yl)-1H-pyrazol-4-yl)pyrimidin-2-ylamino)propan-2-ol | 1 H NMR (400 MHz, DMSO): δ 8.473 (s, 1 H), 8.218 (s, 1 H), 8.052-8.037 (d, 1 H), 7.997-7.992 (d, 1 H), 6.763 (s, 1 H), 6.250 (s, 1 H), 4.681-4.614 (m, 1 H), 3.673 (s, 1 H), 3.141-2.901 (m, 2 H), 2.514-2.490 (d, 3 H), 1.617-1.601 (d, 6 H), 0.883 (s, 3 H). M + H: 392.6 |
| B-8/B | 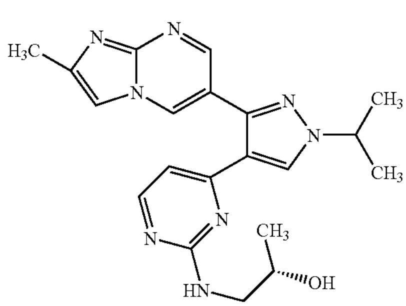 | (2S)-1-(4-(1-isopropyl-3-(2-methylimidazo[1,2-a]pyrimidin-6-yl)-1H-pyrazol-4-yl)pyrimidin-2-ylamino)propan-2-ol | 1 H NMR (300 MHz, MeOH) δ ppm 0.90 (br. s., 3 H) 1.60 (d, 6 H) 2.50 (s, 3 H) 2.92 (br. s., 1 H) 3.08 (br. s., 1 H) 3.69 (br. s., 1 H) 4.57-4.76 (m, 1 H) 6.87 (d, 1 H) 7.73 (s, 1 H) 8.16 (d, 1 H) 8.45 (s, 1 H) 8.84 (br. s., 1 H) 9.16 (br. s., 1 H). M + H: 393 |

TABLE 1-continued

| Ex. No./ Method | Structure Name | ¹H NMR/MS (m/z + 1) M + H |
|---|---|---|
| B-9/B | (2S)-1-(4-(3-(2,3-dimethylimidazo[1,2-a]pyrimidin-6-yl)-1-isopropyl-1H-pyrazol-4-yl)pyrimidin-2-ylamino)propan-2-ol | 1 H NMR (300 MHz, MeOH) δ ppm 0.85 (br. s., 3 H) 1.60 (d, 6 H) 2.44 (s, 3 H) 2.47 (s, 3 H) 2.88 (br. s., 1 H) 3.04 (br. s., 1 H) 3.66 (br. s., 1 H) 4.57-4.73 (m, 1 H) 6.83 (d, 1 H) 8.15 (d, 1 H) 8.42 (s, 1 H) 8.67 (br. s., 1 H) 8.78 (br. s., 1 H). M + H: 409 |
| B-10/B | (2S)-1-(4-(1-isopropyl-3-(5-methyl-5H-pyrrolo[2,3-b]pyrazin-3-yl)-1H-pyrazol-4-yl)pyrimidin-2-ylamino)propan-2-ol | 1 H NMR (300 MHz, MeOH) δ ppm 0.95 (br. s., 3 H) 1.62 (d, 6 H) 2.94 (br. s., 1 H) 3.08 (br. s., 1 H) 3.69 (br. s., 1 H) 3.84 (s, 3 H) 4.61-4.75 (m, 1 H) 6.68 (d, 1 H) 6.83 (d, 1 H) 7.78 (d, 1 H) 8.11 (d, 1 H) 8.33 (br. s., 1 H) 8.69 (br. s., 1 H). M + H: 393 |
| B-11/B | (2S)-1-(4-(3-(3-chloro-1H-pyrrolo[2,3-b]pyridin-5-yl)-1-isopropyl-1H-pyrazol-4-yl)pyrimidin-2-ylamino)propan-2-ol | 1 H NMR (400 MHz, CHLOROFORM-d) δ ppm 1.15 (d, 3 H) 1.63 (d, 6 H) 3.24-3.35 (m, 1 H) 3.41 (dd, 1 H) 3.95 (d, 1 H) 4.56-4.69 (m, 1 H) 5.37- 5.45 (m, 1 H) 6.43 (d, 1 H) 7.31 (d, 1 H) 8.03 (s, 1 H) 8.07 (d, 1 H) 8.22 (s, 1 H) 8.58 (d, 1 H) 8.80 (s, 1 H). M + H 412.2 |
| B-12/B | (2S)-1-(4-(3-(2,3-dihydro-1H-pyrrolo[2,3-b]pyridin-5-yl)-1-isopropyl-1H-pyrazol-4-yl)pyrimidin-2-ylamino)propan-2-ol | 1 H NMR (400 MHz, CHLOROFORM-d) δ ppm 1.23 (d, 3 H) 1.58 (d, 6 H) 3.11 (t, 2 H) 3.34-3.49 (m, 2 H) 3.64-3.73 (m, 2 H) 3.96-4.07 (m, 1 H) 4.50-4.60 (m, 1 H) 4.55 (s, 1 H) 5.38 (t, 1 H) 6.54 (d, 1 H) 7.47 (s, 1 H) 7.97 (s, 1 H) 8.09 (d, 1 H) 8.11 (s, 1 H). M + H: 380.4 |

TABLE 1-continued

| Ex. No./ Method | Structure Name | ¹H NMR/MS (m/z + 1) M + H |
|---|---|---|
| B-13/B | (2S)-1-(4-(1-methyl-3-(1H-pyrrolo[2,3-b]pyridin-5-yl)-1H-pyrazol-4-yl)pyrimidin-2-ylamino)propan-2-ol | 1 H NMR (400 MHz, CHLOROFORM-d) δ ppm 9.46 (br. s., 1 H), 8.54 (d, 1 H), 8.13 (d, 1 H), 8.04 (d, 1 H), 8.01 (s, 1 H), 7.37 (none, 1 H), 6.55 (d, 1 H), 6.43 (d, 1 H), 5.68 (t, 1 H), 4.02 (s, 3 H), 3.88-4.00 (m, 1 H), 3.25-3.48 (m, 2 H), 1.17 (d, 3 H). M + H: 350.2 |
| B-14/B | (2S)-1-(4-(1-(2,2-difluoroethyl)-3-(1H-pyrrolo[2,3-b]pyridin-5-yl)-1H-pyrazol-4-yl)pyrimidin-2-ylamino)propan-2-ol | 1 H NMR (400 MHz, CHLOROFORM-d) δ ppm 9.15 (br. s., 1 H), 8.53 (d, 1 H), 8.12 (d, 1 H), 8.02-8.10 (m, 2 H), 7.36 (dd, 1 H), 6.55 (dd, 1 H), 6.44 (d, 1 H), 6.23 (tt, 1 H), 5.47 (t, 1 H), 4.56 (td, 1 H), 4.23 (br. s., 1 H), 3.86-4.04 (br. m, 1 H), 3.36-3.50 (br. m, 1 H), 3.24-3.35 (m, 1 H), 1.16 (d, 3 H). M + H 400.2 |
| B-15/B | (2S)-1-(4-(1-((3-methyloxetan-3-yl)methyl)-3-(1H-pyrrolo[2,3-b]pyridin-5-yl)-1H-pyrazol-4-yl)pyrimidin-2-ylamino)propan-2-ol | 1 H NMR (400 MHz, CHLOROFORM-d) δ ppm 9.11 (br. s., 1 H), 8.52 (d, 1 H), 8.11 (d, 1 H), 8.06 (d, 1 H), 7.99 (s, 1 H), 7.36 (dd, 1 H), 6.55 (dd, 1 H), 6.44 (d, 1 H), 5.46 (t, 1 H), 4.79 (d, 2 H), 4.47 (d, 2 H), 4.42 (s, 2 H), 3.89-4.03 (br. m, 1 H), 3.36-3.50 (br. m, 1 H), 3.26-3.36 (m, 1 H), 1.38 (s, 3 H), 1.17 (d, 3 H). M + H: 420.0 |
| B-16/B | 4-[3-(6-amino-5-methoxypyridin-3-yl)-1-isopropyl-1H-pyrazol-4-yl]-N-cyclopropylpyrimidin-2-amine | 1 H NMR (400 MHz, ACETONITRILE-d3) δ ppm 8.12 (d, 1 H), 8.07 (s, 1 H), 7.82 (s, 1 H), 7.18 (d, 1 H), 6.58 (d, 1 H), 5.74 (br. s., 1 H), 5.14 (br. s., 2 H), 4.41-4.63 (m, 1 H), 3.79 (s, 3 H), 2.54-2.73 (m, 1 H), 1.52 (d, 6 H), 0.58-0.71 (m, 2 H), 0.30-0.51 (m, 2 H). M + H: 366.2 |

TABLE 1-continued

| Ex. No./ Method | Structure | Structure Name | ¹H NMR/MS (m/z + 1) M + H |
|---|---|---|---|
| B-17/B | 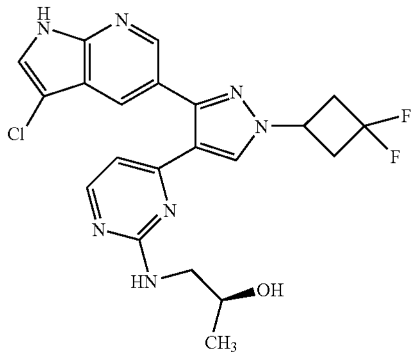 | (2S)-1-({4-[3-(3-chloro-1H-pyrrolo[2,3-b]pyridin-5-yl)-1-(3,3-difluorocyclobutyl)-1H-pyrazol-4-yl]pyrimidin-2-yl}amino)propan-2-ol | 1 H NMR (400 MHz, CHLOROFORM-d) δ ppm 9.28 (br. s., 1 H), 8.57 (d, 1 H), 8.21 (d, 1 H), 8.10 (d, 1 H), 8.06 (s, 1 H), 7.33 (d, 1 H), 6.43 (d, 1 H), 5.53 (br. t, 1 H), 4.61-4.91 (m, 1 H), 4.34 (br. s., 1 H), 3.97 (br. s., 1 H), 3.05-3.48 (m, 6 H), 1.16 (d, 3 H). M + H: 460.0 |
| B-18/B | 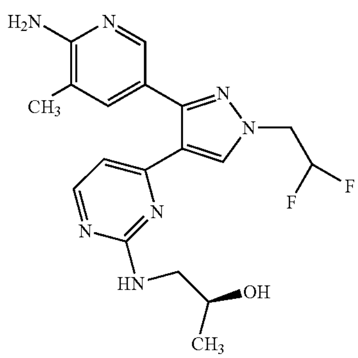 | (2S)-1-({4-[3-(6-amino-5-methylpyridin-3-yl)-1-(2,2-difluoroethyl)-1H-pyrazol-4-yl]pyrimidin-2-yl}amino)propan-2-ol | 1 H NMR (400 MHz, CHLOROFORM-d) δ ppm 8.29 (s, 1 H), 8.12 (d, 1 H), 8.00 (s, 1 H), 7.61 (s, 1 H), 6.52 (d, 1 H), 6.19 (tt, 1 H), 5.78 (br. s., 1 H), 5.21 (br. s., 2 H), 4.52 (td, 2 H), 3.90-4.08 (m, 1 H), 3.17-3.53 (m, 2 H), 2.19 (s, 3 H), 1.23 (d, 3 H). M + H: 390.2 |
| B-19/B | 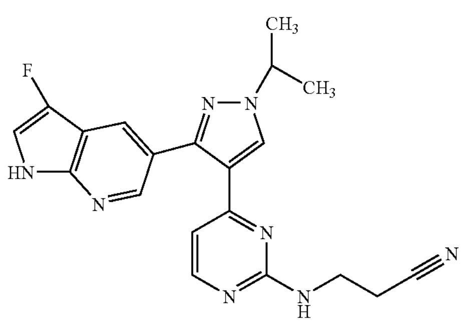 | 3-({4-[3-(3-fluoro-1H-pyrrolo[2,3-b]pyridin-5-yl)-1-isopropyl-1H-pyrazol-4-yl]pyrimidin-2-yl}amino)propanenitrile | 1 H NMR (400 MHz, CHLOROFORM-d) δ ppm 8.39-8.62 (m, 2 H), 8.20 (d, 1 H), 8.12 (d, 1 H), 8.04 (s, 1 H), 7.11 (t, 1 H), 6.52 (d, 1 H), 5.44 (t, 1 H), 4.41-4.74 (m, 1 H), 3.58 (br. s., 2 H), 2.53 (br. s., 2 H), 1.63 (d, 6 H, partially obscured by water). M + H: 391.2 |
| B-20/B | 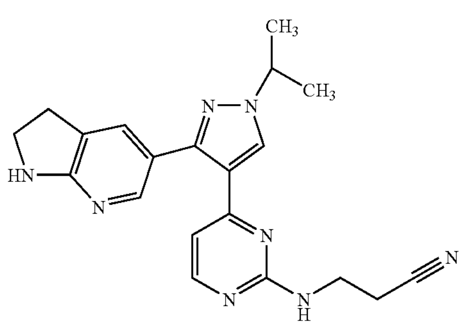 | 3-({4-[3-(2,3-dihydro-1H-pyrrolo[2,3-b]pyridin-5-yl)-1-isopropyl-1H-pyrazol-4-yl]pyrimidin-2-yl}amino)propanenitrile | 1 H NMR (400 MHz, CHLOROFORM-d) δ ppm 8.12 (d, 1 H), 7.94-7.99 (m, 2 H), 7.46 (d, 1 H), 6.60 (d, 1 H), 5.56 (br. t, 1 H), 5.13 (br. s., 1 H), 4.43-4.66 (m, 1 H), 3.50-3.79 (m, 4 H), 3.11 (t, 2 H), 2.66 (t, 2 H), 1.59 (d, 6 H). M + H: 375.2 |

TABLE 1-continued

| Ex. No./ Method | Structure | Structure Name | ¹H NMR/MS (m/z + 1) M + H |
|---|---|---|---|
| B-21/B | 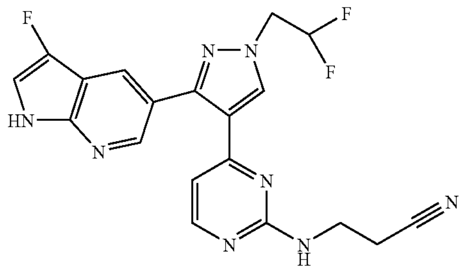 | 3-({4-[1-(2,2-difluoroethyl)-3-(3-fluoro-1H-pyrrolo[2,3-b]pyridin-5-yl)-1H-pyrazol-4-yl]pyrimidin-2-yl}amino)propanenitrile | 1 H NMR (400 MHz, CHLOROFORM-d) δ ppm 8.12 (d, 1 H), 7.94-7.99 (m, 2 H), 7.46 (d, 1 H), 6.60 (d, 1 H), 5.56 (br. t, 1 H), 5.13 (br. s., 1 H), 4.43-4.66 (m, 1 H), 3.50-3.79 (m, 4 H), 3.11 (t, 2 H), 2.66 (t, 2 H), 1.59 (d, 6 H). M + H: 413.2 |
| B-22/B | 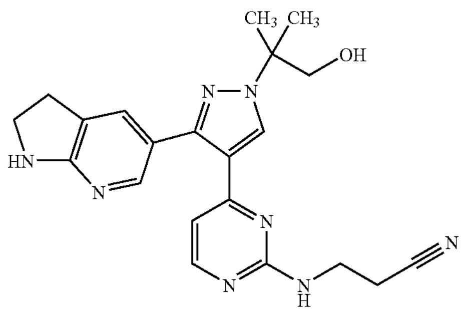 | 3-({4-[3-(2,3-dihydro-1H-pyrrolo[2,3-b]pyridin-5-yl)-1-(2-hydroxy-1,1-dimethylethyl)-1H-pyrazol-4-yl]pyrimidin-2-yl}amino)propanenitrile | 1 H NMR (400 MHz, CHLOROFORM-d/MeOD-d4) δ ppm 7.98 (s, 1 H), 7.96 (d, 1 H), 7.75 (s, 1 H), 7.29 (d, 1 H, partially obscured by Chloroform), 6.47 (d, 1 H), 3.69 (s, 2 H), 3.56 (t, 2 H), 3.48 (t, 2 H), 2.98 (t, 2 H), 2.50 (t, 2 H), 1.49 (s, 6 H). M + H: 405.2 |
| B-23/B | 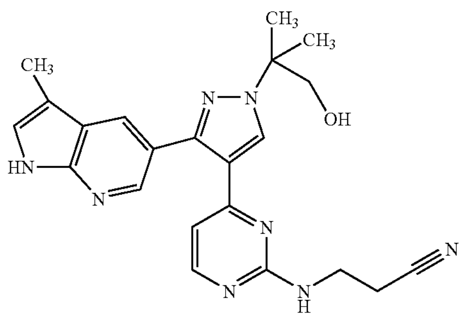 | 3-({4-[1-(2-hydroxy-1,1-dimethylethyl)-3-(3-methyl-1H-pyrrolo[2,3-b]pyridin-5-yl)-1H-pyrazol-4-yl]pyrimidin-2-yl}amino)propanenitrile | 1 H NMR (400 MHz, CHLOROFORM-d) δ ppm 8.73 (br. s., 1 H), 8.42 (d, 1 H), 8.13 (s, 1 H), 8.09 (d, 1 H), 8.06 (d, 1 H), 7.12 (s, 1 H), 6.51 (d, 1 H), 5.45 (t, 1 H), 3.91 (s, 2 H), 3.46-3.71 (br. m, 2 H), 2.53 (br. s., 2 H), 2.33 (s, 3 H), 1.68 (s, 6 H, partially obscured by water). M + H: 417.2 |
| B-24/B | 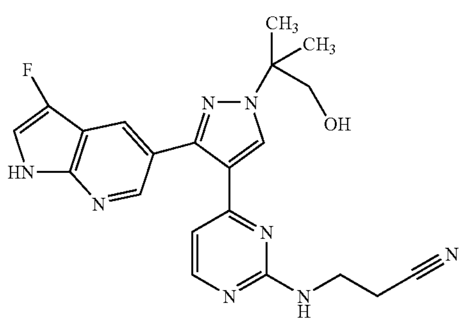 | 3-({4-[3-(3-fluoro-1H-pyrrolo[2,3-b]pyridin-5-yl)-1-(2-hydroxy-1,1-dimethylethyl)-1H-pyrazol-4-yl]pyrimidin-2-yl}amino)propanenitrile | 1 H NMR (400 MHz, CHLOROFORM-d/ METHANOL-d₄) δ ppm 8.31 (d, 1 H), 8.04-8.08 (m, 2 H), 7.95 (d, 1 H), 7.02 (d, 1 H), 6.43 (d, 1 H), 3.74 (s, 2 H), 3.38 (br. s., 2 H), 2.35 (br. s., 2 H), 1.55 (s, 6 H) |
| B-25/B | 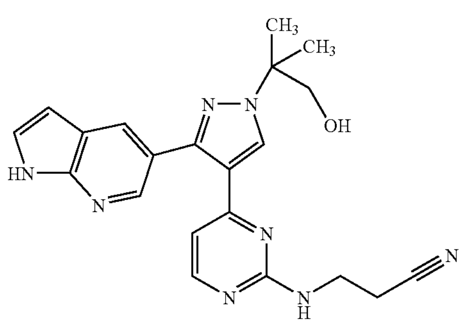 | 3-({4-[1-(2-hydroxy-1,1-dimethylethyl)-3-(1H-pyrrolo[2,3-b]pyridin-5-yl)-1H-pyrazol-4-yl]pyrimidin-2-yl}amino)propanenitrile | 1 H NMR (400 MHz, CHLOROFORM-d) δ ppm 9.52 (br. s., 1 H), 8.46 (s, 1 H), 8.02-8.16 (m, 3 H), 7.37 (d, 1 H), 6.55 (d, 1 H), 6.52 (d, 1 H), 5.59 (t, 1 H), 3.91 (s, 2 H), 3.58 (br. s., 2 H), 2.52 (s, 2 H), 1.67 (s, 6 H). M + H: 403.2 |

TABLE 1-continued

| Ex. No./ Method | Structure | Structure Name | ¹H NMR/MS (m/z + 1) M + H |
|---|---|---|---|
| B-26/B | 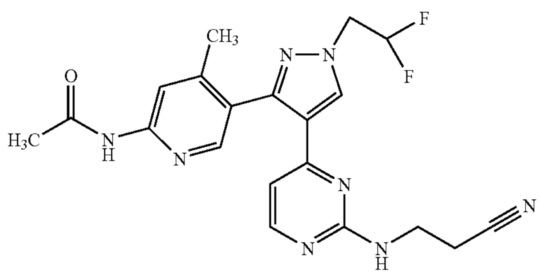 | N-{5-[4-{2-[(2-cyanoethyl)amino]pyrimidin-4-yl}-1-(2,2-difluoroethyl)-1H-pyrazol-3-yl]-4-methylpyridin-2-yl}acetamide | 1 H NMR (400 MHz, CHLOROFORM-d) δ ppm 8.14-8.20 (m, 3 H), 8.12 (d, 1 H), 7.96 (s, 1 H), 6.00-6.38 (m, 2 H), 5.35 (t, 1 H), 4.57 (td, 2 H), 3.53 (br. s., 2 H), 2.55 (br. s., 2 H), 2.25 (s, 3 H), 2.18 (s, 3 H). M + H: 427.2 |
| B-27/B | 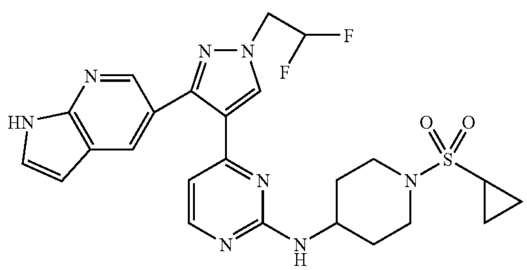 | N-[1-(cyclopropylsulfonyl)piperidin-4-yl]-4-[1-(2,2-difluoroethyl)-3-(1H-pyrrolo[2,3-b]pyridin-5-yl)-1H-pyrazol-4-yl]pyrimidin-2-amine | 1 H NMR (400 MHz, ACETONITRILE-d3) δ ppm 9.72 (br. s., 1 H), 8.37 (d, 1 H), 8.16 (s, 1 H), 8.14 (d, 1 H), 8.07 (d, 1 H), 7.40 (dd, 1 H), 6.65 (br. s., 1 H), 6.51 (dd, 1 H), 6.30 (tt, 1 H), 5.49 (d, 1 H), 4.61 (td, 2 H), 3.40 (br. s., 2 H), 2.23 (br. s., 2 H), 1.68 (br. s., 2 H), 1.29 (br. s., 2 H), 0.94-1.03 (m, 4 H). M + H: 529.2 |
| B-28/B | 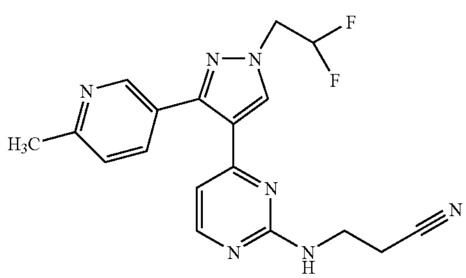 | 3-({4-[1-(2,2-difluoroethyl)-3-(6-methylpyridin-3-yl)-1H-pyrazol-4-yl]pyrimidin-2-yl}amino)propanenitrile | 1 H NMR (400 MHz, ACETONITRILE-d3) δ ppm 8.60 (d, 1 H), 8.19 (s, 1 H), 8.17 (d, 1 H), 7.78 (dd, 1 H), 7.25 (d, 1 H), 6.63 (br. d, 1 H), 6.28 (tt, 1 H), 5.90 (br. t, 1 H), 4.60 (td, 2 H), 3.39 (br. s., 2 H), 2.54 (s, 3 H), 2.46 (br. s., 2 H). M + H: 370.2 |
| B-29/B | 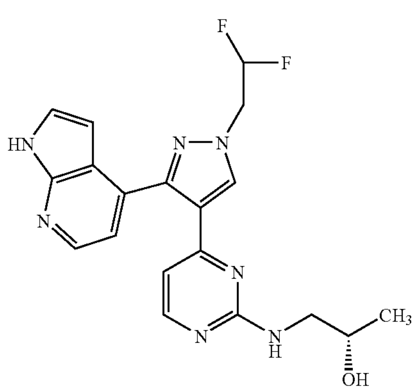 | (2S)-1-({4-[1-(2,2-difluoroethyl)-3-(1H-pyrrolo[2,3-b]pyridin-4-yl)-1H-pyrazol-4-yl]pyrimidin-2-yl}amino)propan-2-ol | 1 H NMR (400 MHz, CHLOROFORM-d) δ ppm 8.87 (br. s., 1 H), 8.37 (d, 1 H), 8.14 (s, 1 H), 8.02 (d, 1 H), 7.31 (dd, 1 H), 7.23 (d, 1 H), 6.04-6.45 (m, 3 H), 5.41 (t, 1 H), 4.60 (td, 2 H), 4.07 (br. s., 1 H), 3.86-4.01 (m, 1 H), 3.36-3.49 (m, 1 H), 3.25 (br. s., 1 H), 1.18 (d, 3 H). M + H: 400.2 |

TABLE 1-continued

| Ex. No./ Method | Structure | Structure Name | ¹H NMR/MS (m/z + 1) M + H |
|---|---|---|---|
| B-30/B | 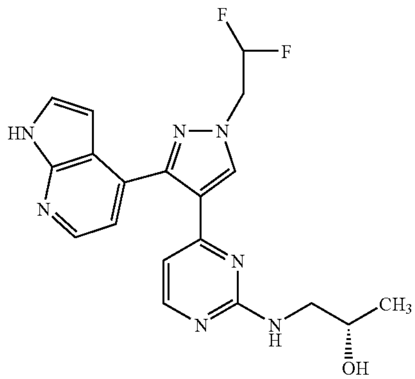 | 3-({4-[3-(5-amino-6-methoxypyrazin-2-yl)-1-tert-butyl-1H-pyrazol-4-yl]pyrimidin-2-yl}amino)propanenitrile | 1 H NMR (400 MHz, CHLOROFORM-d) δ ppm 8.12 (d, 1 H), 8.10 (s, 1 H), 8.01 (s, 1 H), 6.75 (d, 1 H), 5.52 (br. t, 1 H), 4.95 (br. s., 2 H), 3.87 (s, 3 H), 3.71 (q, 2 H), 2.70 (t, 2 H), 1.68 (s, 9 H, partially obscured by water). M + H: 394.2 |
| B-31/B | 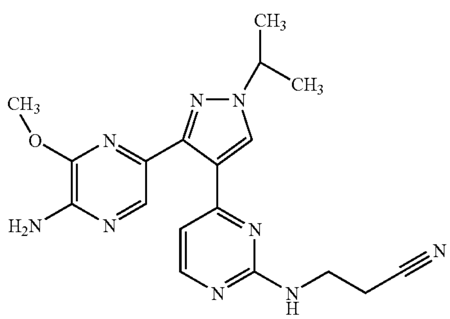 | 3-({4-[3-(5-amino-6-methoxypyrazin-2-yl)-1-isopropyl-1H-pyrazol-4-yl]pyrimidin-2-yl}amino)propanenitrile | 1 H NMR (400 MHz, CHLOROFORM-d) δ ppm 8.13 (d, 1 H), 8.03 (s, 1 H), 7.98 (s, 1 H), 6.74 (d, 1 H), 5.47-5.70 (br. m, 1 H), 4.98 (br. s., 2 H), 4.49-4.74 (m, 1 H), 3.88 (s, 3 H), 3.71 (q, 2 H), 2.70 (t, 2 H), 1.60 (d, 6 H, partially obscured by water). M + H: 380.2 |
| B-32/B | 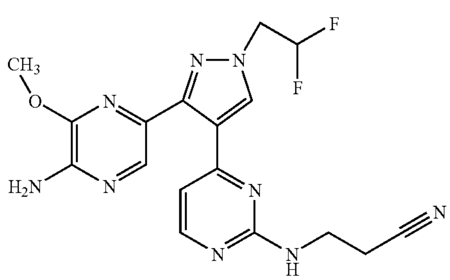 | 3-({4-[3-(5-amino-6-methoxypyrazin-2-yl)-1-(2,2-difluoroethyl)-1H-pyrazol-4-yl]pyrimidin-2-yl}amino)propanenitrile | 1 H NMR (400 MHz, CHLOROFORM-d) δ ppm 8.18 (d, 1 H), 8.04 (s, 1 H), 7.98 (s, 1 H), 6.74 (d, 1 H), 6.21 (tt, 1 H), 5.41 (br. t, 1 H), 4.94 (br. s., 2 H), 4.55 (td, 2 H), 3.87 (s, 3 H), 3.71 (q, 2 H), 2.70 (t, 2 H). M + H: 402.2 |
| B-33/B | 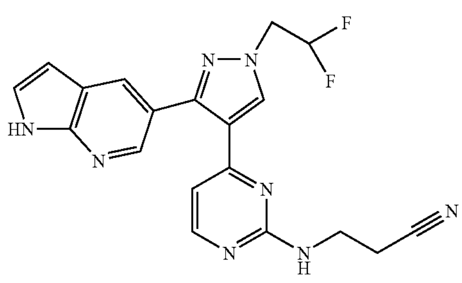 | 3-({4-[3-(5-amino-6-methoxypyrazin-2-yl)-1-(2,2-difluoroethyl)-1H-pyrazol-4-yl]pyrimidin-2-yl}amino)propanenitrile | 1 H NMR (400 MHz, ACETONITRILE-d3) δ ppm 9.73 (br. s., 1 H), 8.37 (d, 1 H), 8.22 (s, 1 H), 8.10 (d, 1 H), 8.08 (d, 1 H), 7.35-7.46 (m, 1 H), 6.54 (d, 1 H), 6.51 (dd, 1 H), 6.30 (tt, 1 H), 5.91 (br. t, 1 H), 4.62 (td, 2 H), 3.39 (br. s., 2 H), 2.40 (br. s., 2 H). M + H: 395.2 |

TABLE 1-continued

| Ex. No./ Method | Structure | Structure Name | ¹H NMR/MS (m/z + 1) M + H |
|---|---|---|---|
| B-34/B | 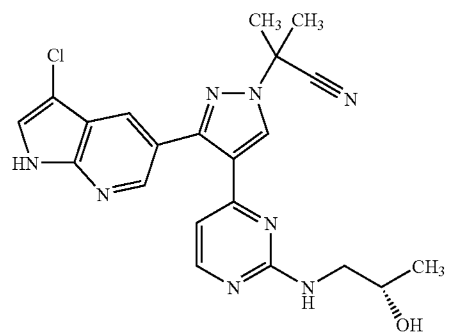 | 2-[3-(3-chloro-1H-pyrrolo[2,3-b]pyridin-5-yl)-4-(2-{[(2S)-2-hydroxypropyl]amino}pyrimidin-4-yl)-1H-pyrazol-1-yl]-2-methylpropanenitrile | 1 H NMR (400 MHz, CHLOROFORM-d) δ ppm 8.81 (br. s., 1 H), 8.58 (d, 1 H), 8.27 (s, 1 H), 8.22 (d, 1 H), 8.12 (d, 1 H), 7.33 (d, 1 H), 6.46 (d, 1 H), 5.45 (br. s., 1 H), 3.95 (br. s., 1 H), 3.42 (br. s., 1 H), 3.18-3.36 (br. m, 1 H), 2.12 (s, 6 H), 1.15 (br. d, 3 H). M + H: 437.2 |
| B-35/B | 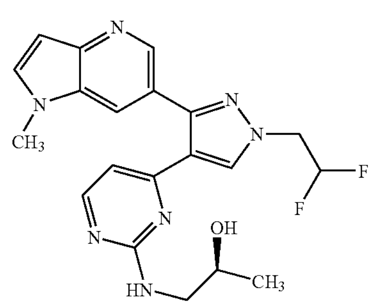 | (2S)-1-({4-[1-(2,2-difluoroethyl)-3-(1-methyl-1H-pyrrolo[3,2-b]pyridin-6-yl)-1H-pyrazol-4-yl]pyrimidin-2-yl}amino)propan-2-ol | 1 H NMR (400 MHz, MeOD) δ ppm 0.88 (br. s., 3 H), 2.91 (br. s., 1 H), 3.10 (br. s., 1 H), 3.31 (br. s., 2 H), 3.67 (br. s., 1 H), 3.86 (s, 3 H), 4.69 (t, 2 H), 6.32 (t, 1 H), 6.62 (br. s., 2 H), 7.57 (d, 1 H), 8.05 (s, 1 H), 8.09 (d, 1 H), 8.36 (s, 1 H), 8.46 (s, 1 H). M + H: 415 |
| B-36/B | 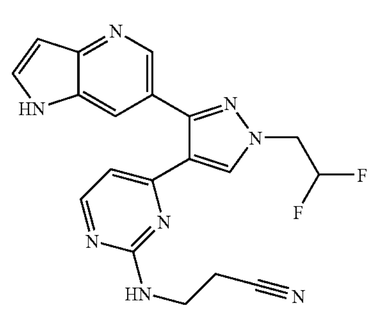 | 3-({4-[1-(2,2-difluoroethyl)-3-(1H-pyrrolo[3,2-b]pyridin-6-yl)-1H-pyrazol-4-yl]pyrimidin-2-yl}amino)propanenitrile | 1 H NMR (400 MHz, MeOD) δ ppm 2.26 (br. s., 2 H), 3.34 (br. s., 2 H), 4.57-4.75 (m, 2 H), 6.12-6.49 (m, 1 H), 6.65 (d, 1 H), 6.68 (br. s., 1 H), 7.65 (d, 1 H), 7.97 (s, 1 H), 8.13 (d, 1 H), 8.38 (s, 1 H), 8.44 (d, 1 H). M + H: 395 |

TABLE 1-continued

| Ex. No./ Method | Structure | Structure Name | ¹H NMR/MS (m/z + 1) M + H |
|---|---|---|---|
| B-37/B | 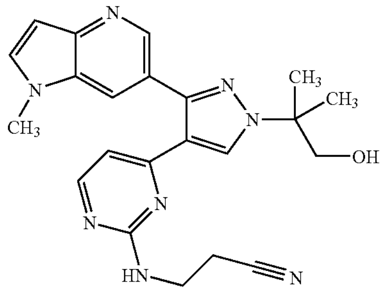 | 3-({4-[1-(2-hydroxy-1,1-dimethylethyl)-3-(1-methyl-1H-pyrrolo[3,2-b]pyridin-6-yl)-1H-pyrazol-4-yl]pyrimidin-2-yl}amino)propanenitrile | 1 H NMR (400 MHz, CHLOROFORM-d) δ ppm 1.68 (s, 6 H), 2.46 (br. s., 2 H), 3.53 (br. s., 2 H), 3.83 (s, 3 H), 3.91 (br. s., 2 H), 4.16 (br. s., 1 H), 5.51 (t, 1 H), 6.50 (d, 1 H), 6.71 (d, 1 H), 7.34 (d, 1 H), 7.81 (s, 1 H), 8.08 (d, 1 H), 8.12 (s, 1 H), 8.55 (d, 1 H). M + H: 417 |
| B-38/B | 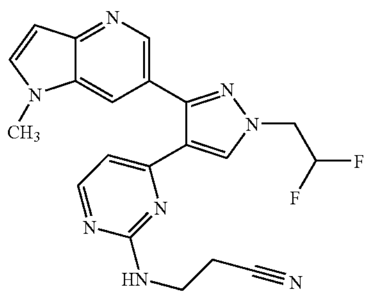 | 3-({4-[1-(2-hydroxy-1,1-dimethylethyl)-3-(1-methyl-1H-pyrrolo[3,2-b]pyridin-6-yl)-1H-pyrazol-4-yl]pyrimidin-2-yl}amino)propanenitrile | 1 H NMR (400 MHz, CHLOROFORM-d) δ ppm 2.46 (br. s., 2 H), 3.53 (br. s., 2 H), 3.84 (s, 3 H), 4.48-4.68 (m, 2 H), 5.54 (t, 1 H), 6.01-6.41 (m, 1 H), 6.53 (d, 1 H), 6.73 (d, 1 H), 7.36 (d, 1 H), 7.85 (s, 1 H), 8.08 (s, 1 H), 8.13 (d, 1 H), 8.59 (d, 1 H). M + H: 409 |
| B-39/B | 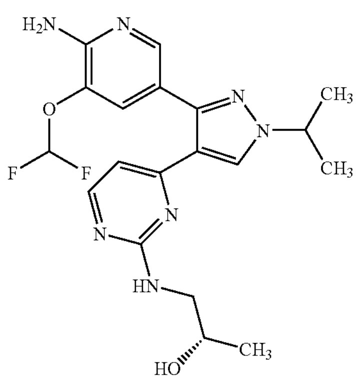 | (2S)-1-[(4-{3-[6-amino-5-(difluoromethoxy)-pyridin-3-yl]-1-isopropyl-1H-pyrazol-4-yl}pyrimidin-2-yl)amino]propan-2-ol | 1 H NMR (400 MHz, CHLOROFORM-d) δ ppm 1.21 (d, 3 H), 1.58 (d, 6 H), 3.28-3.40 (m, 1 H), 3.40-3.58 (m, 1 H), 3.99 (td, 1 H), 4.55 (spt, Hz, 1 H), 4.85 (s, 2 H), 5.46 (t, 1 H), 6.55 (t, 1 H), 6.52 (d, 1 H), 7.56 (s, 1 H), 7.95 (s, 1 H), 8.12 (d, 1 H), 8.24 (d, 1 H). M + H: 420.2 |
| B-40/B | 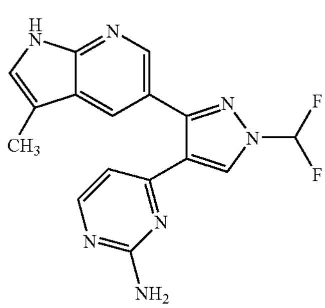 | 4-[1-(difluoromethyl)-3-(3-methyl-1H-pyrrolo[2,3-b]pyridin-5-yl)-1H-pyrazol-4-yl]pyrimidin-2-amine | 1 H NMR (400 MHz, DMSO-d6) δ ppm 2.25 (s, 3 H), 6.38 d, 1 H), 6.60 (s, 2 H), 7.29 (s, 1 H), 7.93 (t, 1 H), 8.10 (d, 1 H), 8.13 (d, 1 H), 8.28 (d, 1 H), 8.68 (s, 1 H), 11.46 (s, 1 H). M + H: 342.0 |

TABLE 1-continued

| Ex. No./Method | Structure | Structure Name | ¹H NMR/MS (m/z + 1) M + H |
|---|---|---|---|
| B-41/B | 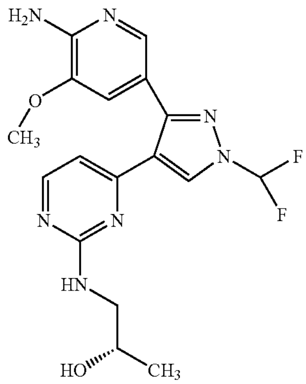 | (2S)-1-({4-[3-(6-amino-5-methoxypyridin-3-yl)-1-(difluoromethyl)-1H-pyrazol-4-yl]pyrimidin-2-yl}amino)propan-2-ol | 1 H NMR (400 MHz, ACETONITRILE-d3) δ ppm 1.07 (d, 3 H), 3.18 (br. s., 1 H), 3.27 (br. s., 1 H), 3.52 (br. s., 1 H), 3.79 (s, 3 H), 5.13 (br. s., 2 H), 5.82 (br. s., 1 H), 6.61 (d, 1 H), 7.16 (s, 1 H), 7.40 (t, 1 H), 7.83 (d, 1 H), 8.17 (d, 1 H), 8.45 (s, 1 H). M + H: 392.0 |
| B-42/B | 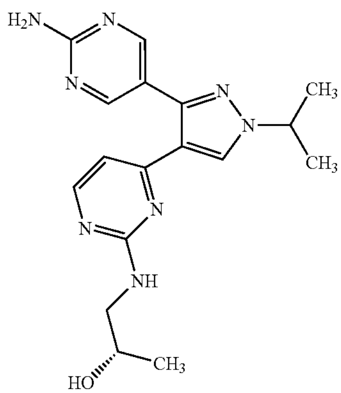 | (2S)-1-({4-[3-(2-aminopyrimidin-5-yl)-1-isopropyl-1H-pyrazol-4-yl]pyrimidin-2-yl}amino)propan-2-ol | 1 H NMR (400 MHz, ACETONITRILE-d3) δ ppm 1.07 (d, 3 H), 1.52 (d, 6 H), 2.93-3.45 (m, 2 H), 3.63 (br. s., 1 H), 3.77 (br. s., 1 H), 4.54 (spt, 1 H), 5.54 (br. s., 2 H), 5.70 (br. s., 1 H), 6.66 (d, 1 H), 8.02-8.25 (m, 2 H), 8.52 (s, 2 H). M + H: 355.2 |
| B-43/B | 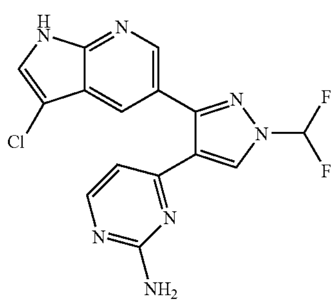 | 4-[3-(3-chloro-1H-pyrrolo[2,3-b]pyridin-5-yl)-1-(difluoromethyl)-1H-pyrazol-4-yl]pyrimidin-2-amine | 1 H NMR (400 MHz, DMSO-d6) δ ppm 6.45 (d, 1 H), 6.58 (br. s., 2 H), 7.77 (d, 1 H), 7.94 (t, 1 H), 8.08 (d, 1 H), 8.16 (d, 1 H), 8.43 (d, 1 H), 8.72 (s, 1 H), 12.17 (br. s., 1 H). M + H: 362.0 |
| B-44/B | 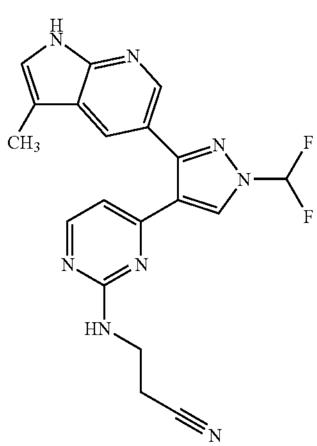 | 3-({4-[1-(difluoromethyl)-3-(3-methyl-1H-pyrrolo[2,3-b]pyridin-5-yl)-1H-pyrazol-4-yl]pyrimidin-2-yl}amino)-propanenitrile | 1 H NMR (400 MHz, CHLOROFORM-d) δ ppm 2.34 (d, 3 H), 2.51 (br. s., 2 H), 3.59 (br. s., 2 H), 5.58 (t, 1 H), 6.57 (d, 1 H), 7.30 (dd, 1 H), 7.15 (s, 1 H), 8.12 (d, 1 H), 8.18 (d, 1 H), 8.41 (s, 1 H), 8.45 (d, 1 H), 8.96 (d, 1 H). M + H: 395.2 |

TABLE 1-continued

| Ex. No./ Method | Structure | Structure Name | ¹H NMR/MS (m/z + 1) M + H |
|---|---|---|---|
| B-45/B | 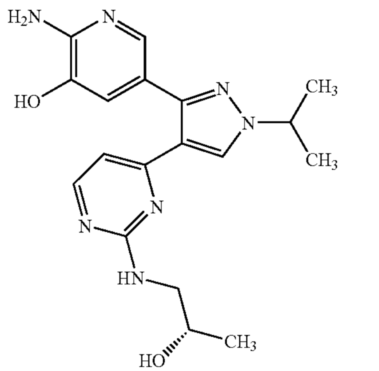 | 2-amino-5-[4-(2-{[(2S)-2-hydroxypropyl]-amino}pyrimidin-4-yl)-1-isopropyl-1H-pyrazol-3-yl]pyridin-3-ol | 1 H NMR (400 MHz, CHLOROFORM-d) δ ppm 1.19 (d, 3 H), 1.55 (d, 6 H), 3.19-3.60 (m, 3 H), 3.88-4.08 (m, 1 H), 4.53 (spt, 1 H), 5.08 (br. s., 2 H), 5.68 (br. s., 1 H), 6.49 (d, 1 H), 7.16 (br. s., 1 H), 7.77-7.94 (m, 2 H), 7.99 (br. s., 1 H). M + H: 370.2 |
| B-46/B | 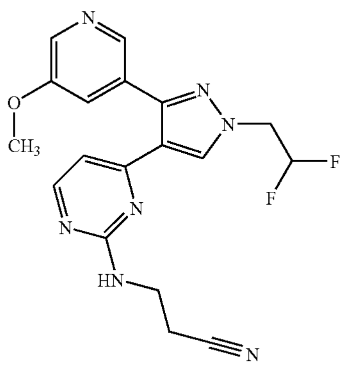 | 3-({4-[1-(2,2-difluoroethyl)-3-(5-methoxypyridin-3-yl)-1H-pyrazol-4-yl]pyrimidin-2-yl}amino)propanenitrile | 1 H NMR (400 MHz, CHLOROFORM-d) δ ppm 2.59 (br. s., 2 H), 3.60 (br. s., 2 H), 3.90 (s, 3 H), 4.56 (td, 2 H), 5.46 (t, 1 H), 6.21 (tt, 1 H), 6.55 (d, 1 H), 7.33-7.53 (m, 1 H), 8.04 (s, 1 H), 8.19 (d, 1 H), 8.35 (br. s., 1 H), 8.41 (s, 1 H). M + H: 386.2 |
| B-47/B | 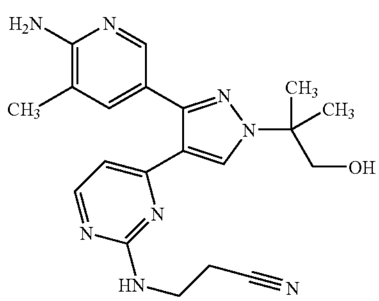 | 3-({4-[3-(6-amino-5-methylpyridin-3-yl)-1-(2-hydroxy-1,1-dimethylethyl)-1H-pyrazol-4-yl]pyrimidin-2-yl}amino)-propanenitrile | 1 H NMR (400 MHz, ACETONITRILE-d3) δ ppm 1.56 (s, 6 H), 2.12 (s, 3 H), 2.54 (br. s., 2 H), 3.48 (d, 2 H) 3.74 (s, 2 H), 5.07 (br. s., 2 H), 5.89 (br. s., 1 H), 6.66 (d, 1 H), 7.22-7.72 (m, 2 H), 8.06 (br. s., 1 H), 8.15 (d, 1 H), 8.18 (s, 1 H). M + H: 393.2 |
| B-48/B | 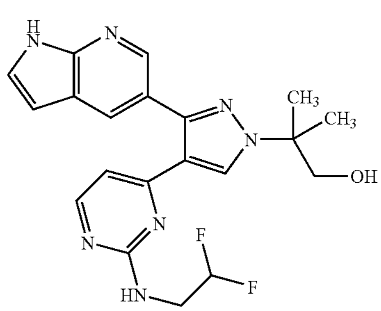 | 2-[4-{2-[(2,2-difluoroethyl)amino]pyrimidin-4-yl}-3-(1H-pyrrolo[2,3-b]pyridin-5-yl)-1H-pyrazol-1-yl]-2-methylpropan-1-ol | 1 H NMR (400 MHz, ACETONITRILE-d3) δ ppm 1.59 (s, 6 H), 3.19-3.71 (m, 3 H), 3.77 (s, 2 H), 5.32-6.10 (m, 2 H), 6.49 (dd, 1 H), 6.60 (d, 1 H), 7.40 (dd, 1 H), 7.90-8.16 (m, 2 H), 8.23 (s, 1 H), 8.41 (br. s., 1 H), 9.97 (br. s., 1 H). M + H: 414.2 |

TABLE 1-continued

| Ex. No./ Method | Structure Name | $^1$H NMR/MS (m/z + 1) M + H |
|---|---|---|
| B-49/B | 3-({4-[1-(2-hydroxy-1,1-dimethylethyl)-3-(5-methoxypyridin-3-yl)-1H-pyrazol-4-yl]pyrimidin-2-yl}amino)propanenitrile | 1 H NMR (400 MHz, ACETONITRILE-d3) δ ppm 1.59 (s, 6 H), 2.46 (br. s., 2 H), 3.25 (br. s., 1 H), 3.38 (br. s., 2 H), 3.76 (s, 2 H), 3.84 (s, 3 H), 5.88 (br. s., 1 H), 6.70 (d, 1 H), 7.47 (br. s., 1 H), 8.17 (d, 1 H), 8.23 (s, 1 H), 8.27 (d, 1 H), 8.35 (s, 1 H). M + H: 394.2 |
| B-50/B | 3-({4-[1-isopropyl-3-(1H-pyrrolo[2,3-b]pyridin-5-yl)-1H-pyrazol-4-yl]pyrimidin-2-yl}amino)-propanenitrile | 1 H NMR (400 MHz, ACETONITRILE-d3) δ ppm 1.55 (d, 6 H), 2.38 (br. s., 2 H), 3.38 (br. s., 2 H), 4.58 (quin, 1 H), 5.85 (t, 1 H), 6.50 (dd, 1 H), 6.56 (d, 1 H), 7.40 (dd, 1 H), 7.92-8.14 (m, 2 H), 8.18 (s, 1 H), 8.38 (d, 1 H), 9.69 (br. s., 1 H). M + H: 373.2 |
| B-51/B | 3-({4-[1-isopropyl-3-(3-methyl-1H-pyrazolo[3,4-b]pyridin-5-yl)-1H-pyrazol-4-yl]pyrimidin-2-yl}amino)propanenitrile | 1 H NMR (400 MHz, ACETONITRILE-d3) δ ppm 1.55 (d, 6 H), 2.36 (br. s., 2 H), 2.52 (s, 3 H), 3.33 (br. s., 2 H), 4.59 (spt, 1 H), 5.84 (br. s., 1 H), 6.64 (d, 1 H), 8.13 (d, 1 H), 8.20 (s, 1 H) 8.25 (d, 1 H), 8.64 (d, 1 H), 11.17 (br. s., 1 H). M + H: 388.2 |
| B-52/B | 3-({4-[3-(5-acetyl-6-aminopyridin-3-yl)-1-isopropyl-1H-pyrazol-4-yl]pyrimidin-2-yl}amino)propanenitrile | 1 H NMR (400 MHz, ACETONITRILE-d3) δ ppm 1.53 (d, 6 H), 2.48 (s, 3 H), 2.55 (br. s., 2 H), 3.46 (br. s., 2 H), 4.56 (spt, 1 H), 5.87 (t, 1 H), 6.70 (d, 1 H), 8.13-8.18 (m, 2 H), 8.27 (br. s., 1 H), 8.41 (d, 1 H). M + H: 391.2 |
| B-53/B | 3-{[4-(1-isopropyl-3-pyridin-3-yl-1H-pyrazol-4-yl)pyrimidin-2-yl]amino}-propanenitrile | 1 H NMR (400 MHz, ACETONITRILE-d3) δ ppm 1.54 (d, 6 H), 2.44 (br. s., 2 H), 3.36 (br. s., 2 H), 4.58 (spt, 1 H), 5.88 (br. s., 1 H), 6.66 (d, 1 H), 7.38 (dd, 1 H), 7.91 (d, 1 H), 8.16 (d, 1 H), 8.17 (s, 1 H), 8.56 (d, 1 H), 8.75 (br. s., 1 H). M + H: 334.2 |

TABLE 1-continued

| Ex. No./ Method | Structure | Structure Name | ¹H NMR/MS (m/z + 1) M + H |
|---|---|---|---|
| B-54/B | 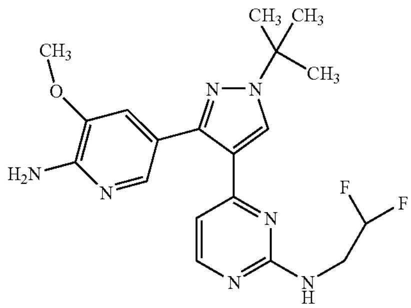 | 4-[3-(6-amino-5-methoxypyridin-3-yl)-1-tert-butyl-1H-pyrazol-4-yl]-N-(2,2-difluoroethyl)pyrimidin-2-amine | 1 H NMR (400 MHz, CHLOROFORM-d) δ ppm 8.11 (d, 1 H), 8.07 (s, 1 H), 7.85 (d, 1 H), 7.12 (d, 1 H), 6.57 (d, 1 H), 5.72-6.14 (m, 1 H), 5.24 (t, 1 H), 4.78 (s, 2 H), 3.85 (s, 3 H), 3.74-3.83 (m, 2 H), 1.67 (s, 9 H). M + H: 404.2 |
| B-55/B | 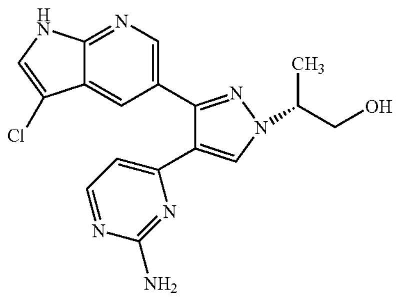 | (2R)-2-[4-(2-aminopyrimidin-4-yl)-3-(3-chloro-1H-pyrrolo[2,3-b]pyridin-5-yl)-1H-pyrazol-1-yl]propan-1-ol | 1 H NMR (400 MHz, DMSO-d6) δ ppm 12.12 (d, 1 H), 8.44 (s, 1 H), 8.43 (d, 1 H), 8.13 (d, 1 H), 8.04 (d, 1 H), 7.75 (d, 1 H), 7.64 (br. s., 2 H) 6.59 (d, 1 H), 4.00-4.27 (m, 3 H), 1.13 (d, 3 H). M + H: 370.2 |
| B-56/B | 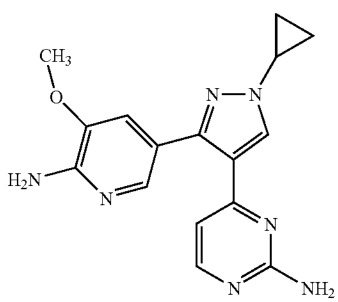 | 4-[3-(6-amino-5-methoxypyridin-3-yl)-1-cyclopropyl-1H-pyrazol-4-yl]pyrimidin-2-amine | 1 H NMR (400 MHz, DMSO-d6) δ ppm 8.18 (s, 1 H), 8.09 (d, 1 H) 7.66 (d, 1 H), 7.15 (d, 1 H), 6.45 (br. s., 2 H), 6.43 (d, 1 H), 5.85 (s, 2 H), 3.79 (td, 1 H), 3.75 (s, 3 H) 1.08-1.15 (m, 2 H), 0.94-1.05 (m, 2 H). M + H: 324.2 |
| B-57/B | 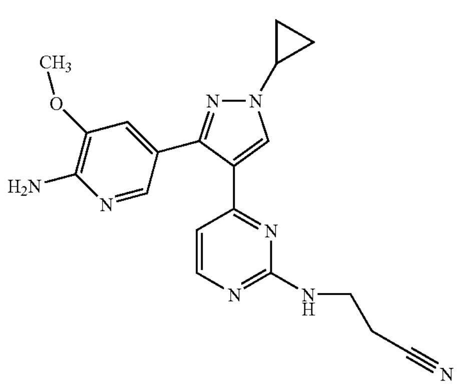 | 3-({4-[3-(6-amino-5-methoxypyridin-3-yl)-1-cyclopropyl-1H-pyrazol-4-yl]pyrimidin-2-yl}amino)-propanenitrile | 1 H NMR (400 MHz, DMSO-d6) δ ppm 8.33 (br. s., 1 H), 8.17 (d, 1 H), 7.65 (s, 1 H), 7.29 (br. s., 1 H), 7.09 (br. s., 1 H), 6.58 (d, 1 H), 5.85 (s, 2 H), 3.80 (td, 1 H), 3.75 (s, 3 H), 3.38-3.49 (m, 2 H), 2.58-2.74 (m, 2 H), 1.10-1.18 (m, 2 H), 0.98-1.05 (m, 2 H). M + H: 377 |

TABLE 1-continued

| Ex. No./ Method | Structure | Structure Name | ¹H NMR/MS (m/z + 1) M + H |
|---|---|---|---|
| B-58/B | 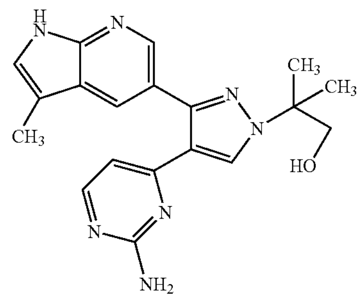 | 2-[4-(2-aminopyrimidin-4-yl)-3-(3-methyl-1H-pyrrolo[2,3-b]pyridin-5-yl)-1H-pyrazol-1-yl]-2-methylpropan-1-ol | 1 H NMR (400 MHz, DMSO-d6) δ ppm 11.39 (br. s., 1 H), 8.25 (d, 1 H), 8.23 (s, 1 H), 8.01 (d, 1 H), 8.00 (d, 1 H), 7.27 (s, 1 H), 6.47 (s, 2 H), 6.26 (d, 1 H) 5.14 (t, 1 H), 3.66 (d, 2 H), 2.26 (s, 3 H), 1.55 (s, 6 H). M + H: 364 |
| B-59/B | 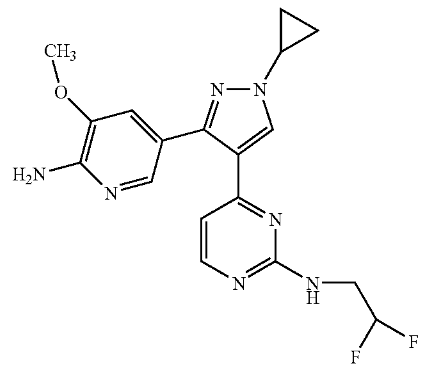 | 4-[3-(6-amino-5-methoxypyridin-3-yl)-1-cyclopropyl-1H-pyrazol-4-yl]-N-(2,2-difluoroethyl)pyrimidin-2-amine | 1 H NMR (400 MHz, DMSO-d6) δ ppm 13.21 (br. s., 1 H), 8.54 (s, 1 H), 8.26 (d, 1 H), 7.91 (br. s., 1 H), 7.50 (br. s., 1 H), 7.40 (br. s., 1 H), 6.84 (d, 1 H), 6.04 (br. s., 1 H), 3.88 (s, 3 H), 3.79-3.86 (m, 1 H), 3.62-3.75 (m, 1 H), 3.44-3.55 (m, 2 H), 1.11-1.21 (m, 2 H), 0.96-1.09 (m, 2 H). M + H: 388 |
| B-60/B | 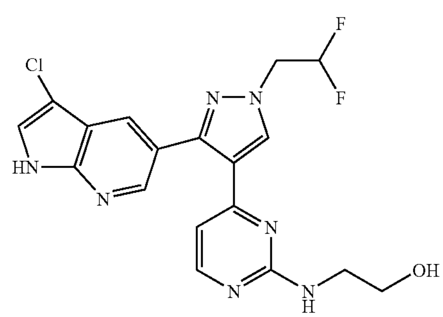 | 4-[3-(3-chloro-1H-pyrrolo[2,3-b]pyridin-5-yl)-1-isopropyl-1H-pyrazol-4-yl]pyrimidin-2-amine | 1 H NMR (300 MHz, DMSO-d6) δ ppm 12.08 (s, 1 H), 8.43 (d, 1 H), 8.36 (s, 1 H), 8.10 (d, 1 H), 8.05 (d, 1 H), 7.74 (d, 1 H), 6.69 (s, 2 H) 6.44 (d, 1 H), 4.51-4.72 (m, 1 H), 1.53 (d, 6 H). M + H: 354 |
| B-61/B | 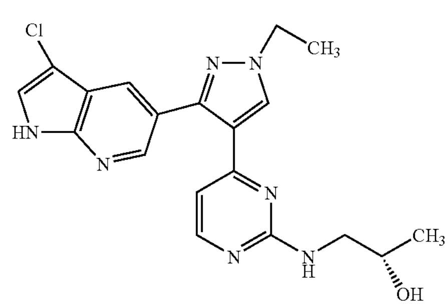 | (2S)-1-({4-[3-(3-chloro-1H-pyrrolo[2,3-b]pyridin-5-yl)-1-ethyl-1H-pyrazol-4-yl]pyrimidin-2-yl}amino)propan-2-ol | 1 H NMR (300 MHz, DMSO-d6) δ ppm 12.08 (s, 1 H), 8.45 (d, 1 H), 8.16 (d, 1 H), 8.03 (d, 1 H), 7.73 (d, 1 H), 7.49 (d, 1 H), 7.13 (d, 1 H), 6.70 (d, 1 H), 4.27 (q, 2 H), 2.76-3.06 (m, 2 H) 2.31 (s, 2 H), 1.50 (t, 3 H), 0.71 (s, 3 H). M + H: 398 |

TABLE 1-continued

| Ex. No./ Method | Structure | Structure Name | ¹H NMR/MS (m/z + 1) M + H |
|---|---|---|---|
| B-62/B | 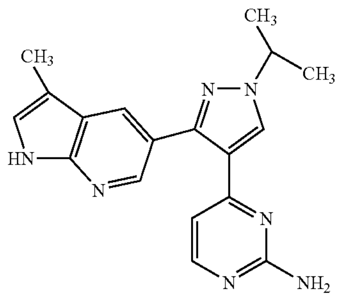 | 4-[1-isopropyl-3-(3-methyl-1H-pyrrolo[2,3-b]pyridin-5-yl)-1H-pyrazol-4-yl]pyrimidin-2-amine | 1 H NMR (300 MHz, DMSO-d6) δ ppm 11.43 (s, 1 H), 8.47 (s, 1 H), 8.31 (d, 1 H), 8.11 (d, 1 H), 8.08 (d, 1 H), 7.57 (s, 2 H) 7.29 (s, 1 H), 6.56 (d, 1 H), 4.54-4.74 (m, 1 H), 2.27 (s, 3 H), 1.52 (d, 6 H). M + H: 334 |
| B-63/B | 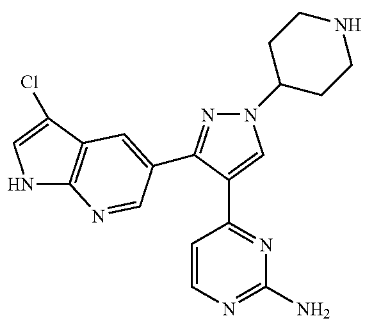 | 4-[3-(3-chloro-1H-pyrrolo[2,3-b]pyridin-5-yl)-1-piperidin-4-yl-1H-pyrazol-4-yl]pyrimidin-2-amine | 1 H NMR (400 MHz, DMSO-d6) δ ppm 12.19 (d, 1 H), 9.21 (d, 1 H), 8.92-9.12 (m, 1 H), 8.68 (s, 1 H), 8.47 (d, 1 H), 8.25 (d, 2 H), 8.08 (d, 1 H), 7.77 (d, 1 H), 6.83 (d, 1 H), 4.59-4.76 (m, 1 H), 3.32-3.51 (m, 2 H), 3.12 (s, 2 H), 2.15-2.38 (m, 4 H). M + H: 395.2 |
| B-64/B | 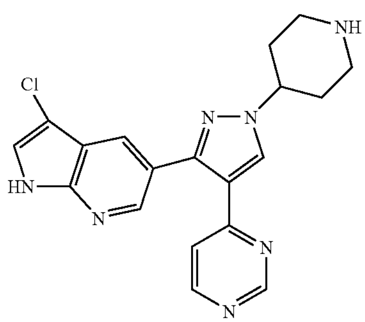 | 3-chloro-5-(1-piperidin-4-yl-4-pyrimidin-4-yl-1H-pyrazol-3-yl)-1H-pyrrolo[2,3-b]pyridine | 1 H NMR (400 MHz, DMSO-d6) δ ppm 12.14 (s, 1 H), 9.04 (d, 1 H), 8.73 (s, 1 H), 8.67 (d, 1 H), 8.63 (s, 1 H), 8.43 (d, 1 H), 8.05 (d, 1 H), 7.75 (d, 1 H), 7.45 (dd, 1 H), 4.59-4.71 (m, 1 H), 3.44 (d, 2 H), 3.04-3.18 (m, 2 H), 2.21-2.37 (m, 4 H). M + H: 380.2 |
| B-65/B | 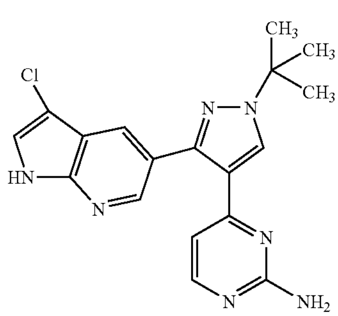 | 4-[1-tert-butyl-3-(3-chloro-1H-pyrrolo[2,3-b]pyridin-5-yl)-1H-pyrazol-4-yl]pyrimidin-2-amine | 1 H NMR (400 MHz, DMSO-d6) δ ppm 12.07 (s, 1 H), 8.41 (d, 1 H), 8.30 (s, 1 H), 8.06 (d, 1 H), 8.03 (d, 1 H), 7.73 (s, 1 H), 6.43 (s, 2 H), 6.37 (d, 1 H), 1.62 (s, 9 H). M + H: 368.2 |

TABLE 1-continued

| Ex. No./ Method | Structure | Structure Name | ¹H NMR/MS (m/z + 1) M + H |
|---|---|---|---|
| B-66/B | 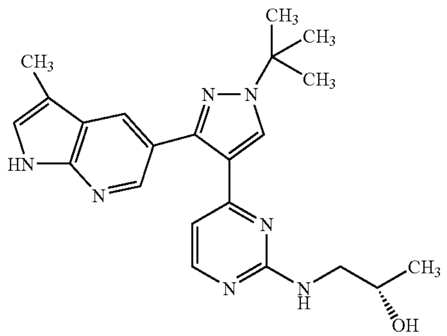 | (2S)-1-({4-[1-tert-butyl-3-(3-methyl-1H-pyrrolo[2,3-b]pyridin-5-yl)-1H-pyrazol-4-yl]pyrimidin-2-yl}amino)propan-2-ol | 1 H NMR (400 MHz, CHLOROFORM-d) δ ppm 8.72 (br. s., 1 H), 8.49 (br. s., 1 H), 8.11 (s, 1 H), 8.10 (d, 1 H), 8.01 (d, 1 H), 7.09 (s, 1 H), 6.42 (d, 1 H), 5.49 (dd, 1 H), 3.89-4.01 (m, 1 H), 3.36-3.48 (m, 1 H), 3.23-3.34 (m, 1 H), 2.32 (d, 2 H), 1.69 (s, 9 H), 1.15 (d, J = 6.32 Hz, 3 H). M + H: 406.25 |
| B-67/B | 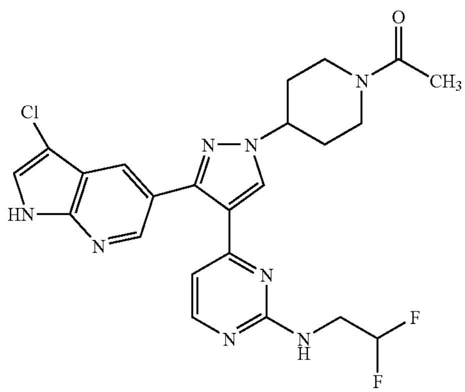 | 4-[1-(1-acetylpiperidin-4-yl)-3-(3-chloro-1H-pyrrolo[2,3-b]pyridin-5-yl)-1H-pyrazol-4-yl]-N-(2,2-difluoroethyl)-pyrimidin-2-amine | 1 H NMR (400 MHz, CHLOROFORM-d) δ ppm 2.06-2.14 (m, 2 H), 2.17 (s, 3 H), 2.22-2.32 (m, 1 H), 2.32-2.39 (m, 1 H), 2.75-2.84 (m, 1 H), 3.24-3.34 (m, 1 H), 3.69 (d, 2 H), 4.03 (d, 1 H), 4.46 (tt, 1 H), 4.83 (d, 1 H), 5.48 (t, 1 H), 5.83 (t, 1 H), 6.49 (d, 1 H), 7.32 (d, 1 H), 8.04 (s, 1 H), 8.13 (d, 1 H), 8.18 (d, 1 H), 8.51 (d, 1 H), 9.81 (br. s., 1 H) |
| B-68/B | 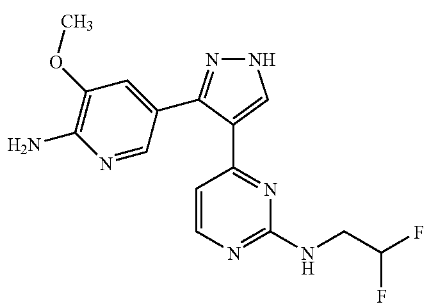 | 4-[3-(6-amino-5-methoxypyridin-3-yl)-1H-pyrazol-4-yl]-N-(2,2-difluoroethyl)-pyrimidin-2-amine | 1 H NMR (400 MHz, DMSO-d6) δ ppm 3.57 (br. s., 2 H), 3.72-3.87 (m, 3 H), 5.82 (s, 1 H), 5.91-6.20 (m, 2 H), 6.50-6.77 (m, 1 H), 7.14 (br. s., 1 H), 7.31 (t, 1 H), 7.53-7.82 (m, 1 H), 7.91-8.44 (m, 1 H), 8.18 (d, 1 H), 13.21 (br. s., 1 H) |
| B-69/B | 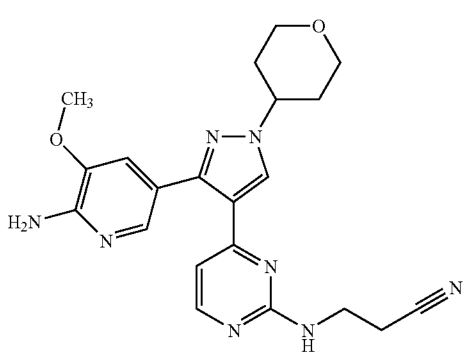 | 3-({4-[3-(6-amino-5-methoxypyridin-3-yl)-1-(tetrahydro-2H-pyran-4-yl)-1H-pyrazol-4-yl]pyrimidin-2-yl}amino)propanenitrile | 1 H NMR (400 MHz, CHLOROFORM-d) δ ppm 2.08-2.24 (m, 4 H), 2.66 (t, 2 H), 3.57 (td, 2 H), 3.68 (q, 2 H), 3.85 (s, 3 H), 4.11-4.18 (m, 2 H), 4.37-4.46 (m, 1 H), 4.81 (s, 2 H), 5.47 (t, 1 H), 6.58 (d, 1 H), 7.11 (d, 1 H), 7.84 (d, 1 H), 8.01 (s, 1 H), 8.13 (d, 1 H) |

TABLE 1-continued

| Ex. No./ Method | Structure | Structure Name | ¹H NMR/MS (m/z + 1) M + H |
|---|---|---|---|
| B-70/B | 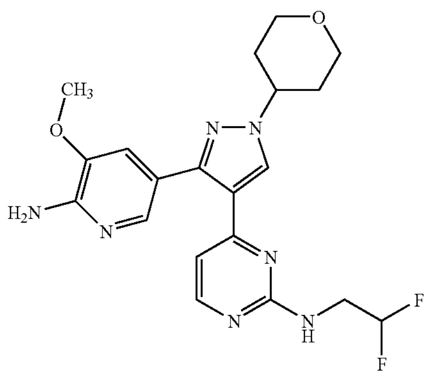 | 4-[3-(6-amino-5-methoxypyridin-3-yl)-1-(tetrahydro-2H-pyran-4-yl)-1H-pyrazol-4-yl]-N-(2,2-difluoroethyl)-pyrimidin-2-amine | 1 H NMR (400 MHz, CHLOROFORM-d) δ ppm 2.09-2.23 (m, 4 H), 3.57 (td, 2 H), 3.73-3.83 (m, 2 H), 3.83-3.87 (m, 3 H), 4.15 (dd, 2 H), 4.37-4.46 (m, 1 H), 4.77 (s, 2 H), 5.25 (t, 1 H), 5.70-6.12 (m, 1 H), 6.58 (d, 1 H), 7.10 (d, 1 H), 7.84 (d, 1 H), 8.01 (s, 1 H), 8.13 (d, 1 H). M + H: 432.2 |
| B-71/B | 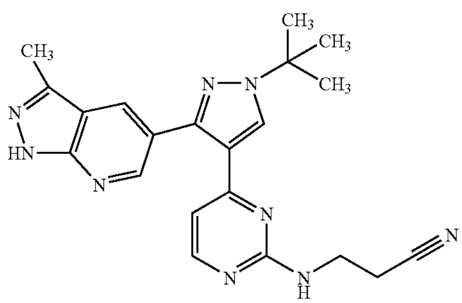 | 3-({4-[1-tert-butyl-3-(3-methyl-1H-pyrazolo[3,4-b]pyridin-5-yl)-1H-pyrazol-4-yl]pyrimidin-2-yl}amino)propanenitrile | 1 H NMR (400 MHz, DMSO-d6) δ ppm 1.63 (s, 9 H), 2.20 (br. s., 1 H), 2.50 (br. s., 3 H), 3.10 (br. s., 1 H), 6.72 (br. s., 1 H), 7.22 (br. s., 1 H), 8.18 (d, 1 H), 8.30 (br. s., 1 H) 8.50 (br. s., 1 H), 8.57 (d, 1 H), 13.25 (s, 1 H). M + H: 402.2 |
| B-72/B | 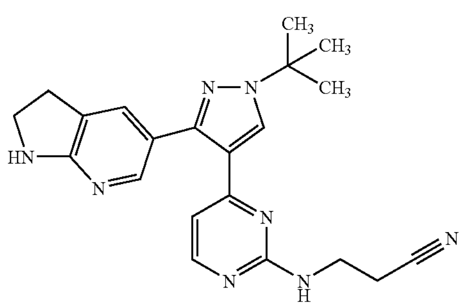 | 3-({4-[1-tert-butyl-3-(2,3-dihydro-1H-pyrrolo[2,3-b]pyridin-5-yl)-1H-pyrazol-4-yl]pyrimidin-2-yl}amino)propanenitrile | 1 H NMR (400 MHz, CHLOROFORM-d) δ ppm 1.66 (s, 9 H), 2.65 (t, 2 H), 3.11 (t, 2 H), 3.59-3.74 (m, 4 H), 4.59 (br. s., 1 H), 5.38-5.52 (m, 1 H), 6.59 (d, 1 H), 7.45 (d, 1 H), 8.01 (d, 1 H), 8.04 (s, 1 H), 8.12 (d, 1 H). M + H: 389.2 |
| B-73/B | 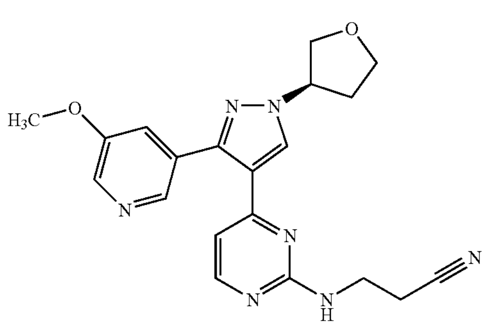 | 3-[(4-{3-(5-methoxypyridin-3-yl)-1-[(3R)-tetrahydrofuran-3-yl]-1H-pyrazol-4-yl}pyrimidin-2-yl)amino]propanenitrile | 1 H NMR (400 MHz, CHLOROFORM-d) δ ppm 2.34-2.49 (m, 1 H), 2.49-2.66 (m, 3 H), 3.59 (br. s., 2 H), 3.87-3.90 (m, 3 H), 3.99 (td, 1 H), 4.11 (dd, 1 H), 4.17-4.23 (m, 2 H), 5.04-5.09 (m, 1 H), 5.39 (t, 1 H), 6.54 (d, 1 H), 7.42 (dd, 1 H), 8.05 (s, 1 H), 8.17 (d, 1 H), 8.33 (d, 1 H), 8.39 (d, 1 H). M + H: 392.2 |

TABLE 1-continued

| Ex. No./ Method | Structure Name | ¹H NMR/MS (m/z + 1) M + H |
|---|---|---|
| B-74/B | 3-({4-[1-tert-butyl-3-(1H-pyrrolo[2,3-b]pyridin-5-yl)-1H-pyrazol-4-yl]pyrimidin-2-yl}amino)-propanenitrile | 1 H NMR (400 MHz, CHLOROFORM-d) δ ppm 1.70 (s, 9 H), 2.51 (br. s., 2 H), 3.58 (br. s., 2 H), 5.47 (t, 1 H), 6.51 (d, 1 H), 6.54 (dd, 1 H), 7.30-7.37 (m, 1 H), 8.08 (d, 1 H), 8.11 (s, 1 H), 8.13 (d, 1 H), 8.50 (d, 1 H), 9.50 (br. s., 1 H). M + H: 387.2 |
| B-75/B | 3-[(4-{3-(1H-pyrrolo[2,3-b]pyridin-5-yl)-1-[(3R)-tetrahydrofuran-3-yl]-1H-pyrazol-4-yl}pyrimidin-2-yl)amino]propanenitrile | 1 H NMR (400 MHz, CHLOROFORM-d) δ ppm 2.32-2.50 (m, 2 H), 2.50-2.64 (m, 2 H), 3.57 (br. s., 2 H), 4.00 (td, 1 H), 4.09-4.17 (m, 1 H), 4.18-4.26 (m, 2 H), 5.06-5.11 (m, 1 H), 5.47 (t, 1 H), 6.52 (d, 1 H), 6.54 (dd, 1 H), 7.36 (dd, 1 H), 8.08-8.13 (m, 3 H), 8.49 (d, 1 H), 9.39 (br. s., 1 H). M + H: 401.2 |
| B-76/B | (2S)-1-({4-[3-(3-chloro-1H-pyrrolo[2,3-b]pyridin-5-yl)-1-(tetrahydro-2H-pyran-4-yl)-1H-pyrazol-4-yl]pyrimidin-2-yl}amino)propan-2-ol | 1 H NMR (400 MHz, CHLOROFORM-d) δ ppm 1.15 (d, 3 H), 2.14-2.26 (m, 4 H), 3.23-3.36 (m, 1 H), 3.42 (dd, 1 H), 3.59 (td, 2 H), 3.96 (td, 1 H), 4.16 (t, 1 H), 4.17-4.37 (m, 2 H), 4.46 (tt, 1 H), 5.54 (t, 1 H), 6.45 (d, 1 H), 7.31 (d, 1 H), 8.05 (s, 1 H), 8.09 (d, 1 H), 8.21 (d, 1 H), 8.57 (d, 1 H), 9.45 (br. s., 1 H). M + H: 454.1 |
| B-77/B | 4-[3-(3-chloro-1H-pyrrolo[2,3-b]pyridin-5-yl)-1-piperidin-4-yl-1H-pyrazol-4-yl]-N-(2,2-difluoroethyl)pyrimidin-2-amine | 1 H NMR (400 MHz, DMSO-d6) δ ppm 1.81 (qd, 2 H), 1.98 (d, 2 H), 2.51-2.61 (m, 2 H), 3.02 (d, 2 H), 4.20-4.29 (m, 1 H), 6.58 (br. s., 1 H), 7.18 (br. s., 1 H), 7.63 (s, 1 H), 7.90 (s, 1 H), 8.10 (d, 1 H), 8.32 (d, 1 H), 8.37 (br. s., 1 H), 11.96 (br. s., 1 H). M + H: 459.2 |

TABLE 1-continued

| Ex. No./ Method | Structure | Structure Name | ¹H NMR/MS (m/z + 1) M + H |
|---|---|---|---|
| B-78/B | 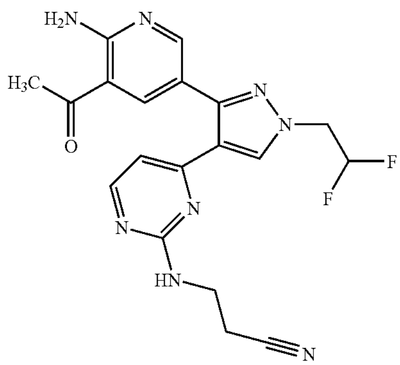 | 3-(4-(3-(5-acetyl-6-aminopyridin-3-yl)-1-(2,2-difluoroethyl)-1H-pyrazol-4-yl)pyrimidin-2-ylamino)-propanenitrile | 1 H NMR (400 MHz, CHLOROFORM-d) δ ppm 2.57 (s, 3 H), 2.64 (br. s., 2 H), 3.65 (q, 2 H), 4.55 (td, 2 H), 5.54 (br. s., 1 H), 6.21 (tt, 1 H), 6.61 (d, 1 H), 8.03 (s, 1 H), 8.21 (d, 1 H), 8.23 (d, 1 H), 8.45 (d, 1 H). M + H: 413.2 |
| B-79/B | 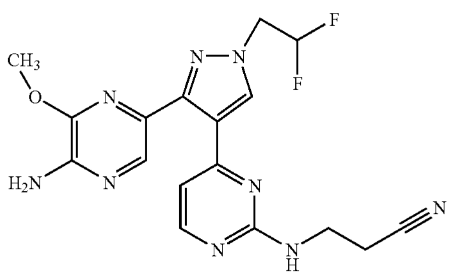 | 3-({4-[3-(5-amino-6-methoxypyrazin-2-yl)-1-(2,2-difluoroethyl)-1H-pyrazol-4-yl]pyrimidin-2-yl}amino)propanenitrile | 1 H NMR (400 MHz, CHLOROFORM-d) δ ppm 8.18 (d, 1 H), 8.04 (s, 1 H), 7.98 (s, 1 H), 6.74 (d, 1 H), 6.21 (tt, 1 H), 5.41 (br. t, 1 H), 4.94 (br. s., 2 H), 4.55 (td, 2 H), 3.87 (s, 3 H), 3.71 (q, 2 H), 2.70 (t, 2 H). M + H: 402.2 |
| B-80/B | 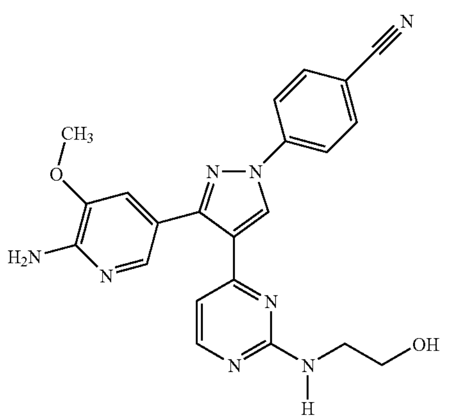 | 4-[3-(6-amino-5-methoxypyridin-3-yl)-4-{2-[(2-hydroxyethyl)-amino]pyrimidin-4-yl}-1H-pyrazol-1-yl]-benzonitrile | 1 H NMR (MeOD): δ 8.94 (1 H, s), 8.20 (1 H, d), 8.13 (2 H, d), 7.91 (2 H, d), 7.84 (1 H, d), 7.33 (1 H, d), 6.75 (1 H, d), 3.89 (3 H, s), 3.66 (1 H, t), 3.47 (1 H, t). M + H: 429 |
| B-81/B | 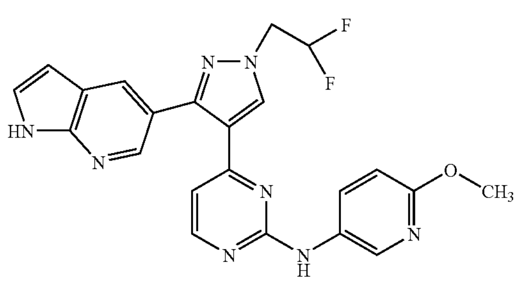 | 4-[1-(2,2-difluoroethyl)-3-(1H-pyrrolo[2,3-b]pyridin-5-yl)-1H-pyrazol-4-yl]-N-(6-methoxypyridin-3-yl)pyrimidin-2-amine | 1 H NMR (MeOD): δ 8.36 (1 H, s), 8.30 (1 H, d), 8.25 (1 H, d), 8.13 (1 H, d), 8.09 (1 H, d), 7.55 (1 H, dd), 7.43 (1 H, d), 6.78 (1 H, d), 6.51 (1 H, d), 6.32 (1 H, t), 6.17 (1 H, m), 4.70 (2 H, td), 3.80 (3 H, s). M + H: 449 |

TABLE 1-continued

| Ex. No./Method | Structure | Structure Name | ¹H NMR/MS (m/z + 1) M + H |
|---|---|---|---|
| B-82/B | 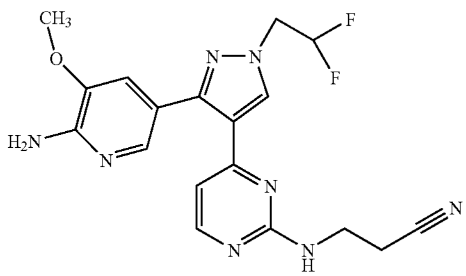 | 3-(4-(3-(6-amino-5-methoxypyridin-3-yl)-1-(2,2-difluoroethyl)-1H-pyrazol-4-yl)pyrimidin-2-ylamino)propanenitrile | 1 H NMR (400 MHz, CHLOROFORM-d) δ ppm 2.66 (t, 2 H), 3.63-3.73 (m, 2 H), 3.86 (s, 3 H), 4.53 (td, 2 H), 4.82 (s, 2 H), 5.42 (t, 1 H), 6.22 (tt, 1 H), 6.60 (d, 1 H), 7.11 (d, 1 H), 7.85 (d, 1 H), 8.03 (s, 1 H), 8.16 (d, 1 H) |
| B-83/B | 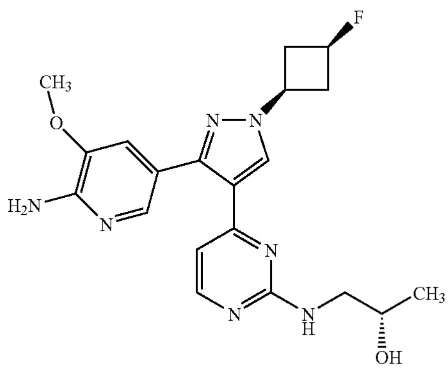 | 3-(4-(3-(6-amino-5-methoxypyridin-3-yl)-1-(2,2-difluoroethyl)-1H-pyrazol-4-yl)pyrimidin-2-ylamino)-propanenitrile | 1 H NMR (400 MHz, CHLOROFORM-d) δ ppm 1.23 (d, 3 H), 2.87-3.10 (m, 4 H), 3.34-3.43 (m, 1 H), 3.50 (br. s., 1 H), 3.87 (s, 3 H), 3.97-4.06 (m, 1 H), 4.33-4.44 (m, 1 H), 4.80 (s, 2 H), 4.97 (dq, 1 H), 5.43 (t, 1 H), 6.53 (d, 1 H), 7.14 (d, 1 H), 7.93 (s, 1 H) 8.02 (s, 1 H), 8.10 (d, 1 H). |
| B-84/B | 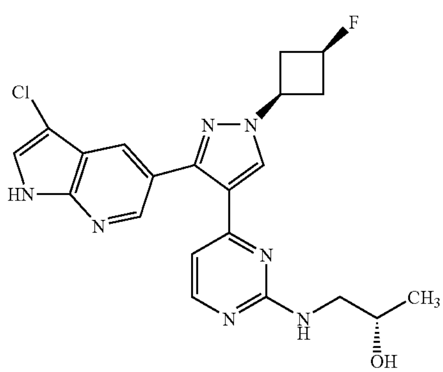 | (S)-1-(4-(3-(3-chloro-1H-pyrrolo[2,3-b]pyridin-5-yl)-1-((1s,3s)-3-fluorocyclobutyl)-1H-pyrazol-4-yl)pyrimidin-2-ylamino)propan-2-ol | 1 H NMR (400 MHz, CHLOROFORM-d) δ ppm 1.13 (d, 3 H), 1.98 (s, 1 H), 2.89-3.14 (m, 4 H), 3.27 (dd, 1 H), 3.34-3.48 (m, 1 H), 3.94 (s, 1 H), 4.42 (q, 1 H), 4.99 (dq, 1 H), 5.96 (s, 1 H), 6.45 (d, 1 H), 7.29 (s, 1 H), 8.05 (s, 1 H), 8.10 (d, 1 H), 8.21 (s, 1 H) 8.56 (s, 1 H), 10.99 (s, 1 H) |
| B-85/B | 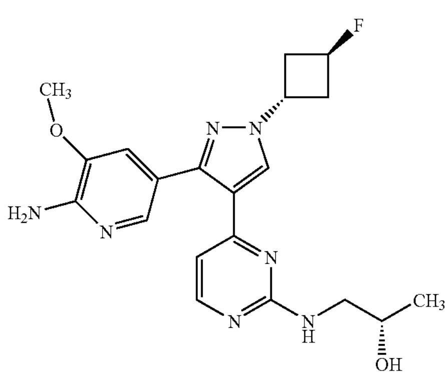 | (S)-1-(4-(3-(6-amino-5-methoxypyridin-3-yl)-1-((1r,3r)-3-fluorocyclobutyl)-1H-pyrazol-4-yl)pyrimidin-2-ylamino)propan-2-ol | 1 H NMR (400 MHz, CHLOROFORM-d) δ ppm 1.23 (d, 3 H), 2.03 (s, 1 H), 2.77-2.91 (m, 2 H), 2.95-3.08 (m, 2 H), 3.34-3.43 (m, 1 H), 3.44-3.54 (m, 1 H), 3.87 (s, 3 H), 3.97-4.06 (m, 1 H), 4.89 (s, 2 H), 5.02-5.12 (m, 1 H), 5.34-5.55 (m, 1 H), 5.44 (t, 1 H), 6.51 (d, 1 H), 7.14 (d, 1 H), 7.95 (d, 1 H), 7.97 (s, 1 H) 8.10 (d, 1 H) |

TABLE 1-continued

| Ex. No./ Method | Structure | Structure Name | ¹H NMR/MS (m/z + 1) M + H |
|---|---|---|---|
| B-86/B | 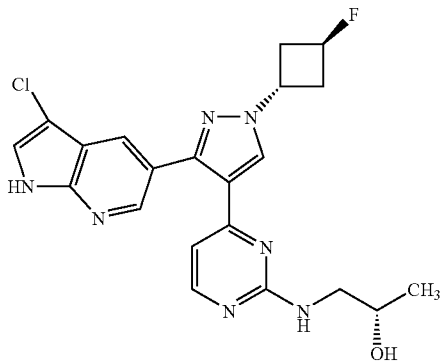 | (S)-1-(4-(3-(3-chloro-1H-pyrrolo[2,3-b]pyridin-5-yl)-1-((1r,3r)-3-fluorocyclobutyl)-1H-pyrazol-4-yl)pyrimidin-2-ylamino)propan-2-ol | 1 H NMR (400 MHz, CHLOROFORM-d) δ ppm 1.15 (d, 3 H), 2.81-2.93 (m, 2 H), 2.99-3.13 (m, 2 H), 3.25-3.35 (m, 1 H), 3.41 (s, 1 H), 3.96 (s, 1 H), 5.07-5.17 (m, 1 H), 5.35-5.58 (m, 1 H), 5.62 (d, 1 H), 6.43 (d, 1 H), 7.32 (d, 1 H), 8.01 (s, 1 H), 8.09 (d, 1 H), 8.21 (d, 1 H), 8.57 (d, 1 H), 9.69 (s, 1 H) |
| B-87/B | 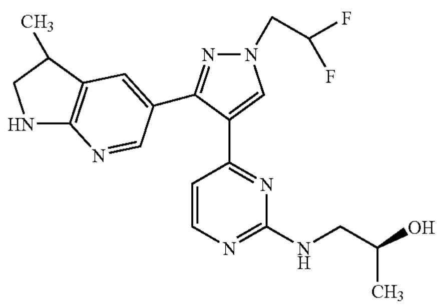 | (2S)-1-(4-(1-(2,2-difluoroethyl)-3-(3-methyl-2,3-dihydro-1H-pyrrolo[2,3-b]pyridin-5-yl)-1H-pyrazol-4-yl)pyrimidin-2-ylamino)propan-2-ol | 1 H NMR (400 MHz, MeOD) δ ppm 1.06-1.23 (m, 3 H), 1.39 (dd, 3 H), 3.32-3.35 (m, 1 H), 3.37-3.58 (m, 2 H), 3.59-3.89 (m, 2 H), 4.07-4.16 (m, 1 H), 4.71 (td, 2 H), 6.31 (tt, 1 H), 7.17 (d, 1 H), 7.82 (d, 2 H), 8.17 (s, 1 H), 8.74 (s, 1 H) |
| B-88/B | 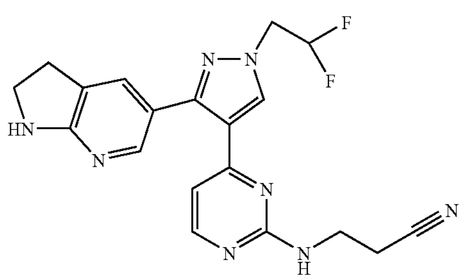 | 3-(4-(1-(2,2-difluoroethyl)-3-(2,3-dihydro-1H-pyrrolo[2,3-b]pyridin-5-yl)-1H-pyrazol-4-yl)pyrimidin-2-ylamino)propanenitrile | 1 H NMR (400 MHz, CHLOROFORM-d) δ ppm 2.62-2.70 (m, 2 H), 3.12 (t, 2 H), 3.63-3.72 (m, 4 H), 4.52 (td, 2 H), 4.68 (s, 1 H), 5.49 (t, 1 H), 6.19 (tt, 1 H), 6.61 (d, 1 H), 7.42 (d, 1 H), 8.00 (s, 2 H), 8.17 (d, 1 H) |
| B-89/B | 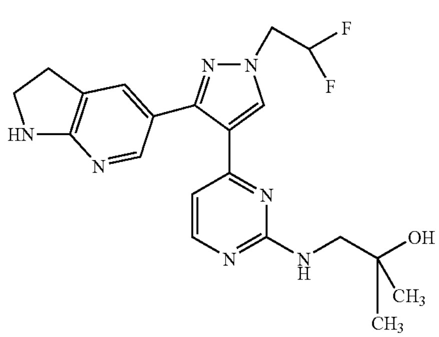 | 1-(4-(1-(2,2-difluoroethyl)-3-(2,3-dihydro-1H-pyrrolo[2,3-b]pyridin-5-yl)-1H-pyrazol-4-yl)pyrimidin-2-ylamino)-2-methylpropan-2-ol | 1 H NMR (400 MHz, CHLOROFORM-d) δ ppm 1.26 (s, 6 H), 3.11 (t, 2 H), 3.42 (d, 2 H), 3.66-3.72 (m, 2 H), 4.51 (td, 2 H), 4.62 (s, 1 H), 5.49 (t, 1 H), 6.19 (tt, 1 H), 6.53 (d, 1 H), 7.42 (d, 1 H), 8.00 (s, 1 H), 8.02 (d, 1 H), 8.11 (d, 1 H). |

TABLE 1-continued

| Ex. No./ Method | Structure | Structure Name | $^1$H NMR/MS (m/z + 1) M + H |
|---|---|---|---|
| B-90/B | 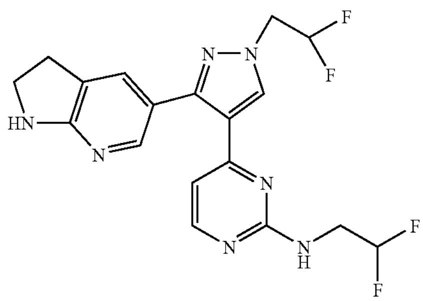 | N-(2,2-difluoroethyl)-4-(1-(2,2-difluoroethyl)-3-(2,3-dihydro-1H-pyrrolo[2,3-b]pyridin-5-yl)-1H-pyrazol-4-yl)pyrimidin-2-amine | 1 H NMR (400 MHz, CHLOROFORM-d) δ ppm 3.11 (t, 2 H), 3.69 (td, 2 H), 3.73-3.85 (m, 2 H), 4.52 (td, 2 H), 4.61 (s, 1 H), 5.29 (t, 1 H), 5.86 (tt, 1 H) 6.21 (tt, 1 H), 6.61 (d, 1 H), 7.42 (d, 1 H), 7.99 (d, 1 H), 8.02 (s, 1 H), 8.16 (d, 1 H). |
| B-91/B | 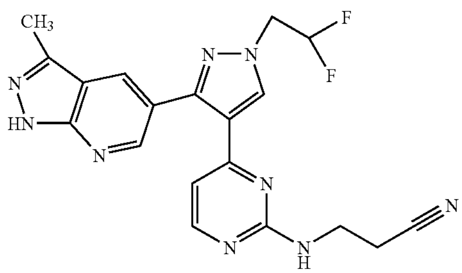 | 3-(4-(1-(2,2-difluoroethyl)-3-(3-methyl-1H-pyrazolo[3,4-b]pyridin-5-yl)-1H-pyrazol-4-yl)pyrimidin-2-ylamino)propanenitrile | 1 H NMR (400 MHz, CHLOROFORM-d) δ ppm 2.47-2.59 (m, 2 H), 2.61 (s, 3 H), 3.57 (s, 2 H), 4.59 (td, 2 H), 5.54 (s, 1 H), 6.24 (tt, 1 H), 6.54 (d, 1 H), 8.08 (s, 1 H), 8.18 (d, 1 H), 8.26 (d, 1 H), 8.70 (d, 1 H), 10.54 (s, 1 H) |
| B-92/B | 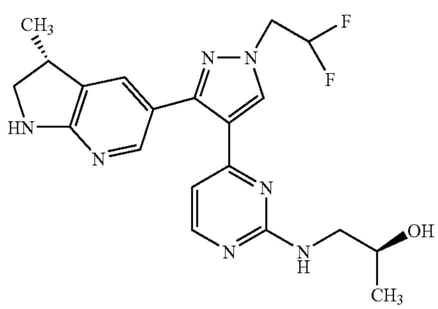 | (S)-1-(4-(1-(2,2-difluoroethyl)-3-((R)-3-methyl-2,3-dihydro-1H-pyrrolo[2,3-b]pyridin-5-yl)-1H-pyrazol-4-yl)pyrimidin-2-ylamino)propan-2-ol | 1 H NMR (400 MHz, CHLOROFORM-d) δ ppm 1.22-1.24 (m, 3 H), 1.35 (d, 3 H), 3.22-3.29 (m, 1 H), 3.36-3.50 (m, 3 H), 3.82 (t, 1 H), 3.98-4.05 (m, 1 H), 4.52 (td, 2 H), 4.56 (s, 1 H), 5.42 (t, 1 H), 6.19 (tt, 1 H), 6.54 (d, 1 H), 7.42 (s, 1 H), 8.01 (s, 1 H), 8.11 (s, 1 H), 8.13 (s, 1 H) |
| B-93/B | 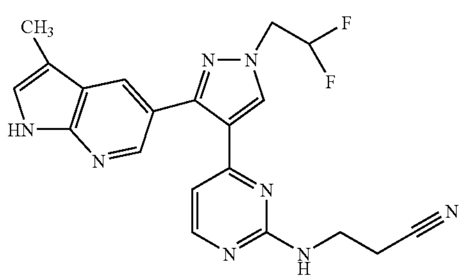 | 3-(4-(1-(2,2-difluoroethyl)-3-(3-methyl-1H-pyrrolo[2,3-b]pyridin-5-yl)-1H-pyrazol-4-yl)pyrimidin-2-ylamino)propanenitrile | 1 H NMR (400 MHz, CHLOROFORM-d) δ ppm 2.33 (d, 3 H), 2.40-2.61 (m, 2 H), 3.52-3.65 (m, 2 H), 4.58 (td, 2 H), 5.40 (t, 1 H), 6.24 (tt, 1 H), 6.52 (d, 1 H), 7.12 (d, 1 H), 8.08 (d, 1 H), 8.09 (s, 1 H), 8.12 (d, 1 H), 8.43 (d, 1 H), 8.57 (s, 1 H) |
| B-94/B | 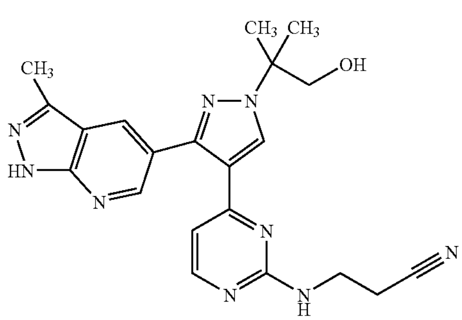 | 3-(4-(1-(1-hydroxy-2-methylpropan-2-yl)-3-(3-methyl-1H-pyrazolo[3,4-b]pyridin-5-yl)-1H-pyrazol-4-yl)pyrimidin-2-ylamino)propanenitrile | 1 H NMR (400 MHz, CHLOROFORM-d) δ ppm 1.69 (s, 6 H), 2.50-2.59 (m, 2 H), 2.62 (s, 3 H), 3.56 (t, 1 H), 3.57-3.65 (m, 2 H), 3.92 (d, 2 H), 5.44 (s, 1 H), 6.52 (d, 1 H), 8.13 (s, 1 H), 8.15 (d, 1 H), 8.23 (d, 1 H), 8.70 (d, 1 H), 10.30 (s, 1 H) |

TABLE 1-continued

| Ex. No./ Method | Structure Name | ¹H NMR/MS (m/z + 1) M + H |
|---|---|---|
| B-95/B | 3-(4-(1-(2,2-difluoroethyl)-3-(2-oxo-2,3-dihydro-1H-pyrrolo[2,3-b]pyridin-5-yl)-1H-pyrazol-4-yl)-pyrimidin-2-ylamino)propanenitrile | 1 H NMR (400 MHz, CHLOROFORM-d) δ ppm 2.58-2.73 (m, 2 H), 3.62 (s, 2 H), 3.63-3.70 (m, 2 H), 4.55 (td, 2 H), 6.20 (tt, 1 H), 6.59 (d, 1 H), 7.70 (s, 1 H), 8.01 (s, 1 H), 8.23 (d, 1 H), 8.39 (s, 1 H) |
| B-96/B | (2S)-1-({4-[3-(3-chloro-1H-pyrrolo[2,3-b]pyridin-5-yl)-1-(2,2-difluoroethyl)-1H-pyrazol-4-yl]pyrimidin-2-yl}amino)propan-2-ol | 1 H NMR (400 MHz, CHLOROFORM-d) δ ppm 9.44 (br. s., 1 H), 8.57 (d, 1 H), 8.21 (d, 1 H), 8.12 (d, 1 H), 8.07 (s, 1 H), 7.31 (d, 1 H), 6.47 (d, 1 H), 6.24 (tt, 1 H), 5.60 (br. s., 1 H), 4.58 (td, 2 H), 4.16 (br. s., 1 H), 3.95 (br. s., 1 H), 3.34-3.50 (br. m, 1 H), 3.23-3.33 (m, 1 H), 1.14 (d, 3 H). M + H: 434.1 |
| B-97/B | (2S)-1-({4-[3-(3-chloro-2-methyl-1H-pyrrolo[2,3-b]pyridin-5-yl)-1-isopropyl-1H-pyrazol-4-yl]pyrimidin-2-yl}amino)propan-2-ol | 1 H NMR (400 MHz, CHLOROFORM-d) δ ppm 9.63 (br. s., 1 H), 8.40 (br. s., 1 H), 8.09 (d, 1 H), 8.00-8.04 (m, 2 H), 6.46 (d, 1 H), 5.94 (br. s., 1 H), 4.49-4.73 (m, 1 H), 4.38 (br. s., 1 H), 3.84-4.12 (br. m, 1 H), 3.39-3.56 (br. m, 1 H), 3.24-3.38 (m, 1 H), 2.38 (br. s., 3 H), 1.63 (d, 6 H, partially obscured by water), 1.17 (d, 3 H). M + H: 426.2 |
| B-98/B | (2S)-1-[(4-{3-(3-chloro-1H-pyrrolo[2,3-b]pyridin-5-yl)-1-[(3-methyloxetan-3-yl)methyl]-1H-pyrazol-4-yl}pyrimidin-2-yl)amino]propan-2-ol | 1 H NMR (300 MHz, CHLOROFORM-d) δ ppm 9.20 (br. s., 1 H), 8.56 (d, 1 H), 8.18 (d, 1 H), 8.09 (d, 1 H), 7.98 (s, 1 H), 7.31 (d, 1 H, partially obscured by chloroform), 6.44 (d, 1 H), 5.52 (br. t, 1 H), 4.79 (d, 2 H), 4.48 (d, 2 H), 4.43 (s, 2 H), 3.86-4.03 (br. m, 1 H), 3.36-3.51 (br. m, 1 H), 3.23-3.35 (m, 1 H), 1.39 (s, 3 H), 1.15 (d, 3 H). M + H: 454.15 |

TABLE 1-continued

| Ex. No./ Method | Structure | Structure Name | ¹H NMR/MS (m/z + 1) M + H |
|---|---|---|---|
| B-99/B | 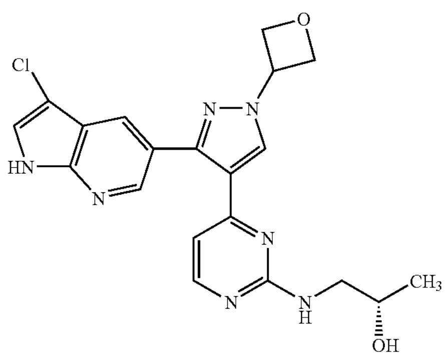 | (2S)-1-({4-[3-(3-chloro-1H-pyrrolo[2,3-b]pyridin-5-yl)-1-oxetan-3-yl-1H-pyrazol-4-yl]pyrimidin-2-yl}amino)propan-2-ol | 1 H NMR (400 MHz, CHLOROFORM-d) δ ppm 9.17 (br. s., 1 H), 8.59 (d, 1 H), 8.23 (d, 1 H), 8.19 (s, 1 H), 8.11 (d, 1 H), 7.33 (d, 1 H), 6.45 (d, 1 H), 5.45-5.65 (m, 2 H), 5.20 (t, J = 6.57 Hz, 2 H), 5.12 (t, 2 H), 3.85-4.03 (br. m, 1 H), 3.37-3.53 (br. m, 1 H), 3.24-3.37 (m, 1 H), 1.16 (d, 3 H). M + H: 426.1 |
| B-100/B | 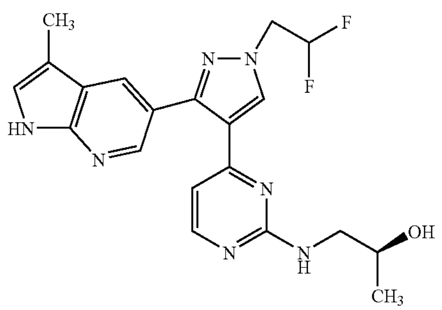 | (2S)-1-({4-[1-(2,2-difluoroethyl)-3-(3-methyl-1H-pyrrolo[2,3-b]pyridin-5-yl)-1H-pyrazol-4-yl]pyrimidin-2-yl}amino)propan-2-ol | 1 H NMR (400 MHz, CHLOROFORM-d) δ ppm 8.64 (br. s., 1 H), 8.48 (d, 1 H), 7.90-8.15 (m, 3 H), 7.11 (s, 1 H), 6.44 (d, 1 H), 6.24 (tt, 1 H), 5.44 (t, 1 H), 4.47-4.67 (m, 2 H), 4.32 (br. s., 1 H), 3.96 (br. s., 1 H), 3.40 (br. s., 1 H), 3.25-3.36 (m, 1 H), 2.33 (s, 3 H), 1.16 (d, 3 H). M + H: 414.1 |
| B-101/B | 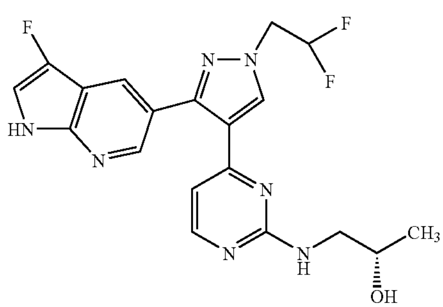 | (2S)-1-({4-[1-(2,2-difluoroethyl)-3-(3-fluoro-1H-pyrrolo[2,3-b]pyridin-5-yl)-1H-pyrazol-4-yl]pyrimidin-2-yl}amino)propan-2-ol | 1 H NMR (400 MHz, CHLOROFORM-d) δ ppm 1.14 (d, 3 H), 3.22-3.34 (m, 1 H), 3.36-3.48 (m, 1 H), 3.95 (s, 1 H), 4.19 (s, 1 H), 4.57 (td, 2 H), 5.68 (s, 1 H), 6.23 (tt, 1 H), 6.47 (d, 1 H), 7.09 (s, 1 H), 8.06 (s, 1 H), 8.12 (d, 1 H), 8.20 (s, 1 H), 8.55 (s, 1 H), 9.33 (s, 1 H). M + H: 418.2 |
| B-102/B | 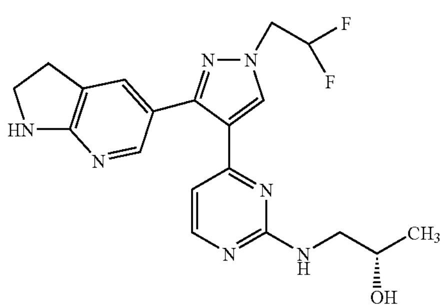 | (2S)-1-({4-[1-(2,2-difluoroethyl)-3-(2,3-dihydro-1H-pyrrolo[2,3-b]pyridin-5-yl)-1H-pyrazol-4-yl]pyrimidin-2-yl}amino)propan-2-ol | 1 H NMR (400 MHz, CHLOROFORM-d) δ ppm 1.22 (d, 3 H), 3.10 (t, 2 H), 3.33-3.41 (m, 1 H), 3.42-3.53 (m, 1 H), 3.68 (t, 2 H), 3.94-4.07 (m, 1 H), 4.50 (td, 2 H), 4.76 (s, 1 H), 5.60 (t, 1 H), 6.18 (tt, 1 H), 6.54 (d, 1 H), 7.43 (s, 1 H), 8.00 (s, 1 H), 8.08 (s, 1 H), 8.12 (d, 1 H). M + H: 402.2 |

TABLE 1-continued

| Ex. No./ Method | Structure | Structure Name | ¹H NMR/MS (m/z + 1) M + H |
|---|---|---|---|
| B-103/B | 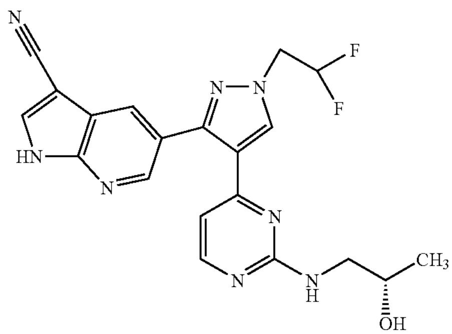 | 5-[1-(2,2-difluoroethyl)-4-(2-{[(2S)-2-hydroxypropyl]amino}pyrimidin-4-yl)-1H-pyrazol-3-yl]-1H-pyrrolo[2,3-b]pyridine-3-carbonitrile | 1 H NMR (400 MHz, MeOD) δ ppm 1.20 (d, 3 H), 2.97 (dd, 1 H), 3.02-3.23 (m, 1 H), 3.60-3.79 (m, 1 H), 4.72 (td, 2 H), 6.34 (tt, 1 H), 6.69 (s, 1 H), 8.14 (d, 1 H), 8.17-8.26 (m, 1 H), 8.29 (s, 1 H), 8.38 (s, 1 H), 8.58 (d, 1 H). M + H: 425.2 |
| B-104/B | 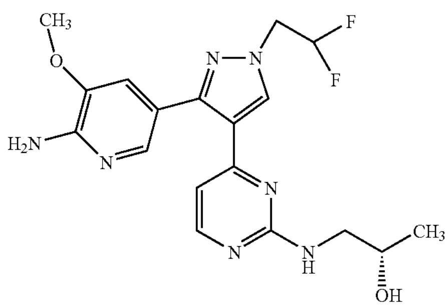 | (2S)-({4-[3-(6-amino-5-methoxypyridin-3-yl)-1-(2,2-difluoroethyl)-1H-pyrazol-4-yl]pyrimidin-2-yl}amino)propan-2-ol | 1 H NMR (400 MHz, CHLOROFORM-d) δ ppm 1.23 (d, 3 H), 3.33-3.42 (m, 1 H), 3.43-3.52 (m, 1 H), 3.86 (s, 3 H), 3.97-4.06 (m, 1 H), 4.52 (td, 2 H), 4.82 (s, 2 H), 5.42 (t, 1 H), 6.20 (tt, 1 H), 6.54 (d, 1 H), 7.12 (d, 1 H), 7.93 (s, 1 H), 8.02 (s, 1 H), 8.12 (d, 1 H). M + H: 406.2 |
| B-105/B | 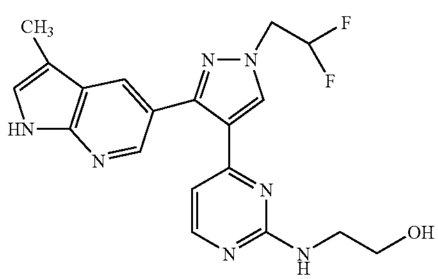 | 2-({4-[1-(2,2-difluoroethyl)-3-(3-methyl-1H-pyrrolo[2,3-b]pyridin-5-yl)-1H-pyrazol-4-yl]pyrimidin-2-yl}amino)ethanol | 1 H NMR (400 MHz, CHLOROFORM-d) δ ppm 2.33 (s, 3 H), 3.48-3.56 (m, 2 H), 3.76 (t, 2 H), 4.57 (td, 2 H), 5.41 (t, 1 H), 6.23 (tt, 1 H), 6.45 (d, 1 H), 7.11 (s, 1 H), 8.08 (d, 1 H), 8.09 (s, 2 H), 8.45-8.49 (m, 1 H), 8.51 (s, 1 H). M + H: 400.2 |
| B-106/B | 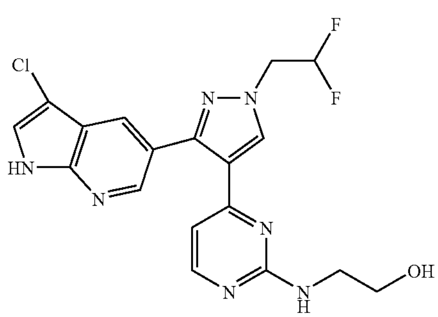 | 2-({4-[3-(3-chloro-1H-pyrrolo[2,3-b]pyridin-5-yl)-1-(2,2-difluoroethyl)-1H-pyrazol-4-yl]pyrimidin-2-yl}amino)ethanol | 1 H NMR (400 MHz, MeOD) δ ppm 3.20-3.30 (m, 2 H), 3.48 (dd, 2 H), 4.71 (td, 2 H), 6.30 (tt, 1 H), 6.61 (d, 1 H), 7.49 (s, 1 H), 8.12 (d, 1 H), 8.16 (d, 1 H), 8.38 (s, 1 H), 8.46 (s, 1 H). M + H: 420.2 |
| B-107/B | 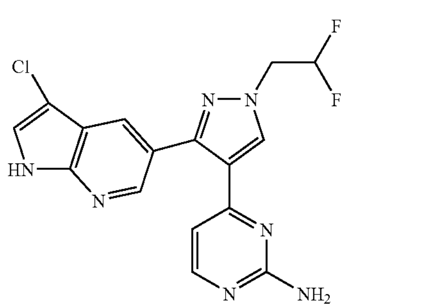 | 4-[3-(3-chloro-1H-pyrrolo[2,3-b]pyridin-5-yl)-1-(2,2-difluoroethyl)-1H-pyrazol-4-yl]pyrimidin-2-amine | 1 H NMR (400 MHz, MeOD) δ ppm 4.70-4.81 (m, 2 H), 6.38 (tt, 1 H), 6.58 (d, 1 H), 7.54 (s, 1 H), 8.14 (d, 1 H), 8.22 (d, 1 H), 8.37 (s, 1 H), 8.52 (d, 1 H). M + H: 376.2 |

TABLE 1-continued

| Ex. No./ Method | Structure | Structure Name | ¹H NMR/MS (m/z + 1) M + H |
|---|---|---|---|
| B-108/B | 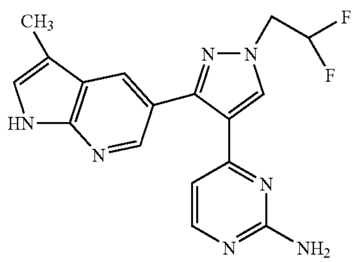 | 4-[1-(2,2-difluoroethyl)-3-(3-methyl-1H-pyrrolo[2,3-b]pyridin-5-yl)-1H-pyrazol-4-yl]pyrimidin-2-amine | 1 H NMR (400 MHz, CHLOROFORM-d) δ ppm 2.33 (s, 3 H), 4.56 (td, 2 H), 5.01 (s, 2 H), 6.23 (td, 1 H), 6.44 (d, 1 H), 7.12 (s, 1 H), 8.08 (d, 1 H), 8.09 (d, 1 H), 8.12 (s, 1 H), 8.44 (d, 1 H), 8.75 (s, 1 H). M + H: 356.2 |
| B-109/B | 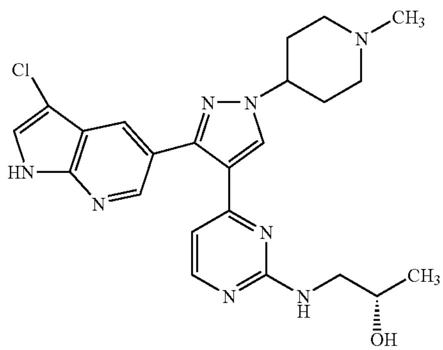 | (2S)-1-({4-[3-(3-chloro-1H-pyrrolo[2,3-b]pyridin-5-yl)-1-(1-methylpiperidin-4-yl)-1H-pyrazol-4-yl]pyrimidin-2-yl}amino)propan-2-ol | 1 H NMR (400 MHz, MeOH-d) δ ppm 8.77 (s, 1 H), 8.45 (s, 1 H), 8.2-8.1 (m, 2 H), 7.53 (s, 1 H), 7.12 (s, 1 H), 4.71 (m, 1 H), 3.74 (d, 2 H), 3.52 (s, 2 H), 2.97 (s, 3 H), 2.73 (m, 2 H), 2.49 (m, 4H), 0.70 (s, 3 H). M + H: 467.2 |
| B-110/B | 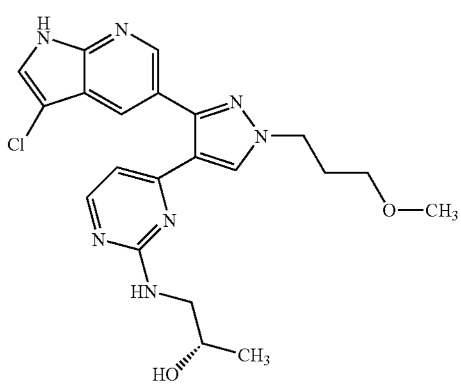 | (2S)-1-({4-[3-(3-chloro-1H-pyrrolo[2,3-b]pyridin-5-yl)-1-(3-methoxypropyl)-1H-pyrazol-4-yl]pyrimidin-2-yl}amino)propan-2-ol | 1 H NMR (400 MHz, CHLOROFORM-d) δ ppm 1.11 (d, 3 H), 2.22 (quin, 2 H), 3.25 (br. s., 1 H), 3.38 (s, 3 H), 3.43 (t, 2 H), 3.92 (br. s., 1 H), 4.33 (t, 2 H), 6.46 (d, 1 H), 7.32 (s, 1 H), 8.03 (d, 1 H), 8.24 (d, 1 H), 8.55 (br. s., 1 H), 10.43 (br. s., 1 H). M + H: 442.2 |
| B-111/B | 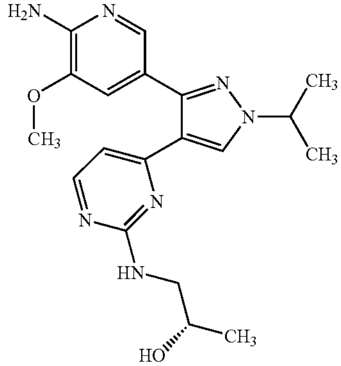 | (2S)-1-({4-[3-(6-amino-5-methoxypyridin-3-yl)-1-isopropyl-1H-pyrazol-4-yl]pyrimidin-2-yl}amino)propan-2-ol | 1 H NMR (400 MHz, CHLOROFORM-d) δ ppm 1.23 (d, 3 H), 1.59 (d, 6 H), 3.34-3.42 (m, 1 H), 3.43-3.53 (m, 1 H), 3.86 (s, 3 H), 3.97-4.06 (m, 1 H), 4.52-4.61 (m, 1 H), 4.83 (s, 2 H), 5.38 (t, 1 H), 6.53 (d, 1 H), 7.15 (d, 1 H), 7.95 (d, 1 H), 7.99 (s, 1 H), 8.09 (d, 1 H). M + H: 384.2 |

TABLE 1-continued

| Ex. No./ Method | Structure | Structure Name | $^1$H NMR/MS (m/z + 1) M + H |
|---|---|---|---|
| B-112/B | 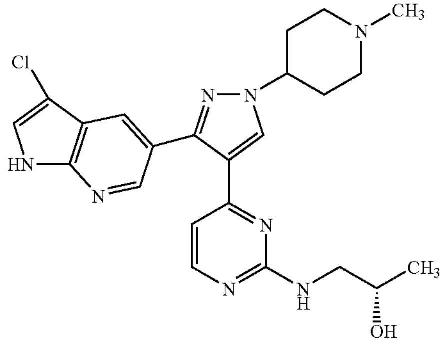 | (2S)-1-({4-[3-(3-chloro-1H-pyrrolo[2,3-b]pyridin-5-yl)-1-(1-methylpiperidin-4-yl)-1H-pyrazol-4-yl]pyrimidin-2-yl}amino)propan-2-ol | 1 H NMR (400 MHz, CHLOROFORM-d) δ ppm 1.06 (d, 3 H), 2.02-2.17 (m, 4 H), 2.21 (d, 2 H), 2.29 (s, 3 H), 2.88-3.04 (m, 2 H), 3.13-3.27 (m, 1 H), 3.27-3.44 (m, 1 H), 3.78-3.98 (m, 1 H), 4.08-4.23 (m, 1 H), 5.48 (br. s., 1 H), 6.37 (d, 1 H), 7.22 (d, 1 H), 7.96 (br. s., 1 H), 8.00 (d, 1 H), 8.13 (d, 1 H), 8.50 (d, 1 H), 9.38 (br. s., 1 H). M + H: 467.2 |
| B-113/B | 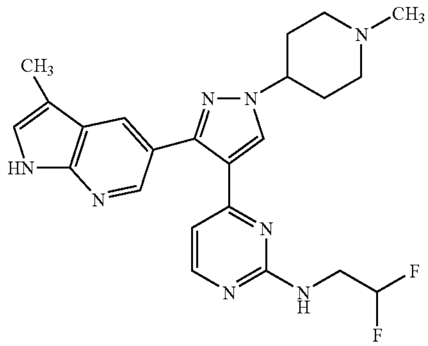 | N-(2,2-difluoroethyl)-4-[1-(1-methylpiperidin-4-yl)-3-(3-methyl-1H-pyrrolo[2,3-b]pyridin-5-yl)-1H-pyrazol-4-yl]pyrimidin-2-amine | 1 H NMR (400 MHz, CHLOROFORM-d) δ ppm 2.09-2.24 (m, 4 H), 2.26-2.33 (m, 5 H), 2.36 (s, 3 H), 2.99-3.08 (m, 2 H), 3.64-3.79 (m, 2 H), 4.19-4.29 (m, 1 H), 5.27-5.36 (m, 1 H), 5.86 (t, 1 H), 6.48 (d, 1 H), 7.10 (d, 1 H), 8.05-8.10 (m, 3 H), 8.43 (d, 1 H), 8.87 (br. s., 1 H). M + H: 453.2 |
| B-114/B | 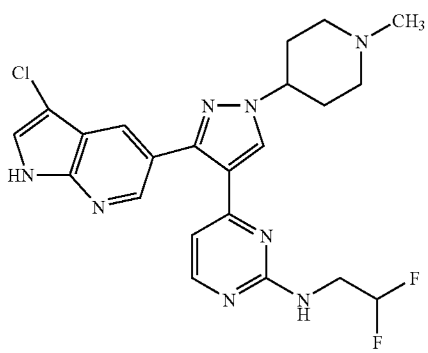 | 4-[3-(3-chloro-1H-pyrrolo[2,3-b]pyridin-5-yl)-1-(1-methylpiperidin-4-yl)-1H-pyrazol-4-yl]-N-(2,2-difluoroethyl)pyrimidin-2-amine | 1 H NMR (400 MHz, DMSO-d6) δ ppm 2.00-2.15 (m, 6 H), 2.23 (s, 3 H), 2.84-3.04 (m, 2 H), 4.15-4.28 (m, 1 H) 5.55-5.87 (m, 1 H), 6.67 (br. s., 1 H), 7.26 (br. s., 1 H), 7.71 (s, 1 H), 7.99 (d, 1 H), 8.19 (d, 1 H), 8.41 (d, 1 H), 8.49 (br. s., 1 H), 12.05 (br. s., 1 H). M + H: 473.2 |
| C-1/C | 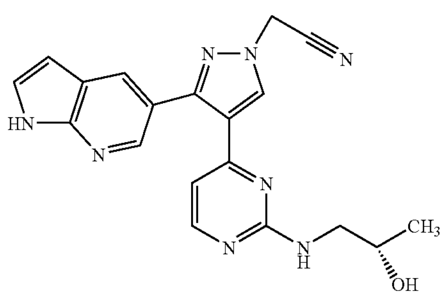 | [4-[2-((S)-2-Hydroxy-propylamino)-pyrimidin-4-yl]-3-(1H-pyrrolo[2,3-b]pyridin-5-yl)-pyrazol-1-yl]-acetonitrile | 1 H NMR (400 MHz, ACETONITRILE-d3) δ ppm 9.78 (br. s., 1 H), 8.42 (d, 1 H), 8.22 (s, 1 H), 8.05-8.14 (m, 2 H), 7.38-7.45 (m, 1 H), 6.42-6.56 (m, 2 H), 5.74 (br. s., 1 H), 5.25 (s, 2 H), 3.72 (br. s., 1 H), 3.19 (br. s., 1 H), 3.04 (br. s., 1 H), 0.95 (br. s., 3 H). M + H: 375.2 |

TABLE 1-continued

| Ex. No./ Method | Structure | Structure Name | $^1$H NMR/MS (m/z + 1) M + H |
|---|---|---|---|
| C-2/C | 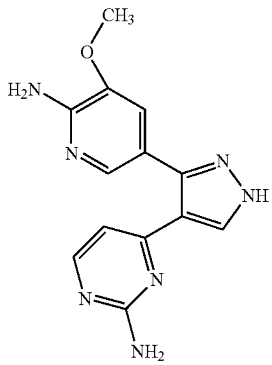 | 4-[3-(6-amino-5-methoxypyridin-3-yl)-1H-pyrazol-4-yl]pyrimidin-2-amine | 1 H NMR (400 MHz, MeOD) δ ppm 13.99 (br. s., 1 H), 8.89 (d, 1 H), 8.74 (s, 1 H), 8.52 (s, 1 H), 8.02 (br. s., 1 H), 7.30 (d, 1 H), 7.26 (s, 2 H), 6.89 (br. s., 1 H), 6.63 (br. s., 1 H), 4.58 (s, 3 H). M + H: 284 |
| D-1/D | 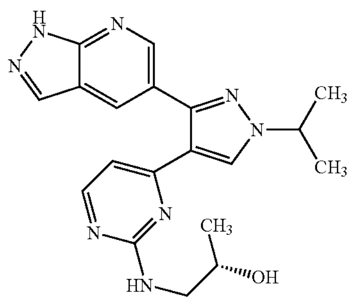 | (2S)-1-(4-(1-isopropyl-3-(1H-pyrazolo[3,4-b]pyridin-5-yl)-1H-pyrazol-4-yl)pyrimidin-2-ylamino)propan-2-ol | 1 H NMR (300 MHz, MeOH) δ ppm 0.84 (br. s., 3 H), 1.59 (d, 6 H), 2.86 (br. s., 1 H), 3.03 (br. s., 1 H), 3.65 (br. s., 1 H), 4.56-4.72 (m, 1 H), 6.68 (br. s., 1 H), 8.09 (d, 1 H), 8.17 (s, 1 H), 8.35 (s, 1 H), 8.39 (br. s., 1 H), 8.69 (br. s., 1 H). M + H 379 |
| D-2/D | 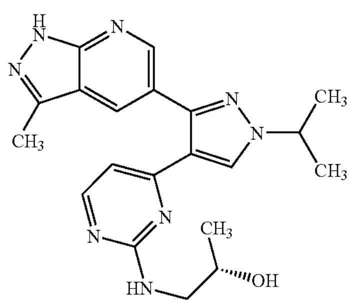 | (2S)-1-(4-(1-isopropyl-3-(3-methyl-1H-pyrazolo[3,4-b]pyridin-5-yl)-1H-pyrazol-4-yl)pyrimidin-2-ylamino)propan-2-ol | 1 H NMR (300 MHz, MeOH) δ ppm 0.84 (br. s., 3 H), 1.60 (d, 6 H), 2.58 (s, 3 H), 2.85 (br. s., 1 H), 3.03 (br. s., 1 H), 3.63 (br. s., 1 H), 4.55-4.73 (m, 1 H), 6.70 (br. s., 1 H), 8.10 (d, 1 H), 8.35 (br. s., 1 H), 8.37 (s, 1 H), 8.64 (s, 1 H). M + H: 393 |
| D-3/D | 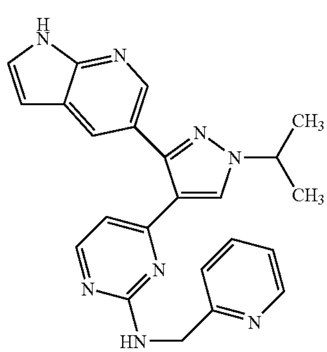 | 4-(1-isopropyl-3-(1H-pyrrolo[2,3-b]pyridin-5-yl)-1H-pyrazol-4-yl)-N-(pyridin-2-ylmethyl)pyrimidin-2-amine | 1 H NMR (400 MHz, ACETONITRILE-d3) δ ppm 9.68 (br. s., 1 H), 8.48 (d, 1 H), 8.38 (d, 1 H), 8.08-8.12 (m, 2 H), 8.06 (d, 1 H), 7.63 (t, 1 H), 7.39 (t, 1 H), 7.10-7.21 (m, 2 H), 6.46-6.51 (m, 2 H), 6.20 (t, 1 H), 4.51-4.61 (m, 1 H), 4.48 (br. s., 2 H), 1.54 (d, 6 H). M + H: 411.2 |

TABLE 1-continued

| Ex. No./ Method | Structure | Structure Name | $^1$H NMR/MS (m/z + 1) M + H |
|---|---|---|---|
| D-4/D | 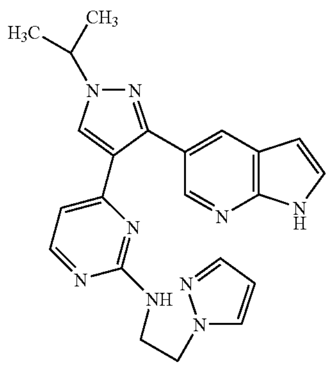 | 4-[1-isopropyl-3-(1H-pyrrolo[2,3-b]pyridin-5-yl)-1H-pyrazol-4-yl]-N-[2-(1H-pyrazol-1-yl)ethyl]pyrimidin-2-amine | 1 H NMR (500 MHz, DMSO-d6) δ ppm 1.51 (d, 6 H), 4.55-4.63 (m, 1 H), 6.16 (br. s., 1 H), 6.47 (br. s., 2 H), 6.86 (br. s., 1 H), 7.39 (br. s., 1 H) 7.47 (br. s., 1 H), 8.10 (br. s., 2 H), 8.32 (br. s., 1 H), 8.38 (br. s., 1 H), 11.64 (br. s., 1 H); four aliphatic protons not visible due to overlap with solvent and water resonances. M + H: 414.2 |
| D-5/D | 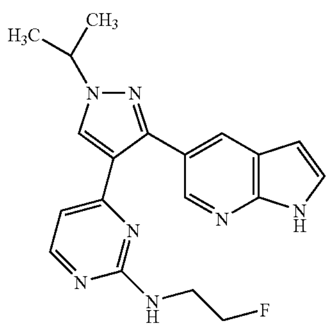 | N-(2-fluoroethyl)-4-[1-isopropyl-3-(1H-pyrrolo[2,3-b]pyridin-5-yl)-1H-pyrazol-4-yl]pyrimidin-2-amine | 1 H NMR (500 MHz, DMSO-d6) δ ppm 1.50 (d, 6 H), 4.55-4.61 (m, 2 H), 4.65-4.70 (m, 1 H), 6.48 (br. s., 1 H), 6.55 (br. s., 1 H), 7.01 (br. s., 1 H), 7.48 (br. s., 1 H), 8.07 (br. s., 1 H), 8.10 (br. s., 1 H), 8.30 (br. s., 1 H), 8.38 (br. s., 1 H), 11.64 (br. s., 1 H); two aliphatic protons not visible due to overlap with solvent and water resonances. M + H: 365.2 |
| D-6/D | 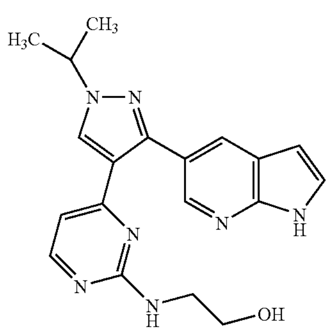 | 2-({4-[1-isopropyl-3-(1H-pyrrolo[2,3-b]pyridin-5-yl)-1H-pyrazol-4-yl]pyrimidin-2-yl}amino)ethanol | 1 H NMR (500 MHz, DMSO-d6) δ ppm 1.50 (d, 6 H), 4.60 (br. m., 1 H), 6.43 (br. s., 1 H), 6.48 (br. s., 1 H), 6.64 (br. s., 1 H), 7.47 (br. s., 1 H), 8.06 (s, 1 H), 8.10 (s, 1 H), 8.33 (br. s., 2 H), 11.64 (br. s., 1 H); four aliphatic protons not visible due to overlap with solvent and water resonances. M + H: 364.2 |
| D-7/D | 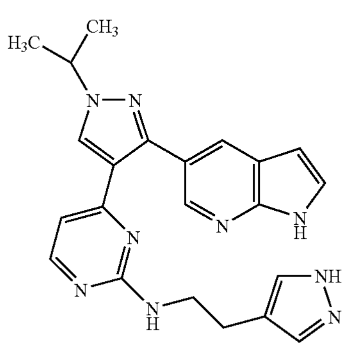 | 4-[1-isopropyl-3-(1H-pyrrolo[2,3-b]pyridin-5-yl)-1H-pyrazol-4-yl]-N-[2-(1H-pyrazol-4-yl)ethyl]pyrimidin-2-amine | 1 H NMR (500 MHz, DMSO-d6) δ ppm 1.50 (d, J = 6.04 Hz, 6 H), 4.55-4.62 (m, 1 H), 6.45 (br. s., 1 H), 6.84 (br. s., 1 H), 7.41 (br. s., 2 H), 7.46 (br. s., 1 H), 8.08 (br. s., 1 H), 8.10 (br. s., 1 H), 8.32 (br. s., 2 H); four aliphatic protons not visible due to overlap with solvent and water resonances. M + H: 413.2 |

TABLE 1-continued

| Ex. No./ Method | Structure | Structure Name | ¹H NMR/MS (m/z + 1) M + H |
|---|---|---|---|
| D-8/D | 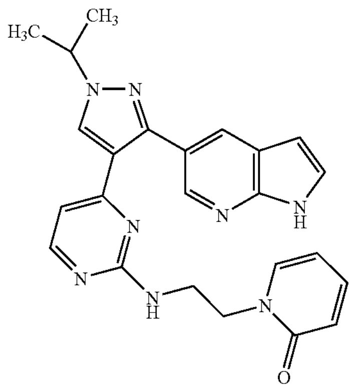 | 1-[2-({4-[1-isopropyl-3-(1H-pyrrolo[2,3-b]pyridin-5-yl)-1H-pyrazol-4-yl]pyrimidin-2-yl}amino)ethyl]pyridin-2(1H)-one | 1 H NMR (500 MHz, DMSO-d6) δ ppm 1.52 (br. s., 6 H), 4.55-4.62 (m, 1 H), 6.06 (br. s., 1 H), 6.32 (br. s., 1 H), 6.42-6.50 (m, 2 H), 6.95 (br. s., 1 H), 7.33 (br. s., 1 H), 7.46 (br. s., 1 H), 8.05 (br. s., 1 H), 8.08 (br. s., 1 H), 8.30 (br. s., 1 H), 8.40 (br. s., 1 H), 11.63 (br. s., 1 H); four aliphatic protons not visible due to overlap with solvent and water resonances. M + H: 441.2 |
| D-9/D | 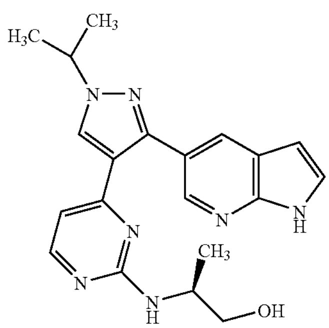 | (2R)-2-({4-[1-isopropyl-3-(1H-pyrrolo[2,3-b]pyridin-5-yl)-1H-pyrazol-4-yl]pyrimidin-2-yl}amino)propan-1-ol | 1 H NMR (500 MHz, DMSO-d6) δ ppm 0.96 (br. s., 3 H), 1.50 (d, 6 H), 4.59 (br. m., 1 H), 4.65 (br. s., 1 H), 6.39 (br. s., 1 H), 6.48 (br. s., 1 H), 7.47 (br. s., 1 H), 8.05 (br. s., 1 H), 8.09 (br. s., 1 H), 8.31 (br. s., 2 H), 11.63 (br. s., 1 H); three aliphatic protons not visible due to overlap with solvent and water resonances. M + H: 378.2 |
| D-10/D | 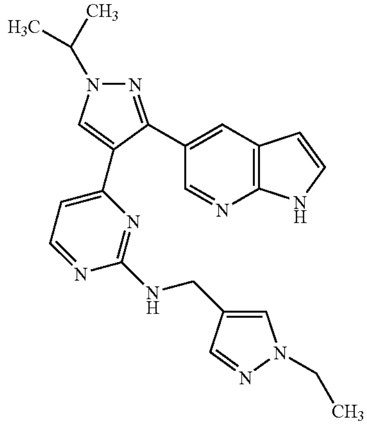 | N-[(1-ethyl-1H-pyrazol-4-yl)methyl]-4-[1-isopropyl-3-(1H-pyrrolo[2,3-b]pyridin-5-yl)-1H-pyrazol-4-yl]pyrimidin-2-amine | 1 H NMR (500 MHz, DMSO-d6) δ ppm 1.28 (t, 3 H), 1.50 (d, 6 H), 3.93-4.03 (m, 2 H), 4.10 (br. s., 1 H), 4.56-4.63 (m, 1 H), 6.47 (br. s., 1 H), 7.05 (br. s., 1 H), 7.17 (br. s., 1 H), 7.34 (br. s., 1 H), 7.46 (br. s., 1 H), 8.08 (br. s., 1 H), 8.11 (br. s., 1 H), 8.35 (br. s., 2 H), 11.63 (br. s., 1 H); two aliphatic protons not visible due to overlap with solvent and water resonances. M + H: 428.2 |

TABLE 1-continued

| Ex. No./ Method | Structure | Structure Name | ¹H NMR/MS (m/z + 1) M + H |
|---|---|---|---|
| D-11/D | 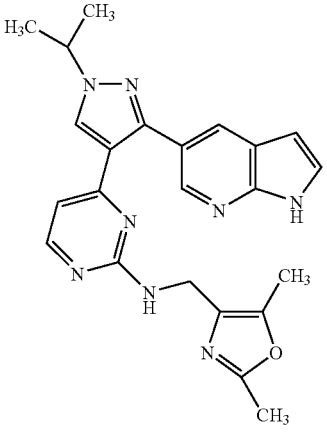 | N-[(2,5-dimethyl-1,3-oxazol-4-yl)methyl]-4-[1-isopropyl-3-(1H-pyrrolo[2,3-b]pyridin-5-yl)-1H-pyrazol-4-yl]pyrimidin-2-amine | 1 H NMR (500 MHz, DMSO-d6) δ ppm 1.50 (d, 6 H), 2.27 (br. s., 3 H), 4.10 (br. s., 2 H), 4.59 (br. m., 1 H), 6.45 (br. s., 1 H), 6.94 (br. s., 1 H), 7.46 (br. s., 1 H), 8.08 (s, 1 H), 8.09 (s, 1 H), 8.31 (br. s., 1 H), 8.35 (br. s., 1 H), 11.63 (br. s., 1 H); three aliphatic protons not visible due to overlap with solvent and water resonances. 429.2 |
| D-12/D | 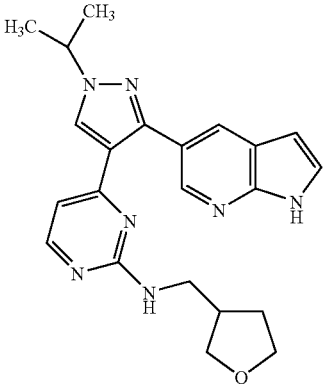 | 4-[1-isopropyl-3-(1H-pyrrolo[2,3-b]pyridin-5-yl)-1H-pyrazol-4-yl]-N-(tetrahydrofuran-3-ylmethyl)pyrimidin-2-amine | 1 H NMR (500 MHz, DMSO-d6) δ ppm 1.50 (d, 6 H), 4.55-4.62 (m, 1 H), 6.47 (br. s., 1 H), 6.96 (br. s., 1 H), 7.46 (br. s., 1 H), 8.05 (br. s., 1 H), 8.09 (br. s., 1 H), 8.30 (br. s., 1 H), 8.36 (br. s., 1 H), 11.61 (br. s., 1 H); nine aliphatic protons not visible due to overlap with solvent and water resonances. M + H: 404.2 |
| D-13/D | 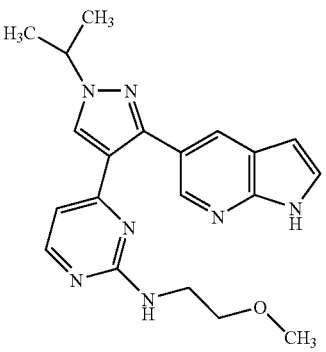 | 4-[1-isopropyl-3-(1H-pyrrolo[2,3-b]pyridin-5-yl)-1H-pyrazol-4-yl]-N-(2-methoxyethyl)-pyrimidin-2-amine | 1 H NMR (500 MHz, DMSO-d6) δ ppm 1.50 (d, 6 H), 4.59 (br. m., 1 H), 6.48 (br. s., 1 H), 6.72 (br. s., 1 H), 7.47 (br. s., 1 H), 8.08 (br. s., 2 H), 8.30 (br. s., 1 H), 8.34 (br. s., 1 H), 11.63 (br. s., 1 H); seven aliphatic protons not visible due to overlap with solvent and water resonances. M + H: 378.2 |

TABLE 1-continued

| Ex. No./ Method | Structure Name | ¹H NMR/MS (m/z + 1) M + H |
|---|---|---|
| D-14/D | 1-ethyl-4-[({4-[1-isopropyl-3-(1H-pyrrolo[2,3-b]pyridin-5-yl)-1H-pyrazol-4-yl]pyrimidin-2-yl}amino)methyl]-pyrrolidin-2-one | 1 H NMR (500 MHz, DMSO-d6) δ ppm 0.93 (br. s., 3 H), 1.50 (d, 6 H), 3.08 (br. s., 2 H), 4.58 (br. m., 1 H), 6.47 (br. s., 1 H), 7.05 (br. s., 1 H), 7.46 (br. s., 1 H), 8.04 (br. s., 1 H), 8.10 (br. s., 1 H), 8.30 (br. s., 1 H), 8.38 (br. s., 1 H), 11.63 (br. s., 1 H); seven aliphatic protons not visible due to overlap with solvent and water resonances. M + H: 445.2 |
| D-15/D | 3-(4-(1-(2,2-difluoroethyl)-3-(1-cyanoethyl-1H-pyrrolo[2,3-b]pyridin-5-yl)-1H-pyrazo[-4-yl)pyrimidin-2-ylamino)propanenitrile | 1 H NMR (400 MHz, CHLOROFORM-d) δ ppm 2.33-2.69 (m, 2 H), 3.02 (t, 2 H), 3.41-3.69 (m, 2 H), 4.56 (td, 2 H), 4.63 (dd, 2 H), 5.52 (t, 1 H), 6.23 (tt, 1 H), 6.54 (s, 1 H), 6.55 (s, 1 H), 7.36 (d, 1 H), 8.07 (s, 1 H) 8.11 (s, 1 H), 8.15 (d, 1 H), 8.47 (s, 1 H) |
| E-1/E | (2S)-1-(4-(3-(3-chloro-1H-pyrrolo[2,3-b]pyridin-5-yl)-1-methyl-1H-pyrazol-4-yl)pyrimidin-2-ylamino)propan-2-ol | 1 H NMR (400 MHz, CHLOROFORM-d) δ ppm 9.41 (br. s., 1 H), 8.56 (br. s., 1 H), 8.20 (d, 1 H), 8.07 (d, 1 H), 8.03 (s, 1 H), 7.31 (s, 1 H), 6.45 (d, 1 H), 5.94 (br. s., 1 H), 4.04 (s, 3 H), 3.96 (br. s., 1 H), 3.40 (br. s., 1 H), 3.25-3.35 (m, 1 H), 1.16 (d, 3 H). M + H: 384.1 |
| E-2/E | (2S)-1-(4-(3-(3-chloro-1H-pyrrolo[2,3-b]pyridin-5-yl)-1-(2,2-difluoroethyl)-1H-pyrazol-4-yl)pyrimidin-2-ylamino)propan-2-ol | 1 H NMR (400 MHz, CHLOROFORM-d) δ ppm 9.44 (br. s., 1 H), 8.57 (d, 1 H), 8.21 (d, 1 H), 8.12 (d, 1 H), 8.07 (s, 1 H), 7.31 (s, 1 H), 6.47 (d, 1 H), 6.24 (tt, 1 H), 5.60 (br. s., 1 H), 4.58 (td, 2 H), 4.16 (br. s., 1 H), 3.95 (br. s., 1 H), 3.34-3.50 (br. m, 1 H), 3.23-3.33 (m, 1 H), 1.14 (d, 3 H). M + H: 434.1 |

TABLE 1-continued

| Ex. No./ Method | Structure | Structure Name | ¹H NMR/MS (m/z + 1) M + H |
|---|---|---|---|
| E-3/E | 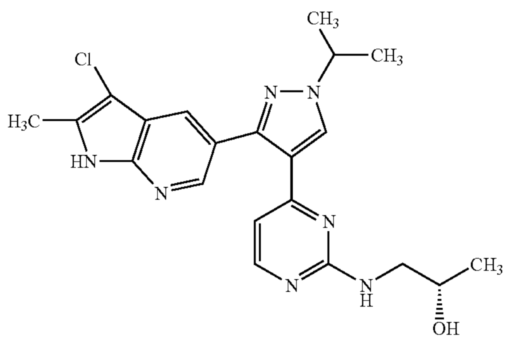 | (2S)-1-(4-(3-(3-chloro-2-methyl-1H-pyrrolo[2,3-b]pyridin-5-yl)-1-isopropyl-1H-pyrazol-4-yl)pyrimidin-2-ylamino)propan-2-ol | 1 H NMR (400 MHz, CHLOROFORM-d) δ ppm 9.63 (br. s., 1 H), 8.40 (br. s., 1 H), 8.09 (d, 1 H), 8.00-8.04 (m, 2 H), 6.46 (d, 1 H), 5.94 (br. s., 1 H), 4.49-4.73 (m, 1 H), 4.38 (br. s., 1 H), 3.84-4.12 (br. m, 1 H), 3.39-3.56 (br. m, 1 H), 3.24-3.38 (m, 1 H), 2.38 (br. s., 3 H), 1.63 (d, 6 H, partially obscured by water), 1.17 (d, J = 6.32 Hz, 3 H). M + H: 426.2 |
| E-4/E | 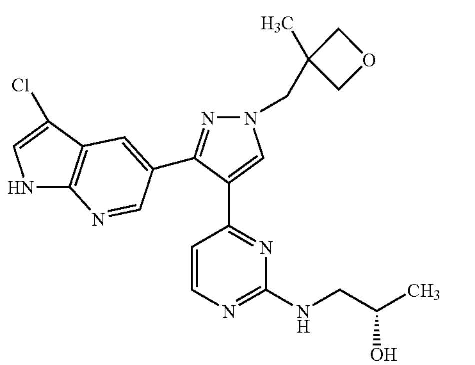 | (2S)-1-(4-(3-(3-chloro-1H-pyrrolo[2,3-b]pyridin-5-yl)-1-((3-methyloxetan-3-yl)methyl)-1H-pyrazol-4-yl)pyrimidin-2-ylamino)propan-2-ol | 1 H NMR (300 MHz, CHLOROFORM-d) δ ppm 9.20 (br. s., 1 H), 8.56 (d, 1 H), 8.18 (d, 1 H), 8.09 (d, 1 H), 7.98 (s, 1 H), 7.31 (d, 1 H, partially obscured by chloroform), 6.44 (d, 1 H), 5.52 (br. t, 1 H), 4.79 (d, 2 H), 4.48 (d, 2 H), 4.43 (s, 2 H), 3.86-4.03 (br. m, 1 H), 3.36-3.51 (br. m, 1 H), 3.23-3.35 (m, 1 H), 1.39 (s, 3 H), 1.15 (d, 3 H). M + H: 454.1 |
| E-5/E | 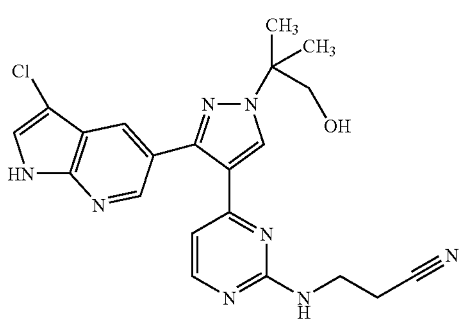 | 3-({4-[3-(3-chloro-1H-pyrrolo[2,3-b]pyridin-5-yl)-1-(2-hydroxy-1,1-dimethylethyl)-1H-pyrazol-4-yl]pyrimidin-2-yl}amino)-propanenitrile | 1 H NMR (400 MHz, DMSO-d6) δ ppm 12.13 (s, 1 H), 8.48 (d, 2 H), 8.23 (d, 1 H), 8.07 (d, 1 H), 7.78 (s, 1 H), 7.32 (t, 1 H), 6.63-6.91 (m, 1 H), 5.15 (t, 1 H), 3.73 (d, 2 H), 3.26 (br. s., 2 H), 2.32 (br. s., 2 H) 1.62 (s, 6 H). M + H: 437.2 |
| E-6/E | 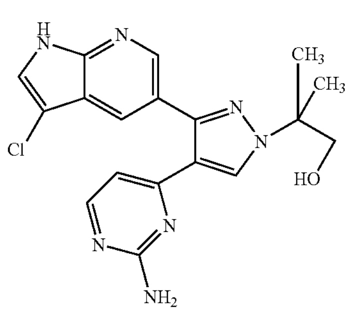 | 2-[4-(2-amino-pyrimidin-4-yl)-3-(3-chloro-1H-pyrrolo[2,3-b]pyridin-5-yl)-1H-pyrazol-1-yl]-2-methylpropan-1-ol | 1 H NMR (400 MHz, DMSO-d6) δ ppm 12.08 (br. s., 1 H), 8.41 (d, 1 H), 8.26 (s, 1 H), 8.05 (d, 1 H), 8.03 (d, 1 H), 7.73 (s, 1 H) 6.45 (s, 2 H), 6.34 (d, 1 H), 5.11 (t, 1 H), 3.67 (d, 2 H), 1.55 (s, 6 H). M + H: 384.2 |

TABLE 1-continued

| Ex. No./ Method | Structure Name | ¹H NMR/MS (m/z + 1) M + H |
|---|---|---|
| F-1/F | 3-chloro-5-(1-isopropyl-4-pyrimidin-4-yl-1H-pyrazol-3-yl)-1H-pyrrolo[2,3-b]pyridine | 1 H NMR (300 MHz, DMSO-d6) δ ppm 12.15 (s, 1 H), 9.06 (d, 1 H), 8.68 (d, 1 H), 8.65 (s, 1 H), 8.48 (d, 1 H), 8.10 (d, 1 H), 7.80 (s, 1 H), 7.45 (dd, 1 H), 4.59-4.80 (m, 1 H), 1.60 (d, 6 H). M + H: 339 |
| F-2/F | 3-chloro-5-[1-(1-methylpiperidin-4-yl)-4-pyrimidin-4-yl-1H-pyrazol-3-yl]-1H-pyrrolo[2,3-b]pyridine | 1 H NMR (400 MHz, CHLOROFORM-d) δ ppm 8.11 (d, 1 H), 8.07 (s, 1 H), 7.85 (d, 1 H), 7.12 (d, 1 H), 6.57 (d, 1 H), 5.72-6.14 (m, 1 H), 5.24 (t, 1 H), 4.78 (s, 2 H), 3.85 (s, 3 H), 3.74-3.83 (m, 2 H), 1.67 (s, 9 H). M + H: 394.2 |
| F-3/F | 5-(1-tert-butyl-4-pyrimidin-4-yl-1H-pyrazol-3-yl)-3-methoxypyridin-2-amine | 1 H NMR (400 MHz, DMSO-d6) δ ppm 9.04 (d, 1 H), 8.62 (d, 1 H), 8.49 (s, 1 H), 7.67 (d, 1 H), 7.41 (dd, 1 H), 7.17 (d, 1 H), 5.89 (s, 2 H), 3.75 (s, 3 H), 1.61 (s, 9 H). M + H: 325.2 |
| G-1/G | (2S)-1-(4-(3-(3-chloro-1H-pyrrolo[2,3-b]pyridin-5-yl)-1-(tetrahydrofuran-3-yl)-1H-pyrazol-4-yl)pyrimidin-2-ylamino)propan-2-ol | 1 H NMR (400 MHz, CDCl3): 611.281 (s, 1 H), 9.81 (s, 1 H), 8.51 (s, 1 H), 8.28 (s, 1 H), 8.217 (m, 1 H), 7.81 (s, 1 H), 7.35 (s, 1 H), 7.19 (s, 1 H), 6.60 (s, 1 H), 5.04 (s, 1 H), 4.19-4.12 (m, 2 H), 4.06-4.02 (m, 1 H), 3.97-3.91 (m, 1 H), 2.94 (s, 2 H), 2.58-2.51 (m, 1 H), 2.49-2.36 (m, 1 H), 0.92 (s, 3 H). M + H: 440 |

TABLE 1-continued

| Ex. No./ Method | Structure | Structure Name | $^1$H NMR/MS (m/z + 1) M + H |
|---|---|---|---|
| G-2/G | 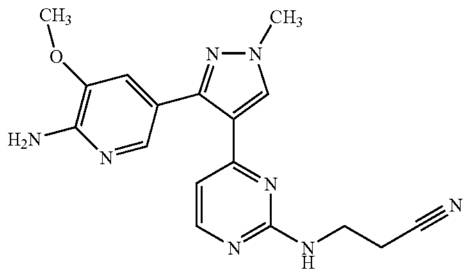 | 3-({4-[3-(6-amino-5-methoxypyridin-3-yl)-1-methyl-1H-pyrazol-4-yl]pyrimidin-2-yl}amino)propanenitrile | 1 H NMR (400 MHz, ACETONITRILE-d3) δ ppm 8.12 (d, 1 H), 8.05 (s, 1 H), 7.73 (d, 1 H), 7.12 (s, 1 H), 6.59 (d, 1 H), 5.91 (br. t, 1 H), 5.05 (br. s., 2 H), 3.90 (s, 3 H), 3.79 (s, 3 H), 3.52 (br. q, 2 H), 2.61 (br. t, 2 H). M + H: 351.2 |
| G-3/G | 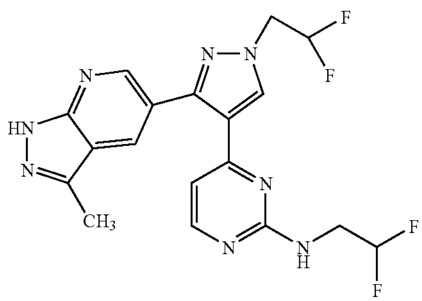 | N-(2,2-difluoroethyl)-4-[1-(2,2-difluoroethyl)-3-(3-methyl-1H-pyrazolo[3,4-b]pyridin-5-yl)-1H-pyrazol-4-yl]pyrimidin-2-amine | 1 H NMR (400 MHz, ACETONITRILE-d3) δ ppm 11.18 (br. s., 1 H), 8.62 (d, 1 H), 8.26 (d, 1 H), 8.24 (s, 1 H), 8.15 (d, 1 H), 6.64 (d, 1 H), 6.30 (tt, 1 H), 5.67-5.93 (br. m, 2 H), 4.63 (td, 2 H), 3.47 (br. s., 2 H), 2.51 (s, 3 H). M + H: 421.2 |
| G-4/G | 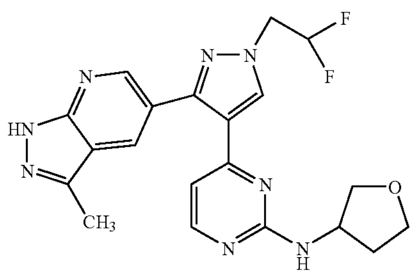 | 4-[1-(2,2-difluoroethyl)-3-(3-methyl-1H-pyrazolo[3,4-b]pyridin-5-yl)-1H-pyrazol-4-yl]-N-(tetrahydrofuran-3-yl)pyrimidin-2-amine | 1 H NMR (400 MHz, CHLOROFORM-d) δ ppm 10.81 (br. s., 1 H), 8.70 (d, 1 H), 8.26 (d, 1 H), 8.16 (d, 1 H), 8.07 (s, 1 H), 6.47 (d, 1 H), 6.23 (tt, 1 H), 5.46 (br. s, 1 H), 4.58 (td, 2 H), 4.41 (br. s, 1 H), 3.92 (q, 1 H), 3.57-3.82 (br. m, 3 H) 2.60 (s, 3 H), 2.15 (br. s, 1 H), 1.81 (br. s, 1 H). M + H: 427.2 |
| G-5/G | 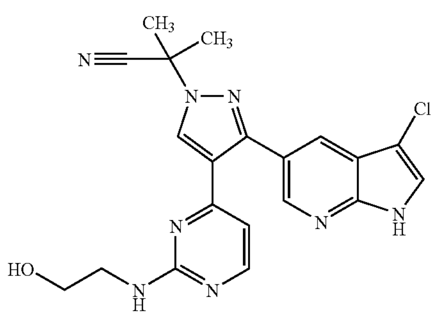 | 2-[3-(3-chloro-1H-pyrollo[2,3-b]pyridin-5-yl)-4-{2-[(2-hydroxyethyl)amino]pyrimidin-4-yl}-1H-pyrazol-1-yl]-2-methylpropanenitrile | 1 H NMR (400 MHz, CHLOROFORM-d) δ ppm 2.12 (s., 6 H), 3.48 (br. s., 2 H), 3.73 (br. S, 2 H), 6.50 (d, 1 H), 7.34 (s, 1 H), 8.08 (d, 1 H), 8.23 (s, 1 H), 8.32 (s, 1 H), 8.57 (s, 1 H), 10.01 (br, s, 1 H). M + H: 423 |
| G-6/G | 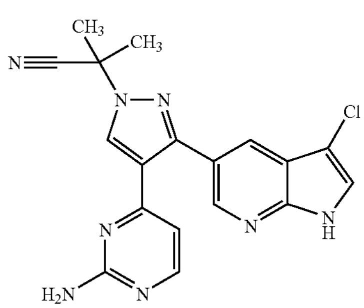 | 2-[4-(2-aminopyrimidin-4-yl)-3-(3-chloro-1H-pyrrolo[2,3-b]pyridin-5-yl)-1H-pyrazol-1-yl]-2-methylpropanenitrile | 1 H NMR (400 MHz, CHLOROFORM-d) δ ppm 2.13 (s., 6 H), 5.68 (br. s., 2 H), 6.49 (d, 1 H), 7.35 (s, 1 H), 8.10 (d, 1 H), 8.24 (s, 1 H), 8.38 (s, 1 H), 8.53 (s, 1 H), 10.06 (br, s, 1 H). M + H: 379 |

TABLE 1-continued

| Ex. No./ Method | Structure | Structure Name | ¹H NMR/MS (m/z + 1) M + H |
|---|---|---|---|
| G-7/G | 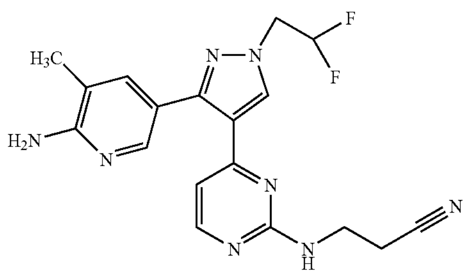 | 3-(4-(3-(6-amino-5-methylpyridin-3-yl)-1-(2,2-difluoroethyl)-1H-pyrazol-4-yl)pyrimidin-2-ylamino)-propanenitrile | 1 H NMR (400 MHz, DMSO-d6) δ ppm 2.09 (s, 3 H) 2.55-2.79 (m, 2 H), 3.36-3.57 (m, 2 H), 4.51-4.84 (m, 2 H), 6.09-6.72 (m, 3 H), 7.36 (br. s., 1 H), 7.48 (br. s., 1 H), 7.94 (br. s., 1 H), 8.19 (d, 1 H), 8.38 (br. s., 1 H), 11.90 (s, 1 H). M + H: 385.2 |
| H-1/H | 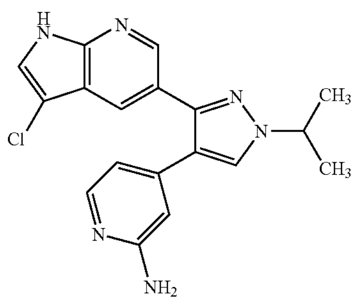 | 4-(3-(3-chloro-1H-pyrrolo[2,3-b]pyridin-5-yl)-1-isopropyl-1H-pyrazol-4-yl)pyridin-2-amine | 1 H NMR (400 MHz, DMSO-d6) δ ppm 1.51 (d, 6 H), 4.43-4.69 (m, 1 H), 6.22-6.63 (m, 4 H), 7.72 (d, 1 H), 7.82 (d, 1 H), 7.92 (d, 1 H), 8.23 (s, 1 H), 8.30 (d, 1 H), 12.08 (d, 1 H). M + H: 353.2 |
| H-2/H | 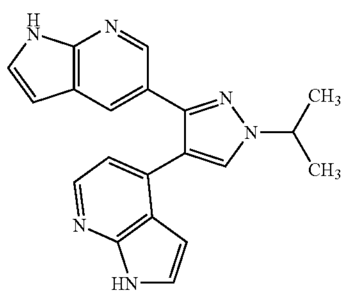 | 4-(1-isopropyl-3-(1H-pyrrolo[2,3-b]pyridin-5-yl)-1H-pyrazol-4-yl)pyridin-2-amine | 1 H NMR (400 MHz, DMSO-d6) δ ppm 1.50 (d, 6 H), 4.45-4.65 (s, 1 H), 5.79 (s, 2 H), 6.25-6.38 (m, 2 H), 6.45 (dd, 1 H), 7.40-7.55 (m, 1 H), 7.71-7.86 (m, 1 H), 7.95 (d, 1 H), 8.09 (s, 1 H), 8.22 (d, 1 H), 11.68 (br. s., 1 H). M + H: 319.2 |
| H-3/H | 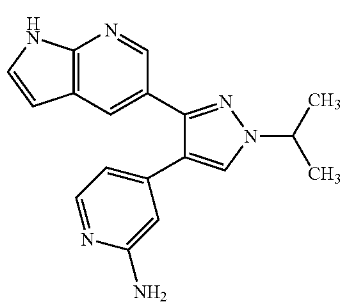 | 4-(1-isopropyl-3-(1H-pyrrolo[2,3-b]pyridin-5-yl)-1H-pyrazol-4-yl)-1H-pyrrolo[2,3-b]pyridine | 1 H NMR (400 MHz, DMSO-d6) δ ppm 1.55 (d, 6 H), 4.56-4.72 (m, 1 H), 6.21 (dd, 1 H), 6.38 (dd, 1 H), 6.79 (d, 1 H), 7.29-7.39 (m, 1 H), 7.39-7.49 (m, 1 H), 7.91 (d, 1 H), 8.06 (d, 1 H), 8.14 (d, 1 H), 8.21 (s, 1 H) 11.62 (br. s., 2 H). M + H: 343.2 |
| H-4/H | 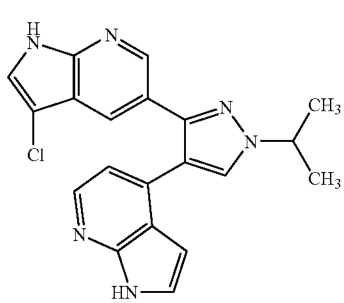 | 3-chloro-5-(1-isopropyl-4-(1H-pyrrolo[2,3-b]pyridin-4-yl)-1H-pyrazol-3-yl)-1H-pyrrolo[2,3-b]pyridine | 1 H NMR (400 MHz, DMSO-d6) δ ppm 1.55 (d, 6 H), 4.53-4.76 (m, 1 H), 6.18 (dd, 1 H), 6.81 (d, 1 H), 7.28-7.42 (m, 1 H), 7.66 (s, 1 H), 7.88 (d, 1 H), 8.09 (d, 1 H), 8.18 (d, 1 H), 8.23 (s, 1 H), 11.64 (br. s., 1 H), 11.99 (br. s., 1 H). M + H: 377.2 |

TABLE 1-continued

| Ex. No./ Method | Structure | Structure Name | ¹H NMR/MS (m/z + 1) M + H |
|---|---|---|---|
| I-1/I | (structure) | (2S)-1-({4-[3-(5-amino-6-methoxypyrazin-2-yl)-1-(2,2-difluoroethyl)-1H-pyrazol-4-yl]pyrimidin-2-yl}amino)propan-2-ol | 1 H NMR (400 MHz ACETONITRILE-d3) δ ppm 8.05-8.15 (m, 2 H), 7.83 (s, 1 H), 6.65 (d, 1 H), 6.27 (tt, 1 H), 5.73 (br. t, 1 H), 5.34 (br. s., 2 H), 4.58 (td, 2 H), 3.81 (br. s., 1 H), 3.76 (s, 3 H), 3.54 (br. s., 1 H), 3.27-3.41 (br. m, 1 H), 3.06-3.23 (br. m, 1 H), 1.08 (d, 3 H). M + H: 407.2 |
| I-2/I | (structure) | (2S)-1-({4-[3-(7-chloro-5H-pyrrolo[2,3-b]pyrazin-2-yl)-1-isopropyl-1H-pyrazol-4-yl]pyrimidin-2-yl}amino)propan-2-ol | 1 H NMR (400 MHz, MeOD) d ppm 8.70 (s. over br. s, 2 H), 8.20 (br. s., 1 H), 7.91 (s, 1 H), 7.27 (d, 1 H), 4.57-4.79 (m, 1 H), 3.66 (br. s., 1 H), 2.91 (br. s., 2 H), 1.64 (d, 6 H), 0.91 (br. s., 3 H). M + H: 413.2 |

Example J

Raf Biochemical Assay

Compounds of the present invention were evaluated for potency against b-Raf using an in vitro kinase assay. Raf kinase activity is measured in vitro by determining transfer of radiolabeled 32-P phosphate from ATP to the specific Raf substrate Mek1. Full-length wild type b-Raf is expressed in recombinant form and purified from bacterial or insect cells. Recombinant Mek1 is purified from E. coli bacterial cells. In one assay format (designated G1), the full-length wild type Mek1 is used as the b-Raf substrate. In a second assay format (designated G2), the full-length K97R Mek1 mutant is used as the b-Raf substrate.

In vitro kinase assays are performed in solution containing the following: 50 mM Hepes (pH 7.4), 5 nM b-Raf, 0.8 μM Mek1, 10 mM MgCl2, 25 μM ATP, 0.002% (v/v) Tween-20, 5 μg/mL leupeptin, 1.2 mM DTT, 2% (v/v) DMSO, 0.2-1.0 μCi [γ-$^{32}$P]ATP per well.

The assays are performed in wells of a 96 well polypropylene round bottom plate, each well containing 43.5 μL assay mix and 1.5 μL inhibitor compound or DMSO vehicle. 15 μL of b-Raf mix is added and the plate is shaken on a plate shaker and preincubated for 10 minutes at ambient temperature. The reaction is started by addition of 15 μL ATP mix and shaking. The reaction is terminated after 40 minutes by addition of 25 μL 0.5 M EDTA (pH 7.4).

60 μL of the stopped reaction is transferred to a well of a 96-well nylon 66 Biodyne A membrane Silent Screen filter plate (Nalge/Nunc: 256081). The wells are filtered and washed five times with 0.85% phosphoric acid. The filter is placed in a tray with about 50 mL 0.85% phosphoric acid and gently rotated for 10 minutes on an orbital shaker. The procedure is repeated once with fresh 0.85% phosphoric acid. Five samples of 0.5 μL of ATP mix are also spotted onto filter paper for calculation of specific activity. The filters are air dried for one hour and sandwiched between cellophane wrap on an Amersham Biosciences Storage Phosphor Screen and developed at least over night. The image is read using a Molecular Dynamics Storm 840 phosphoimager. Volumes of spots are calculated using ImageQuant5.1.

Raf kinase activity is calculated from the specific activity of [32-P] ATP, 32-P incorporation into Mek1, and the concentration of b-Raf.

Example K

Raf Cellular Assay

Compounds of the present invention were evaluated for potency against b-Raf using a cellular assay as follows. The activity of Raf kinases in cells is determined by measuring the level of phosphorylation of Mek1/2 at serine 217/221, the site phosphorylated by Raf kinases in vivo. Mek1/2 Ser phosphorylation is measured using anti-phospho-Mek1/2 antibodies (Cell Signaling #9121) in an ELISA format.

Healthy growing human melanoma A2058 cells (harboring a b-Raf mutation) are used for the assay. A2058 cells are grown in 10% FBS DMEM medium. When the cells are near 85%+confluence, the cells are rinsed with PBS once and trypsinized with trypsin/EDTA for 3 minutes. The cells are resuspended in 10% FBS DMEM and are centrifuged down at 1000 rpm for 5 minutes. The cells are resuspended in 10% FBS DMEM and counted on a cell counter. The cells are seeded at 50,000 cells/well in a volume of 100 μL/well in 10% FBS DMEM in a 96 well flat-bottom plate. The negative control wells receive only 100 μL of 10% FBS DMEM medium without cells. The plate is incubated overnight in a cell culture incubator with 5% $CO_2$ at 37° C.

On day 2, testing compounds are prepared in 10% FBS DMEM medium and serially diluted at 1:3 for 11 test concentrations. Each concentration of the compounds is tested in duplicate. The compound solutions are added at 25 μL/well to the corresponding wells in the cell plate, and 25 μL/well of the vehicle (0.5% DMSO in 10% FBS DMEM) is added to the negative control wells (no cells) and the positive control wells (cells without compounds). The plate is incubated for 1 hour in a cell culture incubator with 5% $CO_2$ at 37° C. After 1 hour of incubation, the medium is removed, 100 μL/well of cell lysis buffer is added into the cell plate, and the plate is shaken for 15 minutes at room temperature. After 15 minutes, the cell lysates are transferred to an ELISA plate (pre-coated with anti-Mek1 anti-body, Cell Signaling #2352), and the plate is incubated with gentle shaking for 2 hours at room temperature. After 2 hours, the contents of the wells are aspirated and the wells are washed 4 times with wash buffer. 100 μL of phospho-Mek1/2 detection antibody (Cell Signaling #9121) is added into each well and the plate is incubated with gentle shaking for 1 hour at room temperature. After 1 hour, the wells are aspirated and washed 4 times with wash buffer. 100 μL of anti-rabbit IgG HRP-linked antibody (Cell Signaling #7074) is added to each well, and the plate is incubated with gentle shaking for 1 hour at room temperature. After 1 hour, the contents of the wells are aspirated and the wells are washed 4 times with wash buffer. 100 μL of TMB substrate solution (Sigma #T0440) is added into each well, and the plate is incubated with gentle shaking at room temperature for 10 to 20 minutes. After color development, 100 μL of stop solution (1N hydrochloric acid) is added to each well to terminate color development. The plate is read at 450 nm on an ELISA plate reader.

TABLE 2

B-Raf Biochemical and Cellular Activity Data

| Ex. No. | pMEK IC50 (μM) | b-Raf $K_i$ (μM) | b-Raf % inhib @ 1 μM |
|---|---|---|---|
| B-1 | 0.154 | 0.0005 | 102 |
| B-2 | 8.67 | 0.012 | 97 |
| B-3 | 0.815 | 0.011 | 98 |
| B-4 | 3.37 | 0.272 | 74 |
| B-5 | 0.007 | 0.0002 | |
| B-6 | 0.044 | 0.0015 | |
| B-7 | 4.01 | 0.0103 | |
| B-8 | 8.49 | 10624 | |
| B-9 | 9.26 | 0.002 | |
| B-10 | 5.96 | 0.005 | |
| B-11 | 0.007 | <0.0001 | |
| B-12 | 0.45 | 0.0016 | |
| B-13 | 6.27 | 0.0227 | |
| B-14 | 0.51 | 0.0007 | 100 |
| B-15 | 3.25 | 0.0062 | |
| C-1 | 0.483 | 0.0039 | |
| D-1 | 1.98 | 0.0033 | |
| D-2 | 0.109 | 0.0003 | |
| D-3 | 1.81 | 0.0083 | 93 |
| D-4 | 0.149 | <0.0001 | 100 |
| D-5 | 0.182 | 0.0005 | 100 |
| D-6 | 0.369 | 0.00136 | 101 |
| D-7 | 0.386 | 0.0005 | 99 |
| D-8 | 0.542 | 0.0007 | 100 |
| D-9 | 0.918 | 0.0016 | 100 |
| D-10 | 0.923 | 0.002 | 100 |
| D-11 | 1.32 | 0.0008 | 100 |
| D-12 | 1.52 | 0.0014 | 99 |
| D-13 | 2.99 | 0.0007 | 100 |
| D-14 | 3.14 | 0.0048 | 99 |
| E-1 | 0.223 | 0.0015 | |
| E-2 | 0.015 | <0.0001 | 100 |
| E-3 | 0.165 | 0.0006 | |
| E-4 | 0.188 | 0.0019 | |

TABLE 3

| Ex. No. | pMEK IC50 (μM) |
|---|---|
| B-16 | 0.024 |
| B-17 | 0.0619 |
| B-18 | 0.58 |
| B-19 | 0.00271 |
| B-20 | 0.00664 |
| B-21 | 0.00195 |
| B-22 | 0.0263 |
| B-23 | 0.000428 |
| B-24 | 0.00326 |
| B-25 | 0.00598 |
| B-26 | 2.2 |
| B-27 | 0.184 |
| B-28 | 0.538 |
| B-29 | 9.39 |
| B-30 | 0.0002 |
| B-31 | 0.0005 |
| B-32 | 0.001 |
| B-33 | 0.00448 |
| B-34 | 0.0295 |
| B-35 | 0.193 |
| B-36 | 0.458 |
| B-37 | 0.044 |
| B-38 | 0.0187 |
| B-39 | 0.0878 |
| B-40 | 0.0482 |
| B-41 | 0.0785 |
| B-42 | 5.65 |
| B-43 | 0.0441 |
| B-44 | 0.00137 |
| B-45 | 0.319 |
| B-46 | 0.016 |
| B-47 | 0.0862 |
| B-48 | 0.0303 |
| B-49 | 0.0224 |
| B-50 | 0.00729 |
| B-51 | 0.011 |
| B-52 | 0.00930 |
| B-53 | 1.32 |
| B-54 | 0.00124 |
| B-55 | 0.0636 |
| B-56 | 0.0833 |
| B-57 | 0.00295 |
| B-58 | 0.00986 |
| B-59 | 0.00686 |
| B-60 | 0.044 |
| B-61 | 0.0673 |
| B-62 | 0.0481 |
| B-63 | 0.0437 |
| B-64 | 0.0617 |
| B-65 | 0.00904 |
| B-66 | 0.00287 |
| B-67 | 0.0092 |

TABLE 3-continued

| Ex. No. | pMEK IC50 (μM) |
|---|---|
| B-68 | 0.0256 |
| B-69 | 0.00298 |
| B-70 | 0.00233 |
| B-71 | 0.0028 |
| B-72 | 0.00815 |
| B-73 | 0.0635 |
| B-74 | 0.00533 |
| B-75 | 0.0238 |
| B-76 | 0.012 |
| B-77 | 0.0304 |
| B-78 | 0.0088 |
| B-79 | 0.001 |
| B-80 | 0.0953 |
| B-81 | 0.0715 |
| B-82 | 0.000627 |
| B-83 | 0.0123 |
| B-84 | 0.0187 |
| B-85 | 0.0219 |
| B-86 | 0.0306 |
| B-87 | 0.51 |
| B-88 | 0.00693 |
| B-89 | 0.284 |
| B-90 | 0.0434 |
| B-91 | 0.00494 |
| B-92 | 0.28 |
| B-93 | 0.000275 |
| B-94 | 0.0133 |
| B-95 | 1.67 |
| B-96 | 0.0141 |
| B-97 | 0.174 |
| B-98 | 0.146 |
| B-99 | 0.235 |
| B-100 | 0.00429 |
| B-101 | 0.107 |
| B-102 | 0.509 |
| B-103 | 3.8 |
| B-104 | 0.00962 |
| B-105 | 0.00946 |
| B-106 | 0.0105 |
| B-107 | 0.00806 |
| B-108 | 0.0112 |
| B-109 | 0.00469 |
| B-110 | 0.144 |
| B-111 | 0.00613 |
| B-112 | 0.0162 |
| B-113 | 0.00148 |
| B-114 | 0.00222 |
| C-2 | 1.31 |

TABLE 3-continued

| Ex. No. | pMEK IC50 (μM) |
|---|---|
| D-15 | 0.107 |
| E-5 | 0.000836 |
| E-6 | 0.00898 |
| F-1 | 0.0499 |
| F-2 | 0.196 |
| F-3 | 0.0554 |
| G-1 | 0.0163 |
| G-2 | 0.00524 |
| G-3 | 0.0229 |
| G-4 | 0.774 |
| G-5 | 0.0199 |
| G-6 | 0.0173 |
| G-7 | 0.0285 |
| H-1 | 0.026 |
| H-2 | 1.02 |
| H-3 | 0.427 |
| H-4 | 0.0663 |
| I-1 | 2.79 |
| I-2 | 0.02 |

We claim:

1. A compound of the formula:

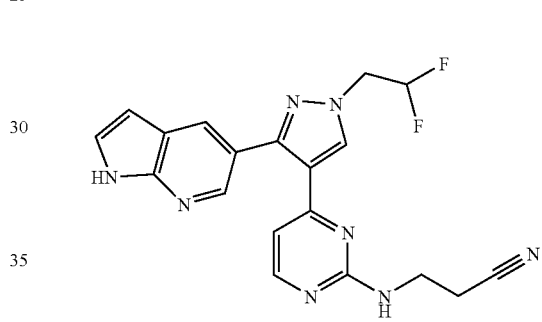

or a pharmaceutically acceptable salt thereof.

2. A pharmaceutical composition comprising the compound according to claim 1, or a pharmaceutically acceptable salt thereof, and a pharmaceutically acceptable carrier or diluent.

* * * * *